(12) United States Patent
Shiboleth et al.

(10) Patent No.: US 11,458,157 B2
(45) Date of Patent: *Oct. 4, 2022

(54) COMPOSITIONS AND METHODS FOR MODIFYING A PREDETERMINED TARGET NUCLEIC ACID SEQUENCE

(71) Applicant: TARGETGENE BIOTECHNOLOGIES LTD., D.N. Hefer (IL)

(72) Inventors: Yoel Moshe Shiboleth, D.N. Hefer (IL); Dan Michael Weinthal, Be'er Sheva (IL)

(73) Assignee: Targetgene Biotechnologies Ltd., D.N. Hefner (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/364,216

(22) PCT Filed: Dec. 16, 2012

(86) PCT No.: PCT/IL2012/050528
§ 371 (c)(1),
(2) Date: Jun. 10, 2014

(87) PCT Pub. No.: WO2013/088446
PCT Pub. Date: Jun. 20, 2013

(65) Prior Publication Data
US 2015/0211023 A1    Jul. 30, 2015

Related U.S. Application Data

(60) Provisional application No. 61/576,423, filed on Dec. 16, 2011.

(51) Int. Cl.
| | |
|---|---|
| *A61K 31/7105* | (2006.01) |
| *C07K 19/00* | (2006.01) |
| *C12N 9/22* | (2006.01) |
| *C12N 15/90* | (2006.01) |
| *C12N 15/62* | (2006.01) |
| *A61K 38/00* | (2006.01) |
| *C12N 15/00* | (2006.01) |
| *C12N 15/10* | (2006.01) |
| *C12N 15/82* | (2006.01) |
| *A61K 31/711* | (2006.01) |
| *A61K 31/7115* | (2006.01) |
| *A61K 31/712* | (2006.01) |
| *A61K 31/7125* | (2006.01) |
| *A61K 31/713* | (2006.01) |
| *A61K 48/00* | (2006.01) |

(52) U.S. Cl.
CPC ........ *A61K 31/7105* (2013.01); *A61K 31/711* (2013.01); *A61K 31/712* (2013.01); *A61K 31/713* (2013.01); *A61K 31/7115* (2013.01); *A61K 31/7125* (2013.01); *A61K 38/00* (2013.01); *C07K 19/00* (2013.01); *C12N 9/22* (2013.01); *C12N 15/00* (2013.01); *C12N 15/102* (2013.01); *C12N 15/62* (2013.01); *C12N 15/825* (2013.01); *C12N 15/8213* (2013.01); *C12N 15/8251* (2013.01); *C12N 15/902* (2013.01); *C12N 15/907* (2013.01); *A61K 48/00* (2013.01); *C07K 2319/01* (2013.01); *C07K 2319/09* (2013.01)

(58) Field of Classification Search
None
See application file for complete search history.

(56) References Cited

U.S. PATENT DOCUMENTS

| | | | |
|---|---|---|---|
| 4,935,357 A | 6/1990 | Szybalski | |
| 5,034,506 A | 7/1991 | Summerton | |
| 5,235,033 A | 8/1993 | Summerton | |
| 6,544,780 B1 | 4/2003 | Wang | |
| 8,697,359 B1 | 4/2014 | Zhang | |
| 8,748,146 B2 | 6/2014 | Lippow et al. | |
| 2003/0105045 A1* | 6/2003 | Stanojevic | C12N 15/113 514/44 A |
| 2003/0228608 A1* | 12/2003 | Friedman-Ohana | C12N 15/102 435/6.18 |

(Continued)

FOREIGN PATENT DOCUMENTS

| | | |
|---|---|---|
| EP | 0234781 A2 * | 2/1987 |
| GB | 1122458.1 | 9/2014 |

(Continued)

OTHER PUBLICATIONS

Written Opinion of the International Search Authority PCT/IL2012/050528, pp. 1-6 dated Mar. 21, 2013.*

(Continued)

*Primary Examiner* — Nancy J Leith

(74) *Attorney, Agent, or Firm* — Arnold & Porter Kaye Scholer

(57) ABSTRACT

Provided herein are compositions and methods for modifying a predetermined nucleic acid sequence. A programmable nucleoprotein molecular complex containing a polypeptide moiety and a specificity conferring nucleic acid (SCNA) which assembles in-vivo, in a target cell, and is capable of interacting with the predetermined target nucleic acid sequence is provided. The programmable nucleoprotein molecular complex is capable of specifically modifying and/or editing a target site within the target nucleic acid sequence and/or modifying the function of the target nucleic acid sequence.

16 Claims, 21 Drawing Sheets
Specification includes a Sequence Listing.

(56) References Cited

U.S. PATENT DOCUMENTS

| | | | |
|---|---|---|---|
| 2005/0026157 A1* | 2/2005 | Baltimore | C12N 9/22 435/6.14 |
| 2007/0042404 A1* | 2/2007 | Zhao | C12N 9/22 435/6.12 |
| 2010/0076057 A1 | 3/2010 | Sontheimer et al. | |
| 2011/0033935 A1 | 2/2011 | Jantz et al. | |
| 2011/0117625 A1* | 5/2011 | Lippow | C12N 9/22 435/196 |
| 2011/0217739 A1 | 9/2011 | Terns et al. | |
| 2012/0324603 A1* | 12/2012 | Hlubek | C12N 9/22 800/298 |
| 2014/0068797 A1* | 3/2014 | Doudna | C12N 15/102 800/18 |
| 2015/0071900 A1* | 3/2015 | Liu | C12N 15/115 424/94.3 |

FOREIGN PATENT DOCUMENTS

| | | |
|---|---|---|
| JP | 63-68083 | 3/1988 |
| JP | 2005-523014 | 8/2005 |
| JP | 2006-502748 | 1/2006 |
| JP | 2007-501626 | 2/2007 |
| UA | 42675 C2 | 11/2001 |
| WO | WO 91/09955 A1 | 7/1991 |
| WO | WO 2004/037977 | 5/2004 |
| WO | WO 2005/014791 | 2/2005 |
| WO | 2006/027099 | 3/2006 |
| WO | WO 2007/025097 | 3/2007 |
| WO | 2011/017315 | 2/2011 |
| WO | WO 2011/072246 | 6/2011 |
| WO | WO 2011/146121 | 11/2011 |
| WO | WO 2011/154393 | 12/2011 |
| WO | 2012/129373 | 9/2012 |
| WO | WO 2013/098244 A1 | 7/2013 |

OTHER PUBLICATIONS

Voytas Annu. Rev. Plant Biol. 2013 64:327-350.*
Kandavelou et al. Engineering and Applications of Chimeric Nucleases Nucleic Acids and Molecular Biology vol. 14 Alfred Pingoud (ed.) Restriction Nucleases Springer-Verlag Berlin Heidelbery 2004, pp. 414-434.*
Shuangyong Xu A universal DNA endonuclease retrieved from SBIR.gov (retrieved from https://www.sbir.gov on Apr. 8, 2016, pp. 1-2, 2005.*
Sorek et al., "CRISPR-Mediated Adaptive Immune Systems in Bacteria and Archaea" 82 Annual Review of Biochemistry 237-266 (Mar. 11, 2013).*
Bibikova et al., "Enhancing Gene Targeting with Designed Zinc Finger Nucleases" 300 Science 764 (2003).*
Sinkunas et al., "Cas3 is a single-stranded DNA nuclease and ATP-dependent helicase in the CRISPR/Cas immune system" 30 The EMBO Journal 1335-1342 (Year: 2011).*
Singwi et al., "Potential Nuclease-Based-Strategies for HIV Gene Therapy" 5 Frontiers in Bioscience d556-579 (Year: 2000).*
Carroll. "Zinc-finger Nucleases as Gene Therapy Agents", Gene Ther., 2008, vol. 15(22), pp. 1463-1468.
Christian et al. "Targeting DNA Double-Strand Breaks with TAL Effector Nucleases", Genetics, 2010, vol. 186, pp. 757-761.
Deltcheva et al. "CRISPR RNA maturation by trans-encoded small RNA and host factor RNase III", Nature, 2011, vol. 47, pp. 602-609.
Gaj et al. "Structure-guided reprogramming of serine recombinase DNA sequence specificity", PNAS, 2011, vol. 108(2), pp. 498-503.
Garneau et al. "The CRISPR/Cas bacterial immune system cleaves bacteriophage plasmid DNA", Nature, 2010, vol. 468, pp. 67-72.
Hale et al. "RNA-Guided RNA Cleavage by a CRISPR RNA-Cas Protein Complex", Cell, 2009, vol. 139, pp. 945-956.
Horvath and Barrangou. "CRISPR/Cas, the Immune System of Bacteria and Archaea", Science, 2010, vol. 327, pp. 167-170.
Jore et al. "Structural basis for CRISPR RNA-guided DNA recognition by Cascade", Nat Struct Mol Biol., 2011, vol. 18(5), pp. 529-536.
Makarova et al. "Evolution and classification of the CRISPR-Cas systems", Nat Rev Mircobiol., 2011, vol. 9(6), pp. 467-477.
Perez-Rodriguez et al. "Envelope stress is a trigger of CRIPSR RNA-mediated DNA silencing in Escherichia coli", Mol Micro., 2010, vol. 79(3), pp. 584-599.
Sapranauskas et al. "The Streptococcus thermophilus CRIPSR/Cas system provides immunity in Escherichia coli", Nucleic Acids Res., 2011, vol. 39(21), pp. 9275-9285.
Wiedenheft et al. "Structures of the RNA-guided surveillance complex from a bacterial immune system", Nature, 2011, vol. 477, pp. 486-490.
International Search Report dated Mar. 21, 2013 in connection with International Application No. PCT/IL2012/050528.
Written Opinion of the International Searching Authority dated Mar. 21, 2013 in connection with PCT International Application No. PCT/IL2012/050528.
Mar. 19, 2015 First Examination Report in connection with New Zealand patent application 626105.
Oct. 10, 2015 extended European search report in connection with European application 12857977.8.
Voytas D. "Plant genome engineering with sequence specific nucleases", Annu Rev Plant Biol, 2013, vol. 64, pp. 327-350, (abstract only).
Vainstein et al., (2011) Permanent genome modifications in plant cells by transient viral vectors. Trends in Biotechnology 29: 363-369.
Vekhoff et al., (2009) Optimized synthesis and enhanced efficacy of novel triplex-forming camptothecin derivatives based on gimatecan. Bioconjug Chem 20(4): 666-72.
Wang et al., (2011) Metal-free cleavage efficiency toward DNA by a novel PNA analog-bridged macrocyclic polyamine. Bioorg Med Chem Lett 21(19): 5866-9.
Watal et al., (2000) Synthesis and evaluation of novel bioconjugates as antiviral agents. Nucleic Acids Symp Ser (44): 179-80.
Watson et al., (2000) Anti-L-selectin aptamers: binding characteristics, pharmacokinetic parameters, and activity against an intravascular target in vivo. Antisense Nucleic Acid Drug Dev 10(2): 63-75.
Wu et al., (2008) Carbon nanotubes protect DNA strands during cellular delivery. ACS Nano 2(10): 2023-8.
Wu et al., (2009) Tape-Arabidopsis Sandwich—a simpler Arabidopsis protoplast isolation method. Plant Methods 5: 16.
Yang et al., (2008) Inhibition of in vitro amplification of targeted DNA fragment and activity of exonuclease I by a fullerene-oligonucleotide conjugate. Biologicals 36(4): 223-6.
Zhang (2008) Quantum dot-A10 RNA aptamer-doxorubicin conjugate. Molecular Imaging and Contrast Agent Database (MICAD) [Internet]. Bethesda (MD): National Center for Biotechnology Information (US); 2004-2013.
Zhang (2008) Thermally cross-linked superparamagnetic iron oxide nanoparticle-A10 RNA aptamer-doxorubicin conjugate. Molecular Imaging and Contrast Agent Database (MICAD) [Internet], Bethesda (MD): National Center for Biotechnology Information (US); 2004-2013.
Ziemba et al., (2003) A bis-alkylating triplex forming oligonucleotide inhibits intracellular reporter gene expression and prevents triplex unwinding due to helicase activity. Biochemistry 42(17): 5013-24.
Oct. 10, 2015 First Office Action in connection with Chinese Patent Application No. 201280062262X.
Antonelli and Stadler (1989) Chemical methods for direct gene transfer to maize protoplasts: I. Efficient transient expression after treatment with the polycation Polybrene. Maize News letter 63: 21-22.
Aström and Strömberg (2001) A method for synthesis of an artificial ribonuclease. Nucleosides Nucleotides Nucleic Acids 20(4-7): 1385-8.
Barnard et al., (1999) 2-5A-DNA conjugate inhibition of respiratory syncytial virus replication: effects of oligonucleotide structure modifications and RNA target site selection. Antiviral Res 41(3): 119-34.
Barrangou (2012) RNA-mediated programmable DNA cleavage. Nat Biotechnol 30(9): 836-8.

(56) References Cited

OTHER PUBLICATIONS

Basu and Wickstrom (1997) Synthesis and characterization of a peptide nucleic acid conjugated to a D-peptide analog of insulin-like growth factor 1 for increased cellular uptake. Bioconjug Chem 8(4): 481-8.
Bonora et al., (2000) PAcM-AN: poly (N-acryloylmorpholine)-conjugated antisense oligonucleotides. Nucleosides Nucleotides Nucleic Acids 19(8): 1281-8.
Brouns (2012) Molecular biology. A Swiss army knife of immunity. Science 337(6096): 808-9.
Chiou et al., (1994) Enhanced resistance to nuclease degradation of nucleic acids complexed to asialoglycoprotein-polylysine carriers. Nucleic Acids Res 22(24): 5439-46.
Citro et al., (1992) Inhibition of leukemia cell proliferation by receptor-mediated uptake of c-myb antisense oligodeoxynucleotides. Proc Natl Acad Sci U S A 89(15): 7031-5.
Cong et al., (2013) Multiplex genome engineering using CRISPR/Cas systems. Science 339(6121): 819-23.
Corey et al., (1995) Strand invasion by oligonucleotide—nuclease conjugates. Bioconjug Chem 6(1): 93-100.
Duval-Valentin et al., (1998) Triple helix-directed psoralen crosslinks are recognized by Uvr(A)BC excinuclease. J Mol Biol 278(4): 815-25.
Eisenschmidt et al., (2005) Developing a programmed restriction endonuclease for highly specific DNA cleavage. Nucleic Acids Res 33(22): 7039-47.
François et al., (1989) Sequence-targeted cleavage of single- and double-stranded DNA by oligothymidylates covalently linked to 1,10-phenanthroline. J Biol Chem 264(10): 5891-8.
Frau et al., (1997) Nuclease activity and binding characteristics of a cationic "manganese porphyrin-bis(benzimidazole) dye (Hoechst 33258)" conjugate. Bioconjug Chem 8(2): 222-31.
Frau et al., (2001) Binding of a porphyrin conjugate of Hoechst 33258 to DNA. II. NMR spectroscopic studies detect multiple binding modes to a 12-mer nonself-complementary duplex DNA. Nucleosides Nucleotides Nucleic Acids 20 (1-2): 145-56.
Frearson et al., (1973) The isolation, culture and regeneration of Petunia leaf protoplasts. Dev Biol 33(1): 130-7.
Fujii et al., (1997) Preparation of DNA-peptide conjugate using oxime resin. Nucleic Acids Symp Ser (37): 71-2.
Gaglione et al., (2011) PNA-based artificial nucleases as antisense and anti-miRNA oligonucleotide agents. Mol Biosyst 7(8): 2490-9.
Gallois and Marinho (1995) Leaf disk transformation using Agrobacterium tumefaciens-expression of heterologous genes in tobacco. Methods Mol Biol 49: 39-48.
Gamper et al., (1993) Facile preparation of nuclease resistant 3' modified oligodeoxynucleotides. Nucleic Acids Res 21 (1): 145-50.
Gasiunas et al., (2012) Cas9-crRNA ribonucleoprotein complex mediates specific DNA cleavage for adaptive immunity in bacteria. Proc Natl Acad Sci U S A 109(39): E2579-86.
Gordon-Kamm et al., (1990) Transformation of Maize Cells and Regeneration of Fertile Transgenic Plants. Plant Cell 2: 603-618.
Hanic-Joyce and Gray (1991) Accurate transcription of a plant mitochondrial gene in vitro. Mol Cell Biol 11: 2035-2039.
Hillier et al., (2004) An electrochemical study of enzymatic oligonucleotide digestion. Bioelectrochemistry 63(1-2): 307-10.
Huston et al., (1988) Protein engineering of antibody binding sites: recovery of specific activity in an anti-digoxin single-chain Fv analogue produced in *Escherichia coli*. Proc Natl Acad Sci U S A 85: 5879-5883.
Hutvanger et al., (2008) Argonaute proteins: key players in RNA silencing. Molecular Cell Biology 9(1): 22-32.
Jinek et al., (2012) A programmable dual-RNA-guided DNA endonuclease in adaptive bacterial immunity. Science 337 (6096):816-21.
Joung et al., (2000) A bacterial two-hybrid selection system for studying protein-DNA and protein-protein interactions. Proc Natl Acad Sci USA 97(13): 7382-7387.
Kaihatsu et al., (2002) Enhanced strand invasion by peptide nucleic acid-peptide conjugates. Biochemistry 41(37): 11118-25.

Kleemann et al., (2005) Nano-carriers for DNA delivery to the lung based upon a TAT-derived peptide covalently coupled to PEG-PEI. J Control Release 109(1-3): 299-316.
Kochevenko and Willmitzer (2003) Chimeric RNA/DNA oligonucleotide-based site-specific modification of the tobacco acetolactate syntase gene. Plant Physiol 132: 174-184.
Kostenko et al., (2002) Downregulation of PGY1/MDR1 mRNA level in human KB cells by antisense oligonucleotide conjugates. RNA accessibility in vitro and intracellular antisense activity. Biochim Biophys Acta 1576(1-2): 143-7.
Kotlo et al., (2003) Nrf2 is an inhibitor of the Fas pathway as identified by Achilles' Heel Method, a new function-based approach to gene identification in human cells. Oncogene 22: 797-806.
Kubo et al., (2003) DNA conjugates as novel functional oligonucleotides. Nucleosides Nucleotides Nucleic Acids 22 (5-8): 1359-61.
Kubo et al., (2004) Control of intracellular delivery of oligonucleotides by signal peptides and genetic expression in human cells. Nucleic Acids Symp Ser (Oxf) (48):303-4.
Kubo et al., (2005) Controlled intracellular localization and enhanced antisense effect of oligonucleotides by chemical conjugation. Org Biomol Chem 3(18): 3257-9.
Kubo et al., (2005) Highly sensitive inhibition of hTERT mRNA expression and telomerase activity by DNA-signal-peptide conjugates. Nucleic Acids Symp Ser (Oxf) (49): 337-8.
Marrs and Urioste (1995) Transient gene expression analysis in electroporated maize protoplasts. Methods Mol Biol 55:133-45.
Mestre et al., (1996) Structure/nuclease activity relationships of DNA cleavers based on cationic metalloporphyrin-oligonucleotide conjugates. Biochemistry 35(28): 9140-9.
Mori et al., (2011) Bridged nucleic acid conjugates at 6'-thlol: synthesis, hybridization properties and nuclease resistances. Org Biomol Chem 9(14): 5272-9.
Mouratou et al., (2002) Development of nonradioactive microtiter plate assays for nuclease activity. Anal Biochem 309 (1): 40-7.
Murata et al., (2003) Novel DNA/polymer conjugate for intelligent antisense reagent with improved nuclease resistance. Bioorg Med Chem Lett 13(22): 3967-70.
Niemeyer (2001) Semi-synthetic nucleic acid-protein conjugates: applications in life sciences and nanobiotechnology. J Biotechnol 82(1): 47-66.
Ossipov and Strömberg (2005) Studies in oligonucleotide-based artificial nuclease systems. intramolecular copper (II) complex formation in an oligonucleotide bis-phenanthroline conjugate. Nucleosides Nucleotides Nucleic Acids 24(5-7): 901-5.
Otvös and Sági (2004) Antisense oligonucleotides with antitumor activity. Magy Onkol 48(3): 221-7 (translated abstract).
Rabe and Niemeyer (2011) Selective covalent conjugation of phosphorothioate DNA oligonucleotides with streptavidin. Molecules 16(8): 6916-26.
Rhodes et al., (1988a) Plant regeneration from protoplasts isolated from embryoganic maize cell cultures. Bintechnology 6:56-60.
Schierling et al., (2012) A novel zinc-finger nuclease platform with a sequence-specific cleavage module. Nucleic Acids Res 40(6): 2623-38.
Sheen (2001) Signal transduction in maize and *Arabidopsis mesophyll* protoplasts. Plant Physiol 127: 1466-1475.
May 2, 2016 Response to Oct. 27, 2015 Communication in connection with European Application No. 12857977.8.
Apr. 25, 2016 Response to Oct. 25, 2015 First Office Action in connection with Chinese Application No. 201280062262X, including English language set of claims.
Apr. 7, 2016 Office Action issued by the Israeli Patent Office in connection with Israeli Application No. 232832, including English language summary.
Aarts et al., "Generation of a mouse mutant by oligonucleotide-mediated gene modification in ES cells," *Nucleic Acids Res* 34:e147 (2006).
Aarts et al., "Progress and prospects: oligonucleotide-directed gene modification in mouse embryonic stem cells: a route to therapeutic application," *Gene Ther*, 18: 213-219 (2011).
Andrieu-Soler et al., "Stable transmission of targeted gene modification using single-stranded oligonucleotides with flanking LNAs," *Nucleic Acids Res*, 33: 3733-3742 (2005).

(56) References Cited

OTHER PUBLICATIONS

Arnould et al., "The I-CreI meganuclease and its engineered derivatives: applications from cell modification to gene therapy," *Protein Eng Des Sel*, 24: 27-31 (2010).
Bardwell et al., "Purification of RNA and RNA-protein complexes by an R17 coat protein affinity method," *Nucleic Acids Res*, 18:6587-6594 (1990).
Beetham et al., "A tool for functional plant genomics: Chimeric RNA/DNA oligonucleotides cause in vivo gene-specific mutations," *Proc Natl Acad Sci USA*, 96: 8774-8778 (1999).
Beumer et al., "Efficient gene targeting in *Drosophila* with zinc-finger nucleases," *Genetics*, 172:2391-2403 (2006).
Beumer et al., "Efficient gene targeting in *Drosophila* by direct embryo injection with zinc-finger nucleases," *Proc Natl Acad Sci USA*, 105:19821-19826 (2008).
Blancafort et al., "Designing transcription factor architectures for drug discovery," *Molecular Pharmacology*, 66:1361-1371 (2004).
Bonner et al., "DNA breakage associated with targeted gene alteration directed by DNA oligonucleotides," *Mutat Res*, 669(1-2):85-94 (2009).
Brenneman et al., "Stimulation of intrachromosomal homologous recombination in human cells by electroporation with site-specific endonucleases," *Proc Natl Acad Sci USA*, 93:3608-3612 (1996).
Chen et al., "The PWWP domain of Dnmt3a and Dnmt3b is required for directing DNA methylation to the major satellite repeats at pericentric heterochromatin," *Molecular and Cellular Biology*, 24(20):9048-9058 (2004).
Chien et al., "The two-hybrid system: a method to identify and clone genes for proteins that interact with a protein of interest," *Proc Natl Acad Sci USA*, 88:9578-9582 (1991).
Chiurazzi et al., "Enhancement of somatic intrachromosomal homologous recombination in *Arabidopsis* by the HO endonuclease," *The Plant Cell*, 8:2057-2066, 1996.
Choulika et al., "Induction of homologous recombination in mammalian chromosomes by using the 1-SceI system of *Saccharomyces cerevisiae*," *Molecular and Cellular Biology*, 115:1968-1973 (1995).
Christian et al., "Targeting DNA double-strand breaks with TAL effector nucleases," *Genetics*, 186:757-761 (2010).
Cilley et al., "Structural mimicry in the phage φ21 N peptide-boxB RNA complex," *RNA*, 9:663-676 (2003).
Collombet et al., "Introduction of plasmid DNA into isolated mitochondria by electroporation. A novel approach toward gene correction for mitochondrial disorders," *The Journal of Biological Chemistry*, 272(8):5342-5347 (1997).
DeGregorio et al., "Translation driven by an cIF4G core domain in vivo," *The EMBO Journal*, 18(17):4865-4874 (1999).
Donoho et al., "Analysis of gene targeting and intrachromosomal homologous recombination stimulated by genomic double-strand breaks in mouse embryonic stem cells," *Molecular and Cellular Biology*, 18(7):4070-4078 (1998).
Dreier et al., "Development of zinc finger domains for recognition of the 5'-CNN-3' family DNA sequences and their use in the construction of artificial transcription factors," *The Journal of Biological Chemistry*, 280(42):35588-35597 (2005).
Epinat et al., "A novel engineered meganuclease induces homologous recombination in yeast and mammalian cells," *Nucleic Acids Res*, 31(11):2952-2962 (2003).
Farré et al., "Gene expression in isolated plant mitochondria: high fidelity of transcription, splicing and editing of a transgene product in electroporated organelles," *Nucleic Acids Research*, 29:2484-2491 (2001).
Finer et al., "Development of the particle inflow gun for DNA delivery to plant cells," *Plant Cell Reports* 11:323-328 (1992).
Folger et al., "Patterns of integration of DNA microinjected into cultured mammalian cells: evidence for homologous recombination between injected plasmid DNA molecules," *Molecular and Cellular Biology*, 2(11):1372-1387 (1982).
Fuks et al., "Dnmt3a binds deacetylases and is recruited by a sequence-specific repressor to silence transcription," *EMBO J*, 20(10):2536-2544 (2001).

Gandhi et al., "Regeneration from leaf protoplasts of *Arabidopsis thaliana* ecotype estland," *Indian Journal of Experimental Biology*, 39:705-709 (2001).
GenBank Accession No. EF447274, "*Zea mays* inositol phosphate kinase 1A (ipd1A) gene, complete cds," Jul. 6, 2007.
GenBank Accession No. AB535096.1, "Targeting vector pTgKCNQ2 DNA, complete sequence," Mar. 1, 2014.
GenBank Accession No. AF067972.2, "*Homo sapiens* DNA cytosine methyltransferase 3 alpha (DNMT3A) mRNA, complete cds," Feb. 12, 2001.
GenBank Accession No. AY230218.1, "Expression vector pDAS112 regulated promoter system for Gram-positive species," Oct. 21, 2003.
GenBank Accession No. EU048870.1, "Cloning vector pSoup, complete sequence," Aug. 19, 2007.
GenBank Accession No. M16770.1, "*Petunia axillaris* subsp. *parodii* CMS-associated fusion protein (CMS-afp), NADH dehydrogenase subunit 3 (nad3), and ribosomal protein S12 (rps12) genes, complete cds; mitochondrial," Jul. 14, 2016.
GenBank Accession No. X07645.1, "Tobacco acetolactate synthase gene, ALS SuRB (EC 4.1.3.18)," Apr. 18, 2005.
GenBank Accession No. X17295.1, "*Arabidopsis* HSP 18.2 gene for 18.2kDa heat shock protein," Apr. 18, 2005.
GenBank Accession No. Y00609.1, "Petunia x hybrid X *Petunia axillaris* subsp. *parodii* mitochondrial ATP synthase subunit 9," Jul. 25, 2016.
GenBank Accession No. NC_000010 GPC_000001302, *Homo sapiens* chromosome 10, GRCh38.p7 Primary Assembly, Jun. 6, 2016.
GenBank Accession No. NT_022517 GPS_003205480, "*Homosapiens* chromosome 3 genomic scaffold, GRCh38.p7 Primary Assembly HSCHR3_CTG1," Jun. 6, 2016.
Guan et al., "Heritable endogenous gene regulation in plants with designed polydactyl zinc finger transcription factors," *Proc Natl Acad Sci USA*, 99(20):13296-13301 (2002).
Hanin et al., "Gene targeting in *Arabidopsis*," *The Plant Journal*, 28(6):671-677 (2001).
Havre et al., "Targeted mutagenesis of simian virus 40 DNA mediated by a triple helix-forming oligonucleotide," *Journal of Virology*, 67(12):7324-7331 (1993).
Holz-Schietinger et al., "Oligomerization of DNMT3A controls the mechanism of de novo DNA methylation," *J Biol Chem*, 286(48):41479-41488 (2011).
Igoucheva et al., "Oligonucleotide-mediated gene targeting in human hepatocytes: implications of mismatch repair," *Oligonucleotides* 18:111-122 (2008).
Igoucheva et al., "A sequence-specific gene correction by an RNA-DNA oligonucleotide in mammalian cells characterized by transfection and nuclear extract using a lacZ shuttle system," *Gene Ther*, 6:1960-1971 (1999).
Igoucheva et al., "Targeted gene correction by small single-stranded oligonucleotides in mammalian cells," *Gene Therapy*, 8:391-399 (2001).
Japanese Office Action dated Dec. 6, 2016, including English translation.
Jin et al., "Resistance to human immunodeficiency virus type 1 (HIV-1) generated by lentivirus vector-mediated delivery of the CCR5Δ32 gene despite detectable expression of the HIV-1 co-receptors," *J Gen Virol*, 89(Pt. 10):2611-2621 (2008).
Kawai et al., "New procedure for DNA transfection with polycation and dimethyl sulfoxide," *Mol Cell Bio*, 14(6):1172-1174 (1984).
Keryer-Bibens et al., "Tethering of proteins to RNAs by bacteriophage proteins," *Biol Cell*, 100:125-138 (2008).
Kim et al., "Cleaving DNA at any predetermined site with adapter-primers and class-IIS restriction enzymes," *Science*, 240:504-506 (1988).
Kim et al., "Hybrid restriction enzymes: zinc finger fusions to Fok I cleavage domain," *Proc Natl Acad Sci USA*, 93:1156-1160 (1996).
Knauert et al., "Triplex forming oligonucleotides: sequence-specific tools for gene targeting," *Hum Mol Genet*, 10(20):2243-2251 (2001).
Koulintchenko et al., "Plant mitochondria actively import DNA via the permeability transition pore complex," *EMBO J*, 22:1245-1254 (2003).

(56) References Cited

OTHER PUBLICATIONS

Kulinski et al., "CEL I Enzymatic Mutation Detection Assay," *Biotechniques* 29:44-48 (2000).
Levy et al., "Transfer of chloramphenicol-resistant mitochondrial DNA into the chimeric mouse," *Transgenic Res*, 8:137-145 (1999).
Lloyd et al., "Targeted mutagenesis using zinc-finger nucleases in *Arabidopsis*," *Proc Natl Acad Sci USA*, 102:2232-2237 (2005).
Majumdar et al., "Cell cycle modulation of gene targeting by a triple helixforming oligonucleotide," *J Biol Chem*, 278:11072-11077 (2003).
Mani et al., "Binding of two zinc finger nuclease monomers to two specific sites is required for effective double-strand DNA cleavage," *Biochem Biophys Res Commun*, 334(4):1191-1197 (2005).
Marcaida et al., "Crystal structure of I-DmoI in complex with its target DNA provides new insights into meganuclease engineering," *Proc Natl Acad Sci USA*, 105(44):16888-16893 (2008).
Marton et al., "Nontransgenic genome modification in plant cells," *Plant Physiol*, 154(3):1079-1087 (2010).
Miller et al., "Human gene targeting by adeno-associated virus vectors is enhanced by DNA double-strand breaks," *Mol Cell Biol*, 23:3550-3557 (2003).
Minczuk et al., "Sequence-specific modification of mitochondrial DNA using a chimeric zinc finger methylase," *Proc Natl Acad Sci USA*, 103:19689-19694 (2006).
Minczuk et al., "Development of a single-chain, quasi-dimeric zinc-finger nuclease for the selective degradation of mutated human mitochondrial DNA," *Nucleic Acids Res*, 36(12):3926-3938 (2008).
Moser et al., "Sequence-specific cleavage of double helical DNA by triple helix formation," *Science*, 238(4825):645-650 (1987).
Munoz et al., "Molecular basis of engineered meganuclease targeting of the endogenous human RAG1 locus," *Nucleic Acids Res*, 39:729-743 (2011).
Nissan et al., "The type III effectors HsvG and HsvB of gall-forming Pantoea agglomerans determine host specificity and function as transcriptional activators," *Mol Microbiol*, 61(5):1118-1131 (2006).
OMIM Entry #116920, "Leukocyte Adhesion Deficiency, Type I; LAD," http://www.omim.org/entry/116920; downloaded Mar. 27, 2017.
OMIM Entry #308240, "Lymphoproliferative Syndrome, X-Linked, 1;XLP1," http://www.omim.org/entry/308240; downloaded Mar. 27, 2017.
OMIM Entry #102700, "Severe Combined Immunodeficiency, Autosomal Recessive, T Cell-Negative, B Cell-Negative, NK Cell-Negative, Due to Adenoine Deaminase Deficiency," https://www.omim.org/entry/102700; downloaded Mar. 27, 2017.
Pierce et al., "Oligonucleotide-directed single-base DNA alterations in mouse embryonic stem cells," *Gene Ther*, 10:24-33 (2003).
Podhajska et al., "Conversion of the FokI endonuclease to a universal restriction enzyme: cleavage of phage M13mp7 DNA at predetermined sites," *Gene*, 40:175-182 (1985).
Porteus, "Mammalian gene targeting with designed zinc finger nucleases," *Mol Ther*, 13(2):pp. 438-446 (2006).
Pruett-Miller et al., "Attenuation of Zinc Finger Nuclease Toxicity by Small-Molecule Regulation of Protein Levels," *PLOS Genetics*, 5:01000376 (2009).
Puchta, "Gene replacement by homologous recombination in plants," *Plant Mol Biol*, 48:173-182 (2002).
Puchta et al., "Two different but related mechanisms are used in plants for the repair of genomic double-strand breaks by homologous recombination," *Proc Nati Acad Sci USA*, 93:5055-5060 (1996).
Rice et al., "Genetic repair of mutations in plant cell-free extracts directed by specific chimeric oligonucleotides," *Plant Physiol*, 123:427-438 (2000).
Rudin et al., "Efficient repair of HO-induced chromosomal breaks in *Saccharomyces cerevisiae* by recombination between flanking homologous sequences," *Mol Cell Biol*, 8(9):3918-3928 (1988).
Salomon et al., "Capture of genomic and T-DNA sequences during doublestrand break repair in somatic plant cells," *The EMBO Journal*, 17(20):6086-6095 (1998).

Scherer et al., "Replacement of chromosome segments with altered DNA sequences constructed in vitro," *Proc Natl Acad Sci USA*, 76:4951-4955 (1979).
Sheen et al., "Green-fluorescent protein as a new vital marker in plant cells," *The Plant Journal*, 8(5):777-784 (1995).
Stege et al., "Controlling gene expression in plants using synthetic zinc finger transcription factors," *Plant J*, 32(6):1077-1086 (2002).
Szczepek et al., "Structure-based redesign of the dimerization interface reduces the toxicity of zinc-finger nucleases," *Nat Biotechnol*, 25(7):786-793 (2007).
Takata et al., "Homologous recombination and non-homologous end-joining pathways of DNA double-strand break repair have overlapping roles in the maintenance of chromosomal integrity in vertebrate cells," *Embo J*, 17(18):5497-5508 (1998).
Tan et al., "Structural variety of arginine-rich RNA-binding peptides," *Proc Natl Acad Sci USA*, 92(12):5282-5286 (1995).
Tovkach et al., "A toolbox and procedural notes for characterizing novel zinc finger nucleases for genome editing in plant cells," *Plant J*, 57(4):747-757 (2009).
Tzfira et al., "Site-specific integration of Agrobacterium tumefaciens T-DNA via double-stranded intermediates," *Plant Physiol.*, 1133:1011-1023 (2003).
Wang et al., (1995) "Targeted mutagenesis in mammalian cells mediated by intracellular triple helix formation," *Mol Cell Biol*, 15:1759-1768 (1995).
Weinthal et al., "Characterization of nuclear localization signals in the type III effectors HsvG and HsvB of the gall-forming bacterium P anto ea agglomerans," *Microbiology*, 157:1500-1508 (2011).
Windbichler et al., "Homing endonuclease mediated gene targeting in Anopheles gambiae cells and embryos," *Nucleic Acids Res*, 35(17):5922-5933 (2007).
Wright et al., "High-frequency homologous recombination in plants mediated by zinc-finger nucleases," *Plant J*, 44(4):693-705 (2005).
Yoon et al., "Targeted gene correction of episomal DNA in mammalian cells mediated by a chimeric RNA•DNA oligonucleotide," *Proc Natl Acad Sci USA*, 93(5):2071-2076 (1996).
Yoon et al., "Transformation of isolated mammalian mitochondria by bacterial conjugation," *Nucleic Acids Res*, 33:e139 (2005).
Zhang et al., "Synthetic zinc finger transcription factor action at an endogenous chromosomal site—Activation of the human erythropoietin gene," *J Biol Chem*, 275(43):33850-33860 (2000).
Zhu et al., "Targeted manipulation of maize genes in vivo using chimeric RNA/DNA oligonucleotides," *Proc Natl Acad Sci USA*, (96):8768-8773 (1999).
Ansari et al., "Modular design of artificial transcription factors," *Current Opinion in Chemical Biology*, 6:765-775 (2002).
Baribault et al., "Embryonic stem cell culture and gene targeting in transgenic mice," *Mol Biol Med*, 6:481-492 (1989).
Beerli et al., "Engineering polydactyl zinc-finger transcription factors," *Nature Biotechnology*, 20:135-141 (2002).
Boynton et al. "Genetics and transformation of mitochondria in the green alga *Chlamydomonas*," *Methods in Enzymology*, 264:279-296 (1996).
Britt et al., "Re-engineering plant gene targeting," *Trends Plant Sci*, 8(2):90-95 (2003).
Brun et al., "Cloning of the PpMSH-2 cDNA of *Physcomitrella patens*, a moss in which gene targeting by homologous recombination occurs at high frequency," *Biochimie*, 83:1003-1008 (2001).
Cai et al., "Targeted transgene integration in plant cells using designed zinc finger nucleases," *Plant Mol Biol*, 69:699-709 (2009).
Capecchi, "Altering the genome by homologous recombination," *Science*, 244(4910):1288-1292 (1989).
Capecchi, "Gene targeting in mice: functional analysis of the mammalian genome for the twenty-first century," *Nat Rev Genet*, 6:507-512 (2005).
Carroll et al., "Design, construction and in vitro testing of zinc finger nucleases," *Nat Protoc*, 1(3):1329-1341 (2006).
Carroll et al., "High-efficiency gene targeting in *Drosophila* with zinc finger nucleases," *Methods in Molecular Biolology*, 649:271-280 (2010).
Chen et al., "Structure and function of eukaryotic DNA methyltransferases," *Current Topics in Developmental Biology*, 60:55-89 (2004).

(56) References Cited

OTHER PUBLICATIONS

Choo et al., "In vivo repression by a site-specific DNA-binding protein designed against an oncogenic sequence," *Nature*, 372:642-645 (1994).
Choulika et al., "The yeast I-Sce I meganuclease induces site-directed chromosomal recombination in mammalian cells," *C R Acad Sci III*, 317:1013-1019(1994).
Collombet et al., "Towards gene therapy of mitochondrial disorders," *Molecular Medicine Today*, 4(1):31-38 (1998).
Connolly et al., "Synthesis and characterization of an octanucleotide containing the EcoR1 recognition sequence with a phosphorothioate group at the cleavage site," *Biochemistry*, 23:3443-3453 (1984).
Corey et al., "Generation of a hybrid sequence-specific single-stranded deoxyribonuclease," *Science*, 238:1401-1403 (1987).
Corey et al., "Generation of a catalytic sequence-specific hybrid DNase," *Biochemistry*, 28:8277-8286 (1989).
Cress et al., "Critical structural elements of the VP16 transcriptional activation domain," *Science*, 251: 87-90 (1991).
Dovzhenko et al., "Efficient regeneration from cotyledon protoplasts in *Arabidopsis thaliana*," *Protoplasma*, 222:107-111 (2003).
Ekker, "Zinc finger-based knockout punches for zebrafish genes," *Zebrafish*, 5(2):121-123 (2008).
Ferrara et al., "Enhanced oligonucleotide-directed gene targeting in mammalian cells following treatment with DNA damaging agents," *Experimental Cell Research*, 300:170-179 (2004).
Galbraith et al., "Flow Cytometric analysis of transgene expression in higher plants: green-fluorescent protein," *Methods in Cell Biol*, 50:3-14 (1995).
Gu et al., "Transplantation and subsequent behavior of mitochondria in cells of *Phytophthora*," *Canadian Journal of Microbiology*, 46:992-997 (2000).
Guilinger et al., "Fusion of catalytically inactive Cas9 to Fok1 nuclease improves the specificity of genome modification," *Nature Biotechnology*, 32:577-582 (2014).
Igoucheva et al., "Targeted single-base correction by RNA-DNA oligonucleotides," *Human Gene Therapy*, 11:2307-2312 (2000).
Iida et al., "Modification of endogenous natural genes by gene targeting in rice and other higher plants," *Plant Mol Biol.*, 59:205-219 (2005).
King et al., "Injection of mitochondria into human cells leads to a rapid replacement of the endogenous mitochondrial DNA," *Cell*, 52:811-819 (1988).
Komor et al., "Programmable editing of a target base in genomic DNA without double-stranded DNA cleavage," *Nature*, 533(7603):420-424 (2016).
Krützfeldt et al., "Silencing of MicroRNAs in vivo with 'antagomirs'," *Nature*, 438:685-689 (2005).
Landgraf et al., "Oligonucleotide-directed nucleic acid scission by micrococcal nuclease," *Biochemistry* 33:10607-10615 (1994).
Mali et al., "CAS9 transcriptional activators for target specificity screening and paired nickases for cooperative genome engineering," *Nature Biotechnology*, 31:833-838 (2013).
Malygin et al., "Dimeric/oligomeric DNA methyltransferases: an unfinished story," *Biol Chem*, 390:835-844 (2009).
Mani et al., "Design, engineering, and characterization of zinc finger nucleases," *Biochem Biophys Res Commun*, 335:447-457 (2005).
Mapp et al., "A TAD further: exogenous control of gene activation," *ACS Chem Biol*, 2(1):62-75 (2007).
McDaniel, "Plant Genetic Engineering Via Organelle Transfer," *In Plant Breeding Reviews*, pp. 283-302, John Wiley & Sons, Inc. (1984).
Midelfort et al., "Substantial energetic improvement with minimal structural perturbation in a high affinity mutant antibody," *J Mol Biol*, 343:685-701 (2004).
Petolino et al., "Zinc finger nuclease-mediated transgene deletion," *Plant Mol Biol*, 73:617-628 (2010).

Pfüdel et al., "Flow cytometry of protoplasts from C4 plants. Photosynthesis: mechanisms and effects," Proceedings of the XIth International Congress on Photosynthesis; Aug. 17-22, 1998; Budapest, Hungary. (1998).
Porteus, "Chimeric nucleases stimulate gene targeting in human cells," *Science*, 300:763 (2003).
Porteus et al., "Gene targeting using zinc finger nucleases," *Nature Biotechnology*, 23:967-973 (2005).
Ran et al., "Double Nicking by RNA-Guided CRISPR Cas9 for Enhanced Genome Editing Specificity," *Cell*, 154:1380-1389 (2013).
Rhodes et al., "Plant Regeneration from Protoplasts Isolated from Embryogenic Maize Cell Cultures," *Nat Biotech*, 6:56-60 (1988).
Seidman, "Oligonucleotide mediated gene targeting in mammalian cells," *Curr Pharm Biotechnol*, 5:421-430 (2004).
Shukla et al., "Precise genome modification in the crop species *Zea mays* using zinc-finger nucleases," *Nature*, 459:437-441 (2009).
Smith, "Homologous recombination in prokaryotes: enzymes and controlling sites," *Genome*, 31:520-527 (1989).
Somers et al., "The effect of conditioned medium on colony formation from 'black mexican sweet' corn protoplasts," *Plant Science*, 53:249-256 (1987).
Soutschek et al., "Therapeutic silencing of an endogenous gene by systemic administration of midified siRNAs," *Nature*, 432:173-178 (2004).
Szostak et al., "The Double-Strand-Break Repair Model for Recombination," *Cell*, 33:25-35 (1983).
Tenzen et al., "Genome modification in human embryonic stem cells," *J Cell Physiol*, 222:278-281 (2010).
Terada et al., "Efficient gene targeting by homologous recombination in rice," *Nat Biotechnol*, 20:1030-1034 (2002).
Tovkach et al., "Validation and expression of zinc finger nucleases in plant cells," *Methods Mol Biol*, 649 315-336 (2010).
Townsend et al., "High-frequency modification of plant genes using engineered zinc-finger nucleases," *Nature*, 459:442-445 (2009).
Tsai et al., "Dimeric CRISPR RNA-guided Fok1 nucleases for highly specific genome editing," *Nature Biotechnology*, 32:569-576 (2014).
Tzfira et al., "*Agrobactcrium* T-DNA integration: molecules and models," *Trends Genet*, 20(8) 375-383 (2004).
Verhoeven et al., "Interspecific transfer of isolated plant mitochondria by microinjection," *Plant Cell Reports*, 14:781-785 (1995).
Weinthal et al., "Genome editing in plant cells by zinc finger nucleases," *Trends Plant Sci*, 15:308-321 (2010).
Whitlow et al., "1.85 Å structure of anti-fluorescein Apr. 4, 2020 Fab," *Protein Engineering*, 8(8):749-761 (1995).
Wintz et al., "A termination codon is created by RNA editing in the petunia mitochondrial atp9 gene transcript," *Current Genetics*, 19:61-64 (1991).
Wintz et al., "Expression of the CMS-associated urfS sequence in transgenic petunia and tobacco," *Plant Mol Biol*, 28:83-92 (1995).
Wyvekens et al., "Dimeric CRISPR RNA-Guided Fok1-dCas9 Nucleases Directed by Truncated gRNAs for Highly Specific Genome Editing," *Human Gene Therapy*, 26(7):425-433 (2015).
Xu et al., "A plasmid-based method to quantitate homologous recombination frequencies in gram-negative bacteria," *Biotechniques*, 6(8):752-760 (1988).
Aparicio et al., "A *Streptomyces glaucescens* endodeoxyribonuclease which shows a strong preference for CC dinucleotide," *Eur. J. Biochem.*, 205:695-699 (1992).
"Award Details: A universal DNA endonuclease", [online], SBIR, 2005, Searched Jul. 7, 2017, internet, https://www.sbir.gov/sbirsearch/details/248288.
Bolotin et al., "Clustered regularly interspaced short palindrome repeats (CRISPRs) have spacers of extrachromosomal origin," *Microbiology*, 151:2551-2561.
Chase et al., "Exonuclease VII of *Escherichia coli*," *J. Biol. Chem.*, 249:4545-4552 (1974).
García-Segura et al., "Purification, molecular and enzymic characterization of an acid RNase from the insect *Ceratitis capitata*," *FEBS J.*, 158:367-370 (1986).
Gates III et al., Endonuclease V of *Escherichia coli*, *J. Biol. Chem.*, 252:1647-1653 (1977).

(56) References Cited

OTHER PUBLICATIONS

Heins et al., "Characterization of a Nuclease Produced by *Staphylococcus aureus*," *J. Biol. Chem.*, 242:1016-1020 (1967).
Japanese Office Action issued in Japanese Patent Application No. 2014-546733 dated Jul. 25, 2017, including English translation.
Kurosawa et al., "Oligonucleotidase Activity of Phosphodiesterase from the Fruit Body of *Flammulina velutipes*," *Agric. Biol. Chem.*, 54:587-592 (1990).
Lehman et al., "The Deoxyribonucleases of *Escherichia coli*," *J. Biol. Chem.*, 239:2628-2636 (1964).
Peebles et al., "Precise Excision of Intervening Sequences from Precursor tRNAs by a Membrane-Associated Yeast Endonuclease," *Cell*, 32:525-536 (1983).
Pingoud Cl al, "Type II restriction endonucleases: structure and mechanism," *CMLS, Cell. Mol. Life Sci.* 62:685-707 (2005).
Wiegand et al., "Specificity of the S1 nuclease from *Aspergillus oryzae*," *J. Biol. Chem.*, 250:8848-8855 (1975).
Yasuda et al., "Human genetically polymorphic deoxyribonuclease: purification, characterization, and multiplicity of urine deoxyribonuclease I," *J. Biochem.*, 108:393-398 (1990).
Yu et al., "The 30-kDa C-terminal domain of the RecB protein is critical for the nuclease activity, but not the helicase activity, of the RecBCD enzyme from *Escherichia coli*," *Proc. Natl. Acad. Sci. USA*, 95:981-986 (1998).
Angelini et al., "Expression of *Helicobacter pylori* CagA domains by library-based construct screening," *FEBS J*, 276:816-824 (2009).
Bath et al., "Many Type IIs Restriction Endonucleases Interact with Two Recognition Sites before Cleaving DNA*," *J. Biol Chem.*, 277(6):4024-4033 (2002).
Beintema et al., "Comparison of the structure of the turtle pancreatic ribonuclease with those of mammalian ribonucleases," *FEBS Letters*, 194:338-342 (1986).
Bitinaite et al., "FokI dimerization is required for DNA cleavage," *Proc. Natl. Acad. Sci. USA*, 95:10570-10575 (1998).
Cerritelli et al., "Ribonuclease H: the enzymes in Eukaryotes," *FEBS J.*, 276:1494-1505 (2009).
Dulon et al., "The bacterial Neo gene confers neomycin resistance to mammalian cochlear hair cells," *NeuroReport*, 10:1189-1193 (1999).
Donis-Keller, "Phy M: an RNase activity specific for U and A residues useful in RNA sequence analysis," *Nucleic Acids Res.*, 8:3133-3142 (1980).
Durai et al., "Zinc finger nucleases: custom-designed molecular scissors for genome engineering of plant and mammalian cells," *Nucleic Acids Res.*, 33(18):5978-5990 (2005).
Feng et al., "The catalytic domain of RNase E shows inherent 3' to 5' directionality in cleavage site selection," *Proc. Natl. Acad. Sci. USA*, 99:14746-14751 (2002).
Gleave et al., "Selectable marker-free transgenic plants without sexual crossing: transient expression of cre recombinase and use of a conditional lethal dominant gene," *Plant Molecular Biology*, 40:223-235 (1999).
Gorman et al., "high efficiency gene transfer into mammalian cells," *Phil. Trans. R. Soc. Lond. B*, 307:343-346 (1984).
Gurevitz et al., "A Cleavage Site of Ribonucelase F," *FEBS J*, 124:553-559 (1982).
He et al., "Identification of a novel component of the nonsense-mediated mRNA decay pathway by use of an interacting protein screen," *Genes & Development*, 9:437-454 (1995).
Jakubauskas et al., "Identification of a single HNH active site in Type IIS restriction endonuclease Eco31I," *J Mol Biol.*, 370(1):157-169 (2007).
Jarrous et al., "Human RNase P: a tRNA-processing enzyme and transcription factor," *Nucleic Acids Res.*, 35:3519-3524 (2007).
Jurėnaitė-Urbanavičienė et al., "Generation of DNA cleavage specificities of type II restriction endonucleases by reassortment of target recognition domains," *Proc. Natl. Acad. Sci. USA*, 104(25):10358-10363 (2007).
Körner et al., "Poly(A) tail shortening by a mammalian poly(A)-specific 3'exoribonuclase," *J. Biol. Chem.*, 272:10448-10456 (1997).

Li et al., "Modularly assembled designer TAL effector nucleases for targeted gene knockout and gene replacement in eukaryotes," *Nucleic Acids Res.*, 39(14):6315-6325 (2011).
Liang et al., "RNase L: Its biological roles and regulation," *Life*, 58:508-514 (2006).
Midelfort et al., "Context-dependent mutations predominate in an engineered high-affinity single chain antibody fragment," *Protein Sci*, 15:324-334 (2006).
Morgan et al., "Inducible Expression and Cytogenic Effects of the EcoRI Restriction Endonuclease in Chinese Hamster Ovary Cells," *Molecular and Cellular Biology*, 8:4204-4211 (1988).
Mullen et al., "Transfer of the bacterial gene for cytosine deaminase to mammalian cells confers lethal sensitivity to 5-fluorocytosine: A negative selection system," *Proc. Natl. Acad. Sci. USA*, 89:33-37 (1992).
Mulligan et al., "Expression of a Bacterial Gene in Mammalian Cells," *Science*, 209:1422-1427 (1980).
Nagy et al., "Creation and Use of a Cre Recombinase Transgenic Database," *Gene Knockout Protocols*, Second Edition, Eds. Kuhn and Würst, Chapter 19, pp. 365-378 (2009).
Nishino et al., "Structure and function of nucleases in DNA repair: shape, grip and blade of the DNA scissors," *Oncogene*, 21:9022-9032 (2002).
Nomenclature Committee of the International Union of Biochemistry and Molecular Biology, "The Enzyme List Class 3—Hydrolases" (2010).
Oh et al., "In Planta Expression Screens of Phytophthora infestans RXLR Effectors Reveal Diverse Phenotypes, Including Activation of the Solanum bumbocastanum Disease Resistance Protein Rpi-blb2," *Plant Cell*, 21:2928-2947 (2009).
O'Hare et al., "Transfoimation of mouse fibroblasts to methotrexate resistance by a recombinant plasmid expressing a prokaryotic dihydrofolate reductase," *Proc. Natl. Acad. Sci. USA*, 78:1527-1531 (1981).
Pace et al., "Ribonuclease T1: Structure, Function, and Stability," *Angewandte Chemie*, 30:343-360 (1991).
Pingoud et al., "Structure and lunction of type II restriction endonucleases," *Nucleic Acids Res.*, 29(18):3705-3727 (2001).
Rawlings et al., "Expression of soluble, active fragments of the morphogenetic protein SpoIIE from Bacillus subtilis using a library-based construct screen," *Protein Engineering, Design & Selection*, 23:817-825 (2010).
Raymond et al., "High-Efficiency FLP and φC31 Site-Specific Recombination in Mammalian Cells," *PLoS One*, 2:e162 (2007).
Sauer, "Functional Expression of the cre-lox Site-Specific Recombination System in the Yeast *Saccharomyces cerevisiae*," *Molecular and Cellular Biology*, 7:2087-2096 (1987).
Schatz et al., "HIV-1 RT-associated ribonuclease H displays both endonuclease and 3'→5' exonuclease activity," *EMBO J.*, 9:1171-1176 (1990).
Schiffer et al., "Assigning a function to a conserved group of proteins: the tRNA 3'-processing enzymes," *EMBO J.*, 21:2769-2777 (2002).
Schröder et al., "Isolation and Characterization of the Novel Polyadenylate- and Polyuridylate-degrading Acid Endoribonuclease V from Calf Thymus," *J. Biol. Chem.*, 255:5108-5112 (1980).
SwisProt, "Enzyme Enzyme nomenclature database," Release 39, Feb. 2006, Accessed on Sep. 15, 2017 at https://web.archive.org/web/20060218084611/http://www.expasy.org:80/enzyme and at https://web.archive.org/web/20030605142953/http://www.expasy.org:80/cgi-bin/enzyme-search-cl.
Wah et al., "Structure of FokI has implications for DNA cleaveage," *Proc. Natl. Acad. Sci. USA*, 95:10564-10569 (1998).
Wah et al., "Structure of the multimodular endonuclease FokI bound to DNA," *Nature*, 388:97-100 (1997).
Wang et al., "CRISPR/Cas9 in Genome Editing and Beyond," *Annu. Rev. Biochem.*, 85:22.1-22.38 (2016).
Zamore, "Thirty-Three Years Later, a Glimpse at the Ribonuclease III Active Site," *Mol. Cell*, 8:1158-1160 (2001).
Zou et al., "Crystal Structure of *Escherichia coli* RNase D, an Exoribonuclease Involved in Structured RNA processing," *Structure*, 13:973-984 (2005).

(56) References Cited

OTHER PUBLICATIONS

Hartl et al., *Genetics: Principles and Analysis, 4th Edition*, Jones and Bartlett Publishers, Boston, MA, pp. 191-193 (1998).
Lewin, *Genes V*, Oxford University Press, Oxford, UK, pp. 113-114 (1994).
Mathews et al., *Biochemistry, 3rd Edition*, Benjamin/Cummings, San Francisco, CA, pp. 88-89 (2000).
Horwich et al., "A leader peptide is sufficient to direct mitochondrial import of a chimeric protein," *The EMBO Journal*, 4(5):1129-1135 (1985).
Kim et al., "Targeted genome engineering vi zinc finger nucleases," *Plant Biotechnol. Rep* 5:9-17 (2011).
Li et al., "TAL Nucleases (TALNs): hybrid proteins composed of TAL effectors and FokI DNA-Cleavage domain," *Nucleic Acids Research*, 39(1):359-372 (2011).
Office Action dated Aug. 19, 2019, in European Patent Application No. 12857977.8.
Office Action dated Sep. 29, 2017 in European Patent Application No. 12857977.8.
Office Action dated Nov. 8, 2019, in Canadian Patent Application No. 2,858,801.
Genna et al., "Second-Shell Basic Residues Expand the Two-Metal-Ion Architecture of DNA and RNA Processing Enzymes," at Graphical Abstract, *Structure*, 26:40-50 (2018).
Qin et al., "Site-Specific Labeling of RNA with Fluorophores and Other Structural Probes," *Methods: A Companion to Methods in Enzymology*, 18:60-70 (1999).
Raybum et al., "Use of biotin-labeled probes to map specific DNA sequences on wheat chromosomes," *The Journal of Heredity*, 76:78-81 (1985).
Huang, "DNA, RNA and Protein Interactions," Chapter 4, pp. 103-144 (1971).
Jones et al., "Protein-RNA interactions: a structural analysis," *Nucleic Acids Research* 29(4):943-954 (2001).

\* cited by examiner

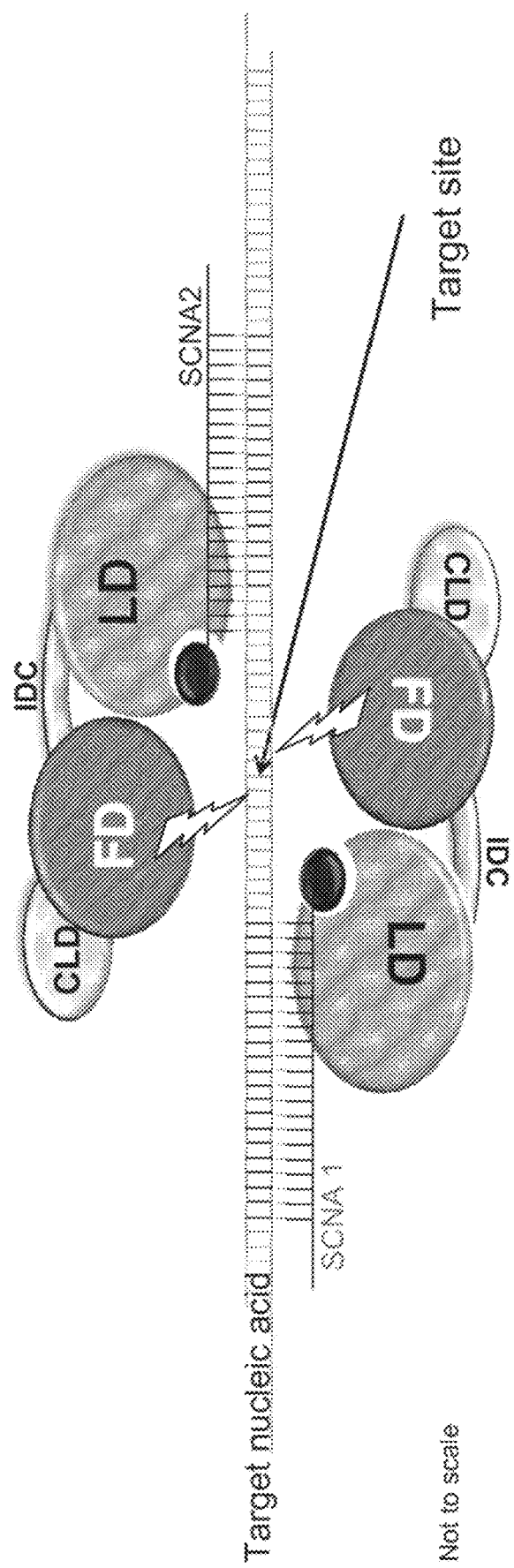

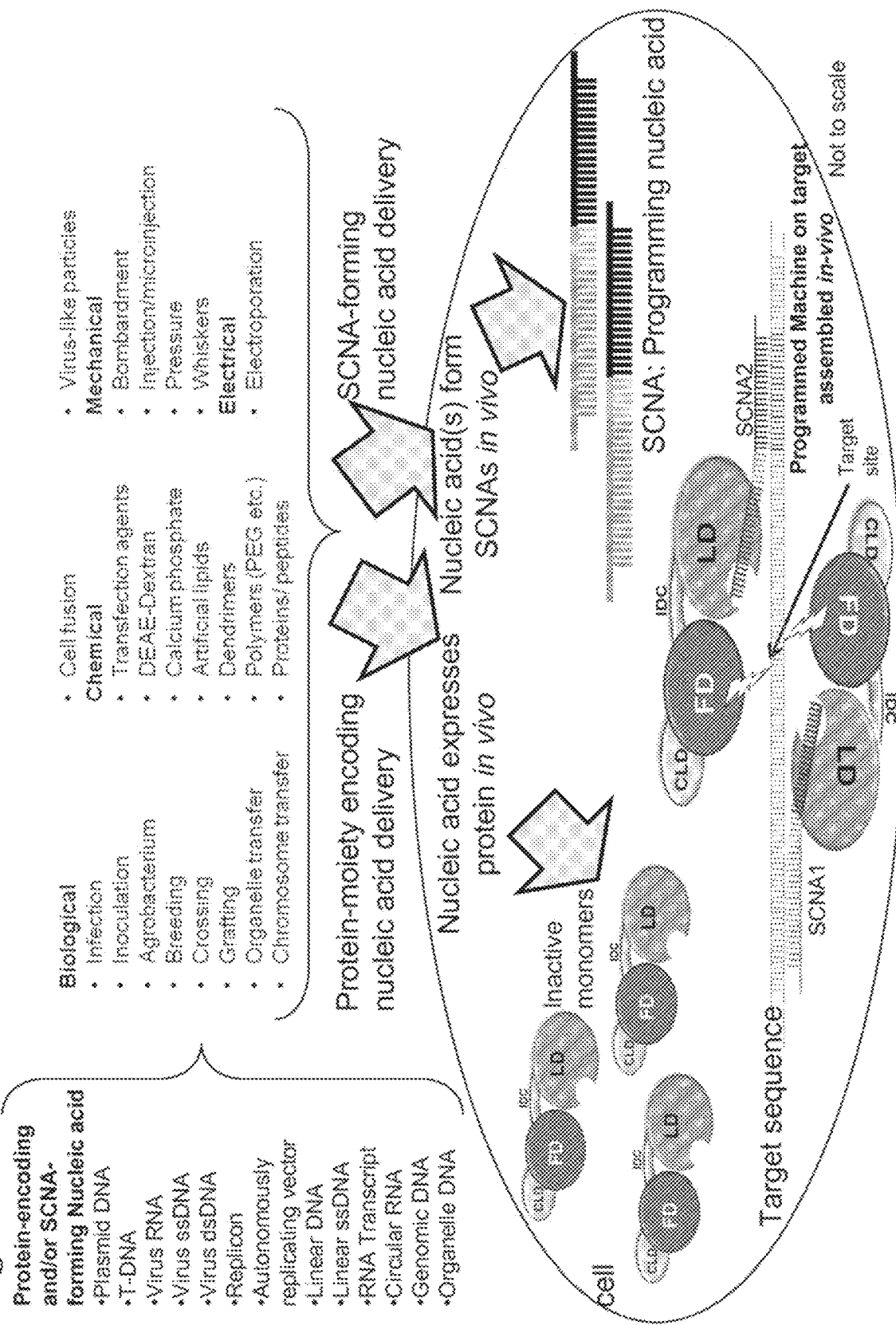

SEQUENCE LISTING

<160> NUMBER OF SEQ ID NOS: 217

<210> SEQ ID NO 1
<211> LENGTH: 13
<212> TYPE: DNA
<213> ORGANISM: Artificial sequence
<220> FEATURE:
<223> OTHER INFORMATION: polynucleotide

<400> SEQUENCE: 1
cucuguaucu ugu                                                      13

<210> SEQ ID NO 2
<211> LENGTH: 25
<212> TYPE: DNA
<213> ORGANISM: Artificial sequence
<220> FEATURE:
<223> OTHER INFORMATION: polynucleotide

<400> SEQUENCE: 2
gtttacccgc caatatatcc tgtca                                         25

<210> SEQ ID NO 3
<211> LENGTH: 7
<212> TYPE: PRT
<213> ORGANISM: Artificial sequence
<220> FEATURE:
<223> OTHER INFORMATION: peptide

<400> SEQUENCE: 3

Pro Lys Lys Lys Arg Lys Val
1               5

<210> SEQ ID NO 4
<211> LENGTH: 25
<212> TYPE: PRT
<213> ORGANISM: Artificial sequence
<220> FEATURE:
<223> OTHER INFORMATION: Peptide

<400> SEQUENCE: 4

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 5
<211> LENGTH: 33
<212> TYPE: PRT
<213> ORGANISM: Artificial sequence
<220> FEATURE:
<223> OTHER INFORMATION: polypeptide

<400> SEQUENCE: 5

Met Leu Ser Ala Leu Ala Arg Pro Ala Ser Ala Ala Leu Arg Arg Ser
1               5                   10                  15

Phe Ser Thr Ser Ala Gln Asn Asn Ala Lys Val Ala Val Leu Gly Ala
            20                  25                  30

Ser

<210> SEQ ID NO 6
<211> LENGTH: 23
<212> TYPE: PRT
<213> ORGANISM: Artificial sequence
<220> FEATURE:

<223> OTHER INFORMATION: polypeptide

<400> SEQUENCE: 6

Met His Ser Arg Ser Ala Leu Leu Tyr Arg Phe Leu Arg Pro Ala Ser
1               5                   10                  15

Arg Cys Phe Ser Ser Ser
            20

<210> SEQ ID NO 7
<211> LENGTH: 5
<212> TYPE: PRT
<213> ORGANISM: Artificial sequence
<220> FEATURE:
<223> OTHER INFORMATION: peptide

<400> SEQUENCE: 7

Gly Gly Ser Gly Gly
1               5

<210> SEQ ID NO 8
<211> LENGTH: 12
<212> TYPE: PRT
<213> ORGANISM: Artificial sequence
<220> FEATURE:
<223> OTHER INFORMATION: peptide

<400> SEQUENCE: 8

Asn Ile His His Val Thr Trp His Met Asp Phe Pro
1               5                   10

<210> SEQ ID NO 9
<211> LENGTH: 7
<212> TYPE: PRT
<213> ORGANISM: Artificial sequence
<220> FEATURE:
<223> OTHER INFORMATION: peptide

<400> SEQUENCE: 9

Pro Asn Ser Leu Ile Val Pro
1               5

<210> SEQ ID NO 10
<211> LENGTH: 6
<212> TYPE: PRT
<213> ORGANISM: Artificial sequence
<220> FEATURE:
<223> OTHER INFORMATION: peptide

<400> SEQUENCE: 10

Thr Gly Leu Asp Ser Pro
1               5

<210> SEQ ID NO 11
<211> LENGTH: 4
<212> TYPE: PRT
<213> ORGANISM: Artificial sequence
<220> FEATURE:
<223> OTHER INFORMATION: peptide

<400> SEQUENCE: 11

Gly Ser Leu Glu
1

<210> SEQ ID NO 12
<211> LENGTH: 461
<212> TYPE: PRT

<213> ORGANISM: Artificial sequence
<220> FEATURE:
<223> OTHER INFORMATION: Artificial peptide

<400> SEQUENCE: 12

```
Met Pro Lys Lys Lys Arg Lys Val Val Lys Ser Glu Leu Glu Lys
1               5                   10                  15

Lys Ser Glu Leu Arg His Lys Leu Lys Tyr Val Pro His Glu Tyr Ile
            20                  25                  30

Glu Leu Ile Glu Ile Ala Arg Asn Ser Thr Gln Asp Arg Ile Leu Glu
            35                  40                  45

Met Lys Val Met Glu Phe Phe Met Lys Val Tyr Gly Tyr Arg Gly Lys
50                  55                  60

His Leu Gly Gly Ser Arg Lys Pro Asp Gly Ala Ile Tyr Thr Val Gly
65                  70                  75                  80

Ser Pro Ile Asp Tyr Gly Val Ile Val Asp Thr Lys Ala Tyr Ser Gly
                85                  90                  95

Gly Tyr Asn Leu Pro Ile Gly Gln Ala Asp Glu Met Gln Arg Tyr Val
            100                 105                 110

Glu Glu Asn Gln Thr Arg Asn Lys His Ile Asn Pro Asn Glu Trp Trp
            115                 120                 125

Lys Val Tyr Pro Ser Ser Val Thr Glu Phe Lys Phe Leu Phe Val Ser
            130                 135                 140

Gly His Phe Lys Gly Asn Tyr Lys Ala Gln Leu Thr Arg Leu Asn His
145                 150                 155                 160

Ile Thr Asn Cys Asn Gly Ala Val Leu Ser Val Glu Glu Leu Leu Ile
                165                 170                 175

Gly Gly Glu Met Ile Lys Ala Gly Thr Leu Thr Leu Glu Glu Val Arg
            180                 185                 190

Arg Lys Phe Asn Asn Gly Glu Ile Asn Phe Gly Ser Leu Glu Gly Gly
            195                 200                 205

Ser Gly Gly Phe Asp Pro Glu Val Gln Leu Gln Gln Ser Gly Pro Glu
            210                 215                 220

Leu Val Lys Pro Gly Ala Ser Val Arg Met Ser Cys Lys Ser Ser Gly
225                 230                 235                 240

Tyr Ile Phe Thr Asp Phe Tyr Met Asn Trp Val Arg Gln Ser His Gly
                245                 250                 255

Lys Ser Leu Asp Tyr Ile Gly Tyr Ile Ser Pro Tyr Ser Gly Val Thr
            260                 265                 270

Gly Tyr Asn Gln Lys Phe Lys Gly Lys Ala Thr Leu Thr Val Asp Lys
            275                 280                 285

Ser Ser Ser Thr Ala Tyr Met Glu Leu Arg Ser Leu Thr Ser Glu Asp
290                 295                 300

Ser Ala Val Tyr Tyr Cys Ala Gly Ser Ser Gly Asn Lys Trp Ala Met
305                 310                 315                 320

Asp Tyr Trp Gly His Gly Ala Ser Val Thr Val Ser Ser Gly Gly Gly
                325                 330                 335

Gly Ser Gly Gly Gly Gly Ser Gly Gly Gly Ser Asp Val Val Met
            340                 345                 350

Thr Gln Thr Pro Leu Ser Leu Pro Val Ser Leu Gly Asp Gln Ala Ser
            355                 360                 365

Ile Ser Cys Arg Ser Ser Gln Ser Leu Val His Ser Asn Gly Asn Thr
            370                 375                 380

Tyr Leu Asn Trp Tyr Leu Gln Lys Ala Gly Gln Ser Pro Lys Leu Leu
```

```
                385               390               395               400
Ile Tyr Lys Val Ser Asn Arg Phe Ser Gly Val Pro Asp Arg Phe Ser
                    405               410               415

Gly Ser Gly Ser Gly Thr Asp Phe Thr Leu Lys Ile Ser Arg Val Glu
                420               425               430

Ala Glu Asp Leu Gly Ile Tyr Phe Cys Ser Gln Thr Thr His Val Pro
            435               440               445

Pro Thr Phe Gly Gly Gly Thr Lys Leu Glu Ile Lys Arg
        450               455               460

<210> SEQ ID NO 13
<211> LENGTH: 1386
<212> TYPE: DNA
<213> ORGANISM: Artificial sequence
<220> FEATURE:
<223> OTHER INFORMATION: Polynucleotide

<400> SEQUENCE: 13
atgcccaaaa agaaacgtaa agttgtgaaa tcggaactcg aagagaagaa atccgagctc     60
aggcataagt tgaagtatgt tccgcacgag tacattgaac taattgagat cgctcgtaac    120
tctacacaag accgtattct tgaaatgaag gtgatggagt ttttcatgaa ggtttatgga    180
tatagaggga agcacttggg tggttctcga aaacctgatg gcgcaatcta cacggttggc    240
tcgccaattg attatggggt gatagtggat actaaggcat actctggtgg atacaatctt    300
cctataggtc aagccgacga aatgcagagg tatgttgaag aaaatcagac aagaaacaag    360
catatcaatc ccaatgagtg gtggaaggtt taccctagct ctgtgaccga attcaaattc    420
ttatttgtct ccggtcactt taagggaaac tataaggctc aattgacaag acttaatcat    480
attacaaact gtaatggtgc agtgctcagt gtcgaagagt tgcttatagg tggggagatg    540
attaaagccg gaacgcttac cttggaagaa gtacgtagaa aattcaataa cggggagata    600
aactttggaa gcttagaggg tggaagtggt ggcttcgatc cggaagtcca gctccaacaa    660
agtggacctg aactagttaa gcctggcgca tccgttagaa tgtcttgtaa atcaagtgga    720
tacatcttta cagatttcta catgaactgg gttaggcaat ctcatgggaa gtctcttgat    780
tacattggct atatctctcc atattctggt gtaactgggt acaatcagaa gtttaaaggt    840
aaggctactt taactgtcga taaatcatct tctacagcgt atatggagtt aagatcactg    900
acatccgaag attcagctgt gtattactgt gctgggagtt ctgggaataa gtgggcgatg    960
gactattggg gccatggtgc ttcggtcacc gtatcaagtg gcggtggcgg atccggtggt   1020
ggtggctcgg tggtggcgg aagtgacgtt gtaatgacac aaaccccact gtctcttcct   1080
gtcagcctag tgatcaggc tagcatttct tgccgatcct cacaatcttt agtgcactcg   1140
aatggaaaca cttatcttaa ctggtacttg cagaaggcag acagtcacc aaaactcttg   1200 atctataaag tttcaaacag attctcagga gttcctgaca ggtttagcgg aagcggatcg   1260
ggaacagatt tcacgctgaa aatctcacgc gttgaggctg aggatctcgg tatttacttt   1320
tgcagccaaa ctactcatgt gccaccgact tttgggggtg aacgaaatt ggagataaag   1380 aggtga                                                              1386

<210> SEQ ID NO 14
<211> LENGTH: 9
<212> TYPE: PRT
<213> ORGANISM: Artificial sequence
<220> FEATURE:
<223> OTHER INFORMATION: peptide
```

<400> SEQUENCE: 14

Gly Ser Leu Glu Gly Gly Ser Gly Gly
1               5

<210> SEQ ID NO 15
<211> LENGTH: 1875
<212> TYPE: DNA
<213> ORGANISM: Artificial sequence
<220> FEATURE:
<223> OTHER INFORMATION: polynucleotide

<400> SEQUENCE: 15

```
gacaacatgt ggagcacgac acacttgtct actccaaaaa tatcaaagat acagtctcag      60
aagaccaaag ggcaattgag acttttcaac aaagggtaat atccggaaac ctcctcggat     120
tccattgccc agctatctgt cactttattg tgaagatagt ggaaaaggaa ggtggctcct     180
acaaatgcca tcattgcgat aaaggaaagg ccatcgttga agatgcctct gccgacagtg     240
gtcccaaaga tggacccca cccacgagga gcatcgtgga aaaagaagac gttccaacca     300
cgtcttcaaa gcaagtggat tgatgtgata acatggtgga gcacgacaca cttgtctact     360
ccaaaaatat caaagataca gtctcagaag accaaagggc aattgagact ttcaacaaa     420
gggtaatatc cggaaacctc ctcggattcc attgcccagc tatctgtcac tttattgtga     480
agatagtgga aaaggaaggt ggctcctaca atgccatca ttgcgataaa ggaaaggcca     540
tcgttgaaga tgcctctgcc gacagtggtc ccaagatgg accccaccc acgaggagca     600
tcgtggaaaa agaagacgtt ccaaccacgt cttcaaagca gtggattga tgtgatatct     660
ccactgacgt aagggatgac gcacaatccc actatccttc gcaagaccct tcctctatat     720
aaggaagttc atttcatttg gagaggacgt cgagagttct caacacaaca tatacaaaac     780
aaacgaatct caagcaatca agcattctac ttctattgca gcaatttaaa tcatttcttt     840
taaagcaaaa gcaattttct gaaaattttc accatttacg aacgatagcc atggccgtcg     900
acaactagtc cagatctgtg tccaagggcg aggagctgtt caccggggtg gtgcccatcc     960
tggtcgagct ggacggcgac gtaaacggcc acaagttcag cgtgtccggc gagggcgagg    1020
gcgatgccac ctacggcaag ctgaccctga gttcatctg caccaccggc aagctgcccg    1080
tgccctggcc caccctcgtg accaccctga cctacggcgt gcagtgcttc agccgctacc    1140
ccgaccacat gaagcagcac gacttcttca gtccgccat gcccgaaggc tacgtccagg    1200
agcgcaccat cttcttcaag gacgacggca actacaagac ccgcgccgag gtgaagttcg    1260
agggcgacac cctggtgaac cgcatcgagc tgaagggcat cgacttcaag gaggacggca    1320
acatcctggg gcacaagctg gagtacaact caacagcca acgtctat atcatggccg    1380
acaagcagaa gaacggcatc aaggtgaact tcaagatccg ccacaacatc gaggacggca    1440
gcgtgcagct cgccgaccac taccagcaga cacccccat cggcgacggc cccgtgctgc    1500
tgcccgacaa ccactacctg agcacccagt ccgccctgag caaagacccc aacgagaagc    1560
gcgatcacat ggtcctgctg gagttcgtga ccgccgccgg gatcactctc ggcatggacg    1620
agctgtacaa gtccggactc taagcttggg tctagagtcc gcaaaaatca ccagtctctc    1680
tctacaaatc tatctctctc tattttttctc cagaataatg tgtgagtagt tcccagataa    1740
gggaattagg gttcttatag ggtttcgctc atgtgttgag catataagaa acccttagta    1800
tgtatttgta tttgtaaaat acttctatca ataaaatttc taattcctaa aaccaaaatc    1860
cagtgacgcg gccgc                                                     1875
```

```
<210> SEQ ID NO 16
<211> LENGTH: 712
<212> TYPE: DNA
<213> ORGANISM: Artificial sequence
<220> FEATURE:
<223> OTHER INFORMATION: polynucleotide

<400> SEQUENCE: 16
atggtgagca agggcgagga ggataacatg gccatcatca aggagttcat gcccttcaag      60
gtgcacatgg agggctccgt gaacggccac gagttcgaga tcgagggcga gggcgagggc     120
cgcccctacg agggcaccca gaccgccaag ctgaaggtga ccaagggtgg cccccctgccc    180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact tcccctccga cggccccgta     420
atgcagaaga agaccatggg ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaagat aa              712

<210> SEQ ID NO 17
<211> LENGTH: 21
<212> TYPE: DNA
<213> ORGANISM: Artificial sequence
<220> FEATURE:
<223> OTHER INFORMATION: polynucleotide

<400> SEQUENCE: 17
gtcgacaact agtccagatc t                                                21

<210> SEQ ID NO 18
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 18
nnnnnngtgt ccaagggcga ggagctgt                                         28

<210> SEQ ID NO 19
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, t or u

<400> SEQUENCE: 19
tttacgaacg atagccatgg ccnnnnnn                                         28
```

```
<210> SEQ ID NO 20
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, t or u

<400> SEQUENCE: 20
nngtccaagg gcgaggagct gttc                                              24

<210> SEQ ID NO 21
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 21
atttacgaac gatagccatg gcnn                                              24

<210> SEQ ID NO 22
<211> LENGTH: 27
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (22)..(27)
<223> OTHER INFORMATION: n is a, c, g, t or u

<400> SEQUENCE: 22
cagctcctcg cccttggaga cnnnnnn                                           27

<210> SEQ ID NO 23
<211> LENGTH: 27
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 23
nnnnnnggcc atggctatcg ttcgtaa                                           27

<210> SEQ ID NO 24
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 24
gaacagctcc tcgcccttgg acnn                                              24
```

```
<210> SEQ ID NO 25
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, t or u

<400> SEQUENCE: 25
nngccatggc tatcgttcgt aaat                                              24

<210> SEQ ID NO 26
<211> LENGTH: 21
<212> TYPE: DNA
<213> ORGANISM: Artificial sequence
<220> FEATURE:
<223> OTHER INFORMATION: polynucleotide

<400> SEQUENCE: 26
gactctaagc ttgggtctag a                                                 21

<210> SEQ ID NO 27
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, or t

<400> SEQUENCE: 27
nntccgcaaa aatcaccagt ctct                                              24

<210> SEQ ID NO 28
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, or t

<400> SEQUENCE: 28
gcatggacga gctgtacaag tcnn                                              24

<210> SEQ ID NO 29
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, or t

<400> SEQUENCE: 29
agagactggt gattttgcg gann                                               24

<210> SEQ ID NO 30
```

```
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, or t

<400> SEQUENCE: 30
nngacttgta cagctcgtcc atgc                                              24

<210> SEQ ID NO 31
<211> LENGTH: 22
<212> TYPE: DNA
<213> ORGANISM: Artificial sequence
<220> FEATURE:
<223> OTHER INFORMATION: polynucleotide

<400> SEQUENCE: 31
ctatccttcg caagacccctt cc                                               22

<210> SEQ ID NO 32
<211> LENGTH: 22
<212> TYPE: DNA
<213> ORGANISM: Artificial sequence
<220> FEATURE:
<223> OTHER INFORMATION: polynucleotide

<400> SEQUENCE: 32
ttatcttgta cagctcgtcc at                                                22

<210> SEQ ID NO 33
<211> LENGTH: 22
<212> TYPE: DNA
<213> ORGANISM: Artificial sequence
<220> FEATURE:
<223> OTHER INFORMATION: polynucleotide

<400> SEQUENCE: 33
ccctataaga accctaattc cc                                                22

<210> SEQ ID NO 34
<211> LENGTH: 20
<212> TYPE: DNA
<213> ORGANISM: Artificial sequence
<220> FEATURE:
<223> OTHER INFORMATION: polynucleotide

<400> SEQUENCE: 34
atggtgagca agggcgagga                                                   20

<210> SEQ ID NO 35
<211> LENGTH: 21
<212> TYPE: DNA
<213> ORGANISM: Artificial sequence
<220> FEATURE:
<223> OTHER INFORMATION: polynucleotide

<400> SEQUENCE: 35
ttctcaagtc atgagcaact c                                                 21

<210> SEQ ID NO 36
<211> LENGTH: 28
<212> TYPE: DNA
<213> ORGANISM: Artificial sequence
```

```
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, or t

<400> SEQUENCE: 36
nnnnnnctgt ggggccatat cccagaac                                              28

<210> SEQ ID NO 37
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, or t

<400> SEQUENCE: 37
gcgggcaccg agttgtattg tannnnnn                                              28

<210> SEQ ID NO 38
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, or t

<400> SEQUENCE: 38
gttctgggat atggccccac agnnnnnn                                              28

<210> SEQ ID NO 39
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, or t

<400> SEQUENCE: 39
nnnnnntaca atacaactcg gtgcccgc                                              28

<210> SEQ ID NO 40
<211> LENGTH: 23
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, or t

<400> SEQUENCE: 40
nngtggggcc atatcccaga act                                                   23

<210> SEQ ID NO 41
<211> LENGTH: 24
<212> TYPE: DNA
```

```
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, or t

<400> SEQUENCE: 41
agcgggcacc gagttgtatt gtnn                                           24

<210> SEQ ID NO 42
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, or t

<400> SEQUENCE: 42
nnacaataca actcggtgcc cgct                                           24

<210> SEQ ID NO 43
<211> LENGTH: 23
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (22)..(23)
<223> OTHER INFORMATION: n is a, c, g, or t

<400> SEQUENCE: 43
agttctggga tatggcccca cnn                                            23

<210> SEQ ID NO 44
<211> LENGTH: 22
<212> TYPE: DNA
<213> ORGANISM: Artificial sequence
<220> FEATURE:
<223> OTHER INFORMATION: polynucleotide

<400> SEQUENCE: 44
gagctagata gcagatgcag at                                             22

<210> SEQ ID NO 45
<211> LENGTH: 22
<212> TYPE: DNA
<213> ORGANISM: Artificial sequence
<220> FEATURE:
<223> OTHER INFORMATION: polynucleotide

<400> SEQUENCE: 45
ctccagaaaa tccctagaaa ca                                             22

<210> SEQ ID NO 46
<211> LENGTH: 1988
<212> TYPE: DNA
<213> ORGANISM: Artificial sequence
<220> FEATURE:
<223> OTHER INFORMATION: polynucleotide

<400> SEQUENCE: 46
ggtgtctgac agcagaagat cctcgatgga gatggatggg gttctgcaag ccgcggatgc   60
```

```
caaggactgg gtttacaagg gggaaggcgc cgcgaatctc atcctcagct acaccggctc    120
gtcgccctcc atggtaagcg ctgagtaggt tcttactgag cgtgcacgca tcgatcactt    180
gactttaggg gctcaatgtg tgattcacgg gtgccgcggc gccattcgag ctccagatcc    240
agtaccgctc gagcaagtga taaaacatgg agcaggacg atcacgtggt cacttgaaaa     300
ttacgtgagg tccggggcga cgatgtacgg cgccggcgaa ctctcaaaca ctcacacaac    360
caaaaccgct tcgtgttcgt ctttgttcca agcgactgtg tgagtgtttg agagttcgcc    420
agcgccgtac atcgtcgccc cggatctgac aaattaagct ttcgttgctt ttccatgatt    480
gtgcattttg tgagcatgca ctgaatacta tgatggatat gtttggagga agcattattc    540
caatttgatg ataagggtgt tatttacact tgttttcagc ttggcaaggt actgcggctc    600
aagaagattc taaaaaacaa gatgagcaag ggcgaggagc tgttcaccgg ggtggtgccc    660
atcctggtcg agctggacgg cgacgtaaac ggccacaagt tcagcgtgtc cggcgagggc    720
gagggcgatg ccacctacgg caagctgacc ctgaagttca tctgcaccac cggcaagctg    780
cccgtgccct ggcccaccct cgtgaccacc ctgacctacg gcgtgcagtg cttcagccgc    840
taccccgacc acatgaagca gcacgacttc ttcaagtccg ccatgcccga aggctacgtc    900
caggagcgca ccatcttctt caaggacgac ggcaactaca agacccgcgc cgaggtgaag    960
ttcgagggcg acaccctggt gaaccgcatc gagctgaagg gcatcgactt caaggaggac   1020
ggcaacatcc tggggcacaa gctggagtac aactacaaca gccacaacgt ctatatcatg   1080
gccgacaagc agaagaacgg catcaaggtg aacttcaaga tccgccacaa catcgaggac   1140
ggcagcgtgc agctcgccga ccactaccag cagaacaccc ccatcggcga cggccccgtg   1200
ctgctgcccg acaaccacta cctgagcacc cagtccgccc tgagcaaaga ccccaacgag   1260
aagcgcgatc acatggtcct gctggagttc gtgaccgccg ccgggatcac tctcggcatg   1320
gacgagctgt acaagtaact caagcctatg cagtgcatgt tatgagccaa cacctgggtg   1380
ccaatcatgt cgatggtggg gtatggttca gattcagttc atttatgtcc tgttattgtg   1440
attttgattg gtaacatatt gacaacctcg acacttggga tcagattcag ttcacttatg   1500
gaagaaattg gagaattgtt ataatttatc tataatcacc cctactgaaa tagaaataac   1560
atggcatcaa tgtgcatgct attggatttt gacacgaata tgctttattc tatcatatgt   1620
tggtaattcc agcaggcagc aggcactact cttttggatcc acgtgacttg acaaagaaat   1680
catgccatct ttccacaatg caggtccgtg tacgtgtttc tagggatttt ctggagcttg   1740
tcgaaaagaa tgttcttagc agccgtcctg ctgggagagt aaatgcaagt tcaattgata   1800
acactgctga tgccgctctt ctaatagcag accactcttt attttctggt acgtactcta   1860
tccctcttct taccataatc tgaatcttgt taaggtttaa aatatatgat tgattaagta   1920
aaatccagag ctctattcat atctcatgca ctgatgtttt gatgaaacac ttgtagcaag   1980
acggttgc                                                             1988
```

<210> SEQ ID NO 47
<211> LENGTH: 2987
<212> TYPE: DNA
<213> ORGANISM: Artificial sequence
<220> FEATURE:
<223> OTHER INFORMATION: polynucleotide

<400> SEQUENCE: 47

```
ggtgtctgac agcagaagat cctcgatgga gatggatggg gttctgcaag ccgcggatgc     60
```

| | |
|---|---|
| caaggactgg gtttacaagg gggaaggcgc cgcgaatctc atcctcagct acaccggctc | 120 |
| gtcgccctcc atggtaagcg ctgagtaggt tcttactgag cgtgcacgca tcgatcactt | 180 |
| gactttaggg gctcaatgtg tgattcacgg gtgccgcggc gccattcgag ctccagatcc | 240 |
| agtaccgctc gagcaagtga taaaacatgg agcaggacg atcacgtggt cacttgaaaa | 300 |
| ttacgtgagg tccggggcga cgatgtacgg cgccggcgaa ctctcaaaca ctcacacaac | 360 |
| caaaaccgct tcgtgttcgt ctttgttcca agcgactgtg tgagtgtttg agagttcgcc | 420 |
| agcgccgtac atcgtcgccc cggatctgac aaattaagct ttcgttgctt ttccatgatt | 480 |
| gtgcattttg tgagcatgca ctgaatacta tgatggatat gtttggagga agcattattc | 540 |
| caatttgatg ataagggtgt tatttacact tgttttcagc ttggcaaggt actgcggctc | 600 |
| aagaagattc taaaaaacaa gtaaatagta taaccggtca acatgtggag cacgacacac | 660 |
| ttgtctactc caaaaatatc aaagatacag tctcagaaga ccaaagggca attgagactt | 720 |
| ttcaacaaag ggtaatatcc ggaaacctcc tcggattcca ttgcccagct atctgtcact | 780 |
| ttattgtgaa gatagtggaa aaggaaggtg gctcctacaa atgccatcat tgcgataaag | 840 |
| gaaaggccat cgttgaagat gcctctgccg acagtggtcc caagatgga ccccaccca | 900 |
| cgaggagcat cgtggaaaaa gaagacgttc caaccacgtc ttcaaagcaa gtggattgat | 960 |
| gtgataacat ggtggagcac gacacacttg tctactccaa aaatatcaaa gatacagtct | 1020 |
| cagaagacca aagggcaatt gagacttttc aacaaagggt aatatccgga aacctcctcg | 1080 |
| gattccattg cccagctatc tgtcacttta ttgtgaagat agtggaaaag gaaggtggct | 1140 |
| cctacaaatg ccatcattgc gataaaggaa aggccatcgt tgaagatgcc tctgccgaca | 1200 |
| gtggtcccaa agatggaccc ccacccacga ggagcatcgt ggaaaaagaa gacgttccaa | 1260 |
| ccacgtcttc aaagcaagtg gattgatgtg atatctccac tgacgtaagg gatgacgcac | 1320 |
| aatcccacta tccttcgcaa gacccttcct ctatataagg aagttcattt catttggaga | 1380 |
| ggacgtcgag agttctcaac acaacatata caaaacaaac gaatctcaag caatcaagca | 1440 |
| ttctacttct attgcagcaa tttaaatcat ttcttttaaa gcaaaagcaa ttttctgaaa | 1500 |
| attttcacca tttacgaacg atagcatgag cccagaacga cgcccggccg acatccgccg | 1560 |
| tgccaccgag gcggacatgc cggcggtctg caccatcgtc aaccactaca tcgagacaag | 1620 |
| cacggtcaac ttccgtaccg agccgcagga accgcaggag tggacggacg acctcgtccg | 1680 |
| tctgcgggag cgctatccct ggctcgtcgc cgaggtggac ggcgaggtcg ccggcatcgc | 1740 |
| ctacgcgggc ccctggaagg cacgcaacgc ctacgactgg acggccgagt cgaccgtgta | 1800 |
| cgtctccccc cgccaccagc ggacgggact gggctccacg ctctacaccc acctgctgaa | 1860 |
| gtccctggag gcacagggct tcaagagcgt ggtcgctgtc atcgggctgc caacgaccc | 1920 |
| gagcgtgcgc atgcacgagg cgctcggata tgccccccgc ggcatgctgc gggcggccgg | 1980 |
| cttcaagcac gggaactggc atgacgtggg tttctggcag ctggacttca gcctgccggt | 2040 |
| accgccccgt ccggtcctgc ccgtcaccga gatctgatcc cgatcgttca acatttggc | 2100 |
| aataaagttt cttaagattg aatcctgttg ccggtcttgc gatgattatc atataatttc | 2160 |
| tgttgaatta cgttaagcat gtaataatta acatgtaatg catgacgtta tttatgagat | 2220 |
| gggtttttat gattagagtc ccgcaattat acatttaata cgcgatagaa acaaaatat | 2280 |
| agcgcgcaaa ctaggataaa ttatcgcgcg cggtgtcatc tatgttacta gatcgggctc | 2340 |
| aagcctatgc agtgcatgtt atgagccaac acctgggtgc caatcatgtc gatggtgggg | 2400 |
| tatggttcag attcagttca tttatgtcct gttattgtga ttttgattgg taacatattg | 2460 |

```
acaacctcga cacttgggat cagattcagt tcacttatgg aagaaattgg agaattgtta    2520
taatttatct ataatcaccc ctactgaaat agaaataaca tggcatcaat gtgcatgcta    2580
ttggattttg acacgaatat gctttattct atcatatgtt ggtaattcca gcaggcagca    2640
ggcactactc tttggatcca cgtgacttga caaagaaatc atgccatctt ccacaatgc     2700 aggtccgtgt acgtgtttct agggattttc tggagcttgt cgaaaagaat gttcttagca    2760
gccgtcctgc tgggagagta aatgcaagtt caattgataa cactgctgat gccgtcttc     2820 taatagcaga ccactcttta ttttctggta cgtactctat ccctcttctt accataatct    2880
gaatcttgtt aaggtttaaa atatatgatt gattaagtaa aatccagagc tctattcata    2940
tctcatgcac tgatgttttg atgaaacact tgtagcaaga cggttgc                  2987
```

<210> SEQ ID NO 48
<211> LENGTH: 1672
<212> TYPE: DNA
<213> ORGANISM: Artificial sequence
<220> FEATURE:
<223> OTHER INFORMATION: polynucleotide

<400> SEQUENCE: 48

```
atggtcattt cttctggttc aagcatgaca tgaacaggca ataaataagt tgagattttg    60
atcacagtaa ctgatacttg aatcgaatca tttagatttt ttttttttt agttacttg     120 tttagtaaat atgttgtcta tgtttgtcac aaaaacgtgg ctcagttctt gtatatatgg   180
agacaaaaaa atccattaaa agattgttga cattctcgga aatttagtgc caactgttat   240
tgcgagaact tactatagtt ttcctttggc gaaaagctaa taatcttaaa tcttgatttt   300
gtcctctttt ctctgagtta gattttctta aattccactt ccgacctatt aagaaatggg   360
cttttgcaaa gaagatccgc ttcactgagc ccgtatctcg aagaggataa tacaacaaca   420
aagcaaaacg gcacgtagtt ttaattgtaa ccaaggattg catttcggtc ttgtttcaac   480
aaacgaaact tcctgaaatg ccaagaaaaa tctggtcatt tcaccacagt gatcattgtg   540
tatgtgttct aaagactcca agcgaaggtt ttagaaaaag gagcattttt tattctattc   600
aagaaactcg aagaacattc tctcttcatc ctctaacttc cctataaata tgtcctttgc   660
taatcagatc aaatcagcag gaaaatcaag aaccaaaagt ctcccgaaaa gcaacgaaca   720
atggatcctg atgatgttgt tgattcttct aaatcttttg tgatggaaaa cttttcttcg   780
taccacggga ctaaacctgg ttatgtagat tccattcaaa aaggtataca aaagccaaaa   840
tctggtacac aaggaaatta tgacgatgat tggaaagggt tttatagtac cgacaataaa   900
tacgacgctg cgggatactc tgtagataat gaaaacccgc tctctggaaa agctggaggc   960
gtggtcaaag tgacgtatcc aggactgacg aaggttctcg cactaaaagt ggataatgcc  1020
gaaactatta agaaagagtt aggtttaagt ctcactgaac cgttgatgga gcaagtcgga  1080
acggaagagt ttatcaaaag gttcggtgat ggtgcttcgc gtgtagtgct cagccttccc  1140
ttcgctgagg ggagttctag cgttgaatat attaataact gggaacaggc gaaagcgtta  1200
agcgtagaac ttgagattaa ttttgaaacc cgtggaaaac gtggccaaga tgcgatgtat  1260
gagtatatgg ctcaagcctg tgcaggaaat cgtgtcaggc gatctctttg tgaaggaacc  1320
ttacttctgt ggtgtgacat aattggacaa actacctaca gagatttaaa gctctaagga  1380
tcccccgggc tgcaggaatt cgatccgcta gcatcgttca acatttggca ataaagtttc  1440
cttaagattg aatcctgttg ccggtcttgc gatgattatc atataatttc tgttgaatta  1500
```

-continued

```
cgttaagcat gtaataatta acatgtaatg catgacgtta tttatgagat gggttttttat    1560 gattagagtc ccgcaattat acatttaata cgcgatagaa acaaaatat agcgcgcaaa      1620 ctaggataaa ttatcgcgcg cggtgtcatc tatgttacta gatcgctagc gg             1672
```

<210> SEQ ID NO 49
<211> LENGTH: 462
<212> TYPE: PRT
<213> ORGANISM: Artificial sequence
<220> FEATURE:
<223> OTHER INFORMATION: polypeptide

<400> SEQUENCE: 49

```
Met Pro Lys Lys Lys Arg Lys Val Val Lys Ser Glu Leu Glu Glu Lys
1               5                   10                  15

Lys Ser Glu Leu Arg His Lys Leu Lys Tyr Val Pro His Glu Tyr Ile
            20                  25                  30

Glu Leu Ile Glu Ile Ala Arg Asn Ser Thr Gln Asp Arg Ile Leu Glu
        35                  40                  45

Met Lys Val Met Glu Phe Phe Met Lys Val Tyr Gly Tyr Arg Gly Lys
    50                  55                  60

His Leu Gly Gly Ser Arg Lys Pro Asp Gly Ala Ile Tyr Thr Val Gly
65                  70                  75                  80

Ser Pro Ile Asp Tyr Gly Val Ile Val Asp Thr Lys Ala Tyr Ser Gly
                85                  90                  95

Gly Tyr Asn Leu Pro Ile Gly Gln Ala Asp Glu Met Gln Arg Tyr Val
            100                 105                 110

Glu Glu Asn Gln Thr Arg Asn Lys His Ile Asn Pro Asn Glu Trp Trp
        115                 120                 125

Lys Val Tyr Pro Ser Ser Val Thr Glu Phe Lys Phe Leu Phe Val Ser
    130                 135                 140

Gly His Phe Lys Gly Asn Tyr Lys Ala Gln Leu Thr Arg Leu Asn His
145                 150                 155                 160

Ile Thr Asn Cys Asn Gly Ala Val Leu Ser Val Glu Glu Leu Leu Ile
                165                 170                 175

Gly Gly Glu Met Ile Lys Ala Gly Thr Leu Thr Leu Glu Glu Val Arg
            180                 185                 190

Arg Lys Phe Asn Asn Gly Glu Ile Asn Phe Gly Gly Ser Gly Gly Ser
        195                 200                 205

Asp Val Val Met Thr Gln Thr Pro Leu Ser Leu Pro Val Ser Leu Gly
    210                 215                 220

Asp Gln Ala Ser Ile Ser Cys Arg Ser Ser Gln Ser Leu Val His Ser
225                 230                 235                 240

Asn Gly Asn Thr Tyr Leu Arg Trp Tyr Leu Gln Lys Pro Gly Gln Ser
                245                 250                 255

Pro Lys Val Leu Ile Tyr Lys Val Ser Asn Arg Phe Ser Gly Val Pro
            260                 265                 270

Asp Arg Phe Ser Gly Ser Gly Ser Gly Thr Asp Phe Thr Leu Lys Ile
        275                 280                 285

Ser Arg Val Glu Ala Glu Asp Leu Gly Val Tyr Phe Cys Ser Gln Ser
    290                 295                 300

Thr His Val Pro Trp Thr Phe Gly Gly Gly Thr Lys Leu Glu Ile Lys
305                 310                 315                 320

Ser Ser Ala Asp Asp Ala Lys Lys Asp Ala Lys Lys Asp Asp Ala
                325                 330                 335
```

```
Lys Lys Asp Asp Ala Lys Lys Asp Gly Val Lys Leu Asp Glu Thr
            340                 345                 350
Gly Gly Gly Leu Val Gln Pro Gly Arg Pro Met Lys Leu Ser Cys Val
        355                 360                 365
Ala Ser Gly Phe Thr Phe Ser Asp Tyr Trp Met Asn Trp Val Arg Gln
370                 375                 380
Ser Pro Glu Lys Gly Leu Glu Trp Val Ala Gln Ile Arg Asn Lys Pro
385                 390                 395                 400
Tyr Asn Tyr Glu Thr Tyr Tyr Ser Asp Ser Val Lys Gly Arg Phe Thr
            405                 410                 415
Ile Ser Arg Asp Asp Ser Lys Ser Ser Val Tyr Leu Gln Met Asn Asn
            420                 425                 430
Leu Arg Val Glu Asp Met Gly Ile Tyr Tyr Cys Thr Gly Ser Tyr Tyr
        435                 440                 445
Gly Met Asp Tyr Trp Gly Gln Gly Thr Ser Val Thr Val Ser
    450                 455                 460

<210> SEQ ID NO 50
<211> LENGTH: 1389
<212> TYPE: DNA
<213> ORGANISM: Artificial sequence
<220> FEATURE:
<223> OTHER INFORMATION: polynucleotide

<400> SEQUENCE: 50
atgccgaaaa agaagaggaa ggtggtgaag agcgaactgg aggagaaaaa gtccgagctc      60
cgccacaagc tgaagtacgt cccgcacgag tacatcgaac tgatcgagat tgccaggaat     120
tccacccagg accgcatcct cgaaatgaag gtcatggaat tcttcatgaa ggtgtacggc     180
taccgcggga acaccctcgg cggcagcagg aagccagatg cgcgatcta tacggtcggg     240
tccccgatcg actatggggt gatcgtcgac accaaagcgt acagcggcgg ctacaacctc     300
ccaattggcc aggcggacga gatgcagagg tatgtggagg agaaccagac cgcaataag      360
cacatcaacc cgaacgagtg gtggaaggtg tacccaagct ccgtgaccga gttcaagttc     420
ctcttcgtgt ccgggcactt caagggcaat tacaaggccc agctgacgcg cctcaaccat     480
atcacgaatt gcaatggcgc cgtcctgtcc gtcgaagagc tgctcatcgg cggggagatg     540
atcaaggcgg gcacgctgac gctggaggaa gtacgtagga aattcaacaa cggggaaatc     600
aatttcgggg gatccggggg cagcgatgtg gtgatgacgc agacccccact gtccctgcca     660
gtgtccctag cgaccaagc gagcatcctc tgtcgcagca gccagtccct cgtgcactcc     720
aacggcaaca cgtatctccg ctggtatctc cagaagccgg ggcagtcccc gaaagtgctg     780
atctacaagg tctccaaccg cttctccggc gtcccggata ggtttagcgg cagcgggtcc     840
ggcaccgact ttaccctgaa aatctccagg gtggaggccg aggatctcgg ggtctacttt     900
tgcagccaga gcacgcacgt cccatggacc tttggggggcg gcacgaaact ggagattaaa     960
agcagcgctg acgatgccaa gaaggacgcg gcgaaaaagg acgacgccaa gaaagacgac    1020
gcgaaaaaag acggcggcgt caagctcgat gaaaccggcg gcggctcgt gcaaccaggc    1080
cgcccgatga gcttagctg cgtggccagc gggttcacct tcagcgacta ctggatgaac    1140
tgggtccgcc aatccccgga aaagggcctg gagtgggtgg cccagatcag gaacaagcca    1200
tataactatg agacgtacta ctccgatagc gtgaagggc gcttcaccat ctccagggac    1260
gacagcaagt cctccgtgta cctccagatg aacaacctac gcgtggagga tatgggcatc    1320
tactactgca ccgggagcta ctacggcatg gactactggg gccagggcac gtccgtcacc    1380
```

```
gtgtcctga                                                              1389

<210> SEQ ID NO 51
<211> LENGTH: 21
<212> TYPE: DNA
<213> ORGANISM: Artificial sequence
<220> FEATURE:
<223> OTHER INFORMATION: polynucleotide

<400> SEQUENCE: 51
gtcctgctaa gcctttgaaa g                                                21

<210> SEQ ID NO 52
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, or t

<400> SEQUENCE: 52
gcatccttcc gtagtgctcc tcnnnnnn                                         28

<210> SEQ ID NO 53
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, or t

<400> SEQUENCE: 53
nnnnnnttgt aattgctggt gctggtat                                         28

<210> SEQ ID NO 54
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, or t

<400> SEQUENCE: 54
nnnnnngagg agcactacgg aaggatgc                                         28

<210> SEQ ID NO 55
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, or t

<400> SEQUENCE: 55
tgcatccttc cgtagtgctc ctnn                                             24
```

<210> SEQ ID NO 56
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, or t

<400> SEQUENCE: 56
nngtaattgc tggtgctggt atgt                                          24

<210> SEQ ID NO 57
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, or t

<400> SEQUENCE: 57
nnaggagcac tacggaagga tgca                                          24

<210> SEQ ID NO 58
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, or t

<400> SEQUENCE: 58
acataccagc accagcaatt acnn                                          24

<210> SEQ ID NO 59
<211> LENGTH: 1865
<212> TYPE: DNA
<213> ORGANISM: Artificial sequence
<220> FEATURE:
<223> OTHER INFORMATION: polynucleotide

<400> SEQUENCE: 59
aaattacgtt gagatgcatg gtctctctct actcaattaa ccaataagg aaaagaatca     60 tatggtcatc aattcgtaaa tcaaaatttt aatttgtgtg gtatttaatc catctacatg   120
tttcgtaagc aacaaaagag cttggtctga aaaccaaaca agaccatatg ggcactcgaa   180
tactccattt tgttatcggc tacttccact agcctcctcc ttcgctgcgt ctcctgtttc   240
tctacttcac gattactcgc taggtaaaag ataagatact aaacaactac tatagccct   300 ttaattcaag tccgtttttt tttgttcttc ttcttttcaa ttatgtgtta aagatacaaa   360
cttttgtctg atttgcttcc accggtttca cctaagatac tcaatttct tacttttgt    420 gtgttttgta attctaattc ttttatagct tcaatttta gattcattga agcagttgtg   480
agttaagttg gagaaaatgg ttgtgtttgg gaatgtttct gcggcgaatt tgccttatca   540
aaacgggttt ttggaggcac tttcatctgg aggttgtgaa ctaatgggac atagctttag   600
ggttcccact tctcaagcgc ttaagacaag aacaaggagg aggagtactg ctggtccttt   660

```
gatggtgagc aagggcgagg aggataacat ggccatcatc aaggagttca tgcccttcaa      720
ggtgcacatg gagggctccg tgaacggcca cgagttcgag atcgagggcg agggcgaggg      780
ccgcccctac gagggcaccc agaccgccaa gctgaaggtg accaagggtg cccccctgcc      840
cttcgcctgg gacatcctgt cccctcagtt catgtacggc tccaaggcct acgtgaagca      900
ccccgccgac atccccgact acttgaagct gtccttcccc gagggcttca gtgggagcg      960 cgtgatgaac ttcgaggacg gcggcgtggt gaccgtgacc caggactcct ccctgcagga     1020
cggcgagttc atctacaagg tgaagctgcg cggcaccaac ttccccctccg acggccccgt     1080 aatgcagaag aagaccatgg gctgggaggc ctcctccgag cggatgtacc ccgaggacgg     1140
cgccctgaag ggcgagatca agcagaggct gaagctgaag gacggcggcc actacgacgc     1200
tgaggtcaag accacctaca aggccaagaa gcccgtgcag ctgcccggcg cctacaacgt     1260
caacatcaag ttggacatca cctcccacaa cgaggactac accatcgtgg aacagtacga     1320
acgcgccgag ggccgccact ccaccggcgg catggacgag ctgtacaagt aaggtatgtc     1380
tacaacttca tttcttactg ctttgtttgg gatctgatgg aattaatgtt catgtgatga     1440
agttcttttg gctctcaaat aattgcagga ttggctggat tgtcaactgc aaagtacctg     1500
gctgatgcag gccacaaacc tctgttgctt gaagcaagag atgttcttgg tggaaaggta     1560
ctttgattgg tctcactttc cgaattactt attgttgttt gcattctca ttcttatatg      1620 atttgctgat tcccaaggc tgtaccaatt atgtttgtga gactacaagg tataactagt      1680
gtttagagtg ttacagctcc taggtaccca atgtatctgt cctgtttgtt gtattagtct     1740
tgtactgccc aatttgtttt ttattatgtt ctaatgtctt cagtcttgtg ctacacaccg     1800 cacaacccctt tccagtttct aggcttaatg tgaatcaaat atagagtagt ttactggaag   1860
atatc                                                                 1865

<210> SEQ ID NO 60
<211> LENGTH: 23
<212> TYPE: DNA
<213> ORGANISM: Artificial sequence
<220> FEATURE:
<223> OTHER INFORMATION: polynucleotide

<400> SEQUENCE: 60
tggttgtgtt tgggaatgtt tct                                               23

<210> SEQ ID NO 61
<211> LENGTH: 26
<212> TYPE: DNA
<213> ORGANISM: Artificial sequence
<220> FEATURE:
<223> OTHER INFORMATION: polynucleotide

<400> SEQUENCE: 61
tatccaaaag atatcttcca gtaaac                                            26

<210> SEQ ID NO 62
<211> LENGTH: 20
<212> TYPE: RNA
<213> ORGANISM: Artificial sequence
<220> FEATURE:
<223> OTHER INFORMATION: polynucleoitde

<400> SEQUENCE: 62
uucaccucua accgggugag                                                   20
```

<210> SEQ ID NO 63
<211> LENGTH: 18
<212> TYPE: PRT
<213> ORGANISM: Artificial sequence
<220> FEATURE:
<223> OTHER INFORMATION: polypeptide

<400> SEQUENCE: 63

Gly Thr Ala Lys Ser Arg Tyr Lys Ala Arg Ala Glu Leu Ile Ala
1               5                   10                  15

Glu Arg

<210> SEQ ID NO 64
<211> LENGTH: 21
<212> TYPE: DNA
<213> ORGANISM: Artificial sequence
<220> FEATURE:
<223> OTHER INFORMATION: polynucleotide

<400> SEQUENCE: 64
ggtcaagtgc cacgtaggat g                                         21

<210> SEQ ID NO 65
<211> LENGTH: 21
<212> TYPE: DNA
<213> ORGANISM: Artificial sequence
<220> FEATURE:
<223> OTHER INFORMATION: polynucleotide

<400> SEQUENCE: 65
ggtcaagtgg cgcgcaggat g                                         21

<210> SEQ ID NO 66
<211> LENGTH: 194
<212> TYPE: PRT
<213> ORGANISM: Artificial sequence
<220> FEATURE:
<223> OTHER INFORMATION: polypeptide

<400> SEQUENCE: 66

Val Lys Ser Glu Leu Glu Glu Lys Lys Ser Glu Leu Arg His Lys Leu
1               5                   10                  15

Lys Tyr Val Pro His Glu Tyr Ile Glu Leu Ile Glu Ile Ala Arg Asn
                20                  25                  30

Ser Thr Gln Asp Arg Ile Leu Glu Met Lys Val Met Glu Phe Phe Met
            35                  40                  45

Lys Val Tyr Gly Tyr Arg Gly Lys His Leu Gly Gly Ser Arg Lys Pro
    50                  55                  60

Asp Gly Ala Ile Tyr Thr Val Gly Ser Pro Ile Asp Tyr Gly Val Ile
65                  70                  75                  80

Val Asp Thr Lys Ala Tyr Ser Gly Gly Tyr Asn Leu Pro Ile Gly Gln
                85                  90                  95

Ala Asp Glu Met Gln Arg Tyr Val Glu Glu Asn Gln Thr Arg Asn Lys
                100                 105                 110

His Ile Asn Pro Asn Glu Trp Trp Lys Val Tyr Pro Ser Ser Val Thr
            115                 120                 125

Glu Phe Lys Phe Leu Phe Val Ser Gly His Phe Lys Gly Asn Tyr Lys
    130                 135                 140

Ala Gln Leu Thr Arg Leu Asn His Ile Thr Asn Cys Asn Gly Ala Val
145                 150                 155                 160

```
Leu Ser Val Glu Glu Leu Leu Ile Gly Gly Glu Met Ile Lys Ala Gly
                165                 170                 175
Thr Leu Thr Leu Glu Glu Val Arg Arg Lys Phe Asn Asn Gly Glu Ile
            180                 185                 190
Asn Phe
```

<210> SEQ ID NO 67
<211> LENGTH: 8
<212> TYPE: PRT
<213> ORGANISM: Artificial sequence
<220> FEATURE:
<223> OTHER INFORMATION: peptide

<400> SEQUENCE: 67

```
Met Pro Lys Lys Lys Arg Lys Val
1               5
```

<210> SEQ ID NO 68
<211> LENGTH: 225
<212> TYPE: PRT
<213> ORGANISM: Artificial sequence
<220> FEATURE:
<223> OTHER INFORMATION: polypeptide

<400> SEQUENCE: 68

```
Met Gly Thr Ala Lys Ser Arg Tyr Lys Ala Arg Arg Ala Glu Leu Ile
1               5                   10                  15
Ala Glu Arg Gly Gly Ser Gly Gly Val Lys Ser Glu Leu Glu Glu Lys
                20                  25                  30
Lys Ser Glu Leu Arg His Lys Leu Lys Tyr Val Pro His Glu Tyr Ile
            35                  40                  45
Glu Leu Ile Glu Ile Ala Arg Asn Ser Thr Gln Asp Arg Ile Leu Glu
        50                  55                  60
Met Lys Val Met Glu Phe Phe Met Lys Val Tyr Gly Tyr Arg Gly Lys
65                  70                  75                  80
His Leu Gly Gly Ser Arg Lys Pro Asp Gly Ala Ile Tyr Thr Val Gly
                85                  90                  95
Ser Pro Ile Asp Tyr Gly Val Ile Val Asp Thr Lys Ala Tyr Ser Gly
            100                 105                 110
Gly Tyr Asn Leu Pro Ile Gly Gln Ala Asp Glu Met Gln Arg Tyr Val
        115                 120                 125
Glu Glu Asn Gln Thr Arg Asn Lys His Ile Asn Pro Asn Glu Trp Trp
130                 135                 140
Lys Val Tyr Pro Ser Ser Val Thr Glu Phe Lys Phe Leu Phe Val Ser
145                 150                 155                 160
Gly His Phe Lys Gly Asn Tyr Lys Ala Gln Leu Thr Arg Leu Asn His
                165                 170                 175
Ile Thr Asn Cys Asn Gly Ala Val Leu Ser Val Glu Glu Leu Leu Ile
            180                 185                 190
Gly Gly Glu Met Ile Lys Ala Gly Thr Leu Thr Leu Glu Glu Val Arg
        195                 200                 205
Arg Lys Phe Asn Asn Gly Glu Ile Asn Phe Pro Lys Lys Lys Arg Lys
    210                 215                 220
Val
225
```

<210> SEQ ID NO 69
<211> LENGTH: 678

```
<212> TYPE: DNA
<213> ORGANISM: Artificial sequence
<220> FEATURE:
<223> OTHER INFORMATION: polypeptide

<400> SEQUENCE: 69
atggggacgg ccaagtccag gtacaaggcg cgcagggccg aactgattgc ggagaggggc    60
ggatccggcg gcgtcaaatc cgagctcgaa gagaagaaga gcgagctgag cacaagctg   120
aagtacgtcc cgcacgagta catcgaactc atcgagatcg ccaggaactc cacccaggac   180
cgcatcctgg agatgaaggt gatggagttc ttcatgaagg tgtacggcta ccgtggcaaa   240
catctggggg gctccaggaa accggatggg gccatctaca ccgtggggag cccgatcgac   300
tacggcgtga tcgtggacac caaagcgtac tccggcggct acaacctccc gattggccag   360
gccgatgaaa tgcagcgcta cgtggaggag aaccagacgc gcaataagca catcaacccg   420
aacgagtggt ggaaggtgta cccgtcctcc gtgaccgagt tcaagttcct gttcgtgagc   480
ggccacttca aggggaacta caaggcccag ctgacccgcc tgaaccacat caccaactgc   540
aatggggcgg tgctctccgt ggaggaactc ctgatcggcg gcgagatgat caaggccggc   600
accctgaccc tggaagaggt acgtagaaag ttcaacaacg gcgagatcaa cttcccgaag   660
aagaagcgca aggtgtga                                                 678

<210> SEQ ID NO 70
<211> LENGTH: 43
<212> TYPE: RNA
<213> ORGANISM: Artificial sequence
<220> FEATURE:
<223> OTHER INFORMATION: polynucleotide
<220> FEATURE:
<221> NAME/KEY: misc_feature
<222> LOCATION: (21)..(21)
<223> OTHER INFORMATION: n is a, c, g, or u

<400> SEQUENCE: 70
uucaccucua accgggugag ngguacugau gcuuucagg aaa                       43

<210> SEQ ID NO 71
<211> LENGTH: 43
<212> TYPE: RNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(23)
<223> OTHER INFORMATION: n is a, c, g, or u

<400> SEQUENCE: 71
auagcguccc cauuguugcu aunuucaccu cuaaccgggu gag                      43

<210> SEQ ID NO 72
<211> LENGTH: 43
<212> TYPE: RNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(23)
<223> OTHER INFORMATION: n is a, c, g, or u

<400> SEQUENCE: 72
uuuccugaaa agcaucagua ccnuucaccu cuaaccgggu gag                      43
```

-continued

<210> SEQ ID NO 73
<211> LENGTH: 42
<212> TYPE: RNA
<213> ORGANISM: Artificial sequence
<220> FEATURE:
<223> OTHER INFORMATION: polynucleotide
<220> FEATURE:
<221> NAME/KEY: misc_feature
<222> LOCATION: (20)..(20)
<223> OTHER INFORMATION: n is a, c, g, or u

<400> SEQUENCE: 73
ucaccucuaa ccgggugagn auagcaacaa uggggacgcu au                              42

<210> SEQ ID NO 74
<211> LENGTH: 8
<212> TYPE: PRT
<213> ORGANISM: Artificial sequence
<220> FEATURE:
<223> OTHER INFORMATION: peptide

<400> SEQUENCE: 74

Gly Gly Ser Gly Gly Glu Ser Lys
1               5

<210> SEQ ID NO 75
<211> LENGTH: 229
<212> TYPE: PRT
<213> ORGANISM: Artificial sequence
<220> FEATURE:
<223> OTHER INFORMATION: polypeptide

<400> SEQUENCE: 75

Met Pro Lys Lys Lys Arg Lys Val Val Lys Ser Glu Leu Glu Lys
1               5                   10                  15

Lys Ser Glu Leu Arg His Lys Leu Lys Tyr Val Pro His Glu Tyr Ile
            20                  25                  30

Glu Leu Ile Glu Ile Ala Arg Asn Ser Thr Gln Asp Arg Ile Leu Glu
        35                  40                  45

Met Lys Val Met Glu Phe Phe Met Lys Val Tyr Gly Tyr Arg Gly Lys
    50                  55                  60

His Leu Gly Gly Ser Arg Lys Pro Asp Gly Ala Ile Tyr Thr Val Gly
65                  70                  75                  80

Ser Pro Ile Asp Tyr Gly Val Ile Val Asp Thr Lys Ala Tyr Ser Gly
                85                  90                  95

Gly Tyr Asn Leu Pro Ile Gly Gln Ala Asp Glu Met Gln Arg Tyr Val
            100                 105                 110

Glu Glu Asn Gln Thr Arg Asn Lys His Ile Asn Pro Asn Glu Trp Trp
        115                 120                 125

Lys Val Tyr Pro Ser Ser Val Thr Glu Phe Lys Phe Leu Phe Val Ser
    130                 135                 140

Gly His Phe Lys Gly Asn Tyr Lys Ala Gln Leu Thr Arg Leu Asn His
145                 150                 155                 160

Ile Thr Asn Cys Asn Gly Ala Val Leu Ser Val Glu Glu Leu Leu Ile
                165                 170                 175

Gly Gly Glu Met Ile Lys Ala Gly Thr Leu Thr Leu Glu Glu Val Arg
            180                 185                 190

Arg Lys Phe Asn Asn Gly Glu Ile Asn Phe Gly Gly Ser Gly Gly Glu
        195                 200                 205

Ser Lys Gly Thr Ala Lys Ser Arg Tyr Lys Ala Arg Arg Ala Glu Leu

Ile Ala Glu Arg Arg
225

<210> SEQ ID NO 76
<211> LENGTH: 690
<212> TYPE: DNA
<213> ORGANISM: Artificial sequence
<220> FEATURE:
<223> OTHER INFORMATION: polypeptide

<400> SEQUENCE: 76

```
atgccaaaga agaagagaaa ggttgttaag tctgaacttg aagaaaagaa gtctgaactt      60
agacataagc ttaagtatgt tccacatgaa tatattgaac ttattgaaat tgctagaaat     120
tctactcaag atagaattct tgaaatgaag gttatggaat tttttatgaa ggtttatgga     180
tatagaggaa agcatcttgg aggatctaga aagccagatg gagctattta tactgttgga     240
tctccaattg attatggagt tattgttgat actaaggctt attctggagg atataatctt     300
ccaattggac aagctgatga atgcaaaga tatgttgaag aaaatcaaac tagaaataag      360
catattaatc caaatgaatg gtggaaggtt tatccatctt ctgttactga atttaagttt     420
cttttttgttt ctggacattt taagggaaat tataaggctc aacttactag acttaatcat     480
attactaatt gtaatggagc tgttctttct gttgaagaac ttcttattgg aggagaaatg     540
attaaggctg aactcttac tcttgaagaa gttagaagaa gtttaataa tggagaaatt       600
aattttggag gatctggagg agaatctaag ggaactgcta agtctagata taaggctaga    660
agagctgaac ttattgctga agaagataa                                       690
```

<210> SEQ ID NO 77
<211> LENGTH: 42
<212> TYPE: RNA
<213> ORGANISM: Artificial sequence
<220> FEATURE:
<223> OTHER INFORMATION: polynucleotide

<400> SEQUENCE: 77

```
uucaccucua accgggugag uacugaugcu uuucaggaaa cu                         42
```

<210> SEQ ID NO 78
<211> LENGTH: 42
<212> TYPE: RNA
<213> ORGANISM: Artificial sequence
<220> FEATURE:
<223> OTHER INFORMATION: polynucleotide

<400> SEQUENCE: 78

```
gauagcgucc ccauuguugc uauucaccuc uaaccggqug ag                         42
```

<210> SEQ ID NO 79
<211> LENGTH: 42
<212> TYPE: RNA
<213> ORGANISM: Artificial
<220> FEATURE:
<223> OTHER INFORMATION: polynucleotide

<400> SEQUENCE: 79

```
aguuccuga aaagcaucag uauucaccuc uaaccgggug ag                          42
```

<210> SEQ ID NO 80
<211> LENGTH: 42
<212> TYPE: RNA

```
<213> ORGANISM: Artificial sequence
<220> FEATURE:
<223> OTHER INFORMATION: polynucleotide

<400> SEQUENCE: 80
uucaccucua accgggugag uagcaacaau ggggacgcua uc                          42

<210> SEQ ID NO 81
<211> LENGTH: 43
<212> TYPE: RNA
<213> ORGANISM: Artificial sequence
<220> FEATURE:
<223> OTHER INFORMATION: polynucleotide
<220> FEATURE:
<221> NAME/KEY: misc_feature
<222> LOCATION: (21)..(21)
<223> OTHER INFORMATION: n is a, c, g, or u

<400> SEQUENCE: 81
uucaccucua accgggugag nucgguacug augcuuuuca gga                         43

<210> SEQ ID NO 82
<211> LENGTH: 43
<212> TYPE: RNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(23)
<223> OTHER INFORMATION: n is a, c, g, or u

<400> SEQUENCE: 82
gcguccccau uguugcuaua acnuucaccu cuaaccgggu gag                         43

<210> SEQ ID NO 83
<211> LENGTH: 43
<212> TYPE: RNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(23)
<223> OTHER INFORMATION: n is a, c, g, or u

<400> SEQUENCE: 83
uccugaaaag caucaguacc ganuucaccu cuaaccgggu gag                         43

<210> SEQ ID NO 84
<211> LENGTH: 43
<212> TYPE: RNA
<213> ORGANISM: Artificial sequence
<220> FEATURE:
<223> OTHER INFORMATION: polynucleotide
<220> FEATURE:
<221> NAME/KEY: misc_feature
<222> LOCATION: (21)..(21)
<223> OTHER INFORMATION: n is a, c, g, or u

<400> SEQUENCE: 84
uucaccucua accgggugag nguuauagca acaaugggga cgc                         43

<210> SEQ ID NO 85
<211> LENGTH: 1995
<212> TYPE: DNA
<213> ORGANISM: Artificial sequence
<220> FEATURE:
<223> OTHER INFORMATION: polynucleotide
```

<400> SEQUENCE: 85

```
atggcggcgg ctgcggcggc tccatctccc tctttctcca aaaccctatc gtcctcctcc      60
tccaaatcct ccaccctcct ccctagatcc accttccctt tcccccacca cccccacaaa     120
accaccccac caccccctcca cctcaccccc acccacattc acagccaacg ccgtcgtttc    180
accatctcca atgtcatttc cactacccaa aaagtttccg agacccaaaa agccgaaact    240
ttcgtttccc gttttgcccc tgacgaaccc agaaagggtt ccgacgttct cgtggaggcc    300
ctcgaaagag aaggggttac ggacgttttt gcgtacccag gcggcgcttc catggagatt    360
caccaagctt tgacgcgctc aagcatcatc cgcaacgtgc taccacgtca cgagcagggt    420
ggtgtcttcg ccgctgaggg ttacgcacgc gccaccggct tccccggcgt ttgcattgcc    480
acctccggcc ctggcgccac caatctcgtc agtggcctcg cggacgccct actggatagc    540
gtccccattg ttgctataac cggtcaagtg ccacgtagga tgatcggtac tgatgctttt    600
caggaaactc cgattgttga ggtaactaga tcgattacca agcataatta tctcgttatg    660
gacgtagagg atattcctag ggttgtacgt gaggcttttt tccttgcgag atcgggccgg    720
cctggccctg ttttgattga tgtacctaag gatattcagc aacaattggt gatacctgac    780
tgggatcagc caatgaggtt gcctggttac atgtctaggt tacctaaatt gcccaatgag    840
atgcttttag aacaaattgt taggcttatt tctgagtcaa agaagcctgt tttgtatgtg    900
gggggtgggt gttcgcaatc gagtgaggag ttgagacgat tcgtggagct caccggtatc    960
cccgtggcaa gtactttgat gggtcttgga gcttttccaa ctggggatga gctttcccctt   1020
tcaatgttgg gtatgcatgg tactgtttat gctaattatg ctgtggacag tagtgattta   1080
ttgctcgcat ttgggggtgag gtttgatgat agagttactg gaaagttaga agcttttgct   1140
agccgagcga aaattgttca cattgatatt gattcagctg agattggaaa gaacaagcag   1200
cctcatgttt ccatttgtgc ggatatcaag ttggcgttac agggtttgaa ttcgatattg   1260
gagagtaagg aaggtaaact gaagttggat ttttctgctt ggaggcagga gttgacggtg   1320
cagaaagtga agtacccgtt gaatttaaa acttttggtg atgctattcc tccgcaatat   1380
gctatccagg ttctagatga gttaactaat gggagtgcta ttataagtac cggtgttggg   1440
cagcaccaga tgtgggctgc tcaatattat aagtacagaa agccacgcca atggttgaca   1500
tctggtggat taggagcgat gggatttggt ttgcccgctg ctattggtgc ggctgttgga   1560
agacctgatg aagttgtggt tgacattgat ggtgatggca gtttcatcat gaatgtgcag   1620
gagctagcaa ctattaaggt ggagaatctc ccagttaaga ttatgttact gaataatcaa   1680
cacttgggaa tggtggttca atgggaggat cggttctata aggctaacag agcacacaca   1740
tacctgggga atccttctaa tgaggcggag atctttccta atatgttgaa atttgcagag   1800
gcttgtggcg tacctgctgc gagagtgaca cacagggatg atcttagagc ggctattcaa   1860
aagatgttag acactcctgg gccatacttg ttggatgtga ttgtacctca tcaggaacat   1920
gttctaccta tgattcccag tggcggggct ttcaaagatg tgatcacaga gggtgacggg   1980
agaagttcct attga                                                    1995
```

<210> SEQ ID NO 86
<211> LENGTH: 1995
<212> TYPE: DNA
<213> ORGANISM: Artificial sequence
<220> FEATURE:
<223> OTHER INFORMATION: polynucleotide

<400> SEQUENCE: 86

```
atggcggcgg ctgcggcggc tccatctccc tctttctcca aaaccctatc gtcctcctcc      60
tccaaatcct ccaccctcct ccctagatcc accttcccttt tcccccacca ccccacaaa     120
accaccccac caccccctcca cctcacccccc cccacattc acagccaacg ccgtcgtttc    180
accatctcca atgtcatttc cactacccaa aaagtttccg agacccaaaa agccgaaact    240
ttcgtttccc gttttgcccc tgacgaaccc agaaagggtt ccgacgttct cgtggaggcc    300
ctcgaaagag aaggggttac ggacgttttt gcgtacccag gcggcgcttc catggagatt    360
caccaagctt tgacgcgctc aagcatcatc cgcaacgtgc taccacgtca cgagcagggt    420
ggtgtcttcg ccgctgaggg ttacgcacgc gccaccggct tccccggcgt ttgcattgcc    480
acctccggcc ctggcgccac caatctcgtc agtggcctcg cggacgccct actggatagc    540
gtcccaatag tagccataac tggtcaagtg gcgcgcagga tgatcggtac cgatgctttt    600
caggaaactc cgattgttga ggtaactaga tcgattacca agcataatta tctcgttatg    660
gacgtagagg atattcctag ggttgtacgt gaggcttttt tccttgcgag atcgggccgg    720
cctggccctg ttttgattga tgtacctaag gatattcagc aacaattggt gatacctgac    780
tgggatcagc caatgaggtt gcctggttac atgtctaggt tacctaaatt gcccaatgag    840
atgcttttag aacaaattgt taggcttatt tctgagtcaa agaagcctgt tttgtatgtg    900
gggggtgggt gttcgcaatc gagtgaggag ttgagacgat cgtggagct caccggtatc    960
cccgtggcaa gtactttgat gggtcttgga gcttttccaa ctggggatga gctttcccttt  1020
tcaatgttgg gtatgcatgg tactgtttat gctaattatg ctgtggacag tagtgattta  1080
ttgctcgcat ttgggtgagt gttgatgat agagttactg gaaagttaga agcttttgct   1140
agccgagcga aaattgttca cattgatatt gattcagctg agattggaaa gaacaagcag  1200
cctcatgttt ccatttgtgc ggatatcaag ttggcgttac agggtttgaa ttcgatattg  1260
gagagtaagg aagtaaact gaagttggat ttttctgctt ggaggcagga gttgacggtg   1320
cagaaagtga agtacccgtt gaatttttaaa acttttggtg atgctattcc tccgcaatat   1380
gctatccagg ttctagatga gttaactaat gggagtgcta ttataagtac cggtgttggg    1440
cagcaccaga tgtgggctgc tcaatattat aagtacagaa agccacgcca atggttgaca    1500
tctggtggat taggagcgat gggatttggt ttgcccgctg ctattggtgc ggctgttgga    1560
agacctgatg aagttgtggt tgacattgat ggtgatggca gtttcatcat gaatgtgcag    1620
gagctagcaa ctattaaggt ggagaatctc ccagttaaga ttatgttact gaataatcaa    1680
cacttgggaa tggtggttca atgggaggat cggttctata aggctaacag agcacacaca    1740
tacctgggga atccttctaa tgaggcggag atctttccta atatgttgaa atttgcagag    1800
gcttgtggcg tacctgctgc gagagtgaca cacagggatg atcttagagc ggctattcaa    1860
aagatgttag acactcctgg gccatacttg ttggatgtga ttgtacctca tcaggaacat    1920
gttctaccta tgattcccag tggcgggggt ttcaaagatg tgatcacaga gggtgacggg    1980
agaagttcct attga                                                    1995
```

<210> SEQ ID NO 87
<211> LENGTH: 286
<212> TYPE: PRT
<213> ORGANISM: Artificial sequence
<220> FEATURE:
<223> OTHER INFORMATION: polypeptide

<400> SEQUENCE: 87

Pro Ala Glu Lys Arg Lys Pro Ile Arg Val Leu Ser Leu Phe Asp Gly
1               5                   10                  15

Ile Ala Thr Gly Leu Leu Val Leu Lys Asp Leu Gly Ile Gln Val Asp
            20                  25                  30

Arg Tyr Ile Ala Ser Glu Val Cys Glu Asp Ser Ile Thr Val Gly Met
        35                  40                  45

Val Arg His Gln Gly Lys Ile Met Tyr Val Gly Asp Val Arg Ser Val
    50                  55                  60

Thr Gln Lys His Ile Gln Glu Trp Gly Pro Phe Asp Leu Val Ile Gly
65                  70                  75                  80

Gly Ser Pro Cys Asn Asp Leu Ser Ile Val Asn Pro Ala Arg Lys Gly
                85                  90                  95

Leu Tyr Glu Gly Thr Gly Ala Leu Phe Phe Glu Phe Tyr Arg Leu Leu
            100                 105                 110

His Asp Ala Arg Pro Lys Glu Gly Asp Asp Arg Pro Phe Phe Trp Leu
        115                 120                 125

Phe Glu Asn Val Val Ala Met Gly Val Ser Asp Lys Arg Asp Ile Ser
    130                 135                 140

Arg Phe Leu Glu Ser Asn Pro Val Met Ile Asp Ala Lys Glu Val Ser
145                 150                 155                 160

Ala Ala His Arg Ala Arg Tyr Phe Trp Gly Asn Leu Pro Gly Met Asn
                165                 170                 175

Arg Pro Leu Ala Ser Thr Val Asn Asp Lys Leu Glu Leu Gln Glu Cys
            180                 185                 190

Leu Glu His Gly Arg Ile Ala Lys Phe Ser Lys Val Arg Thr Ile Thr
        195                 200                 205

Thr Arg Ser Asn Ser Ile Lys Gln Gly Lys Asp Gln His Phe Pro Val
    210                 215                 220

Phe Met Asn Glu Lys Glu Asp Ile Leu Trp Cys Thr Glu Met Glu Arg
225                 230                 235                 240

Val Phe Gly Phe Pro Val His Tyr Thr Asp Val Ser Asn Met Ser Arg
                245                 250                 255

Leu Ala Arg Gln Arg Leu Leu Gly Arg Ser Trp Ser Val Pro Val Ile
            260                 265                 270

Arg His Leu Phe Ala Pro Leu Lys Glu Tyr Phe Ala Cys Val
        275                 280                 285

<210> SEQ ID NO 88
<211> LENGTH: 557
<212> TYPE: PRT
<213> ORGANISM: Artificial sequence
<220> FEATURE:
<223> OTHER INFORMATION: polypeptide

<400> SEQUENCE: 88

Met Pro Lys Lys Lys Arg Lys Val Asp Val Val Met Thr Gln Thr Pro
1               5                   10                  15

Leu Ser Leu Pro Val Ser Leu Gly Asp Gln Ala Ser Ile Ser Cys Arg
            20                  25                  30

Ser Ser Gln Ser Leu Val His Ser Asn Gly Asn Thr Tyr Leu Arg Trp
        35                  40                  45

Tyr Leu Gln Lys Pro Gly Gln Ser Pro Lys Val Leu Ile Tyr Lys Val
    50                  55                  60

Ser Asn Arg Phe Ser Gly Val Pro Asp Arg Phe Ser Gly Ser Gly Ser
65                  70                  75                  80

```
Gly Thr Asp Phe Thr Leu Lys Ile Ser Arg Val Glu Ala Glu Asp Leu
                85                  90                  95

Gly Val Tyr Phe Cys Ser Gln Ser Thr His Val Pro Trp Thr Phe Gly
            100                 105                 110

Gly Gly Thr Lys Leu Glu Ile Lys Ser Ala Asp Asp Ala Lys Lys
        115                 120                 125

Asp Ala Lys Lys Asp Asp Ala Lys Lys Asp Asp Ala Lys Lys Asp
    130                 135                 140

Gly Gly Val Lys Leu Asp Glu Thr Gly Gly Leu Val Gln Pro Gly
145                 150                 155                 160

Arg Pro Met Lys Leu Ser Cys Val Ala Ser Gly Phe Thr Phe Ser Asp
                165                 170                 175

Tyr Trp Met Asn Trp Val Arg Gln Ser Pro Glu Lys Gly Leu Glu Trp
                180                 185                 190

Val Ala Gln Ile Arg Asn Lys Pro Tyr Asn Tyr Glu Thr Tyr Tyr Ser
                195                 200                 205

Asp Ser Val Lys Gly Arg Phe Thr Ile Ser Arg Asp Asp Ser Lys Ser
    210                 215                 220

Ser Val Tyr Leu Gln Met Asn Asn Leu Arg Val Glu Asp Met Gly Ile
225                 230                 235                 240

Tyr Tyr Cys Thr Gly Ser Tyr Tyr Gly Met Asp Tyr Trp Gly Gln Gly
            245                 250                 255

Thr Ser Val Thr Val Ser Gly Ser Leu Glu Gly Gly Ser Gly Gly Pro
            260                 265                 270

Ala Glu Lys Arg Lys Pro Ile Arg Val Leu Ser Leu Phe Asp Gly Ile
            275                 280                 285

Ala Thr Gly Leu Leu Val Leu Lys Asp Leu Gly Ile Gln Val Asp Arg
            290                 295                 300

Tyr Ile Ala Ser Glu Val Cys Glu Asp Ser Ile Thr Val Gly Met Val
305                 310                 315                 320

Arg His Gln Gly Lys Ile Met Tyr Val Gly Asp Val Arg Ser Val Thr
                325                 330                 335

Gln Lys His Ile Gln Glu Trp Gly Pro Phe Asp Leu Val Ile Gly Gly
                340                 345                 350

Ser Pro Cys Asn Asp Leu Ser Ile Val Asn Pro Ala Arg Lys Gly Leu
            355                 360                 365

Tyr Glu Gly Thr Gly Ala Leu Phe Phe Glu Phe Tyr Arg Leu Leu His
    370                 375                 380

Asp Ala Arg Pro Lys Glu Gly Asp Asp Arg Pro Phe Phe Trp Leu Phe
385                 390                 395                 400

Glu Asn Val Val Ala Met Gly Val Ser Asp Lys Arg Asp Ile Ser Arg
                405                 410                 415

Phe Leu Glu Ser Asn Pro Val Met Ile Asp Ala Lys Glu Val Ser Ala
                420                 425                 430

Ala His Arg Ala Arg Tyr Phe Trp Gly Asn Leu Pro Gly Met Asn Arg
            435                 440                 445

Pro Leu Ala Ser Thr Val Asn Asp Lys Leu Glu Leu Gln Glu Cys Leu
    450                 455                 460

Glu His Gly Arg Ile Ala Lys Phe Ser Lys Val Arg Thr Ile Thr Thr
465                 470                 475                 480

Arg Ser Asn Ser Ile Lys Gln Gly Lys Asp Gln His Phe Pro Val Phe
                485                 490                 495
```

```
Met Asn Glu Lys Glu Asp Ile Leu Trp Cys Thr Glu Met Glu Arg Val
            500                 505                 510

Phe Gly Phe Pro Val His Tyr Thr Asp Val Ser Asn Met Ser Arg Leu
        515                 520                 525

Ala Arg Gln Arg Leu Leu Gly Arg Ser Trp Ser Val Pro Val Ile Arg
    530                 535                 540

His Leu Phe Ala Pro Leu Lys Glu Tyr Phe Ala Cys Val
545                 550                 555

<210> SEQ ID NO 89
<211> LENGTH: 1674
<212> TYPE: DNA
<213> ORGANISM: Artificial sequence
<220> FEATURE:
<223> OTHER INFORMATION: polynucleotide

<400> SEQUENCE: 89
atgcctaaga agaagagaaa ggttgatgtt gttatgactc aaactcctct ttctcttcct      60
gtttctcttg gagatcaagc ttctatttct tgtagatctt ctcaatctct tgttcattct     120
aatggaaata cttatcttag atggtatctt caaaagcctg acaatctccc taaggttctt     180
atttataagg tttctaatag attttctgga gttcctgata gattttctgg atctggatct     240
ggaactgatt ttactcttaa gatttctaga gttgaagctg aagatcttgg agtttatttt     300
tgttctcaat ctactcatgt tccttggact tttggaggag aactaagctc tgaaattaag     360
tcttctgctg atgatgctaa gaaggatgct gctaagaagg atgatgctaa gaaggatgat     420
gctaagaagg atggaggagt taagcttgat gaaactggag gaggacttgt tcaacctgga     480
agacctatga agctttcttg tgttgcttct ggatttactt tttctgatta ttggatgaat     540
tgggttagac aatctcctga aagggactt gaatgggttg ctcaaattag aaataagcct     600
tataattatg aaacttatta ttctgattct gttaagggaa gatttactat ttctagagat     660
gattctaagt cttctgttta tcttcaaatg aataatctta gagttgaaga tatgggaatt     720
tattattgta ctggatctta ttatggaatg gattattggg gacaaggaac ttctgttact     780
gtttctggat ctcttgaagg aggatctgga ggacctgctg aaaagagaaa gcctattaga     840
gttctttctc tttttgatgg aattgctact ggacttcttg ttcttaagga tcttggaatt     900
caagttgata gatatattgc ttctgaagtt tgtgaagatt ctattactgt tggaatggtt     960
agacatcaag gaaagattat gtatgttgga gatgttagat ctgttactca aaagcatatt    1020
caagaatggg gacctttga tcttgttatt ggaggatctc cttgtaatga tctttctatt    1080
gttaatcctg ctagaaaggg actttatgaa ggaactggag ctctttttttt tgaattttat    1140 agacttcttc atgatgctag acctaaggaa ggagatgata gacctttttt ttggctttttt    1200 gaaaatgttg ttgctatggg agtttctgat aagagagata tttctagatt tcttgaatct    1260
aatcctgtta tgattgatgc taaggaagtt tctgctgctc atagagctag atatttttgg    1320
ggaaatcttc ctggaatgaa tagacctctt gcttctactg ttaatgataa gcttgaactt    1380
caagaatgtc ttgaacatgg aagaattgct aagttttcta aggttagaac tattactact    1440
agatctaatt ctattaagca aggaaaggat caacattttc ctgtttttat gaatgaaaag    1500
gaagatattc tttggtgtac tgaaatggaa agagttttttg gatttcctgt tcattatact    1560
gatgtttcta atatgtctag acttgctaga caaagacttc ttggaagatc ttggtctgtt    1620
cctgttatta gacatctttt tgctcctctc ttaaggaatatt ttgcttgtgt ttaa         1674
```

<210> SEQ ID NO 90
<211> LENGTH: 1896
<212> TYPE: DNA
<213> ORGANISM: Artificial sequence
<220> FEATURE:
<223> OTHER INFORMATION: polynucleotide

<400> SEQUENCE: 90

```
accggtcaac atgtggagca cgacacactt gtctactcca aaaatatcaa agatacagtc      60
tcagaagacc aaagggcaat tgagactttt caacaaaggg taatatccgg aaacctcctc     120
ggattccatt gcccagctat ctgtcacttt attgtgaaga tagtggaaaa ggaaggtggc     180
tcctacaaat gccatcattg cgataaagga aaggccatcg ttgaagatgc ctctgccgac     240
agtggtccca agatggaccc cccacccacg aggagcatcg tggaaaaaga agacgttcca     300
accacgtctt caaagcaagt ggattgatgt gataacatgg tggagcacga cacacttgtc     360
tactccaaaa atatcaaaga tacagtctca gaagaccaaa gggcaattga acttttcaa     420
caaagggtaa tatccggaaa cctcctcgga ttccattgcc cagctatctg tcactttatt     480
gtgaagatag tggaaaagga aggtggctcc tacaaatgcc atcattgcga taaaggaaag     540
gccatcgttg aagatgcctc tgccgacagt ggtcccaaag atggaccccc acccacgagg     600
agcatcgtgg aaaaagaaga cgttccaacc acgtcttcaa agcaagtgga ttgatgtgat     660
atctccactg acgtaaggga tgacgcacaa tcccactatc cttcgcaaga cccttcctct     720
atataaggaa gttcatttca tttggagagg acgtcgagag ttctcaacac aacatataca     780
aaacaaacga atctcaagca atcaagcatt ctacttctat tgcagcaatt taaatcattt     840
ctttttaaagc aaaagcaatt ttctgaaaat tttcaccatt tacgaacgat agagatctcg     900
agctcaagct tcgaattctg cagtcgacgg taccgcgggc ccgggatcct gatggtgagc     960
aagggcgagg aggataacat ggccatcatc aaggagttca tgcccttcaa ggtgcacatg    1020
gagggctccg tgaacggcca cgagttcgag atcgagggcg agggcgaggg ccgcccctac    1080
gagggcaccc agaccgccaa gctgaaggtg accaagggtg gccccctgcc cttcgcctgg    1140
gacatcctgt cccctcagtt catgtacggc tccaaggcct acgtgaagca ccccgccgac    1200
atccccgact acttgaagct gtccttcccc gagggcttca gtgggagcg cgtgatgaac    1260
ttcgaggacg gcggcgtggt gaccgtgacc caggactcct ccctgcagga cggcgagttc    1320
atctacaagg tgaagctgcg cggcaccaac ttcccctccg acggccccgt aatgcagaag    1380
aagaccatgg gctgggaggc ctcctccgag cggatgtacc ccgaggacgg cgccctgaag    1440
ggcgagatca gcagaggct gaagctgaag gacggcggcc actacgacgc tgaggtcaag    1500
accacctaca aggccaagaa gcccgtgcag ctgccggcg cctacaacgt caacatcaag    1560
ttggacatca cctcccacaa cgaggactac accatcgtgg aacagtacga acgcgccgag    1620
ggccgccact ccaccggcgg catggacgag ctgtacaaga gatccacctg atctagagtc    1680
cgcaaaaatc accagtctct ctctacaaat ctatctctct ctattttct ccagaataat    1740
gtgtgagtag ttcccagata agggaattag ggttcttata gggttcgct catgtgttga    1800
gcatataaga aacccttagt atgtatttgt atttgtaaaa tacttctatc aataaaattt    1860
ctaattccta aaaccaaaat ccagtgacgc ggccgc                            1896
```

<210> SEQ ID NO 91
<211> LENGTH: 28
<212> TYPE: DNA
<213> ORGANISM: Artificial sequence
<220> FEATURE:

<223> OTHER INFORMATION: polynucleotide
<220> FEATURE:
<221> NAME/KEY: misc_feature
<222> LOCATION: (23)..(28)
<223> OTHER INFORMATION: n is a, c, g, or t

<400> SEQUENCE: 91
tcgagctcaa gcttcgaatt ctnnnnnn                                              28

<210> SEQ ID NO 92
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, or t

<400> SEQUENCE: 92
nnnnnngatg gtgagcaagg gcgaggag                                              28

<210> SEQ ID NO 93
<211> LENGTH: 17
<212> TYPE: PRT
<213> ORGANISM: Artificial sequence
<220> FEATURE:
<223> OTHER INFORMATION: peptide

<400> SEQUENCE: 93

Ser Gly Pro Arg Pro Arg Gly Thr Arg Gly Lys Gly Arg Arg Ile Arg
1               5                   10                  15

Arg

<210> SEQ ID NO 94
<211> LENGTH: 31
<212> TYPE: RNA
<213> ORGANISM: Artificial sequence
<220> FEATURE:
<223> OTHER INFORMATION: polynucleotide

<400> SEQUENCE: 94
uucagcucgu guagcucauu agcuccgagc u                                          31

<210> SEQ ID NO 95
<211> LENGTH: 31
<212> TYPE: DNA
<213> ORGANISM: Artificial sequence
<220> FEATURE:
<223> OTHER INFORMATION: polynucleotide

<400> SEQUENCE: 95
ttccatacag tcagtatcaa ttctggaaga a                                          31

<210> SEQ ID NO 96
<211> LENGTH: 22
<212> TYPE: DNA
<213> ORGANISM: Artificial sequence
<220> FEATURE:
<223> OTHER INFORMATION: polypeptide

<400> SEQUENCE: 96
atcaattctg gaagaatttc ca                                                    22

<210> SEQ ID NO 97

```
<210> SEQ ID NO 97
<211> LENGTH: 22
<212> TYPE: DNA
<213> ORGANISM: Artificial sequence
<220> FEATURE:
<223> OTHER INFORMATION: polynucleotide

<400> SEQUENCE: 97
tcattacacc tgcagctctc at                                              22

<210> SEQ ID NO 98
<211> LENGTH: 53
<212> TYPE: DNA
<213> ORGANISM: Artificial sequence
<220> FEATURE:
<223> OTHER INFORMATION: polynucleotide

<400> SEQUENCE: 98
uucagcucgu guagcucauu agcuccgagc uaucaauucu ggaagaauuu cca            53

<210> SEQ ID NO 99
<211> LENGTH: 53
<212> TYPE: DNA
<213> ORGANISM: Artificial sequence
<220> FEATURE:
<223> OTHER INFORMATION: polynucleotide

<400> SEQUENCE: 99
ucauuacacc ugcagcucuc auucagcuc guguagcuca uuagcuccga gcu             53

<210> SEQ ID NO 100
<211> LENGTH: 55
<212> TYPE: RNA
<213> ORGANISM: Artificial sequence
<220> FEATURE:
<223> OTHER INFORMATION: polynucleotide
<220> FEATURE:
<221> NAME/KEY: misc_feature
<222> LOCATION: (32)..(33)
<223> OTHER INFORMATION: n is a, c, g, or u

<400> SEQUENCE: 100
uucagcucgu guagcucauu agcuccgagc unnguaucaa uucuggaaga auuuc          55

<210> SEQ ID NO 101
<211> LENGTH: 56
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (24)..(25)
<223> OTHER INFORMATION: n is a, c, g, t or u

<400> SEQUENCE: 101
caaaaagaag gucuucauua cacnnuucag cucguguagc ucauuagcuc cgagcu         56

<210> SEQ ID NO 102
<211> LENGTH: 32
<212> TYPE: DNA
<213> ORGANISM: Artificial sequence
<220> FEATURE:
<223> OTHER INFORMATION: polynucleotide

<400> SEQUENCE: 102
tttccataca gtcagtatca attctggaag aa                                   32
```

```
<210> SEQ ID NO 103
<211> LENGTH: 31
<212> TYPE: DNA
<213> ORGANISM: Artificial sequence
<220> FEATURE:
<223> OTHER INFORMATION: polynucleotide

<400> SEQUENCE: 103
cagggtggaa caagatggat tatcaagtgt c                              31

<210> SEQ ID NO 104
<211> LENGTH: 53
<212> TYPE: DNA
<213> ORGANISM: Artificial sequence
<220> FEATURE:
<223> OTHER INFORMATION: polynucleotide

<400> SEQUENCE: 104
uucagcucgu guagcucauu agcuccgagc uaagtccaat ctatgacatc aat       53

<210> SEQ ID NO 105
<211> LENGTH: 53
<212> TYPE: DNA
<213> ORGANISM: Artificial sequence
<220> FEATURE:
<223> OTHER INFORMATION: polynucleotide

<400> SEQUENCE: 105
aagatcactt tttatttatg cauucagcuc guguagcuca uuagcuccga gcu       53

<210> SEQ ID NO 106
<211> LENGTH: 55
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (32)..(33)
<223> OTHER INFORMATION: n is a, c, g, t or u

<400> SEQUENCE: 106
uucagcucgu guagcucauu agcuccgagc unnucaaguc caaucuauga cauca     55

<210> SEQ ID NO 107
<211> LENGTH: 55
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 107
gaucacuuuu uauuuaugca cannuucagc ucguguagcu cauuagcucc gagcu     55

<210> SEQ ID NO 108
<211> LENGTH: 31
<212> TYPE: DNA
<213> ORGANISM: Artificial sequence
<220> FEATURE:
<223> OTHER INFORMATION: polynucleotide

<400> SEQUENCE: 108
atatctgtgg gcttgtgaca cggactcaag t                              31
```

<210> SEQ ID NO 109
<211> LENGTH: 53
<212> TYPE: DNA
<213> ORGANISM: Artificial sequence
<220> FEATURE:
<223> OTHER INFORMATION: polynucleotide

<400> SEQUENCE: 109
uucagcucgu guagcucauu agcuccgagc ugggctggtg acccagtcag agt        53

<210> SEQ ID NO 110
<211> LENGTH: 53
<212> TYPE: DNA
<213> ORGANISM: Artificial sequence
<220> FEATURE:
<223> OTHER INFORMATION: polynucleotide

<400> SEQUENCE: 110
ccgatccact ggggagcagg aauucagcuc guguagcuca uuagccccga gcu        53

<210> SEQ ID NO 111
<211> LENGTH: 55
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (32)..(33)
<223> OTHER INFORMATION: n is a, c, g, t or u

<400> SEQUENCE: 111
uucagcucgu guagcucauu agcuccgagc unnugggcug gugacccagu cagag        55

<210> SEQ ID NO 112
<211> LENGTH: 55
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 112
auccacuggg gagcaggaaa uannuucagc ucguguagcu cauuagcucc gagcu        55

<210> SEQ ID NO 113
<211> LENGTH: 7
<212> TYPE: PRT
<213> ORGANISM: Artificial sequence
<220> FEATURE:
<223> OTHER INFORMATION: peptide

<400> SEQUENCE: 113

Gly Ser Gly Gly Ser Gly Pro
1               5

<210> SEQ ID NO 114
<211> LENGTH: 223
<212> TYPE: PRT
<213> ORGANISM: Artificial sequence
<220> FEATURE:
<223> OTHER INFORMATION: polypeptide

<400> SEQUENCE: 114

Met Pro Lys Lys Lys Arg Lys Val Val Lys Ser Glu Leu Glu Glu Lys
1               5                   10                  15

Lys Ser Glu Leu Arg His Lys Leu Lys Tyr Val Pro His Glu Tyr Ile
            20                  25                  30

Glu Leu Ile Glu Ile Ala Arg Asn Ser Thr Gln Asp Arg Ile Leu Glu
        35                  40                  45

Met Lys Val Met Glu Phe Phe Met Lys Val Tyr Gly Tyr Arg Gly Lys
    50                  55                  60

His Leu Gly Gly Ser Arg Lys Pro Asp Gly Ala Ile Tyr Thr Val Gly
65                  70                  75                  80

Ser Pro Ile Asp Tyr Gly Val Ile Val Asp Thr Lys Ala Tyr Ser Gly
                85                  90                  95

Gly Tyr Asn Leu Pro Ile Gly Gln Ala Asp Glu Met Gln Arg Tyr Val
            100                 105                 110

Glu Glu Asn Gln Thr Arg Asn Lys His Ile Asn Pro Asn Glu Trp Trp
        115                 120                 125

Lys Val Tyr Pro Ser Ser Val Thr Glu Phe Lys Phe Leu Phe Val Ser
    130                 135                 140

Gly His Phe Lys Gly Asn Tyr Lys Ala Gln Leu Thr Arg Leu Asn His
145                 150                 155                 160

Ile Thr Asn Cys Asn Gly Ala Val Leu Ser Val Glu Glu Leu Leu Ile
                165                 170                 175

Gly Gly Glu Met Ile Lys Ala Gly Thr Leu Thr Leu Glu Glu Val Arg
            180                 185                 190

Arg Lys Phe Asn Asn Gly Glu Ile Asn Phe Gly Ser Gly Ser Gly
        195                 200                 205

Pro Arg Pro Arg Gly Thr Arg Gly Lys Gly Arg Arg Ile Arg Arg
    210                 215                 220

<210> SEQ ID NO 115
<211> LENGTH: 672
<212> TYPE: DNA
<213> ORGANISM: Artificial sequence
<220> FEATURE:
<223> OTHER INFORMATION: polypeptide

<400> SEQUENCE: 115
atgcccaaga agaagagaaa ggtggtgaag agcgagctgg aggagaagaa gagcgagctg      60
agacacaagc tgaagtacgt gccccacgag tacatcgagc tgatcgagat cgccagaaac     120
agcacccagg acagaatcct ggagatgaag gtgatggagt tcttcatgaa ggtgtacggc     180
tacagaggca agcacctggg cggcagcaga aagcccgacg gcgccatcta caccgtgggc     240
agccccatcg actacggcgt gatcgtggac accaaggcct acagcggcgg ctacaacctg     300
cccatcggcc aggccgacga gatgcagaga tacgtggagg agaaccagac cagaaacaag     360
cacatcaacc ccaacgagtg gtggaaggtg taccccagca gcgtgaccga gttcaagttc     420
ctgttcgtga gcggccactt caagggcaac tacaaggccc agctgaccag actgaaccac     480
atcaccaact gcaacggcgc cgtgctgagc gtggaggagc tgctgatcgg cggcgagatg     540
atcaaggccg gcaccctgac cctggaggag gtgagaagaa agttcaacaa cggcgagatc     600
aacttcggca gcggcggcag cggcccccaga cccagaggca ccagaggcaa gggcagaaga     660
atcagaagat aa                                                         672

<210> SEQ ID NO 116
<211> LENGTH: 7

```
<212> TYPE: PRT
<213> ORGANISM: Artificial sequence
<220> FEATURE:
<223> OTHER INFORMATION: peptide

<400> SEQUENCE: 116

Gly Gly Ser Gly Gly Gly Pro
1               5

<210> SEQ ID NO 117
<211> LENGTH: 31
<212> TYPE: DNA
<213> ORGANISM: Artificial sequence
<220> FEATURE:
<223> OTHER INFORMATION: polynucleotide

<400> SEQUENCE: 117
uucagcucgu guagcucauu agcuccgagc u                              31

<210> SEQ ID NO 118
<211> LENGTH: 31
<212> TYPE: DNA
<213> ORGANISM: Artificial sequence
<220> FEATURE:
<223> OTHER INFORMATION: polynucleotide

<400> SEQUENCE: 118
gcaaaacaat tatttggtta tgccattttg g                              31

<210> SEQ ID NO 119
<211> LENGTH: 53
<212> TYPE: DNA
<213> ORGANISM: Artificial sequence
<220> FEATURE:
<223> OTHER INFORMATION: polynucleotide

<400> SEQUENCE: 119
uucagcucgu guagcucauu agcuccgagc ucaaugaugg auuucgcgcc acg       53

<210> SEQ ID NO 120
<211> LENGTH: 53
<212> TYPE: DNA
<213> ORGANISM: Artificial sequence
<220> FEATURE:
<223> OTHER INFORMATION: polynucleotide

<400> SEQUENCE: 120
uuagcuucgg uuagagcaaa gcuucagcuc guguagcuca uuagcuccga gcu       53

<210> SEQ ID NO 121
<211> LENGTH: 53
<212> TYPE: DNA
<213> ORGANISM: Artificial sequence
<220> FEATURE:
<223> OTHER INFORMATION: polynucleotide

<400> SEQUENCE: 121
uucagcucgu guagcucauu agcuccgagc ugccaaugau ggauuucgcg cca       53

<210> SEQ ID NO 122
<211> LENGTH: 53
<212> TYPE: DNA
<213> ORGANISM: Artificial sequence
<220> FEATURE:
<223> OTHER INFORMATION: polynucleotide

<400> SEQUENCE: 122
```
agcuucgguu agagcaaagc ccuucagcuc guguagcuca uuagcuccga gcu    53

<210> SEQ ID NO 123
<211> LENGTH: 22
<212> TYPE: DNA
<213> ORGANISM: Artificial sequence
<220> FEATURE:
<223> OTHER INFORMATION: polynucleotide

<400> SEQUENCE: 123
atgttagaag gtgcaaaatc aa    22

<210> SEQ ID NO 124
<211> LENGTH: 22
<212> TYPE: DNA
<213> ORGANISM: Artificial sequence
<220> FEATURE:
<223> OTHER INFORMATION: polynucleotide

<400> SEQUENCE: 124
ctaacggact tggaatacga at    22

<210> SEQ ID NO 125
<211> LENGTH: 2833
<212> TYPE: DNA
<213> ORGANISM: Artificial sequence
<220> FEATURE:
<223> OTHER INFORMATION: polynucleotide

<400> SEQUENCE: 125
tgctgtacca tacagtcttt ccgcttaaag aattatattc tctctagcta cttcacagtg    60
tcctttcctt tcgcgtactc ctctgtcttt ttcctatctt ctctcttcta ttaccgagac   120
ccgtacatac aaagatctag gtagctcatc tccttctaag aagtcagatc tccttcctat   180
attctataaa gaataagagc ccttcttaac ttcactcttt aattgtaaag agaggcctca   240
tttaggagcg ctgttttcat ccaactatca atctcgtaag agaataaagc gtggaaagaa   300
aaggttttga ttcgctttat aaagaagaaa gctttttccg gttctaacag gctaattaaa   360
ttagaaacgc gtctgttcac gtcaggtccg aagggatgtg gttgcttttc cttttttgcg   420
tcgagattgg gttggtgttc agtgtaccgc ttgtctagcc tatgctttgc atgaacatct   480
caatgtccaa gataaaaaga acgaggggaa gaatcgacga ggccagtgtt ctcgaagaga   540
aaatcgtgat ggaaaaagcg tgaggagaat tcgaaagtcg atatgttaga aggtgcaaaa   600
tcaatgggtg caggagctgc tacaatcgct tcagcgggag ctgctatcgg tattggaaac   660
gtccttagtt cctcgattca ttccgtgtta ggtatacaaa taacagactt acatcacgat   720
gtcttttttct tcgttattct gatttttggtt ttcgtatcat ggatcttggg tcgcgcttta   780
tggcatttcc actataaaaa aaatccaatc ccgcaaagga ttgttcatgg aactactatc   840
gagattcttc ggaccttatt tcttagtatc atccctatgt tcattgctat accatcattt   900
gccctgtatg ggtattcgga ctataacagt tccgatgaac agtcactcac ttttgacagt   960
tatacgattc cagaagatca tccagaattg ggtcaatcac gtttattaga agtcgacaat  1020
agagtggttg taccagcaaa cagttctctc cgttttattg taacatctgc ggctgtacct  1080
tccttaggtg tcaaaggtga tgctgtgcct tccttaggtg tcaaaggtga tgctgtgcct  1140
tccttaggtg tcaaaggtga tgctgtgcct gggcctgggc gggttttttca gacttggacc  1200
cgagcttttg agcgtttggg cctgttgacg gttgcccatt gcgccggcac cggaacatca  1260

```
agctcgggct cggtagtcag tcttccacag gacgaaatat gggccgccct tgagggcgat    1320
ccccaggccc ttccggaaga cggccaattt cacgccgtcg ccctgaggg gaatccccag    1380 gcccttccgg aagacgggca atttcacgcc gtcccccctg aggggaatcc ccaggccctt    1440
ccggaagacg ggcaatttca ggccgtcgcc cctgagggga tccccaggcc cttccggaa    1500 gacgggcaat tcacgccat cgcctttgac cctcttatag caacacggca agacgcgtgg    1560
aatacgctac ttgtcttgtt gcggcgcagc accaaaattg gcctaaggcc aattttgtta    1620
ctaaagcagg ggaagatctt ggtatagagg aggtcgactt taaaagcgaa cgaaaaacaa    1680
ttgcaaaagc agattgattt ttggcaacgt gaatttaggt tttggaagta aaataagttt    1740
tatttgataa aaattgctaa ttcagtataa ttaatattta cgaggtgaca taacgtatga    1800
aaaaatcaga ggattattcc tcctaaatat aaaaatttaa aatttaggag gaagttatat    1860 atgacttta atattattga attagaaaat tgggatagaa agaatatt tgaacactat    1920 tttaatcagc aaactactta tagcattact aaagaaattg atattacttt gtttaaagat    1980
atgataaaaa agaaaggata tgaaatttat ccctctttaa tttatgcaat tatggaagtt    2040
gtaaataaaa ataaagtgtt tagaacagga attaatagtg agaataaatt aggttattgg    2100
gataagttaa atcctttgta tacagttttt aataagcaaa ctgaaaaatt tactaacatt    2160
tggactgaat ctgataaaaa cttcattct ttttataata attataaaaa tgacttgctt    2220
gaatataaag ataagaaga aatgtttcct aaaaaaccga tacctgaaaa caccataccg    2280
atttcaatga ttccttggat tgattttagt tcatttaatt taaatattgg taacaatagc    2340
agctttttat tgcctattat tacgataggt aaattttata gtgagaataa taaaatttat    2400
ataccagttg ctctgcaact tcatcattct gtatgtgatg gttaccatgc ttcactattt    2460
atgaatgaat ttcaagatat aattcatagg gtagatgatt ggatttagtt tttagatttt    2520
gaaagtgaat ttaattttat acacgtaagt gatcaggagg gaagctaatg catcgtttgc    2580
cccaatgatg gcctttttga tctcattcgt attccaagtc cgttagtcat cgtttacggt    2640
gggtgggtaa gcaggagggg atccctgtgg ttagattaga gtaactggcc gagaaggtta    2700
gcgaggttcc agctatggtg aagtgaaaga tctttcactt cactatagtg ggaaagaaga    2760
caggtgggag cgagcggagc gagagcaaag caagctctag tggtgggttg tcttcgcggt    2820
cccatttcat cga                                                      2833
```

<210> SEQ ID NO 126
<211> LENGTH: 31
<212> TYPE: DNA
<213> ORGANISM: Artificial sequence
<220> FEATURE:
<223> OTHER INFORMATION: polynucleotide

<400> SEQUENCE: 126

```
agacttacat cacgatgtct ttttcttcgt t                                   31
```

<210> SEQ ID NO 127
<211> LENGTH: 53
<212> TYPE: DNA
<213> ORGANISM: Artificial sequence
<220> FEATURE:
<223> OTHER INFORMATION: polynucleotide

<400> SEQUENCE: 127

```
uucagcucgu guagcucauu agcuccgagc uguuauugu auaccuaaca cgg            53
```

```
<210> SEQ ID NO 128
<211> LENGTH: 53
<212> TYPE: DNA
<213> ORGANISM: Artificial sequence
<220> FEATURE:
<223> OTHER INFORMATION: polynucleotide

<400> SEQUENCE: 128
auacgaaaac caaaaucaga auuucagcuc guguagcuca uuagcuccga gcu          53

<210> SEQ ID NO 129
<211> LENGTH: 53
<212> TYPE: DNA
<213> ORGANISM: Artificial sequence
<220> FEATURE:
<223> OTHER INFORMATION: polynucleotide

<400> SEQUENCE: 129
uucagcucgu uagcucauu agcuccgagc ucuguuauuu guauaccuaa cac          53

<210> SEQ ID NO 130
<211> LENGTH: 53
<212> TYPE: DNA
<213> ORGANISM: Artificial sequence
<220> FEATURE:
<223> OTHER INFORMATION: polynucleotide

<400> SEQUENCE: 130
acgaaaacca aaaucagaau aauucagcuc guguagcuca uuagcuccga gcu          53

<210> SEQ ID NO 131
<211> LENGTH: 2852
<212> TYPE: DNA
<213> ORGANISM: Artificial sequence
<220> FEATURE:
<223> OTHER INFORMATION: polynucleotide

<400> SEQUENCE: 131
tgctgtacca tacagtcttt ccgcttaaag aattatattc tctctagcta cttcacagtg     60
tcctttcctt tcgcgtactc ctctgtcttt ttcctatctt ctctcttcta ttaccgagac    120
ccgtacatac aaagatctag gtagctcatc tccttctaag aagtcagatc tccttcctat    180
attctataaa gaataagagc ccttcttaac ttcactcttt aattgtaaag agaggcctca    240
tttaggagcg ctgttttcat ccaactatca atctcgtaag agaataaagc gtggaaaaga    300
aaggttttga ttcgctttat aaagaagaaa gcttttccg gttctaacag gctaattaaa    360
ttagaaacgc gtctgttcac gtcaggtccg aagggatgtg gttgctttc cttttttgcg    420 tcgagattgg gttggtgttc agtgtaccgc ttgtctagcc tatgctttgc atgaacatct    480
caatgtccaa gataaaaga acgagggaa gaatcgacga ggccagtgtt ctcgaagaga    540
aaatcgtgat ggaaaaagcg tgaggagaat tcgaaagtcg atatgttaga aggtgcaaaa    600
tcaatgggtg caggagctgc tacaaatgct tcagcgggag ctgctatcgg tattggaaac    660
gtccttagtt cctcgattca ttccgtggcg cgaaatccat cattggcaaa acaattattt    720
ggttatgcca ttttgggctt tgctctaacc gaagctaatg catcgtttgc cccaatgatg    780 gccttttga tctcattcgt attccaagtc cgttagagga ggtcgacttt aaaagcgaac    840 gaaaacaat tgcaaaagca gattgatttt tggcaacgtg aatttaggtt ttggaagtaa    900
aataagtttt atttgataaa aattgctaat tcagtataat taatatttac gaggtgacat    960
aacgtatgaa aaaatcagag gattattcct cctaaatata aaaatttaaa atttaggagg   1020
```

| | |
|---|---|
| aagttatata tgactttaa tattattgaa ttagaaaatt gggatagaaa agaatatttt | 1080 |
| gaacactatt ttaatcagca aactacttat agcattacta aagaaattga tattactttg | 1140 |
| tttaaagata tgataaaaaa gaaaggatat gaaatttatc cctctttaat ttatgcaatt | 1200 |
| atggaagttg taaataaaaa taaagtgttt agaacaggaa ttaatagtga gaataaatta | 1260 |
| ggttattggg ataagttaaa tcctttgtat acagttttta ataagcaaac tgaaaatttt | 1320 |
| actaacattt ggactgaatc tgataaaaac ttcatttctt tttataataa ttataaaaat | 1380 |
| gacttgcttg aatataaaga taagaagaa atgtttccta aaaaaccgat acctgaaaac | 1440 |
| accataccga tttcaatgat tccttggatt gattttagtt catttaattt aaatattggt | 1500 |
| aacaatagca gcttttttatt gcctattatt acgataggta aattttatag tgagaataat | 1560 |
| aaaatttata taccagttgc tctgcaactt catcattctg tatgtgatgg ttaccatgct | 1620 |
| tcactattta tgaatgaatt tcaagatata attcataggg tagatgattg gatttagttt | 1680 |
| ttagattttg aaagtgaatt taattttata cacgtaagtg atcaggagga aaaaatccaa | 1740 |
| tcccgcaaag gattgttcat ggaactacta tcgagattct tcggaccta tttcttagta | 1800 |
| tcatccctat gttcattgct ataccatcat ttgccctgta tgggtattcg gactataaca | 1860 |
| gttccgatga acagtcactc acttttgaca gttatacgat tccagaagat catccagaat | 1920 |
| tgggtcaatc acgttatta gaagtcgaca atagagtggt tgtaccagca aacagttctc | 1980 |
| tccgtttat tgtaacatct gcggctgtac cttcctagg tgtcaaaggt gatgctgtgc | 2040 |
| cttcctagg tgtcaaaggt gatgctgtgc cttcctagg tgtcaaaggt gatgctgtgc | 2100 |
| ctgggcctgg gcgggttttt cagacttgga cccgagcttt tgagcgtttg ggcctgttga | 2160 |
| cggttgccca ttgcgccggc accggaacat caagctcggg ctcggtagtc agtcttccac | 2220 |
| aggacgaaat atgggccgcc cttgagggcg atccccaggc ccttccggaa gacggccaat | 2280 |
| ttcacgccgt cgcccctgag gggaatcccc aggcccttcc ggaagacggg caatttcacg | 2340 |
| ccgtccccc tgagggggaat ccccaggccc ttccggaaga cgggcaattt caggccgtcg | 2400 |
| cccctgaggg gaatccccag gcccttccgg aagacgggca atttcacgcc atcgcctttg | 2460 |
| accctcttat agcaacacgg caagacgcgt ggaatacgct acttgtcttg ttgcggcgca | 2520 |
| gcaccaaaat tggcctaagg ccaatttgt tactaaagca ggggaagatc ttggtatagg | 2580 |
| aagctaatgc atcgtttgcc ccaatgatgg cctttttgat ctcattcgta ttccaagtcc | 2640 |
| gttagtcatc gtttacggtg ggtgggtaag caggagggga tccctgtggt tagattagag | 2700 |
| taactggccg agaaggttag cgaggttcca gctatggtga agtgaaagat ctttcacttc | 2760 |
| actatagtgg gaaagaagac aggtgggagc gagcggagcg agagcaaagc aagctctagt | 2820 |
| ggtgggttgt cttcgcggtc ccatttcatc ga | 2852 |

<210> SEQ ID NO 132
<211> LENGTH: 399
<212> TYPE: PRT
<213> ORGANISM: Artificial sequence
<220> FEATURE:
<223> OTHER INFORMATION: polypeptide

<400> SEQUENCE: 132

Met Asp Lys Ala Glu Leu Ile Pro Glu Pro Pro Lys Lys Lys Arg Lys
1               5                   10                  15

Val Glu Leu Gly Thr Ala Ala Asn Phe Asn Gln Ser Gly Asn Ile Ala
            20                  25                  30

Asp Ser Ser Leu Ser Phe Thr Phe Thr Asn Ser Ser Asn Gly Pro Asn

```
                35                  40                  45
Leu Ile Thr Thr Gln Thr Asn Ser Gln Ala Leu Ser Gln Pro Ile Ala
 50                  55                  60

Ser Ser Asn Val His Asp Asn Phe Met Asn Asn Glu Ile Thr Ala Ser
 65                  70                  75                  80

Lys Ile Asp Asp Gly Asn Asn Ser Lys Pro Leu Ser Pro Gly Trp Thr
                 85                  90                  95

Asp Gln Thr Ala Tyr Asn Ala Phe Gly Ile Thr Thr Gly Met Phe Asn
                100                 105                 110

Thr Thr Thr Met Asp Asp Val Tyr Asn Tyr Leu Phe Asp Asp Glu Asp
                115                 120                 125

Thr Pro Pro Asn Pro Lys Lys Glu Gly Ser Leu Glu Gly Gly Ser Gly
130                 135                 140

Gly Asp Val Val Met Thr Gln Thr Pro Leu Ser Leu Pro Val Ser Leu
145                 150                 155                 160

Gly Asp Gln Ala Ser Ile Ser Cys Arg Ser Ser Gln Ser Leu Val His
                165                 170                 175

Ser Asn Gly Asn Thr Tyr Leu Arg Trp Tyr Leu Gln Lys Pro Gly Gln
                180                 185                 190

Ser Pro Lys Val Leu Ile Tyr Lys Val Ser Asn Arg Phe Ser Gly Val
                195                 200                 205

Pro Asp Arg Phe Ser Gly Ser Gly Ser Gly Thr Asp Phe Thr Leu Lys
                210                 215                 220

Ile Ser Arg Val Glu Ala Glu Asp Leu Gly Val Tyr Phe Cys Ser Gln
225                 230                 235                 240

Ser Thr His Val Pro Trp Thr Phe Gly Gly Gly Thr Lys Leu Glu Ile
                245                 250                 255

Lys Ser Ser Ala Asp Asp Ala Lys Lys Asp Ala Ala Lys Lys Asp Asp
                260                 265                 270

Ala Lys Lys Asp Asp Ala Lys Lys Asp Gly Gly Val Lys Leu Asp Glu
                275                 280                 285

Thr Gly Gly Gly Leu Val Gln Pro Gly Arg Pro Met Lys Leu Ser Cys
                290                 295                 300

Val Ala Ser Gly Phe Thr Phe Ser Asp Tyr Trp Met Asn Trp Val Arg
305                 310                 315                 320

Gln Ser Pro Glu Lys Gly Leu Glu Trp Val Ala Gln Ile Arg Asn Lys
                325                 330                 335

Pro Tyr Asn Tyr Glu Thr Tyr Tyr Ser Asp Ser Val Lys Gly Arg Phe
                340                 345                 350

Thr Ile Ser Arg Asp Asp Ser Lys Ser Ser Val Tyr Leu Gln Met Asn
                355                 360                 365

Asn Leu Arg Val Glu Asp Met Gly Ile Tyr Tyr Cys Thr Gly Ser Tyr
                370                 375                 380

Tyr Gly Met Asp Tyr Trp Gly Gln Gly Thr Ser Val Thr Val Ser
385                 390                 395
```

<210> SEQ ID NO 133
<211> LENGTH: 21
<212> TYPE: DNA
<213> ORGANISM: Artificial sequence
<220> FEATURE:
<223> OTHER INFORMATION: polynucleotide

<400> SEQUENCE: 133
gggcatctgg accctcctac c        21

<210> SEQ ID NO 134
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, t or u

<400> SEQUENCE: 134
aggattgctc aacaaccatg ctnnnnnn                                    28

<210> SEQ ID NO 135
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 135
nnnnnntctg gtgagccctc tcctgccc                                    28

<210> SEQ ID NO 136
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 136
ggaggattgc tcaacaacca tgnn                                        24

<210> SEQ ID NO 137
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, t or u

<400> SEQUENCE: 137
nnctggtgag ccctctcctg cccg                                        24

<210> SEQ ID NO 138
<211> LENGTH: 21
<212> TYPE: DNA
<213> ORGANISM: Artificial sequence
<220> FEATURE:
<223> OTHER INFORMATION: polynucleotide

<400> SEQUENCE: 138
tacgtctgtt gctagattat c                                           21

<210> SEQ ID NO 139

```
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, t or u

<400> SEQUENCE: 139
atgcttttat tttacaggtt ctnnnnnn                                        28

<210> SEQ ID NO 140
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 140
nnnnnngtcc aaaagtgtta atgcccaa                                        28

<210> SEQ ID NO 141
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 141
tcatgctttt attttacagg ttnn                                            24

<210> SEQ ID NO 142
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, t or u

<400> SEQUENCE: 142
nntccaaaag tgttaatgcc caag                                            24

<210> SEQ ID NO 143
<211> LENGTH: 21
<212> TYPE: DNA
<213> ORGANISM: Artificial sequence
<220> FEATURE:
<223> OTHER INFORMATION: polynucleotide

<400> SEQUENCE: 143
cagttgagac tcagaacttg g                                               21

<210> SEQ ID NO 144
<211> LENGTH: 29
<212> TYPE: DNA
<213> ORGANISM: Artificial sequence
```

```
<220> FEATURE:
<223> OTHER INFORMATION: polynucleotide
<220> FEATURE:
<221> NAME/KEY: misc_feature
<222> LOCATION: (24)..(29)
<223> OTHER INFORMATION: n is a, c, g, t or u

<400> SEQUENCE: 144
ggaattgagg aagactgtta ctannnnnn                                           29

<210> SEQ ID NO 145
<211> LENGTH: 34
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 145
nnnnnnaagg cctgcatcat gatggccaat tctc                                     34

<210> SEQ ID NO 146
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 146
ggaattgagg aagactgtta ctnn                                                24

<210> SEQ ID NO 147
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, t or u

<400> SEQUENCE: 147
nnggcctgca tcatgatggc caat                                                24

<210> SEQ ID NO 148
<211> LENGTH: 18
<212> TYPE: DNA
<213> ORGANISM: Artificial sequence
<220> FEATURE:
<223> OTHER INFORMATION: polynucleotide

<400> SEQUENCE: 148
catgctttta ttttacag                                                       18

<210> SEQ ID NO 149
<211> LENGTH: 20
<212> TYPE: DNA
<213> ORGANISM: Artificial sequence
<220> FEATURE:
<223> OTHER INFORMATION: polynucleotide
```

```
<400> SEQUENCE: 149
ctgtgacttt cactgtaatc                                              20

<210> SEQ ID NO 150
<211> LENGTH: 21
<212> TYPE: DNA
<213> ORGANISM: Artificial sequence
<220> FEATURE:
<223> OTHER INFORMATION: polynucleotide

<400> SEQUENCE: 150
caattgtgaa ttcacataga a                                            21

<210> SEQ ID NO 151
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, t or u

<400> SEQUENCE: 151
ggtgtcatat tatacaatat ttnnnnnn                                     28

<210> SEQ ID NO 152
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 152
nnnnnnaaca ttaaattata atgtttga                                     28

<210> SEQ ID NO 153
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 153
ttggtgtcat attatacaat atnn                                         24

<210> SEQ ID NO 154
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, t or u

<400> SEQUENCE: 154
nnacattaaa ttataatgtt tgac                                         24
```

<210> SEQ ID NO 155
<211> LENGTH: 22
<212> TYPE: DNA
<213> ORGANISM: Artificial sequence
<220> FEATURE:
<223> OTHER INFORMATION: polynucleotide

<400> SEQUENCE: 155
ctttgtttat aactctgaga ag                                              22

<210> SEQ ID NO 156
<211> LENGTH: 22
<212> TYPE: DNA
<213> ORGANISM: Artificial sequence
<220> FEATURE:
<223> OTHER INFORMATION: polynucleotide

<400> SEQUENCE: 156
tcaaaatgct tttgatgcct ga                                              22

<210> SEQ ID NO 157
<211> LENGTH: 1200
<212> TYPE: DNA
<213> ORGANISM: Artificial sequence
<220> FEATURE:
<223> OTHER INFORMATION: polynucleotide

<400> SEQUENCE: 157
atggacaagg cagagttgat ccctgaacca cctaagaaaa agagaaaggt ggagctcgga     60
acagcagcta acttcaacca gtctggaaac attgcagact cttctttgtc ttttactttc    120
acaaattctt ctaatggacc aaacttgatt acaacacaga caaactcaca ggctttgtct    180
cagccaatcg cttcttctaa tgtgcacgac aacttcatga caacgagat tacagcttca     240
aagatcgatg acgtaacaa ttctaagcct ctttctcctg atggactga ccagactgca      300
tacaacgcat tcggaatcac aacaggtatg ttcaacacaa ctactatgga tgatgtgtac    360
aattaccttt tgatgacga ggacacacca ccaaacccaa agaaagaggg atcacttgag     420
ggtggatccg gaggagacgt ggtgatgaca cagacaccat tgtctttgcc tgtgtcccta    480
ggagaccagg catcaatctc atgcaggtca tctcagtctc ttgtgcactc taatggtaac    540
acttatttga ggtggtactt gcagaagcca ggtcagtctc caaaggtgct tatctataag    600
gtttctaaca gattctcagg agtgccagat aggttctcag gatcaggatc tggaacagac    660
tttacattga gatttcaag ggttgaggca gaggaccttg gagtgtactt ctgctctcag     720
tcaacacacg ttccatggac tttcggtgga ggaacaaaac ttgagattaa atctagcgct    780
gacgacgcta agaaggacgc tgctaagaag gatgacgcta aaaaggacga cgcaaagaag    840
gacggtggtg tgaagcttga cgagactgga ggtggtttgg tgcagcctgg aaggcctatg    900
aaactttcat gcgtggcttc tggattcaca ttctctgact actggatgaa ctgggttagg    960
cagtcacctg agaagggttt ggaatgggtg gctcagatca ggaacaagcc ttacaactat   1020
gagacttact actctgattc tgtgaaagga aggttcacta tctcaaggga cgattcaaag   1080
tcttctgttt accttcagat gaataactta cgcgtagaag acatgggtat ctattactgt   1140
actggatctt actacggtat ggactattgg ggacaggta catcagtgac agtgtcatga   1200

<210> SEQ ID NO 158
<211> LENGTH: 20
<212> TYPE: DNA

```
<213> ORGANISM: Artificial sequence
<220> FEATURE:
<223> OTHER INFORMATION: polynucleotide

<400> SEQUENCE: 158
tagggcgctg gcaagtgtag                                                  20

<210> SEQ ID NO 159
<211> LENGTH: 20
<212> TYPE: DNA
<213> ORGANISM: Artificial sequence
<220> FEATURE:
<223> OTHER INFORMATION: polynucleotide

<400> SEQUENCE: 159
cataacaccc cttgtattac                                                  20

<210> SEQ ID NO 160
<211> LENGTH: 1120
<212> TYPE: DNA
<213> ORGANISM: Artificial sequence
<220> FEATURE:
<223> OTHER INFORMATION: polynucleotide

<400> SEQUENCE: 160
caggtggcac ttttcgggga aatgtgcgcg gaacccctat ttgtttattt ttctaaatac      60
attcaaatat gtatccgctc atgagacaat aaccctgata aatgcttcaa taatattgaa     120
aaaggaagag tatgagtatt caacatttcc gtgtcgccct tattcccttt tttgcggcat     180
tttgccttcc tgttttttgct cacccagaaa cgctggtgaa agtaaaagat gctgaagatc    240
agttgggtgc acgagtgggt tacatcgaac tggatctcaa cagcggtaag atccttgaga    300
gttttcgccc cgaagaacgt tttccaatga tgagcacttt taaagttctg ctatgtggcg    360
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgcttttttt gcacaacatg ggggatcatg    600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac    1020
tttagattga tttaaaactt cattttttaat ttaaaaggat ctaggtgaag atcctttttg    1080
ataatctcat gaacaataaa actgtctgct tacataaaca                           1120

<210> SEQ ID NO 161
<211> LENGTH: 21
<212> TYPE: DNA
<213> ORGANISM: Artificial sequence
<220> FEATURE:
<223> OTHER INFORMATION: polynucleotide

<400> SEQUENCE: 161
tatgagtatt caacatttcc g                                                21
```

<210> SEQ ID NO 162
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, t or u

<400> SEQUENCE: 162 ataatattg aaaaaggaag agnnnnnn                                          28

<210> SEQ ID NO 163
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 163
nnnnnntgtc gcccttattc ccttttt                                          28

<210> SEQ ID NO 164
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 164
nnnnnnctct tccttttca atattatt                                          28

<210> SEQ ID NO 165
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, t or u

<400> SEQUENCE: 165
aaaaaaggga ataagggcga cannnnnn                                         28

<210> SEQ ID NO 166
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 166
caataatatt gaaaaaggaa gann                                              24

<210> SEQ ID NO 167
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, t or u

<400> SEQUENCE: 167 nntcgcccctt attcccttttt ttgc                                            24

<210> SEQ ID NO 168
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, t or u

<400> SEQUENCE: 168
nntcttcctt tttcaatatt attg                                              24

<210> SEQ ID NO 169
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 169
gcaaaaaagg gaataagggc gann                                              24

<210> SEQ ID NO 170
<211> LENGTH: 21
<212> TYPE: DNA
<213> ORGANISM: Artificial sequence
<220> FEATURE:
<223> OTHER INFORMATION: polynucleotide

<400> SEQUENCE: 170
agcattggta actgtcagac c                                                 21

<210> SEQ ID NO 171
<211> LENGTH: 28
<212> TYPE: DNA
<213> ORGANISM: Artificial sequence
<220> FEATURE:
<223> OTHER INFORMATION: polynucloeitde
<220> FEATURE:
<221> NAME/KEY: misc_feature
<222> LOCATION: (23)..(28)
<223> OTHER INFORMATION: n is a, c, g, t or u

<400> SEQUENCE: 171
gagataggtg cctcactgat tannnnnn                                          28

-continued

```
<210> SEQ ID NO 172
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 172
nnnnnnaagt ttactcatat atacttta                                        28

<210> SEQ ID NO 173
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 173
nnnnnntaat cagtgaggca cctatctc                                        28

<210> SEQ ID NO 174
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, t or u

<400> SEQUENCE: 174
taaagtatat atgagtaaac ttnnnnnn                                        28

<210> SEQ ID NO 175
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 175
tgagataggt gcctcactga ttnn                                            24

<210> SEQ ID NO 176
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
<223> OTHER INFORMATION: n is a, c, g, t or u

<400> SEQUENCE: 176
nngtttactc atatatactt taga                                            24
```

<210> SEQ ID NO 177
<211> LENGTH: 24
<212> TYPE: DNA
<213> ORGANISM: Artificial sequence
<220> FEATURE:
<223> OTHER INFORMATION: polynucloeitde
<220> FEATURE:
<221> NAME/KEY: misc_feature
<222> LOCATION: (1)..(2)
<223> OTHER INFORMATION: n is a, c, g, t or u

<400> SEQUENCE: 177
nnaatcagtg aggcacctat ctca                                            24

<210> SEQ ID NO 178
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 178
tctaaagtat atatgagtaa acnn                                            24

<210> SEQ ID NO 179
<211> LENGTH: 1902
<212> TYPE: DNA
<213> ORGANISM: Artificial sequence
<220> FEATURE:
<223> OTHER INFORMATION: polynucleotide

<400> SEQUENCE: 179
gagtattcta tagtgtcacc taaatagctt ggcgtaatca tggtcatagc tgtttcctgt      60
gtgaaattgt tatccgctca caattccaca caacatacga gccggaagca taaagtgtaa     120
agcctggggt gcctaatgag tgagctaact cacattaatt gcgttgcgct cactgcccgc     180
tttccagtcg ggaaacctgt cgtgccagct gcattaatga atcggccaac gcgcggggag     240
aggcggtttg cgtattgggc gctcttccgc ttcctcgctc actgactcgc tgcgctcggt     300
cgttcggctg cggcgagcgg tatcagctca ctcaaaggcg gtaatacggt tatccacaga     360
atcaggggat aacgcaggaa agaacatgaa ttaattctca tgtttgacag cttatcatcg     420
attagcttta atgcggtagt ttatcacagt taaattgcta acgcagtcag gcaccgtgta     480
tgaaatctaa caatgcgctc atcgtcatcc tcggcaccgt caccctggat gctgtaggca     540
taggcttggt tatgccggta ctgccgggcc tcttgcggga tatcgtccat tccgacagca     600
tcgccagtca ctatggcgtg ctgctagcgc tatatgcgtt gatgcaattt ctatgcgcac     660
ccgttctcgg agcactgtcc gaccgctttg gccgccgccc agtcctgctc gcttcgctac     720
ttggagccac tatcgactac gcgatcatgg cgaccacacc cgtcctgtgg attctctacg     780
ccggacgcat cgtggccggc atcaccggcg ccacaggtgc ggttgctggc gcctatatcg     840
ccgacatcac cgatgggaa gatcgggctc gccacttcgg gctcatgagc gcttgtttcg     900
gcgtgggtat ggtggcaggc cccgtggccg gggactgtt gggcgccatc tccttacatg     960
caccattcct tgcggcggcg gtgctcaacg gcctcaacct actactgggc tgcttcctaa    1020
tgcaggagtc gcataaggga gagcgccgac cgatgccctt gagagccttc aacccagtca    1080
gctccttccg gtgggcgcgg ggcatgacta tcgtcgccgc acttatgact gtcttcttta    1140

```
tcatgcaact cgtaggacag gtgccggcag cgctctgggt catttttcggc gaggaccgct    1200 ttcgctggag cgcgacgatg atcggcctgt cgcttgcgt attcggaatc ttgcacgccc     1260
tcgctcaagc cttcgtcact ggtcccgcca ccaaacgttt cggcgagaag caggccatta    1320
tcgccggcat ggcggccgac gcgctgggct acgtcttgct ggcgttcgcg acgcgaggct    1380
ggatggcctt ccccattatg attcttctcg cttccggcgg catcgggatg cccgcgttgc    1440
aggccatgct gtccaggcag gtagatgacg accatcaggg acagcttcaa ggatcgctcg    1500
cggctcttac cagcctaact tcgatcactg gaccgctgat cgtcacggcg atttatgccg    1560
cctcggcgag cacatggaac gggttggcat ggattgtagg cgccgcccta taccttgtct    1620
gcctccccgc gttgcgtcgc ggtgcatgga gccgggccac ctcgacctga atggaagccg    1680
gcggcacctc gctaacggat tcaccactcc aagaattgga gccaatcaat tcttgcggag    1740
aactgtgaat gcgcaaacca acccttgtat cggggaagaa cagtatgtcg agctattttt    1800
tgacttactg gggatcaagc ctgattggga gaaaataaaa tattatattt tactggatga    1860
attgttttag tacctagatg tggcgcaacg atgccggcga ca                        1902

<210> SEQ ID NO 180
<211> LENGTH: 204
<212> TYPE: DNA
<213> ORGANISM: Artificial sequence
<220> FEATURE:
<223> OTHER INFORMATION: polynucleotide

<400> SEQUENCE: 180
ggactgtaga ggttccgggt gacagccctc cgacgggtga cagccctccg acgggtgaca     60
gccctccgaa ttctagagga tccgggtgac agccctccga cgggtgacag ccctccgacg    120
ggtgacagcc ctccgaattc gagctcggta cccggggatc tgtcgacctc gatcgagatc    180
ttcgcaagac ccttcctcta tata                                            204

<210> SEQ ID NO 181
<211> LENGTH: 1875
<212> TYPE: DNA
<213> ORGANISM: Artificial sequence
<220> FEATURE:
<223> OTHER INFORMATION: polynucleotide

<400> SEQUENCE: 181
gacaacatgt ggagcacgac acacttgtct actccaaaaa tatcaaagat acagtctcag     60
aagaccaaag gcaattgag actttttcaac aaagggtaat atccggaaac ctcctcggat    120
tccattgccc agctatctgt cactttattg tgaagatagt ggaaaaggaa ggtggctcct    180
acaaatgcca tcattgcgat aaaggaaagg ccatcgttga agatgcctct gccgacagtg    240
gtcccaaaga tggacccccca cccacgagga gcatcgtgga aaagaagac gttccaacca    300 cgtcttcaaa gcaagtggat tgatgtgata acatggtgga gcacgacaca cttgtctact    360
ccaaaaatat caaagataca gtctcagaag accaaagggc aattgagact tttcaacaaa    420
gggtaatatc cggaaacctc ctcggattcc attgcccagc tatctgtcac tttattgtga    480
agatagtgga aaaggaaggt ggctcctaca atgccatca ttgcgataaa ggaaaggcca    540
tcgttgaaga tgcctctgcc gacagtggtc ccaaagatgg accccaccc acgaggagca    600 tcgtggaaaa agaagacgtt ccaaccacgt cttcaaagca gtggattga tgtgatatct    660 ccactgacgt aagggatgac gcacaatccc actatccttc gcaagaccct tcctctatat    720
```

```
aaggaagttc atttcatttg gagaggacgt cgagagttct caacacaaca tatacaaaac    780
aaacgaatct caagcaatca agcattctac ttctattgca gcaatttaaa tcatttcttt    840
taaagcaaaa gcaattttct gaaaattttc accatttacg aacgatagcc atggccgtcg    900
acaactagtc cagatctgtg tccaagggcg aggagctgtt caccggggtg gtgcccatcc    960
tggtcgagct ggacggcgac gtaaacggcc acaagttcag cgtgtccggc gagggcgagg   1020
gcgatgccac ctacggcaag ctgaccctga agttcatctg caccaccggc aagctgcccg   1080
tgccctggcc caccctcgtg accaccctga cctacggcgt gcagtgcttc agccgctacc   1140
ccgaccacat gaagcagcac gacttcttca gtccgccat gcccgaaggc tacgtccagg    1200
agcgcaccat cttcttcaag gacgacggca actacaagac ccgcgccgag gtgaagttcg   1260
agggcgacac cctggtgaac cgcatcgagc tgaagggcat cgacttcaag gaggacggca   1320
acatcctggg gcacaagctg gagtacaact acaacagcca caacgtctat atcatggccg   1380
acaagcagaa gaacggcatc aaggtgaact tcaagatccg ccacaacatc gaggacggca   1440
gcgtgcagct cgccgaccac taccagcaga acaccccat cggcgacggc cccgtgctgc    1500
tgcccgacaa ccactacctg agcacccagt ccgccctgag caaagacccc aacgagaagc   1560
gcgatcacat ggtcctgctg gagttcgtga ccgccgccgg gatcactctc ggcatggacg   1620
agctgtacaa gtccggactc taagcttggg tctagagtcc gcaaaaatca ccagtctctc   1680
tctacaaatc tatctctctc tattttctc cagaataatg tgtgagtagt tcccagataa    1740
gggaattagg gttcttatag ggtttcgctc atgtgttgag catataagaa acccttagta   1800
tgtatttgta tttgtaaaat acttctatca ataaatttc taattcctaa aaccaaaatc    1860
cagtgacgcg gccgc                                                    1875
```

<210> SEQ ID NO 182
<211> LENGTH: 22
<212> TYPE: DNA
<213> ORGANISM: Artificial sequence
<220> FEATURE:
<223> OTHER INFORMATION: polynucleotide

<400> SEQUENCE: 182

```
atctcaagtc tctaggactg gt                                              22
```

<210> SEQ ID NO 183
<211> LENGTH: 22
<212> TYPE: DNA
<213> ORGANISM: Artificial sequence
<220> FEATURE:
<223> OTHER INFORMATION: polynucleotide

<400> SEQUENCE: 183

```
atctgtgagc aaaggcgagg ag                                              22
```

<210> SEQ ID NO 184
<211> LENGTH: 68
<212> TYPE: DNA
<213> ORGANISM: Artificial sequence
<220> FEATURE:
<223> OTHER INFORMATION: polynucleotide

<400> SEQUENCE: 184

```
ccatgggatc tcaagtctct aggactggtc ttcaaaatct ttctcactag tttctacgat    60
cttggcca                                                              68
```

```
<210> SEQ ID NO 185
<211> LENGTH: 62
<212> TYPE: DNA
<213> ORGANISM: Artificial sequence
<220> FEATURE:
<223> OTHER INFORMATION: polynucleotide

<400> SEQUENCE: 185
ccatgggatc tcaagtctct aggactggtc aaaatctttc tcactagttt ctacgctggc    60
ca                                                                  62

<210> SEQ ID NO 186
<211> LENGTH: 56
<212> TYPE: DNA
<213> ORGANISM: Artificial sequence
<220> FEATURE:
<223> OTHER INFORMATION: polynucleotide

<400> SEQUENCE: 186
ccatgggatc tcaagtctct aggactggta atctttctca ctagttacgc tggcca        56

<210> SEQ ID NO 187
<211> LENGTH: 53
<212> TYPE: DNA
<213> ORGANISM: Artificial sequence
<220> FEATURE:
<223> OTHER INFORMATION: polynucleotide

<400> SEQUENCE: 187
ccatgggatc tcaagtctct aggactggta atctttcttg atcagtctgg cca           53

<210> SEQ ID NO 188
<211> LENGTH: 52
<212> TYPE: DNA
<213> ORGANISM: Artificial sequence
<220> FEATURE:
<223> OTHER INFORMATION: polynucleotide

<400> SEQUENCE: 188
ccatgggatc tcaagtctct aggactggta atctttcttg atcagctggc ca            52

<210> SEQ ID NO 189
<211> LENGTH: 51
<212> TYPE: DNA
<213> ORGANISM: Artificial sequence
<220> FEATURE:
<223> OTHER INFORMATION: polynucleotide

<400> SEQUENCE: 189
ccatgggatc tcaagtctct aggactggta atctttcttg atcactggcc a             51

<210> SEQ ID NO 190
<211> LENGTH: 50
<212> TYPE: DNA
<213> ORGANISM: Artificial sequence
<220> FEATURE:
<223> OTHER INFORMATION: polynucleotide

<400> SEQUENCE: 190
ccatgggatc tcaagtctct aggactggtc tttctcacta gttctggcca               50

<210> SEQ ID NO 191
<211> LENGTH: 44
<212> TYPE: DNA
<213> ORGANISM: Artificial sequence
<220> FEATURE:
```

<223> OTHER INFORMATION: polynucleotide

<400> SEQUENCE: 191

| ccatgggatc tcaagtctct aggactggtc ttcactagtg gcca | 44 |

<210> SEQ ID NO 192
<211> LENGTH: 37
<212> TYPE: DNA
<213> ORGANISM: Artificial sequence
<220> FEATURE:
<223> OTHER INFORMATION: polynucleotide

<400> SEQUENCE: 192

| aggaagttca tttcatttgg rgaggacacg ctgaacc | 37 |

<210> SEQ ID NO 193
<211> LENGTH: 720
<212> TYPE: DNA
<213> ORGANISM: Artificial sequence
<220> FEATURE:
<223> OTHER INFORMATION: polynucleotide

<400> SEQUENCE: 193

| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagtaa | 720 |

<210> SEQ ID NO 194
<211> LENGTH: 1809
<212> TYPE: DNA
<213> ORGANISM: Artificial sequence
<220> FEATURE:
<223> OTHER INFORMATION: polynucleotide

<400> SEQUENCE: 194

| atgttacgtc ctgtagaaac cccaacccgt gaaatcaaaa aactcgacgg cctgtgggca | 60 |
| ttcagtctgg atcgcgaaaa ctgtggaatt gatcagcgtt ggtgggaaag cgcgttacaa | 120 |
| gaaagccggg caattgctgt gccaggcagt tttaacgatc agttcgccga tgcagatatt | 180 |
| cgtaattatg cgggcaacgt ctggtatcag cgcgaagtct ttataccgaa aggttgggca | 240 |
| ggccagcgta tcgtgctgcg tttcgatgcg gtcactcatt acggcaaagt gtgggtcaat | 300 |
| aatcaggaag tgatggagca tcagggcggc tatacgccat ttgaagccga tgtcacgccg | 360 |
| tatgttattg ccgggaaaag tgtacgtatc accgtttgtg tgaacaacga actgaactgg | 420 |
| cagactatcc cgccgggaat ggtgattacc gacgaaaacg gcaagaaaaa gcagtcttac | 480 |
| ttccatgatt tctttaacta tgccggaatc catcgcagcg taatgctcta caccacgccg | 540 |

```
aacacctggg tggacgatat caccgtggtg acgcatgtcg cgcaagactg taaccacgcg      600
tctgttgact ggcaggtggt ggccaatggt gatgtcagcg ttgaactgcg tgatgcggat      660
caacaggtgg ttgcaactgg acaaggcact agcgggactt tgcaagtggt gaatccgcac      720
ctctggcaac cgggtgaagg ttatctctat gaactgtgcg tcacagccaa agccagaca      780 gagtgtgata tctacccgct tcgcgtcggc atccggtcag tggcagtgaa gggccaacag      840
ttcctgatta accacaaacc gttctacttt actggctttg gtcgtcatga agatgcggac      900
ttacgtggca aaggattcga taacgtgctg atggtgcacg accacgcatt aatggactgg      960
attggggcca actcctaccg tacctcgcat taccctracg ctgaagagat gctcgactgg     1020
gcagatgaac atggcatcgt ggtgattgat gaaactgctg ctgtcggctt taacctctct     1080
ttaggcattg gtttcgaagc gggcaacaag ccgaaagaac tgtacagcga agaggcagtc     1140 aacgggaaa ctcagcaagc gcacttacag gcgattaaag agctgatagc gcgtgacaaa     1200
aaccacccaa gcgtggtgat gtggagtatt gccaacgaac cggatacccg tccgcaagtg     1260
cacgggaata tttcgccact ggcggaagca acgcgtaaac tcgacccgac gcgtccgatc     1320
acctgcgtca atgtaatgtt ctgcgacgct cacaccgata ccatcagcga tctctttgat     1380
gtgctgtgcc tgaaccgtta ttacggatgg tatgtccaaa gcggcgattt ggaaacggca     1440
gagaaggtac tggaaaaaga acttctggcc tggcaggaga aactgcatca gccgattatc     1500
atcaccgaat acgcgtgga tacgttagcc gggctgcact caatgtacac cgacatgtgg     1560
agtgaagagt atcagtgtgc atggctggat atgtatcacc gcgtctttga tcgcgtcagc     1620
gccgtcgtcg gtgaacaggt atggaatttc gccgattttg cgacctcgca aggcatattg     1680
cgcgttggcg gtaacaagaa agggatcttc actcgcgacc gcaaaccgaa gtcggcggct     1740
tttctgctgc aaaaacgctg gactggcatg aacttcggtg aaaaaccgca gcagggaggc     1800
aaacaatga                                                             1809

<210> SEQ ID NO 195
<211> LENGTH: 211
<212> TYPE: DNA
<213> ORGANISM: Artificial sequence
<220> FEATURE:
<223> OTHER INFORMATION: polynucleotide

<400> SEQUENCE: 195
gtccgcaaaa atcaccagtc tctctctaca aatctatctc tctctatttt tctccagaat       60
aatgtgtgag tagttcccag ataagggaat tagggttctt atagggtttc gctcatgtgt      120
tgagcatata agaaacccct agtatgtatt tgtatttgta aaatacttct atcaataaaa      180
tttctaattc ctaaaaccaa atccagtga c                                      211

<210> SEQ ID NO 196
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (19)..(24)
<223> OTHER INFORMATION: n is a, c, g, t or u

<400> SEQUENCE: 196
cgggtgacag ccctccgann nnnn                                              24
```

<210> SEQ ID NO 197
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 197
nnnnnntcgg agggctgtca cccg                                          24

<210> SEQ ID NO 198
<211> LENGTH: 152
<212> TYPE: DNA
<213> ORGANISM: Artificial sequence
<220> FEATURE:
<223> OTHER INFORMATION: polynucleotide

<400> SEQUENCE: 198
tcttcgctat tacgccagct ggcgaaaggg ggatgtgctg caaggcgatt aagttgggta   60
acgccagggt tttcccagtc acgacgttgt aaaacgacgg ccagtgccac ccataatacc  120
cataatagct gtttgccaac cggttctata ta                                152

<210> SEQ ID NO 199
<211> LENGTH: 37
<212> TYPE: DNA
<213> ORGANISM: Artificial sequence
<220> FEATURE:
<223> OTHER INFORMATION: polynucleotide

<400> SEQUENCE: 199
aggaagttca tttcatttgg rgaggacacg ctgaacc                            37

<210> SEQ ID NO 200
<211> LENGTH: 720
<212> TYPE: DNA
<213> ORGANISM: Artificial sequence
<220> FEATURE:
<223> OTHER INFORMATION: polynucleotide

<400> SEQUENCE: 200
atggtgagca agggcgagga gctgttcacc ggggtggtgc ccatcctggt cgagctggac   60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctgggcac  420 aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtaa  720

<210> SEQ ID NO 201
<211> LENGTH: 1809
<212> TYPE: DNA
<213> ORGANISM: Artificial sequence
<220> FEATURE:
<223> OTHER INFORMATION: polynucleotide

<400> SEQUENCE: 201

```
atgttacgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat tgaagccga tgtcacgccg     360
tatgttattg ccgggaaaag tgtacgtatc accgtttgtg tgaacaacga actgaactgg     420
cagactatcc cgccgggaat ggtgattacc gacgaaaacg gcaagaaaaa gcagtcttac     480
ttccatgatt tctttaacta tgccggaatc catcgcagcg taatgctcta caccacgccg     540
aacacctggg tggacgatat caccgtggtg acgcatgtcg cgcaagactg taaccacgcg     600
tctgttgact ggcaggtggt ggccaatggt gatgtcagcg ttgaactgcg tgatgcggat     660
caacaggtgg ttgcaactgg acaaggcact agcgggactt tgcaagtggt gaatccgcac     720
ctctggcaac cgggtgaagg ttatctctat gaactgtgcg tcacagccaa agccagaca     780
gagtgtgata tctacccgct tcgcgtcggc atccggtcag tggcagtgaa gggccaacag     840
ttcctgatta accacaaacc gttctacttt actggctttg gtcgtcatga agatgcggac     900
ttacgtggca aaggattcga taacgtgctg atggtgcacg accacgcatt aatggactgg     960
attggggcca actcctaccg tacctcgcat taccctacg ctgaagagat gctcgactgg    1020
gcagatgaac atggcatcgt ggtgattgat gaaactgctg ctgtcggctt taacctctct    1080
ttaggcattg gtttcgaagc gggcaacaag ccgaaagaac tgtacagcga agaggcagtc    1140
aacggggaaa ctcagcaagc gcacttacag gcgattaaag agctgatagc gcgtgacaaa    1200
aaccacccaa gcgtggtgat gtggagtatt gccaacgaac cggatacccg tccgcaagtg    1260
cacgggaata tttcgccact ggcggaagca acgcgtaaac tcgacccgac gcgtccgatc    1320
acctgcgtca atgtaatgtt ctgcgacgct cacaccgata ccatcagcga tctctttgat    1380
gtgctgtgcc tgaaccgtta ttacggatgg tatgtccaaa gcggcgattt ggaaacggca    1440
gagaaggtac tggaaaaaga acttctggcc tggcaggaga aactgcatca gccgattatc    1500
atcaccgaat acggcgtgga tacgttagcc gggctgcact caatgtacac cgacatgtgg    1560
agtgaagagt atcagtgtgc atggctggat atgtatcacc gcgtctttga tcgcgtcagc    1620
gccgtcgtcg gtgaacaggt atggaatttc gccgatttg cgacctcgca aggcatattg    1680
cgcgttggcg gtaacaagaa agggatcttc actcgcgacc gcaaaccgaa gtcggcggct    1740
tttctgctgc aaaaacgctg gactggcatg aacttcggtg aaaaaccgca gcagggaggc    1800
aaacaatga                                                            1809
```

<210> SEQ ID NO 202
<211> LENGTH: 211
<212> TYPE: DNA
<213> ORGANISM: Artificial sequence
<220> FEATURE:
<223> OTHER INFORMATION: polynucloeitde

<400> SEQUENCE: 202

```
gtccgcaaaa atcaccagtc tctctctaca aatctatctc tctctatttt tctccagaat    60
aatgtgtgag tagttcccag ataagggaat tagggttctt atagggtttc gctcatgtgt   120
tgagcatata agaaacccctt agtatgtatt tgtatttgta aaatacttct atcaataaaa   180
tttctaattc ctaaaaccaa aatccagtga c                                   211
```

<210> SEQ ID NO 203
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, t or u

<400> SEQUENCE: 203

```
gccagggttt tcccagtcac gannnnnn                                        28
```

<210> SEQ ID NO 204
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(6)
<223> OTHER INFORMATION: n is a, c, g, t or u

<400> SEQUENCE: 204

```
nnnnnntcgt gactgggaaa accctggc                                        28
```

<210> SEQ ID NO 205
<211> LENGTH: 238
<212> TYPE: PRT
<213> ORGANISM: Artificial sequence
<220> FEATURE:
<223> OTHER INFORMATION: polypeptide

<400> SEQUENCE: 205

```
Met His Ser Arg Ser Ala Leu Leu Tyr Arg Phe Leu Arg Pro Ala Ser
1               5                   10                  15

Arg Cys Phe Ser Ser Ser Val Lys Ser Glu Leu Glu Glu Lys Lys
            20                  25                  30

Ser Glu Leu Arg His Lys Leu Lys Tyr Val Pro His Glu Tyr Ile Glu
        35                  40                  45

Leu Ile Glu Ile Ala Arg Asn Ser Thr Gln Asp Arg Ile Leu Glu Met
    50                  55                  60

Lys Val Met Glu Phe Phe Met Lys Val Tyr Gly Tyr Arg Gly Lys His
65                  70                  75                  80

Leu Gly Gly Ser Arg Lys Pro Asp Gly Ala Ile Tyr Thr Val Gly Ser
                85                  90                  95

Pro Ile Asp Tyr Gly Val Ile Val Asp Thr Lys Ala Tyr Ser Gly Gly
            100                 105                 110

Tyr Asn Leu Pro Ile Gly Gln Ala Asp Glu Met Gln Arg Tyr Val Glu
        115                 120                 125

Glu Asn Gln Thr Arg Asn Lys His Ile Asn Pro Asn Glu Trp Trp Lys
    130                 135                 140
```

-continued

Val Tyr Pro Ser Ser Val Thr Glu Phe Lys Phe Leu Phe Val Ser Gly
145                 150                 155                 160

His Phe Lys Gly Asn Tyr Lys Ala Gln Leu Thr Arg Leu Asn His Ile
                165                 170                 175

Thr Asn Cys Asn Gly Ala Val Leu Ser Val Glu Glu Leu Leu Ile Gly
            180                 185                 190

Gly Glu Met Ile Lys Ala Gly Thr Leu Thr Leu Glu Glu Val Arg Arg
        195                 200                 205

Lys Phe Asn Asn Gly Glu Ile Asn Phe Gly Ser Gly Ser Gly Pro
    210                 215                 220

Arg Pro Arg Gly Thr Arg Gly Lys Gly Arg Ile Arg Arg
225                 230                 235

<210> SEQ ID NO 206
<211> LENGTH: 717
<212> TYPE: DNA
<213> ORGANISM: Artificial sequence
<220> FEATURE:
<223> OTHER INFORMATION: polynucleotide

<400> SEQUENCE: 206
atgcattcta gatctgctct tctttataga tttcttagac cagcttctag atgtttttct       60
tcttcttctg ttaagtctga acttgaagaa aagaagtctg aacttagaca taagcttaag      120
tatgttccac atgaatatat tgaacttatt gaaattgcta gaaattctac tcaagataga      180
attcttgaaa tgaaggttat ggaattttt atgaaggttt atggatatag aggaaagcat       240
cttggaggat ctagaaagcc agatggagct atttatactt ttggatctcc aattgattat      300
ggagttattg ttgatactaa ggcttattct ggaggatata atcttccaat tggacaagct      360
gatgaaatgc aaagatatgt tgaagaaaat caaactagaa ataagcatat taatccaaat      420
gaatggtgga aggtttatcc atcttctgtt actgaattta gtttcttttt tgtttctgga      480 catttaagg gaaattataa ggctcaactt actagactta atcatattac taattgtaat       540
ggagctgttc tttctgttga agaacttctt attggaggag aaatgattaa ggctggaact      600
cttactcttg aagaagttag aagaaagttt aataatggag aaattaattt tggatctgga      660
ggatctggac caagaccaag aggaactaga ggaaagggaa gagaattag aagataa         717

<210> SEQ ID NO 207
<211> LENGTH: 43
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (21)..(21)
<223> OTHER INFORMATION: n is a, c, g, t or u

<400> SEQUENCE: 207
uucaccucua accgggugag nuccaagggc gaggagcugu uca                         43

<210> SEQ ID NO 208
<211> LENGTH: 43
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(23)
<223> OTHER INFORMATION: n is a, c, g, t or u

```
<400> SEQUENCE: 208
accauuuacg aacgauagcc aunuucaccu cuaaccgggu gag        43

<210> SEQ ID NO 209
<211> LENGTH: 43
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (21)..(21)
<223> OTHER INFORMATION: n is a, c, g, t or u

<400> SEQUENCE: 209
uucaccucua accgggugag nauggcuauc guucguaaau ggu        43

<210> SEQ ID NO 210
<211> LENGTH: 43
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(23)
<223> OTHER INFORMATION: n is a, c, g, t or u

<400> SEQUENCE: 210
ugaacagcuc cucgcccuug ganuucaccu cuaaccgggu gag        43

<210> SEQ ID NO 211
<211> LENGTH: 24
<212> TYPE: DNA
<213> ORGANISM: Artificial sequence
<220> FEATURE:
<223> OTHER INFORMATION: polynucleoitde
<220> FEATURE:
<221> NAME/KEY: misc_feature
<222> LOCATION: (1)..(2)
<223> OTHER INFORMATION: n is a, c, g, t or u

<400> SEQUENCE: 211
nntgtccaag ggcgaggagc tgtt                             24

<210> SEQ ID NO 212
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 212
catttacgaa cgatagccat ggnn                             24

<210> SEQ ID NO 213
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (1)..(2)
```

```
<223> OTHER INFORMATION: n is a, c, g, t or u

<400> SEQUENCE: 213
nnccatggct atcgttcgta aatg                                              24

<210> SEQ ID NO 214
<211> LENGTH: 24
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(24)
<223> OTHER INFORMATION: n is a, c, g, t or u

<400> SEQUENCE: 214
aacagctcct cgcccttgga cann                                              24

<210> SEQ ID NO 215
<211> LENGTH: 6
<212> TYPE: PRT
<213> ORGANISM: Artificial sequence
<220> FEATURE:
<223> OTHER INFORMATION: peptide

<400> SEQUENCE: 215

Ala Cys Thr Ala Gly Thr
1               5

<210> SEQ ID NO 216
<211> LENGTH: 6
<212> TYPE: PRT
<213> ORGANISM: Artificial sequence
<220> FEATURE:
<223> OTHER INFORMATION: peptide

<400> SEQUENCE: 216

Thr Gly Ala Thr Cys Ala
1               5

<210> SEQ ID NO 217
<211> LENGTH: 28
<212> TYPE: DNA
<213> ORGANISM: Artificial sequence
<220> FEATURE:
<223> OTHER INFORMATION: polynucleotide
<220> FEATURE:
<221> NAME/KEY: misc_feature
<222> LOCATION: (23)..(28)
<223> OTHER INFORMATION: n is a, c, g, t or u

<400> SEQUENCE: 217
ataccagcac cagcaattac aannnnnn                                          28
```

COMPOSITIONS AND METHODS FOR MODIFYING A PREDETERMINED TARGET NUCLEIC ACID SEQUENCE

CROSS-REFERENCE TO RELATED APPLICATIONS

This application is the national stage application of PCT Patent Application No. PCT/IL2012/050528, filed Dec. 16, 2012, which claims benefit under 35 U.S.C. § 119(e) to U.S. Provisional Patent Application No. 61/576,423, filed Dec. 16, 2011, each of which are incorporated herein by reference in their entirety.

SEQUENCE LISTING

A sequence listing submitted in computer readable format is hereby incorporated by reference. The computer readable file is named SEQ LIST_ST25.txt and contains 128,802 bytes as measured in Microsoft Windows®.

FIELD OF THE INVENTION

The present invention relates to compositions and methods for targeting and modifying nucleic acid sequences utilizing a programmable molecular complex.

BACKGROUND OF THE INVENTION

A major area of interest in biology and medicine is targeted alteration of genomic nucleotide sequences. Such alterations include insertion, deletion and replacement of endogenous chromosomal nucleic acid sequences. Past attempts have been made by others to alter genomic sequences by different techniques.

Gene targeting is a biotechnological tool desired for genome manipulation or genome functional modification. Gene targeting can induce a change in a specific genomic location which may or may not, be related to coding sequences.

In a gene targeting event, a predefined endogenous gene, or another predefined endogenous nucleic acid sequence, is either targeted for cleavage resulting in deletion, mutation, insertion or replacement or targeted for chemical modification by targeted gene-functional modification. One advantage of gene-targeting over untargeted transgenic organism production is the possibility to modify or delete existing genomic sequences without insertion of foreign DNA, or alternatively, place a foreign donor DNA, by insertion or replacement, in a predefined locus. It is advantageous to be able to thus manipulate a sequence without superfluous sequences, as these are undesired by breeders, farmers, consumers and regulatory agencies, and while many techniques for avoiding such sequences have been suggested, each suffers from its own shortcomings.

The strategies for gene targeting in Eukaryotes are dependent on two cellular dsDNA break repair mechanisms: The homologous recombination (HR) and non-homologous-end-joining (NHEJ) repair pathways. In NHEJ gene insertions depend on the existence of a dsDNA break which may occur randomly (e.g. through radiation or oxidative damage) or be directed by a nuclease such as a TALE nuclease (TALEN), meganuclease or a zinc-finger nuclease (ZFN). HR can be induced by dsDNA breaks. In HR, a dsDNA break is not essential, but may improve the efficiency if located near the recombination site.

Extensive research has been conducted on HR mediated gene targeting which functions usefully well in many organisms such as bacteria, yeast and the primitive plant, moss. HR has also been utilized in higher organisms such as *Drosophila*, mice, and humans. Rates of HR in these organisms are about $10^{-6}$, and can be increased to over $10^{-2}$, in assisted HR, by creating a gene specific DSB. Low rates of transformants are one reason these methods are not prevalent in gene therapy or breeding programs.

Various techniques for modifying nucleic acids in-vivo have been suggested and can be divided into enzyme based or nucleotide based methods. In general, enzyme based methods use a DNA-binding protein which has both a desired catalytic activity and the ability to bind the desired target sequence through a protein-nucleic-acid interaction in a manner similar to restriction enzymes. Examples include meganucleases which are naturally occurring or engineered rare sequence cutting enzymes, zinc finger nucleases (ZFNs) or transcription activator-like nucleases (TALENs) which contain the FoId catalytic nuclease subunit linked to a modified DNA binding domain and can cut one predetermined sequence each. In ZFNs the binding domain is comprised of chains of amino-acids folding into customized zinc finger domains. In TALENs, similarly, 34 amino acid repeats originating from transcription factors fold into a huge DNA-binding domain. In the event of gene targeting, these enzymes can cleave genomic DNA to form a double strand break (DSB) or create a nick which can be repaired by one of two repair pathways, non-homologous end joining (NHEJ) or homologous recombination (HR). The NHEJ pathway can potentially result in specific mutations, deletions, insertions or replacement events. The HR pathway results in replacement of the targeted sequence by a supplied donor sequence. One disadvantage of these protein-only based methods is the long and laborious necessity to design and supply a different protein for every desired target sequence. Other disadvantages include the somewhat limited subset of nucleic acid triplets or sequences recognized by ZFNs and meganucleases respectively. Moreover, even a six-Zinc-finger ZFN, which is very difficult to construct, is limited to a binding site of only 18 nucleotides, and as 18 nucleotides are statistically not sufficient to confer sequence specificity in the sequence space, or complexity, of a whole genome these must be supplied as heterodimers. Moreover, the nature of ZFNs and TALENs requires functionality screening and even successful nucleases may show poor gene-targeting efficiency.

For nucleotide based methods, nucleic acids are supplied to the organism and endogenous processes bring about DNA repair or gene-targeting through unassisted homologous recombination or integration of the oligonucleotide into the genome. These nucleic acids can be supplied using viral-vectors, plasmid vectors, T-DNA vectors and double-stranded DNA oligonucleotides. Shorter nucleotides termed Triple-helix forming oligonucleotides (TFOs) are used for Oligonucleotide-based mismatch repair, and can attain repair of point mutations or up to 4 nucleotide repair. There is ample evidence that these methods too are dependent on the formation of DSBs which can be random, randomly induced or locally induced by enzymatic or chemical modifications through enzymes or reactive chemicals covalently bound to the supplied nucleic acid. Double strand breaks (DSB) in DNA are necessary for HR. Specific pre-existing DSBs are not essential but improve efficiency. Natural breaks in DNA are randomly located and rare, and thus efficiency, thus, must be low ($10^{-6}$). DSBs can be randomly induced by ionizing radiation or oxidizing chemicals, improving efficiency at the expense of genotoxicity. In an improvement to this system, assisted HR or repair has been performed in the past using non-enzymatic DNA cleavage assisted by chemical modification of the terminus of a nucleic acid. These modifications include EDTA-Fe or photoactivatable Psoralen and were used for the production of a sequence specific DSB in dsDNA when incorporated in vitro to form a triple helix. An additional method uses oligonucleotides, or modified oligonucleotides, derived from single-stranded DNA (ssDNA), otherwise known as "small synthetic single-stranded oligodeoxynucleotides (ODNs or ssODNs). However, while oligonucleotide based methods may result in relatively efficient point mutations in mammalian cell genomes, these are restricted to this mode of editing.

Oligonucleotide-enzyme conjugates are a combination of the two methods comprising of a nucleic acid covalently bound in-vitro to a catalytic enzyme prior to supplying the conjugate to the organism. These methods, in contrast to enzyme-only methods are modular, allowing preparation of conjugates aimed at a diversity of target sequences. The main disadvantage of oligonucleotide-enzyme conjugates is that they cannot self-assemble in vivo, thereby severely limiting their usefulness for genome editing in vivo. Additional critical disadvantage of such systems known in the art is that in uses of these conjugates the enzyme component is active as a monomer, and thus any binding of the enzyme to a nucleic acid, specific or not, will result in cleavage. Such non-specific cleavage severely reduces the safety of such systems, as they might introduce undesired changes/mutations at undesired locations.

Non-conjugated oligonucleotide-protein systems have also been used to cleave a ssDNA substrate. In this system a Class-IIS Restriction Enzyme, FokI, which cleaves outside its recognition site was used in vitro, in conjunction with a hairpin forming oligonucleotide which reconstitutes the FokI recognition sequence, with a PolIk enzyme and dNTPs to create a double-strand section of DNA primed by the oligonucleotide to be cleaved. In this system, not only the intended sequence is cleaved, but any naturally occurring FokI site will be recognized and the sequence adjacent to it will be cleaved. As FokI has only a 5-nucleotide recognition site this implies there are thousands of potential cleavage sites in a whole genome, rendering this system useless for genome editing.

In higher plants and humans, in contrast to other organisms where HR can be used for gene-targeting, the NHEJ pathway is the predominant endogenous mechanism. The plant DNA-repair machinery does not permit efficient HR between donor and chromosomal DNA. Indeed, it is widely accepted that foreign donor DNA molecules, which are often delivered by *Agrobacterium*-mediated genetic transformation, are recognized by the plant Non-Homologous End Joining (NHEJ) pathway, which leads to their random integration throughout the host genome. Most current plant transformation methods, thus, are not considered gene targeting, as in these methods, sequences are randomly inserted in the genome, and as an undesirable side effect, may disrupt an existing gene, and are often inserted in multiple copies, or contain undesired plasmid, marker or bacterial sequence remnants.

Methods for induction of specific dsDNA breaks, useful for assisted HR and directed NHEJ, utilize expression of nucleases in vivo. These include rare-sequence cutting nucleases (rare-cutters) such as meganucleases or chimeric meganucleases, derived from homing endonucleases, custom-made recombinant Zinc-Finger-Nucleases (ZFNs), or custom-made recombinant TAL effector nucleases. In these methods, recognition of the cleaved target site, is achieved by the interaction of a protein domain or subunit which naturally recognizes a specific nucleotide sequence, or is engineered specifically to recognize a specific nucleotide sequence and is not based on polynucleotide-polynucleotide hybridization or base-pairing. For example, Zinc Finger Nucleases are chimeric proteins, constructed as hybrids between the FokI nuclease subunit and synthetic zinc-finger (ZF) domains. Zinc Finger Nucleases do not contain a nucleic acid component. ZFNs are designed to specifically recognize nucleotide triplets through a combination of several ZF motifs. ZFNs cannot be constructed to recognize all sequences due to their inherent ability to recognize only a limited subset of nucleotide triplets. Use of ZFN heterodimers, whereby two different ZFNs, which are inactive as a monomer are delivered concomitantly, has a positive effect on specificity, though this complicates the design further and reduces the choice of target sequences. ZFNs have also been utilized to create artificial transcription factors both for activation and for repression of genes, for altering gene regulation. However, such Zinc finger based transcription factors cannot bind all sequences, being limited in length of recognition site and limited to several specific tri-nucleotide motifs, and thus cannot be utilized to activate or suppress all possible genes.

For example, Schierling et. al., disclose a novel zinc finger nuclease platform with a sequence-specific cleavage module. For example, Eisenschmidt K, et. al. disclose a programmed restriction endonuclease for highly specific DNA cleavage. For example, WO 2006/027099 is directed to enzyme conjugates with a programmable specificity, which react in a highly specific manner with DNA.

Kubo et. al., for example, disclose the control of intracellular delivery of oligonucleotides by signal peptides and genetic expression in human cells. Jinek et. al., disclose a programmable Dual-RNA-Guided DNA endonuclease in adaptive bacterial immunity.

WO 2012/129373, for example, is directed to methods for producing a complex transgenic trait locus.

Nevertheless, there is still an unmet need in the art for safe, reliable, modular, and inexpensive compositions and methods that allow the specific targeting and modifying of target nucleic acid sequences in-vivo.

SUMMARY OF THE INVENTION

The present invention provides compositions and methods for targeting and modifying nucleic acid sequences, in-vivo or in-vitro. According to some embodiments the novel composite programmable molecular complex (nucleoprotein complex) provided herein is used to edit or functionally modify a predetermined nucleic acid sequence target precisely, reliably and cost effectively.

In some embodiments, the molecular complex disclosed herein is used for gene-targeting and/or targeted gene-functional modification including, but not limited to, generation of breaks in one or two strands of the target nucleic acid to initiate gene mutation, deletion, gene replacement, and integration of a foreign nucleic acid molecule, or for its chemical, conformational, or biological functional modification.

According to some embodiments, the molecular complex disclosed herein comprises a) a chimeric polypeptide (that may be encoded by a polynucleotide molecule), the chimeric polypeptide comprising: (i) a functional (effector) domain (FD) capable of modifying a target site; and (ii) a linking domain (LD); and (b) a specificity conferring nucleic acid (SCNA), the SCNA comprising: (i) a nucleotide sequence complementary to a region of a target nucleic acid flanking the target site; and (ii) a recognition region capable of specifically attaching to the linking domain of the polypeptide; whereby assembly of the polypeptide and the SCNA within a host/target cell forms a functional, programmable, nucleoprotein molecular complex, capable of specifically modifying the target nucleic acid at the target site.

In some embodiments, the present invention provides an advantageous composition comprising a protein effector module (or a nucleic acid molecule encoding the same) and a programming/targeting nucleic-acid module which can self-assemble in-vivo into a specific, active nucleic acid modifying molecular nucleoprotein complex. In this complex, the nucleic acid, also termed herein as a "programming moiety", "programming oligonucleotide" or "specificity-conferring nucleic acid" (SCNA) provides the specificity and binding capabilities of the molecular complex to the target nucleic acid through base-pairing of said specificity-conferring nucleic acid and a target nucleic acid. The protein effector component or module of this complex is designed to bind/link/attach to the specificity determining nucleic acid by a chemical moiety attached to the oligonucleotide, a modification of a nucleotide or nucleotides on the oligonucleotide, a specific recognition sequence on the oligonucleotide, and the like, or combinations thereof. Advantageously, the compositions and methods disclosed herein confer higher specificity with a wide range of desired target sequences, are less genotoxic, modular in their assembly, reliable, utilize a single platform without customization, practical for independent use outside of specialized core-facilities, and have a shorter development time frame and reduced costs.

The activity of the protein module may result in the modification of the target nucleic acid sequence and/or the functional modification of the target nucleic acid. Target nucleic acid modification may include, but is not limited to: mutation, deletion, insertion, replacement, binding, digestion, nicking, methylation, acetylation, ligation, recombination, helix unwinding, chemical modification, labeling, activation, and inactivation or any combinations thereof. Target nucleic acid functional modification may lead to, but is not limited to: changes in transcriptional activation, transcriptional inactivation, alternative splicing, chromatin rearrangement, pathogen inactivation, virus inactivation, change in cellular localization, compartmentalization of nucleic acid, and the like, or combinations thereof. Any editing action or other modification effected by the protein moiety is directed or guided to an intended (predefined) specific target nucleic acid by its linkage to the specificity-conferring nucleic acid. Advantageously, use of each single type of protein component may be combined with an unlimited assortment of nucleotide-sequences of specificity determining nucleic acids concomitantly or separately, to allow similar action on different sections of intended target nucleic acid. This allows overcoming shortcoming of state of the art methods, by providing a versatile, reliable and cost effective methods and compositions for modifying predetermined nucleic acid sequence targets. Thus, if used in one receptacle or organism, only one type of protein is to be provided with any combination or multiplicity of specificity determining nucleic acid types. This also includes the possibility to concomitantly use more than one type of protein component with more than one type of specificity determining nucleic acids.

According to some embodiments, the complex disclosed herein is modular and can self-assemble within a target cell either in vivo or in vitro, allowing the supply of one type of protein moiety at a time with one or a multiplicity of specificity-determining oligonucleotides concomitantly. Furthermore, in some embodiments, the protein component can be delivered to a desired cell(s) and expressed in vivo, awaiting the delivery of any appropriate SCNA at a later time. In some embodiments, the protein component and the SCNA may be delivered simultaneously, or essentially simultaneously. Thus, the combination of the protein component and the SCNA, preferably within the desired target cell, may accomplish the induction of specific genomic double strand breaks (DSBs), or any other desired nucleic acid modification, in vivo. The methods of the present invention are not limited to the introduction of point mutations to the target nucleic acid, as the molecular complex can target any nucleic-acid sequence or pair of sequences, cut/restrict/cleave in close proximity to them, and consequentially delete a small or large nucleic acid section, or cut/restrict/cleave the sequence in order to initiate a removal, or an insertion, or a replacement of any nucleic acid sequence.

Advantageously, the present invention, in embodiments thereof, discloses for the first time expression of a protein component in-vivo and its binding/attachment to the SCNA (s) by self-assembling in-vivo to form a molecular complex in-vivo, without the need of prior covalent/chemical linking between the protein moiety and the targeting nucleic acid. According to embodiments of the present invention, in contrast to the oligonucleotide-based systems known in the art, the SCNA bound to the protein is not intended to function as a donor, but rather as a specificity conferring moiety, and does not become part of the modified nucleic acid. Furthermore, in some embodiments of the present invention, the SCNA can be expressed in vivo in a manner that causes the assembly of all the components of the molecular complex with a single delivery event. Furthermore, according to some embodiments, the effector protein can be designed to be active only upon it's dimerization (i.e. it must form a dimer to be active), whereby the dimerization can be controlled such that an active dimer can only form when it is targeted/programmed by an SCNA and bound to its target site, for example, when the molecular distances between the monomeric partners (proteins) of the dimer are precise enough. Thus, advantageously, the molecular complex is activated only at its intended target site, thereby enhancing specificity and reliability. According to further embodiments, one protein component may be expressed to form/produce homo-dimers, each programmed/targeted by a different oligonucleotide conferring specificity. Additionally, as viral expression systems, which are known in the art for use for protein expression in-vivo, are often limited to the production of one protein due to size constraints, and are often exclusive to similar viruses due to cross protection, using one protein component has thus a critical advantage for that mode of delivery. Furthermore, in contrast to other methods known in the art (such as ZFNs and meganucleases), which have a limited subset of recognition sequences, the programming oligonucleotides (SCNAs) disclosed herein, have an infinite repertoire of sequences, thus conceivably achieving extreme sequence specificity in high complexity genomes. Moreover, as many programming oligonucleotides can be supplied concomitantly with a single protein effector moiety, it is possible to modify more than one target at the same time, providing additional advantages over methods know in the art. This can be useful, for example, for rapidly knocking out a multiplicity of genes, or for inserting several different traits in different locations, or for tagging several different locations with one donor nucleotide tag.

According to some embodiments, since an unprogrammed protein component (i.e. a protein not attached/linked to a programming oligonucleotide) has no or very low affinity to target nucleic acids, improved specificity and safety and reduced genotoxicity are advantageously obtained. As detailed above, the effector or catalytic domain of the protein component is only active upon dimerization, whereby at least two programming oligonucleotides (SCNAs) must bind the target flanking sequences to cause protein dimerization and activation. Two sufficiently long programming oligonucleotides can impart the very high theoretical specificity needed in high complexity genomes by creating extensive complementarity with the binding sites. Since the unprogrammed expressed protein has no affinity to the target nucleic acid it does not bind, and/or modify the target nucleic acid. Thus, in applications where, for example, the programming oligonucleotides are delivered/supplied separately to the target cell (which already expresses the unprogrammed protein component), or in conditions where oligonucleotides are depleted from the target cell (for example, by dilution or degradation) no unspecific cleavage can occur, thereby increasing safety and reducing genotoxicity.

Thus, according to embodiments of the present invention, both directed non-homologous-end-joining (NHEJ) and assisted homologous recombination (HR) may be utilized specifically and in a programmable manner to achieve one or more of the following:

1) Mutate a DNA sequence by cleaving inside it, creating a double strand break (DSB), to be somewhat degraded by the endogenous nucleases and re-ligated by the endogenous NHEJ DNA repair mechanism to create either an in-frame deletion and/or a frame-shift mutation of the DNA. As opposed to T-DNA or transposon insertion lines in plants, this method of deletion or mutation of an endogenous gene leaves behind no foreign DNA and the plant might be termed non-transgenic by some definitions. In NHEJ one or more nucleotides may also be added in the DSB in a yet uncharacterized endogenous mechanism, essentially achieving the same effect of frame shifting or mutation.
2) Delete a stretch of DNA sequence by cleaving two sequences flanking it, to be re-ligated by the endogenous NHEJ DNA repair mechanism, or by assisted HR by cleaving in or near the sequence to be deleted and supplying a donor DNA which is subsequently recombined into the target, and which contains sequences flanking the sequence to be deleted in the target.
3) Insert a donor nucleic acid into a DSB by cleaving a target nucleic acid and supplying a Donor DNA to be either ligated directly into the gap by the NHEJ mechanism, or preferably, supplying a donor that has homology to the ends of the gap to be recombined and ligated into the gap by assisted HR.
4) Replace a target nucleic acid sequence by cleaving both sequences flanking it, and supplying a donor nucleic acid to be inserted, to be ligated within the target flanking sequence either by NHEJ, or preferably, recombined and ligated by HR, by adding sequences similar to the target nucleic acid, or those flanking it, at the termini of the donor.

According to some embodiments, and without wishing to be bound to theory or mechanisms, the advantages of the compositions and methods disclosed herein, include the creation of a general enzymatic complex construction scheme that can target an unlimited selection of sequences. Once a protein component has been optimized for a specific purpose (e.g. dsDNA cleavage), this same protein can be used with an unlimited selection of programming nucleic acid (SCNA) sequences. Thus, the diversity of target sequences to be affected is achieved by the design of the SCNA, without the difficult and time-consuming necessity of protein re-design and optimization, which is inherent in other methods known in the art, such as, TALENs, ZFNs and Meganucleases, where the protein itself must be changed and adapted for every target sequence. Designing and preparing synthetic SCNAs is relatively simple, rapid and relatively inexpensive. It is also possible, in some embodiments of this invention, to produce SCNAs in-vivo, circumventing the necessity to deliver chemically synthesized SCNAs to a cell. Furthermore, SCNAs can be designed to base pair to almost any desired target sequence, and thus, can direct the molecular complex to almost any target sequence. Moreover, several target sequences may be used in the same cell concomitantly. For example, in editing functions which require more than one cleavage site, such as deletion or replacement of specific stretches of nucleic acid, by simply providing four different SCNAs and one protein moiety.

According to some embodiments, there is thus provided a nucleo-protein composition for modifying a predetermined target site in a target nucleic acid sequence in a target cell, the composition comprising: a polynucleotide molecule encoding a polypeptide, or a polypeptide, said polypeptide comprising: (i) a functional (effector) domain (FD) capable of modifying said target site, the functional domain being devoid of a specific nucleic acid binding site; and (ii) a linking domain (LD), capable of interacting with a specificity conferring nucleic acid (SCNA), wherein the linking domain being devoid of a specific target nucleic acid binding site; and; (b) the specificity conferring nucleic acid (SCNA) or a nucleic acid encoding for the SCNA, the SCNA comprising: (i) a nucleotide sequence complementary to a region of the target nucleic acid flanking the target site; and (ii) a recognition region capable of specifically attaching to the linking domain of the polypeptide with high binding affinity; whereby assembly of the polypeptide and the SCNA within the target cell forms a functional nucleoprotein complex, capable of specifically modifying said target nucleic acid at the target site.

In some embodiments, the functional domain comprises a catalytic domain. In some embodiments, the polypeptide further comprises a subcellular localization domain.

In some embodiments, modifying the target nucleic acid is selected from: mutation, deletion, insertion, replacement, binding, digestion, double-strand-break creation, nicking, methylation, acetylation, ligation, recombination, helix unwinding, chemical modification, labelling, activation and inactivation.

According to some embodiments, the SCNA comprises a nucleic acid molecule selected from the group consisting of a single-strand DNA, a single strand RNA, a double strand RNA, a modified DNA, a modified RNA, a locked-nucleic acid (LNA) and a peptide-nucleic acid (PNA) or combinations thereof.

In some embodiments, the recognition region of the SCNA comprises a modification selected from 5'-end modification, 3'-end modification, and internal modification. In some embodiments, the chemical modification is selected from the group consisting of a nucleotide modification, and addition of a non nucleotide moiety. In some embodiments, the non nucleotide moiety is selected from: Biotin, Fluorescein, Amine-linkers, oligo-peptides, Aminoallyl, a dye molecule, fluorophores, Digoxigenin, Acrydite, Adenylation, Azide, NHS-Ester, Cholesteryl-TEG, Alkynes, Photocleavable Biotin, Thiol, Dithiol. In some embodiments, the nucleotide modification is selected from the group consisting of phosphate, 2-Aminopurine, Trimer-20, 2,6-Diaminopurine, 5-Bromo-deoxiUridine, DeoxiUridine, Inverted dT, dideoxi-nucleotides, 5-methyl deoxyCytidine, deoxyInosine, 5-nitroindole, 2-O-methyl RNA bases, Iso-dC, Iso-dG, Fluorine modified bases and Phosphorothioate bonds. In some embodiments, the modification is selected from the group consisting of a nucleotide modification, Biotin, Fluorescein, Amine-linkers, oligo-peptides, Aminoallyl, a dye molecule, fluorophores, Digoxygenin, Acrydite, Adenylation, Azide, NHS-Ester, Cholesteryl-TEG, Alkynes, Photocleavable Biotin, Thiol, Dithiol, Modified bases, phosphate, 2-Aminopurine, Trimer-20, 2,6-Diaminopurine, 5-Bromo-deoxiUridine, DeoxiUridine, Inverted dT, dideoxi-nucleotides, 5-methyl deoxyCytidine, deoxyInosine, 5-nitroindole, 2-O-methyl RNA bases, Iso-dC, Iso-dG, Flourine modified bases and Phosphorothioate bonds, and proteins covalently bound by their interaction with the specific nucleotide sequences. In some embodiments, proteins covalently bound by their interaction with the specific nucleotide sequences may be selected from, but not limited to: *Agrobacterium* VirD2 protein, Picornavirus VPg, Topoisomerase, PhiX174 phage A protein, PhiX A* protein and any variants thereof.

In some embodiments, the attachment/binding/association between the modification on the SCNA and the linking domain results from an interaction of a binding-pair selected from non-covalent interaction of a binding-pair selected from, but not limited to: Biotin-Avidin; Biotin-Streptavidin; Biotin-modified forms of Avidin; protein-protein; protein-nucleic acid interactions; ligand-receptor interactions; ligand-substrate interactions; antibody-antigen; single chain antibody-antigen; antibody or single chain antibody-hapten; hormone-hormone binding protein; receptor-agonist; receptor-receptor antagonist; IgG-protein A; enzyme-enzyme cofactor; enzyme-enzyme inhibitor; single-strand DNA-VirE2; StickyC-dsDNA; RISC-RNA; viral coat protein-nucleic acid; anti-Fluorescein single-chain variable fragment antibody (anti-FAM ScFV)-Fluorescein; anti-DIG single-chain variable fragment (scFv) immunoglobin (DIG-ScFv)-Digoxigenin (DIG) and *Agrobacterium* VirD2-VirD2 binding protein; and any variants thereof.

In some embodiments, the recognition region of the SCNA comprises a nucleotide motif capable of specifically attaching/binding/associating to the linking domain of the chimeric protein. In some embodiments, the attachment/association/binding between the nucleotide motif and the linking domain is selected from, but not limited to: Zinc finger protein-Zinc finger motif; restriction enzyme recognition domain-restriction enzyme recognition sequence; DNA binding domain of transcription factor-DNA motif; repressor-operator; Leucine zipper-promoter; Helix loop helix-E box domain; RNA binding motifs comprising Arginine-Rich Motif domains, $\alpha\beta$ protein domains, RNA Recognition Motif (RRM) domains, K-Homology Domains, Double Stranded RNA Binding Motifs, RNA-binding Zinc Fingers, and RNA-Targeting Enzymes-cognate specific RNA sequence; HIV-rev protein-Stem IIB of the HIV rev response element (RRE); Bovine immunodeficiency virus (BIV) Tat main binding domain-loop 1 of the BIV transacting response element (TAR) sequence; Phage lambda, phi21, and P22 Nproteins—The boxB loop hairpins in the N-utilization (nut) sites in their respective RNAs.

According to some embodiments, there is provided a method for modifying a predetermined target site within a target nucleic acid sequence by a programmable nucleoprotein molecular complex, the method comprising the steps of: a) delivering a nucleic acid sequence encoding a programmable chimeric protein (polypeptide) or the protein (polypeptide) to a host cell; b) delivering a specificity-conferring nucleic acid (SCNA) molecule, or a nucleic acid encoding for the SCNA to said host cell; c) binding of said chimeric protein to the SCNA, thereby targeting the chimeric protein to the predetermined target nucleic acid sequence within the host cell, to form an active programmed nucleoprotein complex; and d) allowing the modification of the predetermined target site of the target nucleic acid sequence by said active programmed nucleoprotein molecular complex.

In some embodiments, there is provided a method for modifying a predetermined target site within a target nucleic acid sequence by a programmable nucleoprotein molecular complex, the method comprising the steps of:
a. delivering a nucleic acid sequence encoding a programmable chimeric polypeptide to a host cell, said chimeric polypeptide comprising:
 (i) a functional domain capable of modifying said target site, the functional domain being devoid of a specific nucleic acid binding site; and
 (ii) a linking domain that is capable of interacting with a specificity conferring nucleic acid, wherein the linking domain being devoid of a specific target-nucleic acid binding site;
b. delivering a specificity-conferring nucleic acid (SCNA) molecule, or a nucleic acid encoding the SCNA to said host cell, said SCNA molecule comprising:
 (i) a nucleotide sequence complementary to a region of the target nucleic acid flanking the target site; and
 (ii) a recognition region capable of specifically attaching to the linking domain of the polypeptide with high binding affinity;
wherein expression of the polypeptide in the cell harboring the SCNA enables attachment of said chimeric polypeptide to the SCNA, forming an active programmed nucleoprotein complex, thereby targeting the chimeric polypeptide to the predetermined target nucleic acid sequence within the host cell, enabling the modification of the predetermined target site of the target nucleic acid sequence by said active programmed nucleoprotein molecular complex.

In some embodiments, the target nucleic acid is DNA. In some embodiments, the target DNA is genomic DNA. In some embodiments, the target nucleic acid sequence is an extra-chromosomal nucleic acid sequence. In some embodiments, the extra-chromosomal target nucleic acid sequence resides in an organelle selected from the group consisting of mitochondria, chloroplast, amyloplast and chromoplast. In some embodiments, the target nucleic acid sequence is a viral nucleic acid sequence. In some embodiments, the target nucleic acid sequence is a prokaryotic nucleic acid sequence. In some embodiments, the target nucleic acid sequence is a synthetic nucleic acid sequence.

In some embodiments, the modification is selected from mutation, deletion, insertion, replacement, binding, digestion, double-strand-break creation, nicking, methylation, acetylation, ligation, recombination, helix unwinding, chemical modification, labelling, activation and inactivation.

In some embodiments, the chimeric protein (polypeptide) comprises a protein moiety having a nucleic acid modifying activity. In some embodiments, the chimeric protein comprises a protein moiety having a nucleic acid functional modifier, wherein the functional modification is selected from the group consisting of transcriptional activation, transcriptional inactivation, RNA transcript silencing, alternative RNA splicing, chromatin rearrangement, cellular parasite and virus inactivation and change in cellular localization or compartmentalization of said target nucleic acid sequence.

In some embodiments, the SCNA comprises a molecule selected from the group consisting of a single-strand DNA, a single strand RNA, a double strand RNA, a modified DNA, a modified RNA, a locked-nucleic acid (LNA) and a peptide-nucleic acid (PNA) or combinations thereof. In some embodiments, the SCNA comprises a specificity-defining sequence configured to specifically interact with the target nucleic acid. The interaction between the SCNA and the target nucleic acid is through base pairing, selected from the group consisting of a full double helix base pairing, a partial double helix base pairing, a full triple helix base pairing, a partial triple helix base pairing, and D-loops or branched forms, formed by said base pairing.

In additional embodiments, the SCNA comprises a recognition region, configured to associate/bind/attach with a linking domain of the chimeric protein. In some embodiments, the recognition region comprises a modification selected from the group consisting of 5'-end modification, 3'-end modification, and internal modification. The modification may be selected from, but not limited to nucleotide modification, Biotin, Fluorescein, Amine-linkers, oligo-peptides, Aminoallyl, a dye molecule, fluorophores, Digoxygenin, Acrydite, Adenylation, Azide, NHS-Ester, Cholesteryl-TEG, Alkynes, Photocleavable Biotin, Thiol, Dithiol, Modified bases, phosphate, 2-Aminopurine, Trimer-20, 2,6-Diaminopurine, 5-Bromo-deoxiUridine, DeoxiUridine, Inverted dT, dideoxi-nucleotides, 5-methyl deoxyCytidine, deoxyInosine, 5-nitroindole, 2-O-methyl RNA bases, Iso-dC, Iso-dG, Flourine modified bases and Phosphorothioate bonds, and proteins covalently bound by their interaction with the specific nucleotide sequences. The proteins covalently bound by their interaction with the specific nucleotide sequences are selected from Agrobacterium VirD2 protein, Picornavirus VPg, Topoisomerase, PhiX174 phage A protein, PhiX A* protein and any variants thereof.

In some embodiments, the association/binding/attachment between the modification on the SCNA and the linking domain results from a non-covalent interaction of a binding-pair selected from: Biotin-Avidin; Biotin-Streptavidin; Biotin-modified forms of Avidin; Protein-protein interactions; protein-nucleic acid interactions; ligand-receptor interactions; ligand-substrate interactions; antibody-antigen interactions; single chain antibody-antigen; antibody or single chain antibody-hapten interactions; hormone-hormone binding protein; receptor-agonist; receptor-receptor antagonist; anti-Fluorescein single-chain variable fragment antibody (anti-FAM ScFV)-Fluorescein; anti-DIG single-chain variable fragment (scFv) immunoglobin (DIG-ScFv)-Digoxigenin (DIG); IgG-protein A; enzyme-enzyme cofactor; enzyme-enzyme inhibitor; single-strand DNA-VirE2; StickyC-dsDNA; RISC-RNA; viral coat protein-nucleic acid and Agrobacterium VirD2-VirD2 binding protein; and any variants thereof.

In some embodiments, binding/association between the specificity conferring nucleic acid sequence and the linking domain of the protein moiety is covalently created in vivo. In some embodiments, the covalent association of the linking domain and the SCNA results from a biological interaction of Agrobacterium VirD2-Right border sequence or any variants thereof, and is created in a bacterium comprising Agrobacterium.

In some embodiments, the recognition region comprises a nucleotide motif capable of interacting/attaching/binding with the linking domain of the chimeric protein. In some embodiments, the interaction pair is selected from: Zinc finger protein-Zinc finger motif; restriction enzyme recognition domain-restriction enzyme recognition sequence; DNA binding domain of transcription factor-DNA motif; repressor-operator; Leucine zipper-promoter; Helix loop helix-E box domain; RNA binding motifs comprising Arginine-Rich Motif domains, αβ protein domains, RNA Recognition Motif (RRM) domains, K-Homology Domains, Double Stranded RNA Binding Motifs, RNA-binding Zinc Fingers, and RNA-Targeting Enzymes-cognate specific RNA sequence; HIV-rev protein-Stem IIB of the HIV rev response element (RRE); Bovine immunodeficiency virus (BIV) Tat main binding domain-loop 1 of the BIV trans-acting response element (TAR) sequence; Phage lambda, phi21, and P22 Nproteins—The boxB loop hairpins in the N-utilization (nut) sites in their respective RNAs.

According to some embodiments, the predetermined target nucleic acid sequence is involved in a genetic trait, and the modification results in changes in the transcription or translation of a genetic element, by a technical procedure selected from the group consisting of permanently replacing, knocking-out, temporarily or permanently enhancing, shutting-off, knocking-down, and frameshifting. In some embodiments, the genetic trait is modified by editing the genetic element sequence itself, its regulatory sequences, genes regulating the gene of interest or their regulatory sequences in a regulatory chain of events.

According to further embodiments, there is provided a nucleo-protein complex, wherein a physical association between the protein moiety and the specificity conferring nucleic acid moiety form a programmed functional complex. In some embodiments, the physical association between the linking domain of the protein moiety and the SCNA is based on an affinity interaction selected from the group consisting of ligand-receptor, ligand-substrate, hydrogen bonds, van der Waals bonds, ionic bonds and hydrophobic interaction.

According to some embodiments, there is provided a host cell having a predetermined genetic modification in a predetermined target site, created by the method disclosed herein. In some embodiments, the host cell may be any type of cell, such as, but not limited to: vertebrate cell, mammalian cell, human cell, animal cell, plant cell, invertebrate cell, nematodal cell, insect cell, and a stem cell.

According to some embodiments, there is provided a transgenic organism or knock out organism, having a predetermined genetic modification formed by the method described herein. In some embodiments, the organism is a plant or an animal.

According to some embodiments, there is provided a method of treating a genetic disease in an organism, the method comprising introducing into a cell of the organism the nucleoprotein programmable molecular complex.

According to some embodiments, there is provided a host cell comprising:

a) a polypeptide comprising: (i) a functional domain capable of modifying a target site in a target nucleic acid sequence in the cell, the functional domain being devoid of a specific nucleic acid binding site; and (ii) a linking domain that is capable of interacting with a specificity conferring nucleic acid and being devoid of a specific target-nucleic acid binding site; and;

(b) a specificity conferring nucleic acid (SCNA) comprising:
  (i) a nucleotide sequence complementary to a region of the target nucleic acid flanking the target site; and (ii) a recognition region capable of specifically attaching to the linking domain of the polypeptide;
whereby assembly of the polypeptide and the SCNA within the host cell forms a functional nucleoprotein complex, capable of specifically modifying the target nucleic acid at the target site.

In some embodiments, there is provided a host cell harbouring: (a) a polynucleotide molecule encoding for a polypeptide, the polypeptide comprising: (i) a functional domain capable of modifying a target site in a target nucleic acid sequence in the cell, the functional domain being devoid of a specific nucleic acid binding site; and (ii) a linking domain that is capable of interacting with a specificity conferring nucleic acid and being devoid of a specific target-nucleic acid binding site; and (b) a specificity conferring nucleic acid (SCNA) comprising: (i) a nucleotide sequence complementary to a region of the target nucleic acid flanking the target site; and (ii) a recognition region capable of specifically attaching to the linking domain of the polypeptide; whereby assembly of the polypeptide and the SCNA within the host cell forms a functional nucleoprotein complex, capable of specifically modifying the target nucleic acid at the target site.

BRIEF DESCRIPTION OF THE DRAWINGS

FIGS. 2A-B are schematic cartoons showing the assembly of the programmable molecular complex, according to some embodiments;

FIG. 6 is a general scheme demonstrating the delivery of the programmable molecular complex to a cell using an in-vivo produced SCNA, according to some embodiments;

DETAILED DESCRIPTION OF THE INVENTION

Figure 1A:
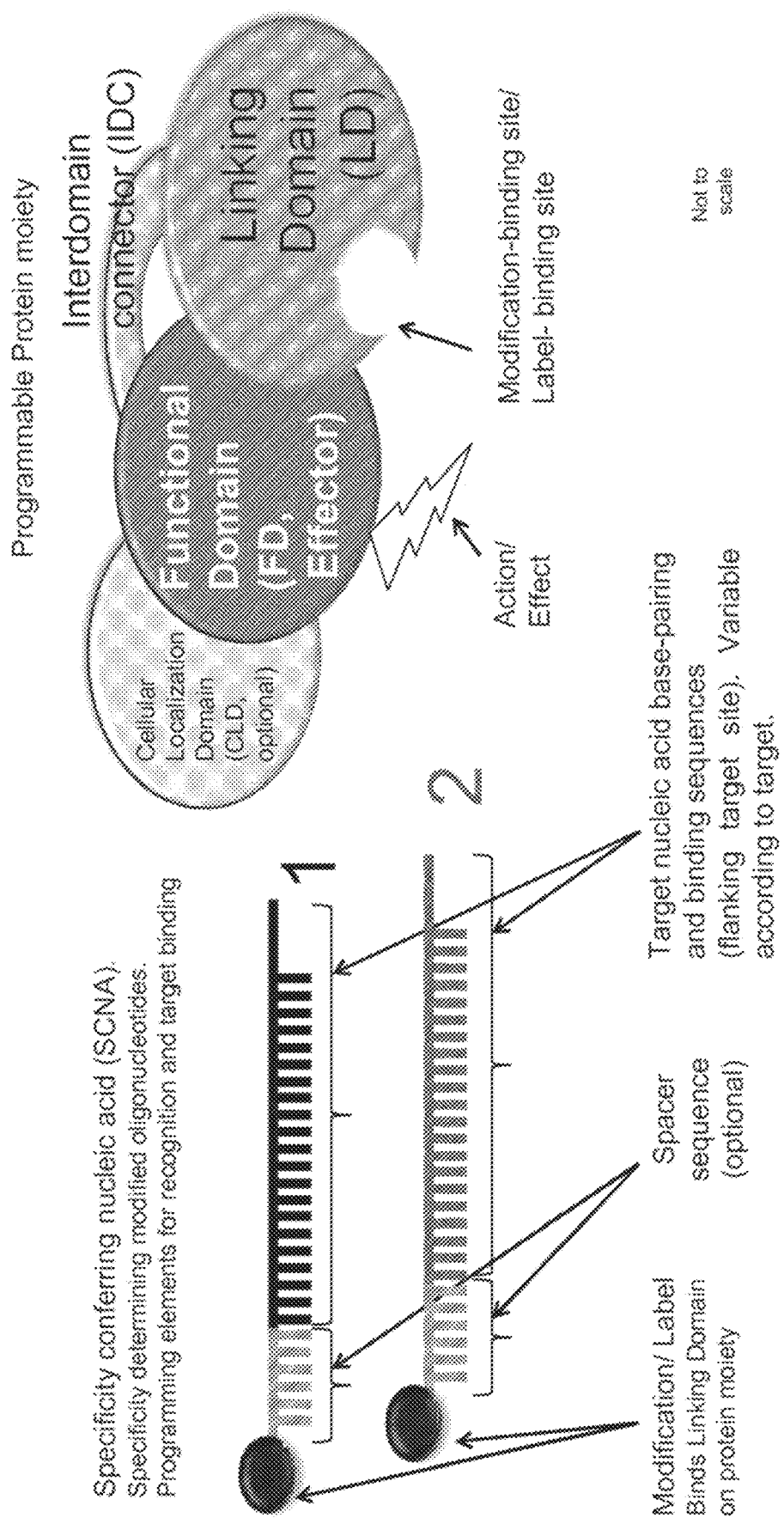
FIGS. 1A-B are schematic cartoons showing elements/components of a programmable molecular complex, according to some embodiments.

According to some embodiments, there are provided compositions and methods for modifying a predetermined target nucleic acid. Specifically disclosed are methods for modifying a target sequence in-vivo, using a composition which comprises a programmable molecular complex. The programmable molecular complex (also referred to herein as a "nucleo-protein complex") comprises a protein moiety, (also referred to herein as a "programmable moiety"), and a nucleic acid moiety, (also referred to herein as a "specificity-conferring nucleic acid" (SCNA) or "the programming nucleic acid"). According to some embodiments, the components of the molecular complex self-assemble in-vivo in a living cell, organism, tissue, callus, organ or part thereof, whether differentiated or not, in the presence of a target nucleic acid sequence(s) to form an active, programmed functional molecular complex.

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

Definitions about

As used herein, the term "about" refers to +/−10%.

administering

"Administering" is directed to providing a pharmaceutical agent or composition to a subject, and includes, but is not limited to, administering by a medical professional and self-administering.

"Parenteral administration," means administration not through the intestines. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Chemoembolization" means a procedure in which the blood supply to a tumor is blocked surgically or mechanically and chemotherapeutic agents are administered directly into the tumor.

antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

autonomously replicating vectors

"Autonomously replicating vectors" are defined here as to comprise any natural or un-natural nucleic acid sequence capable of replicating within a host, comprising but not limited to viruses, modified viruses, certain recombinant vectors and plasmids, replicons and intracellular parasites.

cell

"Cell" is defined here as to comprise any type of cell, prokaryotic or a eukaryotic cell, isolated or not, cultured or not, differentiated or not, and comprising also higher level organizations of cells such as tissues, organs, calli, organisms or parts thereof. Exemplary cells include, but are not limited to: vertebrate cells, mammalian cells, human cells, plant cells, animal cells, invertebrate cells, nematodal cells, insect cells, stem cells, and the like.

complement

"Complement" or "complementary" as used herein means Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules. Partial complementary may mean less than 100% complementarity, for example 80% complementarity.

delivery vector

"delivery vector" or "delivery vectors" is directed to any delivery vector which can be used in the present invention to put into cell contact or deliver inside cells or subcellular compartments agents/chemicals and molecules (proteins or nucleic acids) needed in the present invention. It includes, but is not limited to, transducing vectors, liposomal delivery vectors, plasmid delivery vectors, viral delivery vectors, bacterial delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, nucleic acid(s), proteins), or other vectors such as plasmids and T-DNA. These delivery vectors are molecule carriers.

dose

"Dose" as used herein means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

dosage unit

"Dosage unit" as used herein means a form in which a pharmaceutical agent is provided. In certain embodiments, a dosage unit is a vial containing lyophilized oligonucleotide. In certain embodiments, a dosage unit is a vial containing reconstituted oligonucleotide.

donor nucleic acid

"Donor nucleic acid" is defined here as any nucleic acid supplied to an organism or receptacle to be inserted or recombined wholly or partially into the target sequence either by DNA repair mechanisms, homologous recombination (HR), or by non-homologous end-joining (NHEJ).

duration

"Duration" as used herein means the period of time during which an activity or event continues. In certain embodiments, the duration of treatment is the period of time during which doses of a pharmaceutical agent or pharmaceutical composition are administered.

expression vector

"Expression vector" as used herein means any nucleic acid designed to artificially encode an exogenous protein or proteins in a host cell. Examples for expression vectors comprise plasmid DNA, T-DNA, Virus-RNA, ssDNA or dsDNA, Replicons, autonomously replicating vectors, linear ssDNA, linear dsDNA, phi polymerase products, RNA transcript, circular RNA, and in some applications of this invention, genomic and organellar DNA transferred into the host cell.

fragment

"Fragment" is used herein to indicate a non-full length part of a nucleic acid or polypeptide. Thus, a fragment is itself also a nucleic acid or polypeptide, respectively.

gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

gene targeting

"Gene targeting" is used herein as any genetic technique that induces a permanent change to a target nucleic acid sequence including deletion, insertion, mutation and replacement of nucleotides in a target sequence.

genomic modification

"Genomic modification" is used herein as any modification generated in a genome or a chromosome or extrachromosomal DNA or organellar DNA of an organism as the result of gene targeting or gene-functional modification.

host cell

"Host cell" used herein may be a naturally occurring cell or a transformed cell that may contain a vector. Host cells may be cultured cells, explants, cells in vivo, and the like. Host cells may be prokaryotic cells such as *E. coli*, or eukaryotic cells such as plant, yeast, insect, amphibian, or mammalian cells, such as CHO and HeLa.

According to some embodiments, said host cell is a whole or partial, differentiated or undifferentiated, cell in organism, organ, tissue or callus.

identity

"Identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

inhibit

"Inhibit" as used herein may mean prevent, suppress, repress, reduce or eliminate.

in-vitro

"In-vitro" is defined herein as an artificial environment outside the membranes of a whole or partial, differentiated or undifferentiated, living organism, organ, tissue, callus or cell. In some embodiments, the term in-vitro is not inside a viable cell.

in-vivo

"In-vivo" is defined herein as inside a whole or partial, differentiated or undifferentiated, organism, organ, tissue, callus or cell.

kits

A kit as used herein may comprise the compositions described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

label

"Label" as used herein means a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

mismatch

"Mismatch" means a nucleobase of a first nucleic acid that is not capable of pairing with a nucleobase at a corresponding position of a second nucleic acid.

modified oligonucleotide

"Modified oligonucleotide" as used herein means an oligonucleotide having one or more modifications relative to a naturally occurring terminus, sugar, nucleobase, and/or internucleoside linkage.

modulation

"Modulation" as used herein means a perturbation of function and/or activity and/or structure. In certain embodiments, modulation means an increase in gene expression. In certain embodiments, modulation means a decrease in gene expression.

mutant

"Mutant" as used herein refers to a sequence in which at least a portion of the functionality of the sequence has been lost, for example, changes to the sequence in a promoter or enhancer region will affect at least partially the expression of a coding sequence in an organism. As used herein, the term "mutation," refers to any change in a sequence in a nucleic acid sequence that may arise such as from a deletion, addition, substitution, or rearrangement. The mutation may also affect one or more steps that the sequence is involved in. For example, a change in a DNA sequence may lead to the synthesis of an altered mRNA and/or a protein that is active, partially active or inactive.

nucleic acid

"Nucleic acid sequence" or "oligonucleotide" or "polynucleotide" as used herein mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods. A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, NH2, NHR, NR2 or CN, wherein R is C1-C6 alkyl, alkenyl or alkynyl and halo is F, Cl, Br or I. Modified nucleotides also include nucleotides conjugated with cholesterol through, e.g., a hydroxyprolinol linkage. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver. Mixtures of naturally occurring nucleic acids and analogs may be made; alternatively, mixtures of different nucleic acid analogs, and mixtures of naturally occurring nucleic acids and analogs may be made.

operably linked

"Operably linked" used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, CaMV 35S promoter, NOS promoter, heat-shock promoters, Steroid-regulated promoters, Metal-regulated promoters, Seed promoters and plant ubiquitin promoters.

recombinant host cells

"Recombinant host cells" refers to cells which have been transformed with vectors constructed using recombinant DNA techniques.

selectable marker

"Selectable marker" used herein may mean any gene which confers a phenotype on a host cell, tissue, organ, callus or organism in which it is expressed to facilitate their identification and/or selection of those which are transfected or transformed with a genetic construct. Representative examples of selectable markers include the ampicillin-resistance gene (AmpR), tetracycline-resistance gene (TcR), bacterial kanamycin-resistance gene (KanR), zeocin resistance gene, the AURI-C gene which confers resistance to the antibiotic aureobasidin A, phosphinothricin-resistance gene (Bar), neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene. In some embodiments of this invention a selectable marker can be produced from a modification of an endogenous gene, for example abolishment of a chemokine receptor expressed and displayed on the surface of a cell when a mutation of this gene results in a frame-shift mutation and can then be negatively selected with an antibody, or for example a W568L mutation in the Tobacco Acetolactate synthase gene which results in resistance the herbicides chlorsulfuron and imazaquin.

stringent hybridization conditions

"Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength and pH. The $T_m$ may be the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

complementary

"complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

substantially Identical

"Substantially identical" as used herein means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

target nucleic acid

"Target nucleic acid" or "target sequence" as used herein is any desired predetermined nucleic acid sequence to be acted upon, including but not limited to coding or non-coding sequences, genes, exons or introns, regulatory sequences, intergenic sequences, synthetic sequences and intracellular parasite sequences. In some embodiments, the target nucleic acid resides within a target cell, tissue, organ or organism. The target nucleic acid comprises a target site, which includes one or more nucleotides within the target sequence, which are modified to any extent by the methods and compositions disclosed herein. For example, the target site may comprise one nucleotide. For example, the target site may comprise 1-300 nucleotides. For example, the target site may comprise about 1-100 nucleotides. For example, the target site may comprise about 1-50 nucleotides. For example, the target site may comprise about 1-35 nucleotides. In some embodiments, a target nucleic acid may include more than one target site, that may be identical or different.

targeted gene-functional modification

"Targeted gene-functional modification" and "target gene modification" are directed to any genetic technique that results in a permanent or temporary alteration in a target nucleic acid, including but not limited to deletion, insertion, mutation, replacement, nicking, methylation, acetylation, ligation, recombination, helix unwinding, chemical modification, labelling, activation, inactivation and repression of one or more nucleotides in a target sequence.

therapy

"Therapy" as used herein means a disease treatment method. In certain embodiments, therapy includes, but is not limited to, chemotherapy, surgical resection, transplant, and/or chemoembolization.

transgenic organism

The term is directed to an organism having one or more target gene modification(s) in it's genome, introduced by the compositions and methods disclosed herein. For example, modification is selected from: insertion, mutation, replacement of one or more nucleotides, nicking, methylation, acetylation, ligation, recombination, helix unwinding, chemical modification, labelling, activation, inactivation and/or repression. The organism may be any type of organism, such as, human, animal, plant, and the like.

transient expression

"Transient expression" or "transiently expressing" used herein may refer to the transcription, or translation from a provided nucleic acid in a whole or partial, differentiated or undifferentiated, organism, organ, tissue, callus or cell, said expression being limited due to non-integration of the provided nucleic acid into the stable nucleic acids of the organism, organ, tissue, callus or cell comprising the genome or organellar nucleic acids. Vectors for transient expression comprise provided linear or circular ssDNA, dsDNA or RNA, plasmids, autonomously replicating vectors, viruses, in-vitro transcripts, T-DNA, synthetic nucleic acids and modified derivatives thereof. Thus, while transient expression is non-hereditable by definition, it may be expressed continuously in cell lineages and autonomously transferred from cell to cell due to nucleic acid replication outside of a chromosome or an organellar-genome.

treat

"Treat" or "treating" used herein when referring to protection of a subject from a condition may mean preventing, suppressing, repressing, or eliminating the condition. Preventing the condition involves administering a composition described herein to a subject prior to onset of the condition. Suppressing the condition involves administering the composition to a subject after induction of the condition but before its clinical appearance. Repressing the condition involves administering the composition to a subject after clinical appearance of the condition such that the condition is reduced or prevented from worsening. Elimination of the condition involves administering the composition to a subject after clinical appearance of the condition such that the subject no longer suffers from the condition.

variant

"Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

vector

"Vector" as used herein means a nucleic acid sequence used for the purpose of nucleic acid delivery. A vector may be used in this invention to bring about genetic transformation, the expression of a protein, the transcription of an RNA, or to be used directly as a Donor for homologous recombination or non-homologous end-joining. A vector may be a plasmid DNA, T-DNA, Virus-RNA, ssDNA or dsDNA, Replicons, autonomously replicating vectors, linear or circular ssDNA, linear or circular dsDNA, branched phi polymerase products, nucleic acid dendrimers, RNA transcript, circular RNA, bacteriophage, bacterial artificial chromosome or yeast artificial chromosome and in some applications of this invention, genomic and organellar DNA transferred into the host cell. A vector may be either non-replicating, a self-replicating extrachromosomal vector or a vector which integrates into a host genome.

wild type

As used herein, the term "wild type" sequence refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

According to some embodiments, the composition comprising the programmable molecular complex which comprises a protein (polypeptidic) moiety, and a nucleic acid moiety, self-assemble in-vivo in a living cell, organism, tissue, callus, organ or part thereof, in the presence of a target nucleic acid sequence(s) to form an active, programmed functional molecular complexes.

According to some embodiments, the various programmed molecular complexes can be constructed to permanently or transiently modify an existing or imminent eukaryotic, prokaryotic, synthetic, intracellular parasite or viral target sequence such as that found in a genome, a nucleus, a chromosome, a cytoplasm, an organelle, or an extra-chromosomal nucleic acid. The target modification performed by the action of the molecular complex comprises heritable and non-heritable, permanent and transient genetic changes/modifications. In some embodiments, the target is comprised of a nucleic acid involved in a genetic trait of interest which would be advantageous to alter. Alterations in the targeted sequence include, for example, but not limited to: permanent deletion, mutation, insertion of nucleic acids, and replacement of a targeted sequence with another nucleic acid sequence, knocking-out, frame-shifting, or any change in any fashion of the transcription or translation of a gene, its regulatory sequences, the genes regulating the gene of interest or their regulatory sequences in a regulatory chain of events. Permanent changes to the target nucleic acid include, for example, genetic material editing or sequence alterations such as nucleic-acid mutation, deletion, insertion, replacement and recombination. Transient changes to the target sequence include, for example, binding, digestion, nicking, helix unwinding, activation, inactivation, chemical modification, methylation, acetylation and labelling of the target nucleic acid. Target modification include, for example, target functional modification which can lead in the cell to changes in transcriptional activation, transcriptional inactivation, RNA silencing, alternative RNA splicing, chromatin rearrangement, intracellular parasite inactivation, and changes in cellular localization or compartmentalization of the target nucleic acid.

According to some embodiments, and without wishing to be bound to any theory or mechanism, the design of the programmable molecular complex, is based on its ability to self-assemble, its ability to target a predefined intended sequence on a target nucleic acid, and its ability to act upon the target sequence in a predetermined fashion. The components of the complex are modular and adjustable to be suitable for 1) particular types of molecular action required, 2) the target, and 3) the desired nucleic acid delivery method used for its expression in-vivo. The methods and compositions of the present disclosure have several advantages over other systems known in the art. For example, the protein moieties of the complex are inactive as monomers, and only correct spacing, within a limited range, of the two SCNA oligonucleotides that bind the target nucleic acid at a predetermined sequence, will result in placement of the effector domains of the protein moieties such that they dimerize and are able to specifically act upon the desired, predetermined target site. Such a setting, whereby only dimers of programmed molecular complexes (i.e. complex which comprises a protein moiety linked to the SCNA, which is bound to the target nucleic acid), reduces or completely eliminates potential off-site or non-specific cleavage, since the protein moiety by itself does not bind the target nucleic acid and does not act as a monomer.

According to some embodiments, the active portion (functional domain), of the molecular complex is designed to be activated only upon dimerization of the functional domain of the protein moiety. The unprogrammed protein component is designed to have low or practically no non-specific affinity to nucleic acid sequence and to the target site. Thus, while for all types of modifications a single type of monomer of the protein moiety needs to be expressed, for the minimal functions of point modification, such as, for example, a point mutation mediated by a nuclease domain, or alternatively, a point methylation mediated by a methylase domain, two SCNAs, designed to bind sequences flanking the target site, should be present to affect the correct spacing of the proteins and allow both their binding and their dimerization with each other. This advantageously enhances the sequence-specificity of the complex. In some embodiments, for the editing functions of deletion and replacement, two different sites flanking the region of interest may need to be cleaved concomitantly. In such embodiment, even in this case, only one exogenous protein component needs to be expressed along with four SCNAs. When the oligonucleotides are depleted, either by dilution or by degradation, the unprogrammed expressed protein has no affinity to the target nucleic acid and will cease to act upon it (i.e, in this case, cease cleaving the target nucleic acid).

According to some embodiments the protein (polypeptide) moiety may be expressed as separate polypeptides or as one contiguous protein (polypeptide). In some embodiments, the protein moiety (component) may have one or more identifiable domain(s), identifiable according to structure and/or function (utility). In some embodiments, one structural domain may have more than one utility domain, that is, a separable structural domain may have several functions. According to some embodiments, the protein moiety may comprise one or more of the following structural and/or utility domains: a) an "effector domain" (functional domain), that can interact with and consequently affect the target nucleic acid; and/or b) a "linking domain", that can directly or indirectly specifically bind the SCNA; and/or c) a "cellular localization domain"; and/or d) inter-domain connectors or spacers; and any combination thereof.

According to some embodiments, the "Effector Domain" (also termed herein as "Functional Domain"), interacts with the target nucleic acid after assembly of the molecular complex and exert the intended effect on the target sequence. In some exemplary embodiments, this domain has an enzymatic or catalytic function, comprising a nucleic acid modifying activity. In some embodiments, this domain may be derived from active domains derived from whole, or portions of, or modified portions of proteins of known function such as, a DNA binding protein, a nuclease, a methylase, a methylated DNA binding factor, a transcription factor, a chromatin remodelling factor, a polymerase, a demethylase, an acetylase, a deacetylase, a kinase, a phosphatase, an integrase, a recombinase, a ligase, a topoisomerase, a girase and a helicase. In some embodiments, the functional domain may be constructed by fusing amino-acid sequence(s) of active domains derived from whole, or portions of, or modified portions of proteins of known function comprising a DNA binding protein, a nuclease, a methylase, a methylated DNA binding factor, a transcription factor, a chromatin remodelling factor, a polymerase, a demethylase, an acetylase, a deacetylase, a kinase, a phosphatase, an integrase, a recombinase, a ligase, a topoisomerase, a girase and a helicase. In some embodiments, for an effector domain which is or is derived from a nuclease, the DNA-binding recognition domain of the nuclease may be removed. For example, when the effector domain is derived from a FokI nuclease, the FokI site recognition and binding domains are absent in the Effector domain of the protein moiety. In some embodiments, the effector domain is devoid of a specific target-nucleic acid binding site, i.e., it cannot specifically bind a specific target sequence.

According to some embodiments, the "Linking Domain" is designed to directly or indirectly specifically bind/attach the SCNA (and in particular, to the SCNA recognition region). The binding/attachment between the linking domain and the SCNA can be direct, or indirect through, for example, a modification on the SCNA. The attachments/binding/linking between the linking domain and the SCNA enables in vivo the assemblage of the SCNA with the protein moiety. In some embodiments, the linking domain is constructed by fusing the amino-acid sequence of the protein moiety to amino-acids incorporating a domain which specifically binds a nucleotide sequence or a chemical or a biological element on the specificity-conferring nucleic acid. The physical interaction between the Linking Domain and the Specificity Conferring Nucleic Acid can be due to, but is not limited to, an affinity due to one or more of the following types of interactions; ligand-receptor, ligand-substrate, Hydrogen bonds, van der Waals bonds, Covalent bonds formed in-vivo, Ionic bonds and hydrophobic interactions. Non-covalent binding examples comprise, one or more, of fragments or portions or modified forms of the following: binding-pair examples: Biotin-Avidin; Biotin-Streptavidin; Biotin-modified forms of Avidin; Protein-protein; nucleic acid-protein; ligand-receptor; substrate-ligand; antigen-antibody; antigen-single chain antibody; hapten-antibody or -single chain antibody; hormone-hormone binding protein; agonist-receptor; receptor antagonist-receptor; protein A-IgG; enzyme cofactor-enzyme; enzyme inhibitor-enzyme; single-strand DNA-VirE2; dsDNA-StickyC; RNA-Argonaute family protein; dsRNA-RnaseIII family protein; nucleic acid-viral coat protein and *Agrobacterium* VirD2 or parts thereof-VirD2 binding protein, whereby each of the Specificity-Conferring Nucleic Acid and Linking Domain comprise one of the pair members. In an exemplary embodiment, the Linking Domain contains a single chain antibody ScFV capable of binding the dye Fluorescein which in turn is chemically linked via a linker to a 5'-terminus or a 3'-terminus of the Specificity-Conferring Nucleic Acid, thus enabling the association of the protein moiety and the nucleic acid moiety of the programmable complex. In some embodiments, the Linking Domain is derived from the *C. elegans* PUF5 binding element eight triple-helical repeat, and the Specificity-conferring nucleic acid (SCNA) contains the RNA sequence as set forth in SEQ ID NO:1 (CUCUGUAUCUUGU) at or sufficiently near one of its termini. In this embodiment the protein and SCNA are directly brought together without the need for a chemical modification on the SCNA, permitting its biosynthesis in-vivo as a transcript and thus enabling the in-vivo association of the protein moiety and the nucleic acid moiety of the programmable complex. In some exemplary embodiments, an RNA sequence/molecule capable of forming secondary or tertiary structures (such as hairpin loop), located within the SCNA, interacts with the linking domain of the protein moiety, which is an RNA-motif-binding Linking Domain, derived from the viral TAT proteins (such as, HIV, BIV, and the like). In some exemplary embodiments, a 20-mer boxB RNA hairpin binding sequence from bacteriophage Phi21 is located on the SCNA and is capable of binding/attaching it's counterpart linking Domain on the protein moiety, which is derived from the RNA-binding protein (RBP) bacteriophage Phi21 NProtein. In another exemplary embodiment, which allows the production of the SCNA in-vivo, the Linking Domain is derived from a protein which binds *Agrobacterium* VirD2 protein, comprising VirD2-binding proteins found in bacteria comprising VBP1, VBP2 and VBP3 and artificial single chain antibodies designed to bind VirD2. In this embodiment, the SCNA is produced as a ssDNA from a T-DNA in an *Agrobacterium*, where it is covalently bound at its 5'-terminus to tyrosine 29 of VirD2 which is required for the covalent association, whereby the covalent binding occurs in-vivo. The catalysis occurs in the bacterium and the complex is subsequently exported from the bacterium through a bacterial secretion system into a eukaryotic cell comprising whole or partial plant-, animal- and human-cells, tissues, calli and organs. In this embodiment, the VirD2-binding domain in the Linking Domain binds the VirD2 protein attached to the SCNA thus enabling the association of the protein moiety and the nucleic acid moiety of the programmable complex. In this embodiment, modifications to VirD2 expressed in the bacterium could be designed that would decrease DNA integration and could be of benefit to avoid non-specific DNA integration. Examples of Covalent binding formed in vivo in the target organism, comprise, respectively, on the recognition region of the SCNA, and in the Linking domain, one or more, of fragments or portions or modified forms of, but not limited to, the following binding-pair example paired by a dash symbol; the RB sequence of T-DNA GTTTACCCGC-CAATATATCCTGTCA (SEQ ID NO: 2)-*Agrobacterium* VirD2; Picornavirus RNA-VPg; DNA-Topoisomerase; PhiX174 phage origin sequence on ssDNA-PhiX174 phage A protein or PhiX A* protein, and the like. In one exemplary embodiment of such an in-vivo SCNA-Linking Domain attachment, a synthetic ssDNA oligonucleotide containing an RB sequence at or near its 5'-terminus is delivered to a cell where it encounters the protein moiety. The protein harbours a portion of VirD2 capable of cleaving the RB sequence and subsequently binds the rest of the oligonucleotide containing the sequence TCA at its 5' end, an appropriate spacer, and a target-base-pairing sequence, thus effectively "programming" the molecular complex in-vivo. In some embodiments, the linking domain is devoid of a specific target-nucleic acid binding site, i.e., it cannot specifically bind a specific target sequence.

According to some embodiments, a "cellular localization domain" which can localize the protein moiety or the programmed protein moiety or the assembled complex to a specific cellular or sub cellular localization in a living cell, may optionally be part of the protein moiety. The cellular localization domain may be constructed by fusing the amino-acid sequence of the protein moiety to amino-acids incorporating a domain comprising a Nuclear localization signal (NLS); a Mitochondrial leader sequence (MLS); a Chloroplast leader sequence; and/or any sequences designed to transport or lead or localize a protein to a nucleic acid containing organelle, a cellular compartment or any subdivision of a cell. In some exemplary embodiments, the organism is eukaryotic and the cellular localization domain comprises a nuclear localization domain (NLS) which allows the protein access to the nucleus and the genomic DNA within. The sequence of said NLS may comprise any functional NLS positively charged sequence comprising, for example, the SV40NLS sequence PKKKRKV (SEQ ID NO: 3). In another exemplary embodiment, this domain is comprised of a leader sequence enabling the entry of the protein moiety or of the programmed nucleo-protein into an organelle, enabling the desired modification of the organelle DNA by the complex. In another exemplary embodiment, a sequence derived from the Yeast mitochondrial Cox4p (MLSLRQSIRFFKPATRTLCSSRYLL (SEQ ID NO: 4)) or a sequence derived from the human malate dehydrogenase mitochondrial leader sequence (MLS) (MLSALA-RPASAALRRSFSTSAQNNAKVAVLGAS (SEQ ID NO:

5)) or derived from the *Arabidopsis* Lipoic acid synthase (NCBI Ref. Seq. ID: NP_179682.1 designated herein as SEQ ID NO: 6: MHSRSALLYRFLRPASRCFSSSS) may be used to localize the complex into a mitochondrial matrix to modify mitochondrial DNA. One use of this application may include the curing of maternally inherited mitochondrial DNA defects in various Eukaryotes, such as Chronic Progressive External Ophthalmoplegia Syndrome in Humans. Another example is inducing defects to bring about male sterility in plants used for hybrid plant production. In one embodiment the mitochondrial target is an ATPase and reconstitutes the function of the pcf locus in *Petunia*.

According to further embodiments, optional various interdomain connectors or spacers designed to allow the desired function of the complex by serving as molecular adapters or hinges. Many such connectors may be foreseen by those skilled in the art. Choice of connector may affect the specificity of the programmed molecular complex by affecting the range of target nucleic acid in reach of the functional domain active site. In one exemplary embodiment, the C' of the Linking Domain and the N' of the Functional Domain are flexibly connected with the amino acids GGSGG (SEQ ID NO: 7), spanning about 15 Angstroms. In another embodiment, a rigid Alpha-helix linker with the amino acids NIHHVTWHMDFP (SEQ ID NO: 8) spanning about 16 Angstrom is used. In another embodiment, a rigid helical linker with the amino acids PNSLIVP (SEQ ID NO: 9) spanning about 16.88 Angstrom is used. In another embodiment, a disordered coiled linker with the amino acids TGLDSP (SEQ ID NO: 10) spanning about 15.55 Angstrom is used. Extra amino acids encoded by restriction enzyme sites may be added in the interdomain connector to facilitate exchanging protein modules (e.g. GSLE (SEQ ID NO: 11) encoding BamHI/XhoI).

According to some embodiments, the nucleic-acid moiety of the molecular complex, termed herein "Specificity-conferring nucleic acid" (SCNA) or "programming nucleic acid" comprises one or more portions (regions) and functions. One portion (region) defines the target region to be acted upon, and contains the specificity-defining sequence. The specificity-defining sequence in the SCNA defines its specificity to the target nucleic acid by base pairing. This pairing may form, for example, but not limited to: a full or partial double helix, a full or partial triple helix, D-loops and branched forms, and may be the result of hydrogen bonds or Hoogsteen hydrogen bonds or combinations thereof. In some embodiments, the specificity-defining sequence is capable of interacting with the target nucleic acids, at regions which are proximate to, or flanking the target site. In some embodiments, the specificity-defining sequence of the SCNA does not bind/interact with the target site. In some embodiments, the specificity-defining sequence may include any number of nucleotides. For example, the specificity-defining sequence may be at a length of about 3-200 nucleotides. For example, the specificity-defining sequence may be at a length of about 10-100 nucleotides. For example, the specificity-defining sequence may be at a length of about 15-50 nucleotides. For example, the specificity-defining sequence may be at a length of over about 18 nucleotides.

According to some embodiments, a second portion of the SCNA, is the recognition region (portion), which is a region that can specifically bind/attach/recognize the linking domain of the protein moiety. In some embodiments, this recognition region may be and/or include a modification or a Linking-Domain-recognition sequence (also termed herein as SCNA nucleotide motif or SCNA linking domain-binding nucleotide sequence). The recognition region may be an integral part or may be linked (for example, covalently) to the specificity-defining sequence, and may be composed of a sequence or a modification which enables the binding of the SCNA to the Linking Domain of the protein moiety, as detailed above.

In some embodiments, the SCNA is comprised of but not limited to, a molecule of the following types: single-strand DNA, single strand RNA, double strand RNA, modified DNA, modified RNA, locked-nucleic acid (LNA), peptide-nucleic acid (PNA) and any combinations of the above. In some embodiments, the SCNA may additionally include one or a multiplicity of modifications which may enhance its stability, enhance its specificity to the target, modify its affinity to nucleic acids and/or enable its binding to the Linking Domain of the complex. The modifications may be positioned at its 5' end, at its 3' end, as spacers and/or internally on the SCNA. Exemplary modifications include, but are not limited to, Nucleotides, Biotin, Fluorescein, Amine-linkers, oligo-peptides, Aminoallyl, a dye molecule, fluorophores, Digoxygenin, Acrydite, Adenylation, Azide, NHS-Ester, Cholesteryl-TEG, Alkynes, Photocleavable Biotin, Thiol, Dithiol, Modified bases, phosphate, 2-Aminopurine, Trimer-20, 2,6-Diaminopurine, 5-Bromo-deoxiUridine, DeoxiUridine, Inverted dT, dideoxi-nucleotides, 5-methyl deoxyCytidine, deoxyInosine, 5-nitroindole, 2-O-methyl RNA bases, Iso-dC, Iso-dG, Flourine modified bases, Phosphorothioate bonds and the *Agrobacterium* VirD2 protein and parts of said VirD2 and modifications of VirD2.

According to some embodiments, the SCNA may further include optional spacer sequences that may be used for optimizing the molecular distances and degrees of freedom necessary to bring together the linking domain and a target nucleic acid. In some embodiments, the spacer sequences may be at a length of about 0-100 nucleotides. For example, the spacer may be at a length of about 0-6 nucleotides.

According to some embodiments, the SCNA may be produced chemically and/or biologically, in-vitro and in-vivo, and the modification may be pre-synthesized or added post-synthesis. In some exemplary embodiments, the SCNA is produced chemically and is composed of phosphorothioate-modified ssDNA which is modified at one of its termini by the linking of a C6-Fluorescein dye molecule. This SCNA is consequently delivered to a cell, (for example, by particle bombardment, Polyethylene glycol transfection, liposomes, viral particles, silicon-carbide whiskers and/or electroporation) where it encounters both the protein component of the molecular complex, which comprises a Linking Domain comprising a single chain antibody ScFV capable of binding the dye Fluorescein, thus programming the molecular complex, and delivering/targeting the complex to its intended target nucleotide sequence. According to some embodiments, the SCNA does not bind/interact with the target site.

Figure 1B:
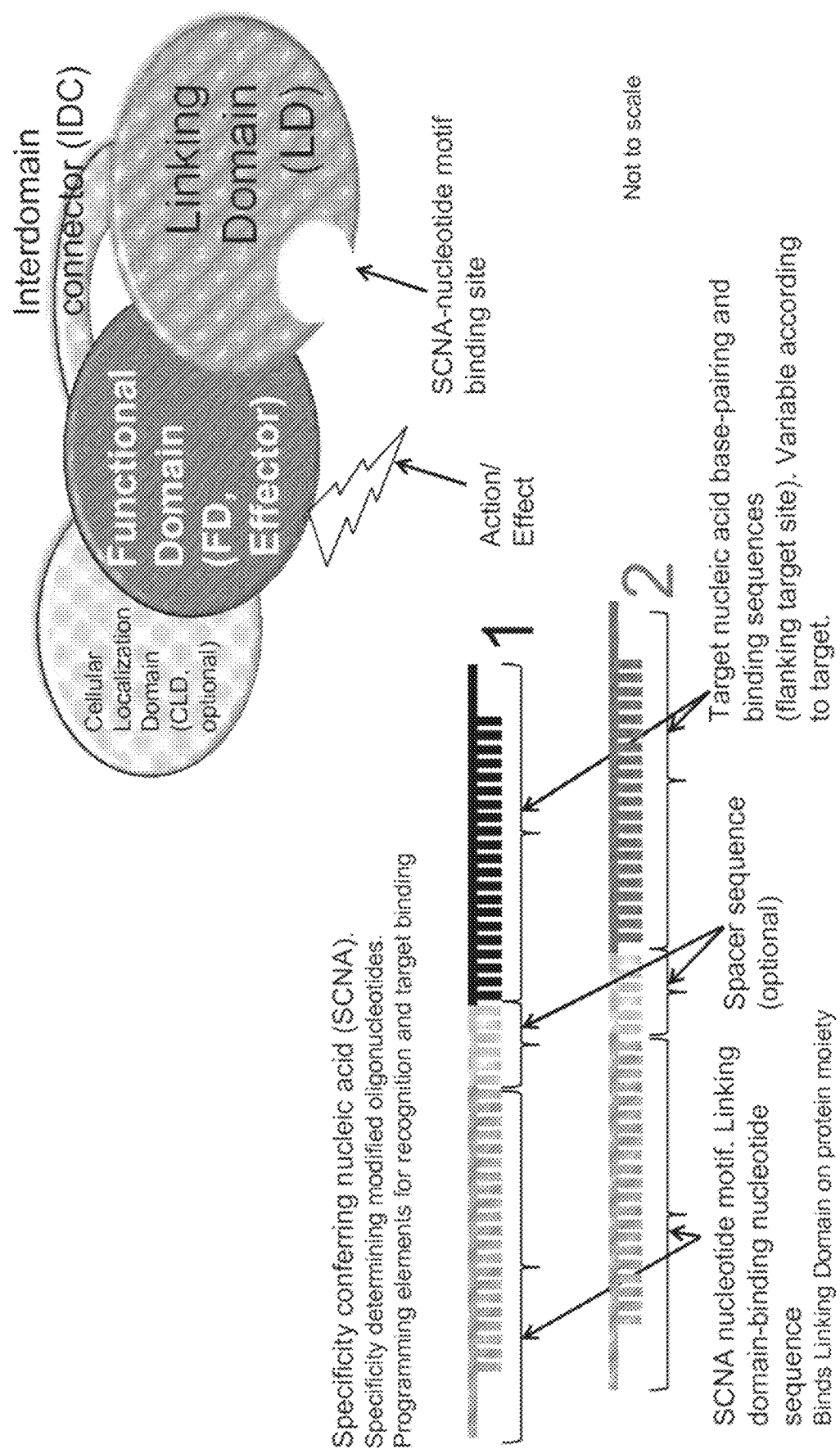

Reference is now made to FIGS. 1A-B which are schematic cartoons (not to scale) showing elements/components of a programmable molecular complex, according to some embodiments. The schematic cartoons (not to scale) of FIGS. 1A-B, show a molecule of a programmable protein moiety as a monomer, and two molecules of specificity conferring nucleic acids (SCNA). As shown in FIGS. 1A-B, the protein moiety is a polypeptide (a chain of amino-acids) arranged into several structural/functional domains: a linking domain (LD), a functional or Effector Domain (FD); an optional Cellular Localization Domain (CLD) and an optional interdomain connector(s) (IDC), each defined by their role in the molecular complex. The function of the linking domain is to bind the SCNA. The function of the Effector domain is to interact with the target nucleic acid and structurally modify the target site and/or modify it's function and/or the function of the entire target nucleic acid. The function of the optional cellular localization domain is to localize the protein complex to the same cellular or subcellular compartment as the target nucleic acid. The function of the optional interdomain connectors is to allow optimal molecular distances and degrees of freedom between domains for the proper function of the complex. The SCNAs are comprised of a nucleic acid chain or a modified nucleic acid chain (comb shape) and include a modification, preferably at one of its termini (shown in FIG. 1A as black oval) for binding to the protein moiety, or a sequence, (termed the SCNA-nucleotide motif, or Linking-domain-binding nucleotide sequence or Linking-Domain-recognition sequence or segment, shown in FIG. 1B, arrow marked comb), which can bind the linking domain on the protein moiety. In the non-limiting example presented in FIGS. 1A-B, the specificity determining portion of the SCNA is single stranded. In some embodiments, the SCNA may form double strand segments/regions (by self annealing, such as forming hairpin loops). The specificity of the SCNA to a predetermined target nucleic acid sequence is achieved through a stretch of base-pairing nucleic acids or modified nucleic acids (Target nucleic acid base-pairing, comb shape), also termed the variable sequence, which may include any number of nucleotides, such as, 3-200 nucleotides, and any ranges thereof. For example, the length can be 10-100 nucleotides. For example, the length can be at least 18 nucleotides. Optional spacer sequences (Spacer sequence, comb shape), may be present for optimizing the molecular distances and degrees of freedom necessary to bring together the linking domain and a target nucleic acid. In some embodiments, the spacer sequences may be at a length of about 0-100 nucleotides. For example, the spacer may be at a length of about 0-6 nucleotides. Action or effect of the functional domain of the protein moiety, which occurs upon binding to the SCNA linking domain and dimerization and its consequent co-localization to the target nucleic acid, is portrayed as a lightning symbol ("Action/Effect").

Figure 2B:
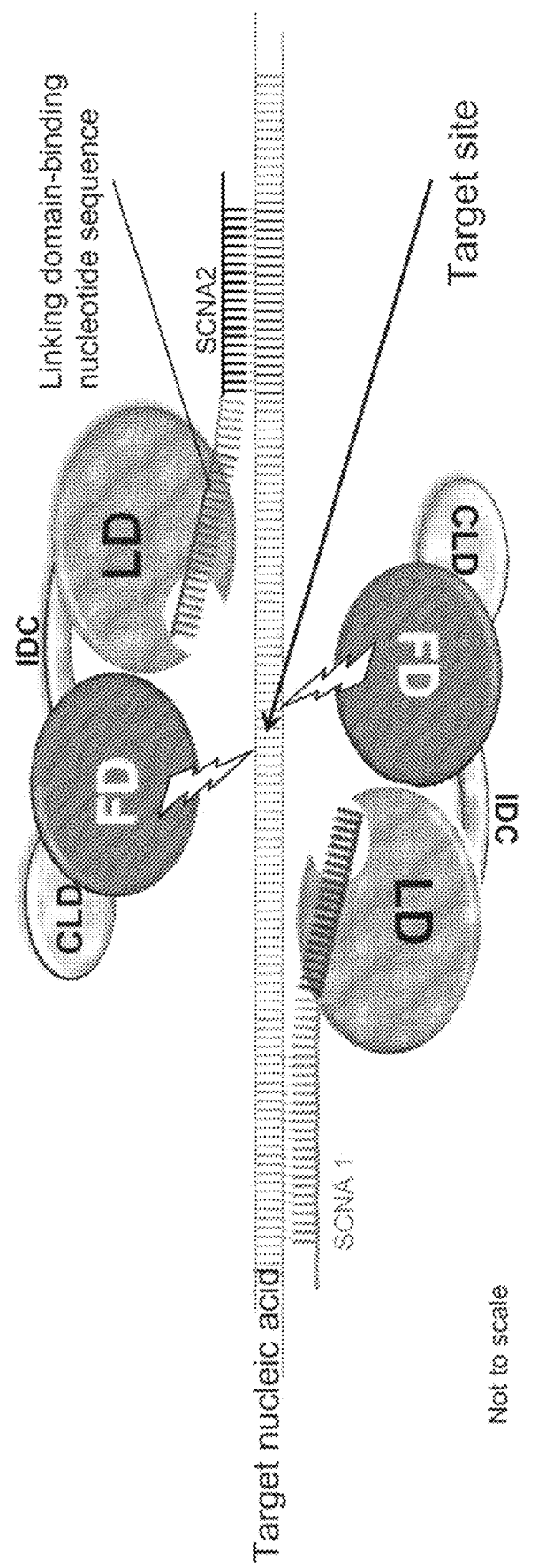

Reference is now made to FIGS. 2A-B, which are schematic cartoons showing the assembly of the programmable molecular complex, according to some embodiments. The schematic cartoons (not to scale) of FIGS. 2A-B demonstrate mode of assembly of the components of the programmable molecular complex on a target nucleic acid. In the example shown in FIGS. 2A-B, two protein monomers bind two different SCNAs, each having a different specificity determinant in its variable sequence region. These SCNAs base pair and bind with predefined homologous sequences on a target nucleic acid (marked in the FIGS. as "Target nucleic acid"). This base pairing can form a double- or a triple-helix with the Target nucleic acid, depending whether the target is double- or single-stranded (illustrated in these figures, as dsDNA). Both SCNAs can bind either the same strand or opposite strands as required, in an optimized distance. The SCNAs can bind the protein Linking Domain through a modification on their terminus (FIG. 2A) or through an SCNA-nucleotide motif (FIG. 2B). Upon assembly the Functional Domain prompts its effect on the predetermined target site (marked as "Target site") on the target nucleic acid.

Figure 3:
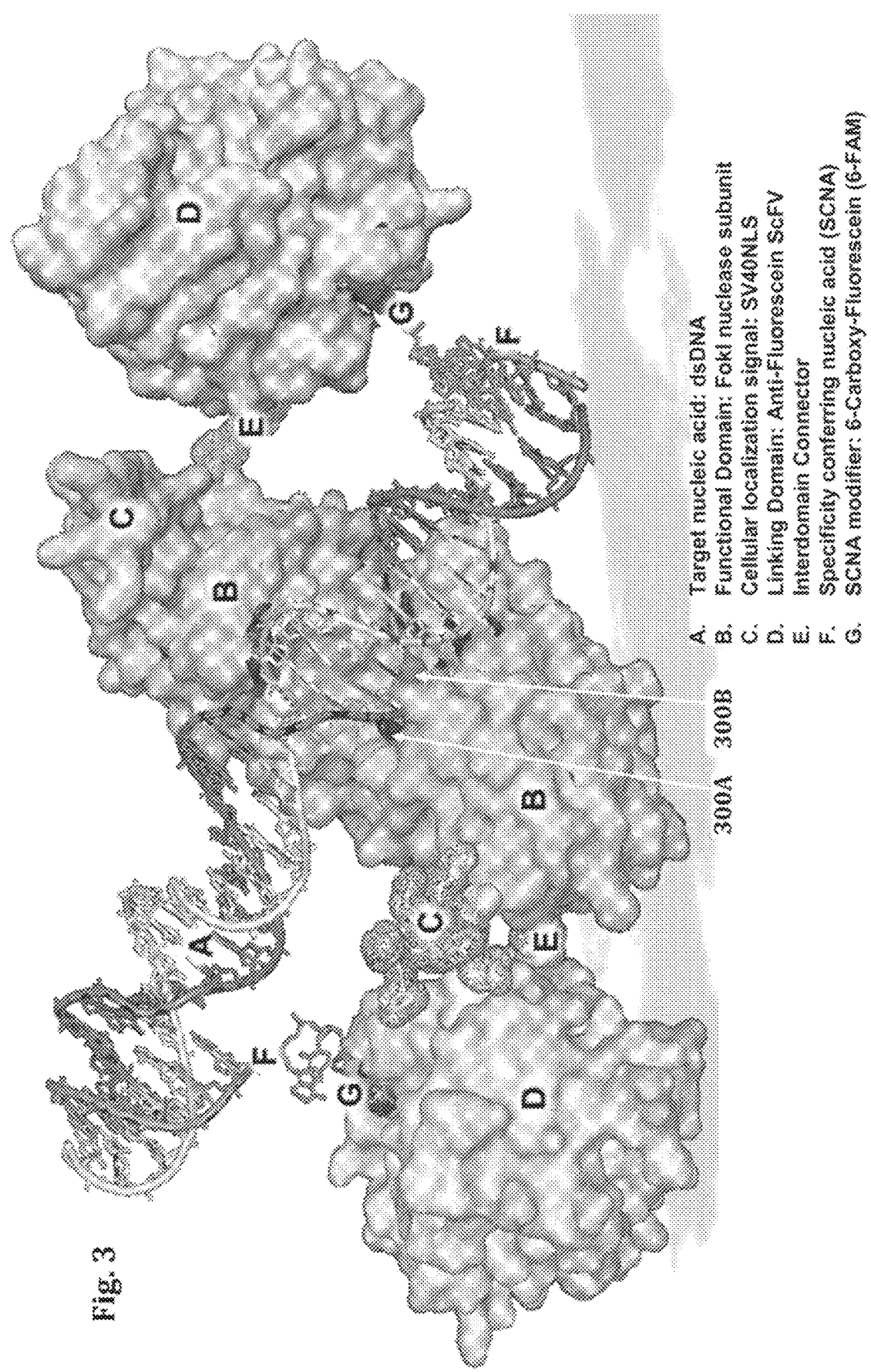
FIG. 3 demonstrates a 3D Modeled example of a molecular complex designed for cleavage of a predefined nuclear dsDNA target sequence, according to some embodiments.

Reference is now made to FIG. 3, which demonstrates a 3D Modeled example of a molecular complex designed for cleavage of a predefined nuclear dsDNA target sequence, according to some embodiments. A programmed dimerized protein moiety is shown in association with its Target dsDNA (A, shown in part). Each monomer of the protein moiety is comprised of a Functional Domain derived from a FokI nuclease subunit (B); a cellular localization domain derived from the SV40NLS (C); a Linking Domain derived from an anti-Fluorescein single-chain variable fragment antibody (anti-FAM ScFV, D) and an interdomain connector (E). Each Linking Domain (D) is shown bound to a Specificity Conferring Nucleic Acid, SCNA ssDNA (F, shown in part) through its modifier 6-carboxy Fluorescein molecule (G), which is covalently bound to the terminus of each SCNA. Expected cleavage sites (target site) of the target dsDNA (shown as balls on the helix backbone) are marked with arrows 300A-B. Each SCNA is depicted here as forming a partial triple-helix occupying the major groove of the dsDNA target-flanking sequence.

Figure 4A:
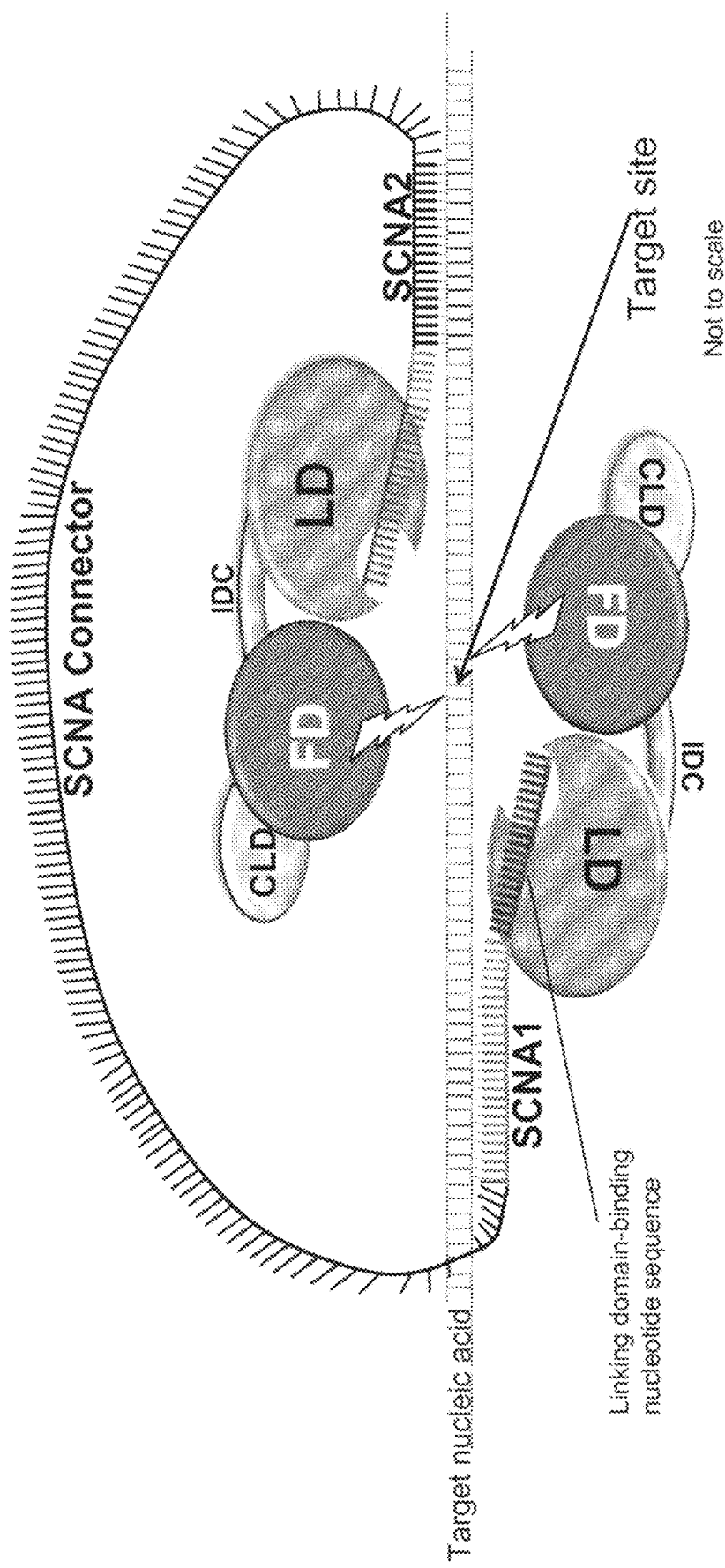
FIGS. 4A-B are schematic drawings (not to scale) of exemplary mode of assembly of the components of the programmable molecular complex on a target nucleic acid, according to some embodiments.
Figure 4B:
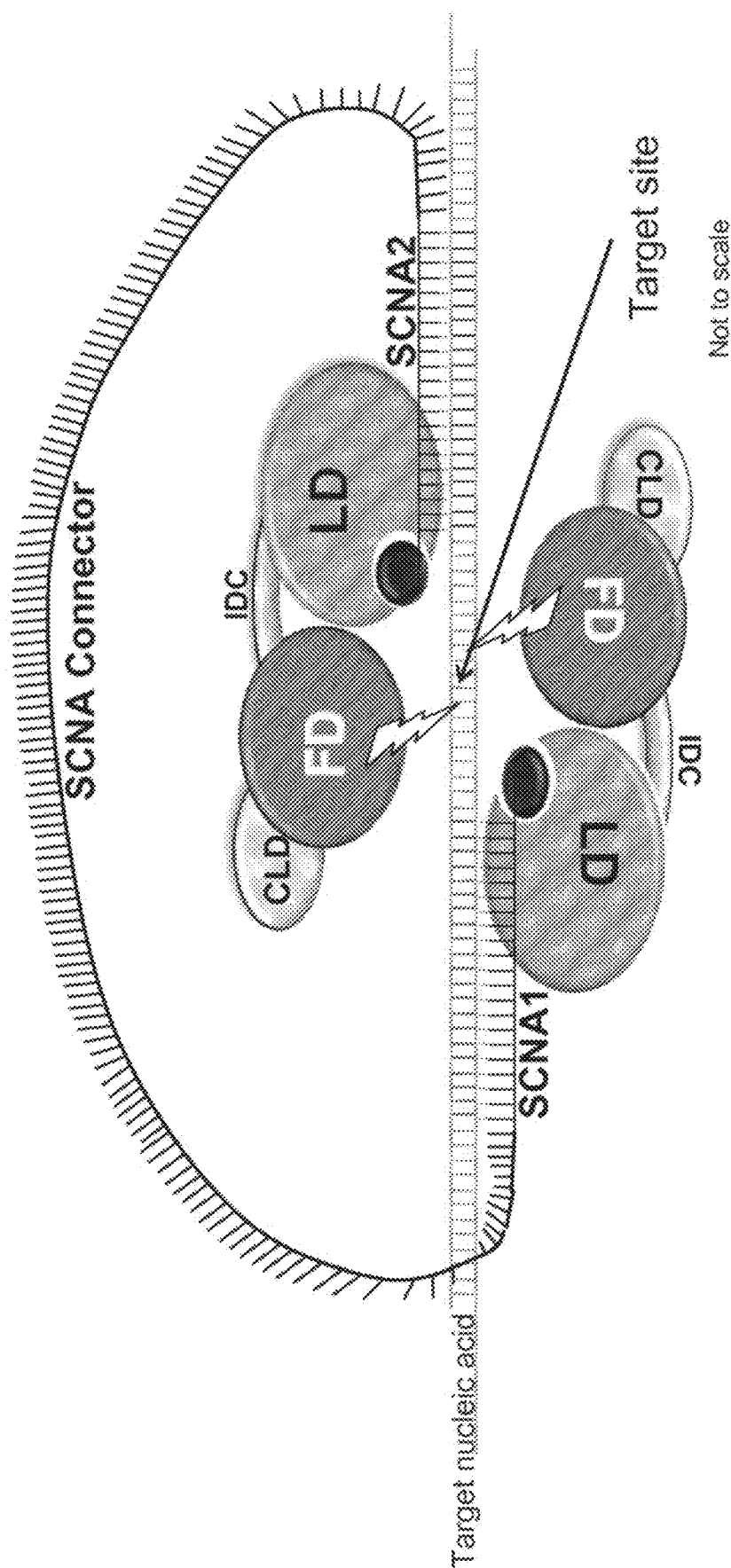

Reference is now made to FIGS. 4A-B, which are schematic drawings (not to scale) of exemplary mode of assembly of the components of the programmable molecular complex on a target nucleic acid, according to some embodiments. As shown in the non limiting examples presented in FIGS. 4A-B, two monomers of the protein moiety bind two different SCNAs (SCNA1, SCNA2), each having a different specificity determinant in the variable sequence region. As shown in the figures, both SCNAs reside on a single nucleic acid and are connected with a sequence of undetermined sequence or length which does not base-pair with the Target, referred to herein as the"SCNA connector". The SCNA connector may include any sequence of nucleotides, at any length (X(n)). In some embodiments, X(n) signifies an undetermined length of RNA nucleotides connecting the two specificity conferring regions to each other. In some embodiments, for linear DNA, the expected optimal length (n) is about, for example, between 10-100 nucleotides. For example, the length is about 35-73 nucleotides (nts). For example, the length is over about 70 nucleotides. For example, the length is shorter than about 35 nucleotides. These SCNAs base pair and bind with predefined homologous (corresponding) sequences on the target nucleic acid. This base pairing can form a double- or a triple-helix with the target nucleic acid, depending whether the target is double- or single-stranded (in the example illustrated in FIGS. 4A-B, dsDNA). In some embodiments, both SCNAs can bind either the same strand or opposite strands of the target nucleic acid as required, in a distance optimized to achieve a desired result. In some embodiments, only one dual connected SCNA containing nucleic acid is needed to target a target site, by flanking both ends of the target site. In some embodiments, the SCNAs can bind the binding site of the Linking Domain (indentation in Linking domain) of the protein moiety, via SCNA-nucleotide motifs on both SCNAs (marked combs in Linking domain binding site, FIG. 4A, or through a modification on both termini (black ovals in Linking domain binding site, FIG. 4B). Upon assembly, the Functional Domain may prompt its effect on the target site in the target nucleic acid.

According to some embodiments, methods for delivery of the SCNA into the organism or cell comprise the multitude of methods known to those skilled in the art and are generally those optimal for the organism or cell type used in the relevant circumstance. These can include delivery of nucleic acid by the biological methods of: infection using autonomously replicating vectors, transgenic virus infection or transduction, including the use of deconstructed or partial viruses, inoculation, *Agrobacterium* T-DNA delivery, breeding, crossing, grafting, organelle transfer, chromosome transfer, cell fusion; the chemical mediated uptake methods of: using transfection agents, DEAE-Dextran, Calcium phosphate, artificial lipids, dendrimers, polymers (PEG etc.), proteins/peptides, virus-like particles; the mechanical methods of: bombardment, injection/microinjection, pressure, whiskers; and the electrical method of electroporation, and any method that alters the cellular plasma membrane, allowing nucleic acids to actively or passively enter the cell.

According to some embodiments, methods for delivery of the nucleic acid encoding the protein module into the organism or cell comprise the multitude of methods known to those skilled in the art and are generally those optimal for the organism or cell type used in the relevant circumstance. These can include delivery of nucleic acid by crossing or breeding an organism with a transgenic organism carrying the gene or by the biological methods of: infection using autonomously replicating vectors, transgenic virus infection or transduction, including the use of deconstructed or partial viruses, inoculation, *Agrobacterium* T-DNA delivery, grafting, organelle transfer, chromosome transfer, cell fusion; the chemical mediated uptake methods of: using transfection agents, DEAE-Dextran, Calcium phosphate, artificial lipids, dendrimers, polymers (PEG etc.), proteins/peptides, virus-like particles; the mechanical methods of: bombardment, injection/microinjection, pressure, whiskers; and the electrical method of electroporation, and any method that alters the cellular plasma membrane, allowing nucleic acids to actively or passively enter the cell.

According to some embodiments, methods for delivery of "donor DNA", in the subgroup of uses requiring such a DNA comprising gene-insertion or gene replacement, comprise similar methods to those described for delivery of the nucleic acid which encodes the protein module. This DNA can be either single stranded, double stranded or partially double stranded, linear or circular. This DNA can be supplied on a single vector or on several vectors, concurrently or separately from the nucleic acid encoding the protein component of the molecular complex and from the specificity-determining programming nucleic acid. Thus, nucleic acids can be delivered, by choosing from the appropriate aforementioned delivery methods, to a plant or a part of a plant, to a plant tissue or organ such as an embryo, pollen, ovum, anther, stigma, whole flower, cotyledon, leaf, root, stem, petiole, to isolated plant cells such as protoplasts, or to differentiated or undifferentiated cultured plant tissue, callus, or cells. In some embodiments, nucleic acids can be delivered to a fungus, including unicellular and multicellular fungi, and to a member of the animal kingdom including invertebrates (such as arthropods and nematodes), vertebrates (such as birds, fish, mammals, reptiles, and amphibians) and to parts of these organisms including organs, cultured organs, tissues, cultured tissues, isolated cells, cell cultures, cell lines and stem cells such as human embryonic stem cells or human hematopoietic stem cells.

Figure 5:
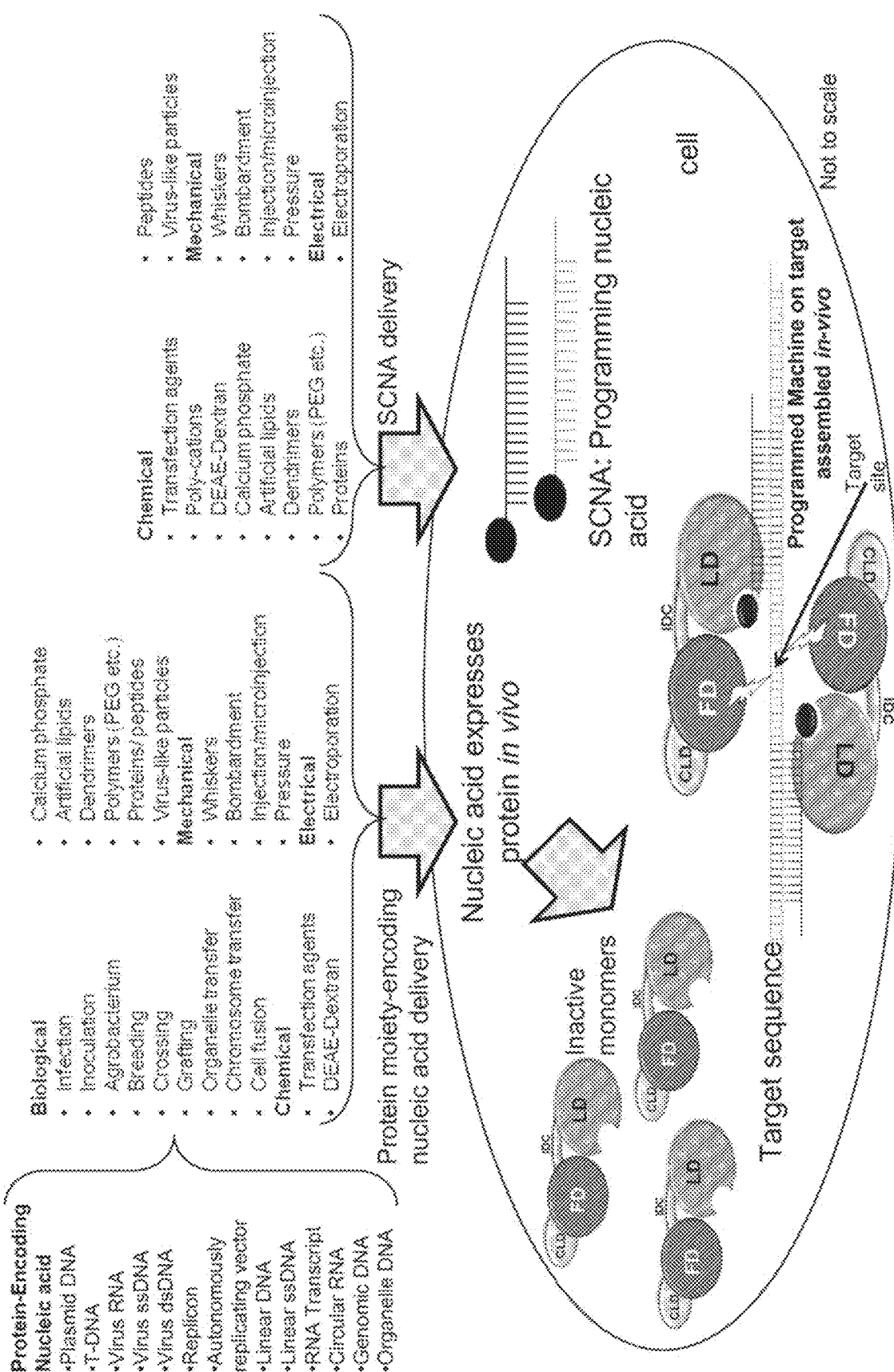
FIG. 5 is a schematic scheme demonstrating the delivery of the programmable molecular complex to a cell using in-vitro produced SCNAs, according to some embodiments.

Reference is now made to FIG. 5 which shows a schematic illustration demonstrating delivery options of the programmable molecular complex to a cell using in-vitro produced SCNAs, according to some embodiments. A general scheme for selecting an appropriate delivery method is shown. A nucleic acid molecule encoding for the protein moiety is selected from the left hand column and delivered using applicable methods selected from the next two columns. A synthetic SCNA is supplied through methods selected from those shown in the two right columns. Within the target cell, a nucleic acid encoding for the protein brings about the expression of the protein by its translation in-vivo from a template RNA molecule. If the delivered nucleic acid molecule is comprised of dsDNA, it may first transcribe to RNA (via a designated promoter). If the delivered nucleic acid molecule is comprised of ssDNA it may first be complemented to dsDNA and then transcribed. If the delivered nucleic acid molecule is comprised of RNA, such as that encoding a virus or another autonomously replicating vector, it may proceed through replication via a minus strand before being translated. The translated protein can then be localized to the desired subcellular compartment, according to its localization signal (if present). The SCNAs may be delivered concomitantly or separately from the nucleic acid molecule encoding for the protein moiety by the same or different delivery method. Once the SCNA, protein moiety and Target nucleic acid are co-localized within the cell, they may assemble to form an active molecular dimeric complex. Donor DNA, if required, may also be delivered separately or simultaneously.

Reference is now made to FIG. 6, which is a general scheme demonstrating the delivery of the programmable molecular complex to a cell using an in-vivo produced SCNA, according to some embodiments. A nucleic acid molecule encoding the protein moiety is selected from the left hand column and delivered using applicable methods selected from the next three columns. In-vivo produced SCNAs are encoded by a nucleic acid molecule provided for that purpose and introduced into the cell using these same methods. The nucleic acid molecules encoding for the protein moiety and/or the SCNA may be delivered separately or concomitantly. In the cell, the nucleic acid encoding the SCNA expresses the SCNA by transcription or nucleic acid cleavage. If the delivered nucleic acid molecule is comprised of dsDNA, it may be first transcribed to RNA via a designated promoter. If the delivered nucleic acid molecule is comprised of ssDNA it may first be complemented to dsDNA and then transcribed. If the delivered nucleic acid molecule is comprised of RNA such as that encoding a virus or another autonomously replicating vector, it may proceed through replication via a minus strand. Within the cell, the nucleic acid encoding the protein is expressed via its translation in-vivo from an RNA molecule produced in a manner similar to that described for the SCNA. The translated protein can then be localized to the desired subcellular compartment, according to its localization signal (if present). The nucleic acid molecules encoding for the protein moiety and/or the nucleic acid molecules encoding for the SCNAs may be delivered concomitantly (at the same time) or separately, by identical or different delivery methods. Once the SCNA, protein moiety and Target nucleic acid are co-localized within the cell, they may assemble to form an active molecular dimeric complex. Donor DNA, if required, may also be delivered separately or simultaneously.

According to some embodiments, the biological synthesis in-vivo of the SCNA may be performed by several routes, such as, but not limited to: (a) the use of *Agrobacterium* to synthesize both nucleic acid and the Linking-Domain-binding moiety, in this example VirD2, which also catalyzes their covalent linking. *Agrobacterium* then facilitates the transfer to a cell of a ssDNA covalently bound to VirD2, (b) the use of *Agrobacterium* to transfer a T-DNA to a cell, said T-DNA comprising promoters driving the synthesis in the cell of RNA SCNAs having an RNA domain that binds the Linking Domain of the complex upon their converging. Thus, the complex, expressed in the target cell, assembles through an RNA-protein interaction, (c) the use of autonomously replicating vectors comprising viruses and viral-based expression vectors to deliver a replicon to a cell, said replicon comprising subgenomic promoters driving the synthesis of RNA SCNAs having an RNA domain that binds the Linking Domain of the complex upon their converging. Thus, the complex, expressed in the target cell, assembles through an RNA-protein interaction.

Figure 7A:
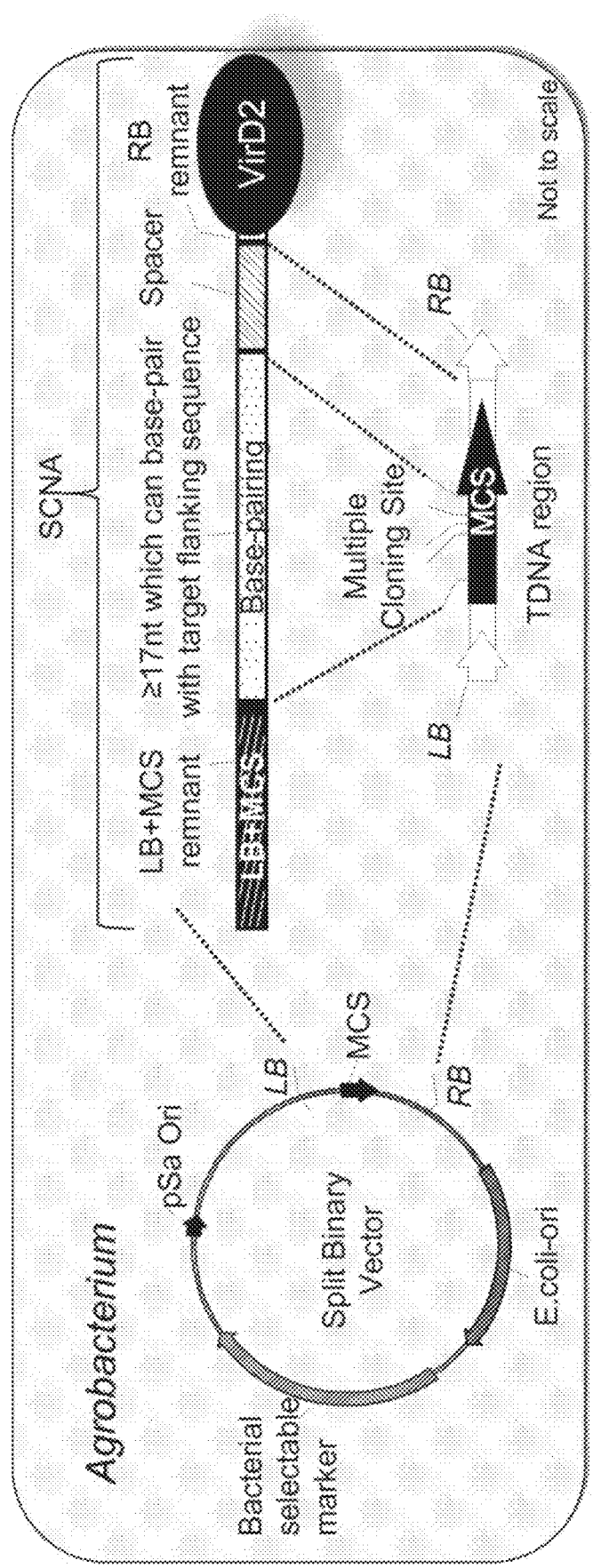
FIGS. 7A-B are schemes showing non-limiting examples of the delivery of the programming nucleic acid moiety of the molecular complex to a cell using a single-strand DNA SCNA produced in *Agrobacterium* (FIG. 7A) and bacterial secretion system (FIG. 7B), according to some embodiments.
Figure 7B:
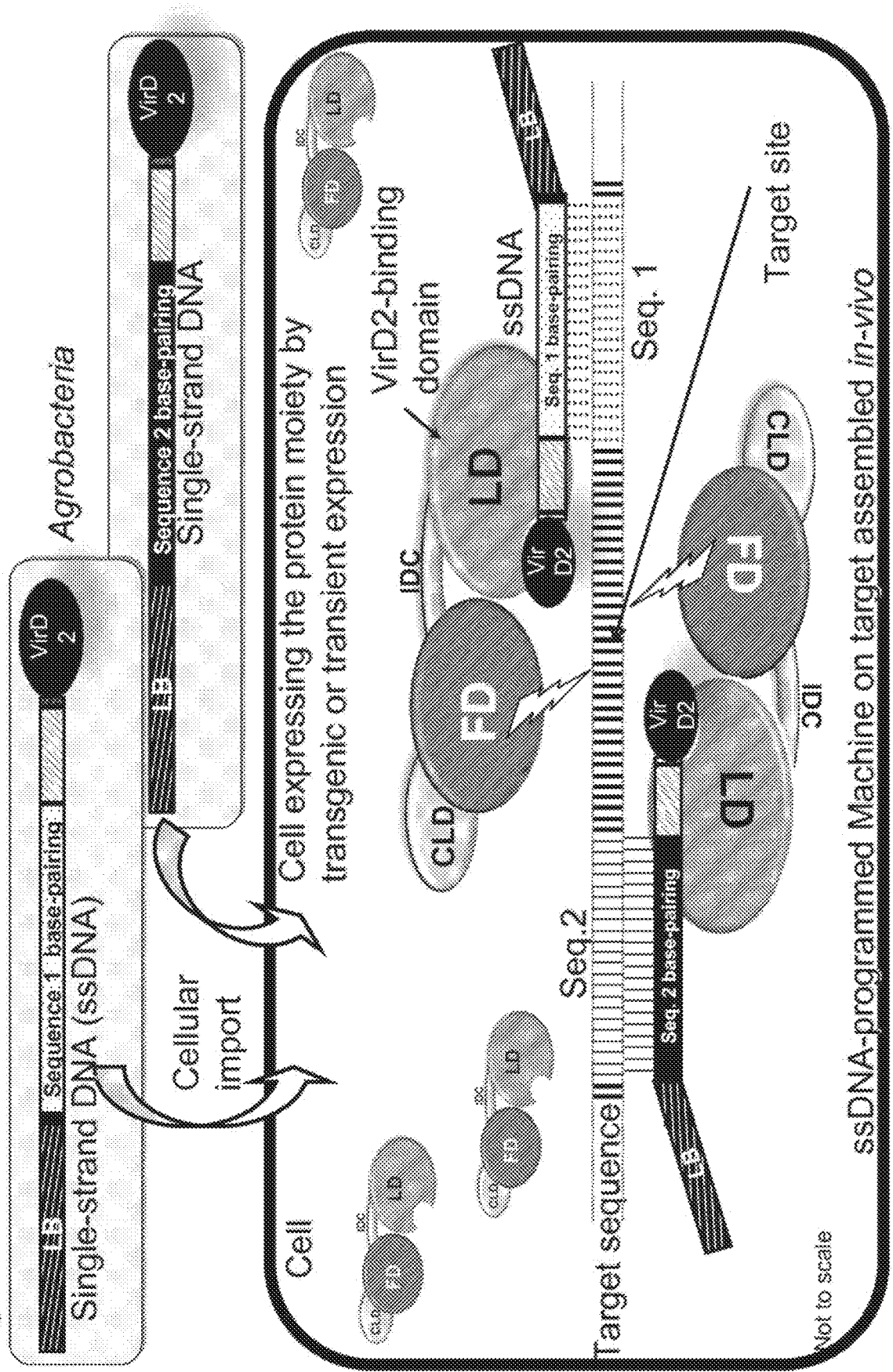

Reference is now made to FIGS. 7A-B which are schematic drawings (not to scale) showing non-limiting examples of delivery of the SCNA to a cell using a single-strand DNA produced in *Agrobacterium*. Shown in FIG. 7A is a non-limiting example of the use of *Agrobacterium* for production of ssDNA SCNA bound to a protein, VirD2, in vivo, at its 5' end. As shown in this example, the targeting variable SCNA sequence is inserted into a multiple cloning site (MCS) in a plasmid capable of replicating in *Agrobacterium*. *Agrobacterium* is then transformed with this plasmid. The Ti plasmid Right Border (RB) sequence on the plasmid is cleaved and ssDNA is bound by VirD2 in the bacterium. 3 nucleotides of the RB sequence are left behind at the 5' of the sequence after cleavage, and 21 nucleotides of the Ti plasmid left Border (LB) sequence are left behind after cleavage at the 3' of the sequence. The LB sequence can further aid in SCNA stabilization and in screening for unwanted integration events. Mutated forms of Agrobacteria, (for example, those missing VirE1 or VirE2 or with partial VirD2 functionality) are useful for the inhibition of unwanted integration events. *Agrobacterium* then exports the T-DNA comprising the SCNA bound to VirD2 into the cell. Shown in FIG. 7B is a non-limiting example of the use of a bacterial secretion system to deliver SCNAs to a host cell. One or a multiplicity of agrobacteria transformed with different T-DNAs encoding different SCNA sequences are used to infect one cell. The VirD2-bound ssDNA SCNA thus created in the bacteria and exported to the host cell can then encounter and bind the Linking Domain of the protein moiety through an interaction between the VirD2 protein and the VirD2-binding domain in the Linking Domain in the host cell. An example for such a VirD2-binding Linking Domain comprises an artificial single-chain variable fragment of an antibody (scFv) produced against VirD2. The SCNA can thus bring about the assembly of the molecular complex on a Target nucleic acid.

Figure 8A:
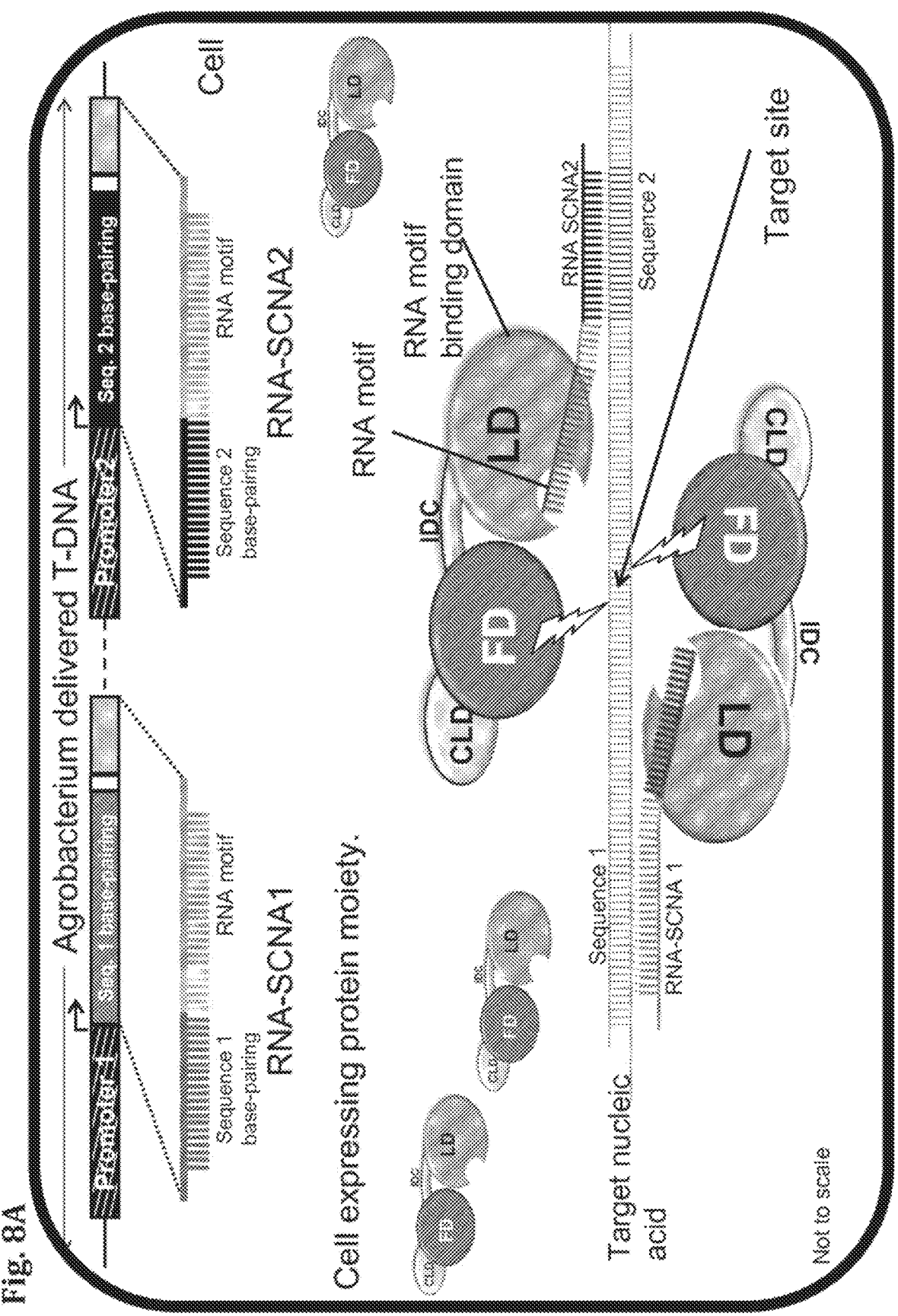
FIGS. 8A-B schematic illustration demonstrating the delivery of the programming moiety of the programmable molecular complex to a cell using RNA SCNAs produced *Agrobacterium* (FIG. 8A) or by an autonomously replicating vector such as a virus (FIG. 8B), according to some embodiments.
Figure 8B:
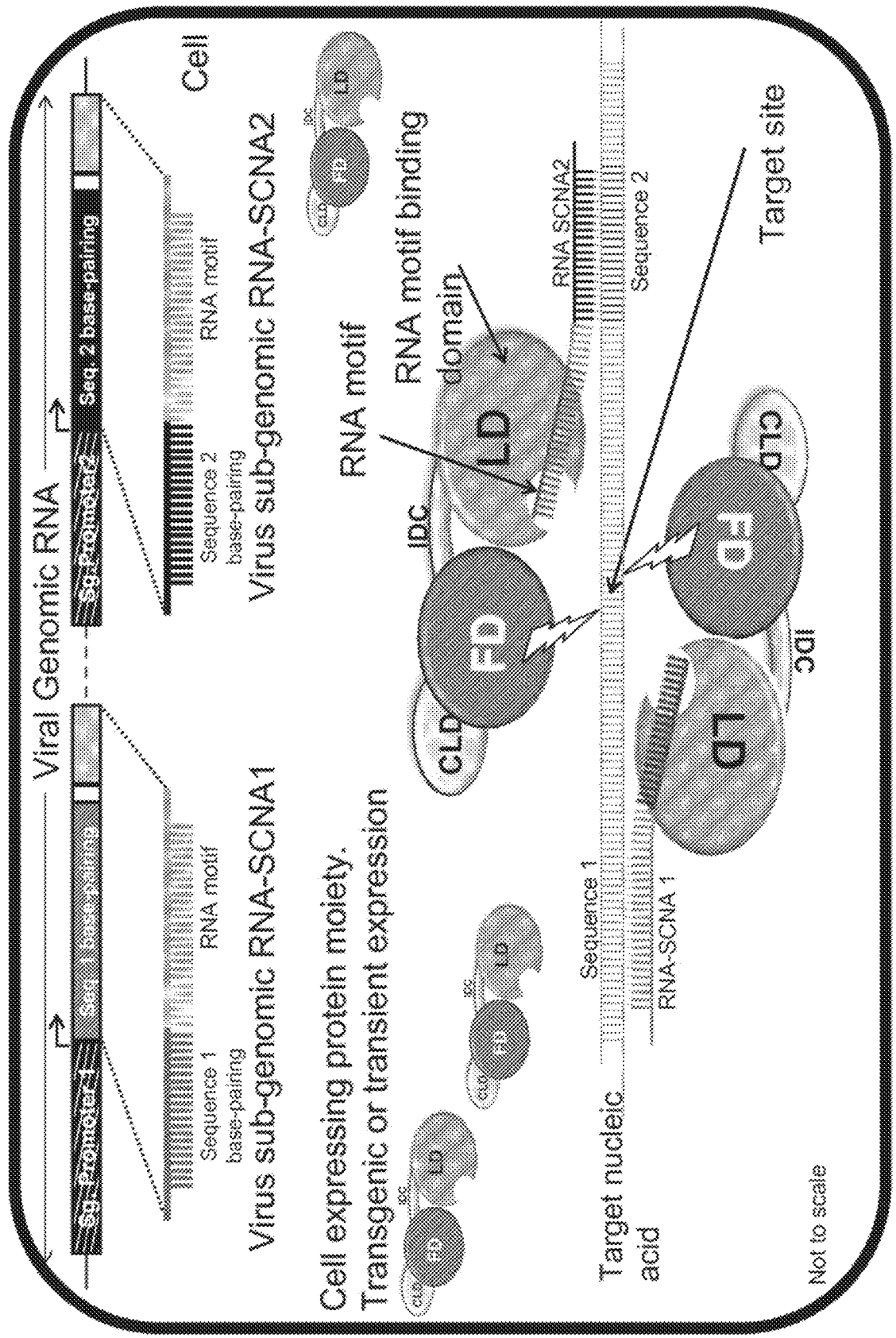

Reference is now made to FIGS. 8A-B which are schematic illustrations demonstrating the delivery of SCNA to a cell using RNA SCNAs produced inside the host cell, from an *Agrobacterium* delivered T-DNA (FIG. 8A) or from a nucleic acid delivered by an autonomously replicating vector such as a virus (FIG. 8B). The RNA SCNAs presented in these figures include an SCNA-RNA motif (marked combs) which can bind a corresponding RNA-binding motif of the Linking Domain of the protein moiety. As shown in FIG. 8A, the SCNA sequences are inserted into a multiple cloning site (MCS) in a plasmid capable of replicating in *Agrobacterium* and containing the appropriate Eukaryotic promoters for the transcription of one or a multiplicity of RNA SCNAs in the infected cell. FIG. 8B: The SCNA sequence(s) is/are inserted into the genome of a virus or a virus-derived autonomously replicating vector each under the control of a sub-genomic (sg) promoter for the transcription of one or a multiplicity of RNA SCNAs in the infected cell. In the non-limiting examples shown in FIGS. 8A-B, the nucleic acid molecule encoding for the protein-moiety coding may be delivered to the target cell beforehand, together with (concomitantly) or after the delivery of the SCNA encoding nucleic acid molecule. When the protein moiety and the SCNA are expressed in the cell, the assembly of the molecular complex on the target nucleic acid occurs.

Figure 9:
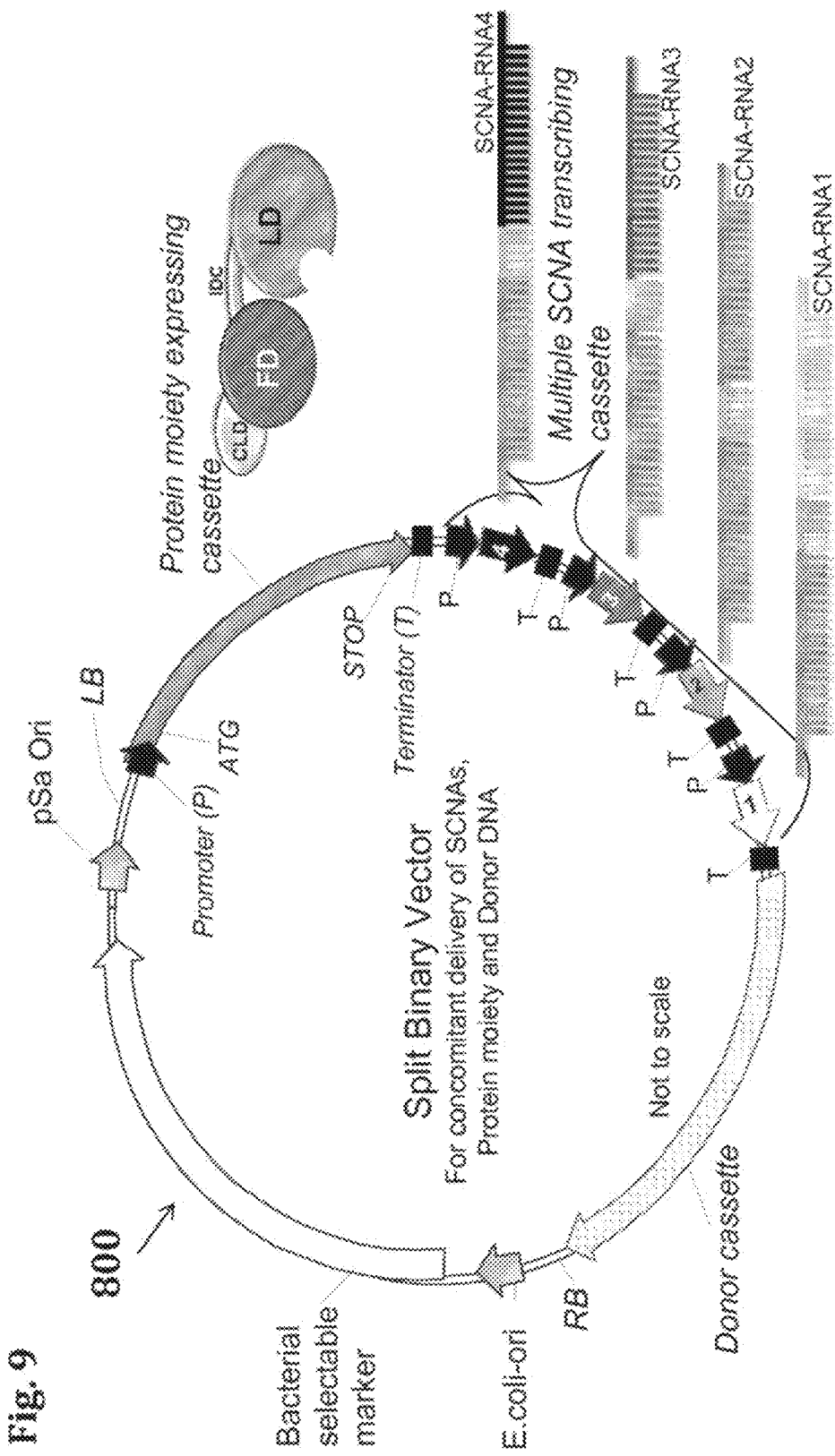
FIG. 9 shows a schematic illustration (not to scale) of a non-limiting example of a delivery vehicle or vector for concomitant delivery of the composition comprising the components necessary for the assembly of a programmable molecular complex to a susceptible target Eukaryotic cell in a single delivery event, according to some embodiments.

Reference is now made to FIG. 9, which shows a schematic illustration (not to scale) of a non-limiting example of a delivery vehicle or vector for concomitant delivery of the composition comprising the components necessary for the assembly of a programmable molecular complex to a susceptible target Eukaryotic cell in a single delivery event, according to some embodiments. For the non-limiting example shown in FIG. 9, the desired action is replacement of a genomic DNA stretch (the target nucleic acid), with a predetermined sequence the "Donor cassette". Accordingly, the domains of the protein moiety include: a Functional Domain, derived from a nuclease and having a nucleic cleavage activity; a cellular localization domain, which is a nuclear localization signal (NLS); and Linking Domain capable of recognizing and binding an RNA motif on the SCNAs. In the example shown in FIG. 9, a biological delivery system is used. *Agrobacterium* is transformed with a plasmid vector, such as plasmid (800), which contains various functional/structural sequences, such as, bacterial selectable marker, various origins of replication sites (*E. Coli*-ori, pSa Ori), LB sequence, promoter regions (designated as (P)), the protein moiety expressing sequence (comprising an ATG start codon and an in-frame STOP codon), Terminator site (T), multiple SCNA transcribing cassettes (shown as four SCNA transcribing cassettes, each comprising a promoter and terminator sequences), a Donor cassette, and RB site. The plasmid vector (transfected *Agrobacterium*) is then brought into contact with the target organism cells. *Agrobacterium* then forms a T-DNA from the region between the Right border (RB) and the Left border (LB) sequences and secretes it into the Eukaryotic cell. The ssDNA of the T-DNA is delivered to the nucleus, complemented in-vivo to become dsDNA, and transcribed to RNA from the compatible promoters (P) on the plasmid. The thus formed transcript of the protein moiety is translated to form the designated protein. Transcripts from the SCNA cassette which comprise an RNA motif sequence are bound by a specific RNA sequence-binding domain in the protein moiety. The Donor cassette contains a sufficiently long sequence that can recombine with the target nucleic acid in the presence of a double strand break (DSB) formed adjacent to the recombination site. The SCNAs are designed to target and hybridize sequences flanking the sequence to be replaced. In some embodiments, a similar plasmid, lacking border sequences, or a linear DNA of similar construction, can further be used to transfect cells in a non-biological delivery system, to the same effect.

According to some embodiments, and as detailed above, alterations/modifications in the targeted sequence include, for example, but not limited to: permanent deletion, mutation, insertion of nucleic acids, and replacement of a targeted sequence with another nucleic acid sequence, knocking-out, frame-shifting, or any change in any fashion of the transcription or translation of a gene, its regulatory sequences, the genes regulating the gene of interest or their regulatory sequences in a regulatory chain of events.

Figure 10:
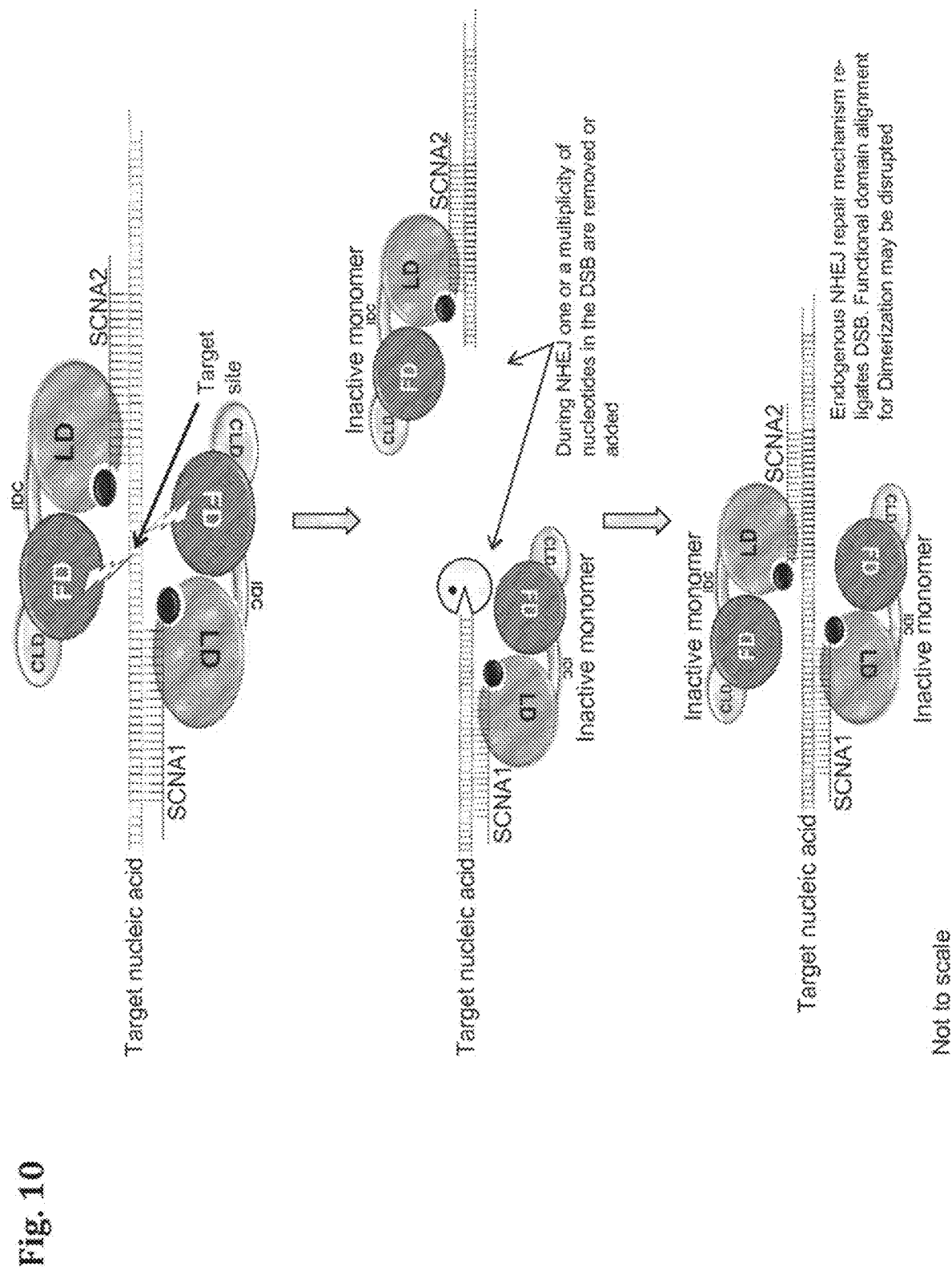
FIG. 10 is a schematic illustration (not to scale) demonstrating the use of a programmed molecular complex to create a mutation in a Target nucleic acid, according to some embodiments.

Reference is now made to FIG. 10, which is a schematic illustration (not to scale) demonstrating the use of a programmed molecular complex to create a mutation in a Target nucleic acid, according to some embodiments. As shown in the non limiting example presented in FIG. 10, the Functional Domain of the protein moiety is derived from a nuclease, and the mutation of the target site on the target nucleic acid is achieved through the creation of a dsDNA break (DSB) in the Target nucleic acid in a predefined location. The SCNA-programmed molecular complexes self-assemble by SCNA base-pairing with a corresponding target sequence on the target nucleic acid. Upon assembly of the components of the complex, the Functional Domain is dimerized and the nuclease is activated, cleaving the target site, which is located, in this example, at or near the midpoint, between the two SCNA molecules, thereby creating a DSB (for example, the DSB can have 4 nucleotide 5'-overhangs such as those created by the restriction enzyme FokI). Cellular Non homologous end-joining (NHEJ) repair mechanisms attempt to repair the DSB and while doing so may: 1) make a perfect ligation—while the complex may continue to recleave the same sequence for repeated attempts at mutation until depletion of complex components, 2) add one or a multiplicity of nucleotides thus widening the distance between the SCNAs and abolishing Functional Domain dimerization, thereby ending the action of the complex, or 3) remove one or a multiplicity of nucleotides ("pacman" figure), thus narrowing the distance between the SCNAs and abolishing the Functional Domain dimerization, thereby ending the action of the complex. When any of options 2 or 3 occur within the cell, a mutation is achieved.

Figure 11:
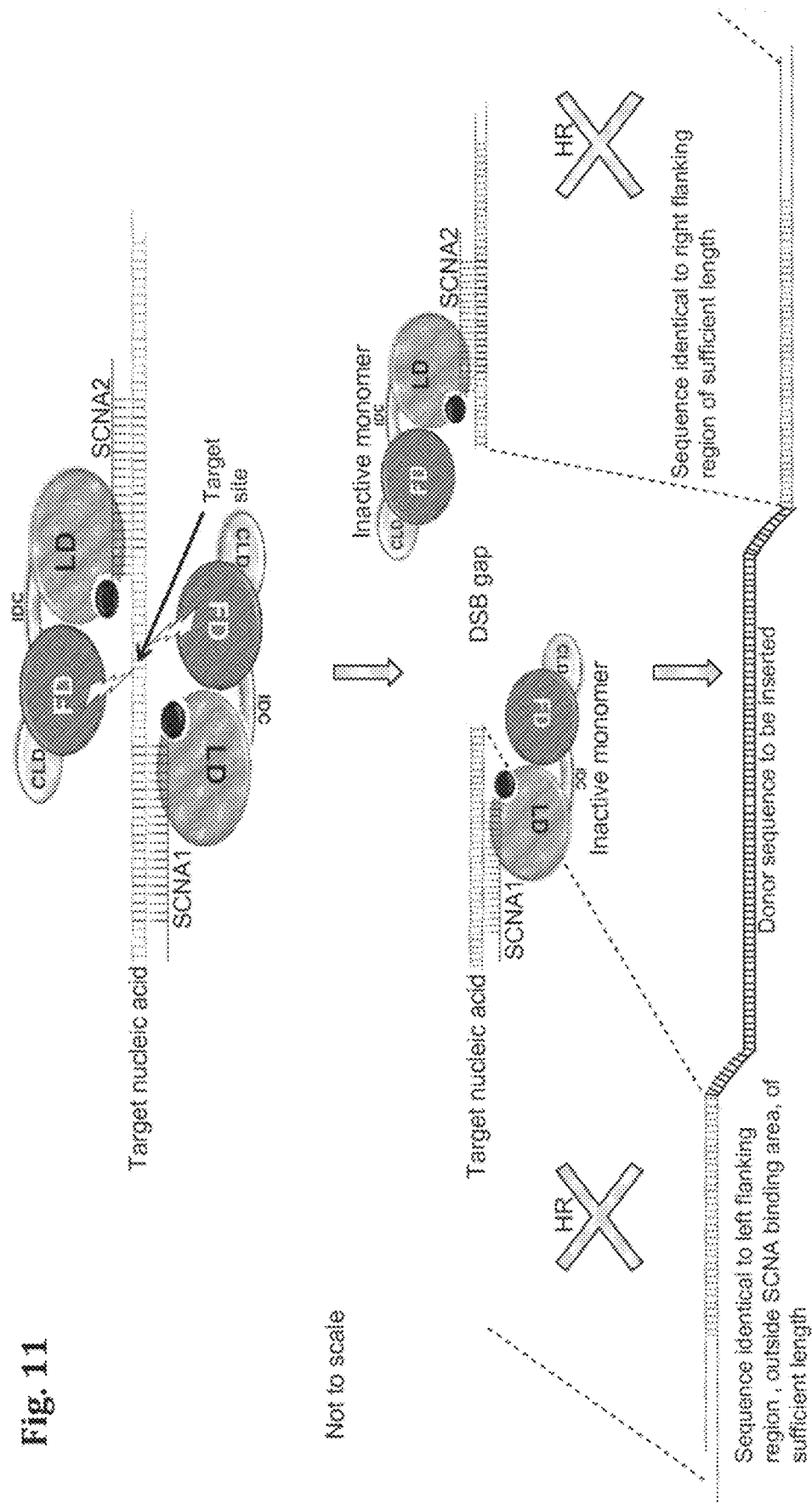
FIG. 11 is a schematic illustration (not to scale) demonstrating the use of a programmed molecular complex to insert one or a multiplicity of nucleotides into a Target nucleic acid using a supplied Donor nucleic acid, according to some embodiments.

Reference is now made to FIG. 11, which is a schematic illustration (not to scale) demonstrating the use of a programmed molecular complex to insert one or a multiplicity of nucleotides into a Target nucleic acid using a supplied Donor nucleic acid, according to some embodiments. As shown in the non limiting example presented in FIG. 11, the Functional Domain of the protein moiety is derived from a nuclease, and a dsDNA break (DSB) in the target nucleic acid at a predefined location (target site) assists the process of Homologous Recombination (HR). The SCNA-programmed molecular complexes self-assemble by SCNA base-pairing with a corresponding target sequence. Upon assembly of the components of the complex, the Functional Domain is dimerized and the nuclease is activated, thereby cleaving the target nucleic acid at the target site, which may be located, for example, at or near the midpoint between the two SCNA molecules, thereby creating a DSB. The Donor DNA contains the sequence to be inserted and sufficiently long stretches of nucleotides, flanking this sequence which are essentially identical to the Target sequence flanking the intended DSB point. These flanking sequences may then recombine (X) with the target nucleic acid through the cellular process of HR, thus replacing a predetermined stretch of nucleotides in the Target nucleic acid, and in effect bringing about an Insertion of the desired sequence. Upon recombination and Insertion of the predetermined Donor sequence, the distance between the SCNAs is widened, thus interfering with dimerization of the Functional Domain, thereby ending the action of the complex. In occasions when perfect re-ligation by NHEJ occurs, the activated programmed complex may continue to recleave the same sequence for repeated attempts at insertion.

Figure 12:
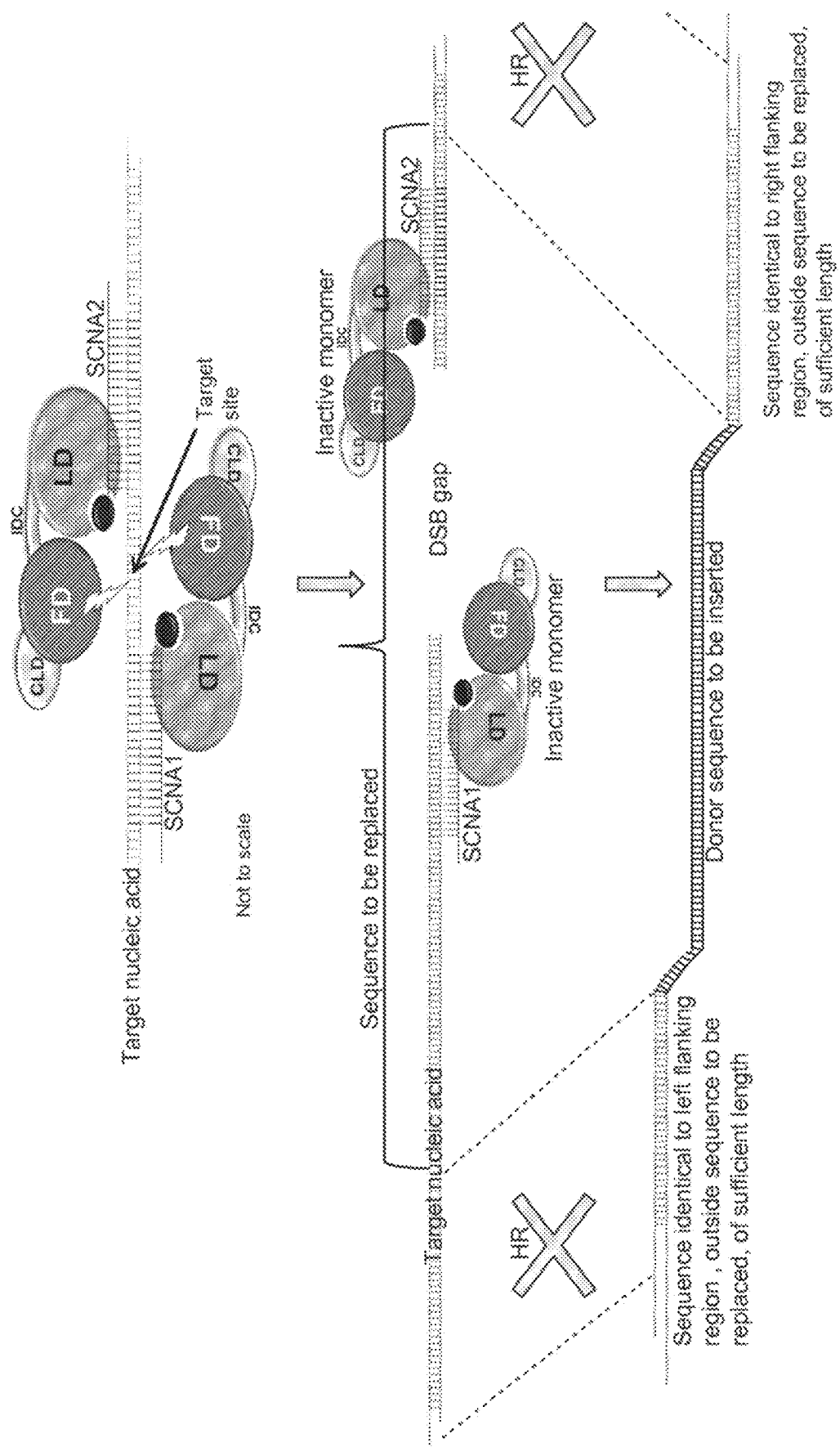
FIG. 12 is a schematic illustration (not to scale) demonstrating the use of a programmed molecular complex to replace one or a multiplicity of nucleotides in a Target nucleic acid using a supplied Donor nucleic acid, according to some embodiments

Reference is now made to FIG. 12, which is a schematic illustration (not to scale) demonstrating the use of a programmed molecular complex in the replacement, insertion and/or deletion of one or a multiplicity of nucleotides in a Target nucleic acid using a supplied Donor nucleic acid, according to some embodiments. As shown in the non limiting example presented in FIG. 12, the Functional Domain of the protein moiety is derived from a nuclease, and a dsDNA break (DSB) in the Target nucleic acid in a predefined location (target site) assists the process of Homologous Recombination (HR). SCNA-programmed molecular complexes self-assemble by SCNA base-pairing with a predetermined target sequence. Upon assembly of the components of the complex, the Functional Domain is dimerized and the nuclease is activated, cleaving the target nucleic acid at the target site, which may be located, for example, at or near the midpoint between the two SCNA molecules, thereby creating a DSB. The Donor DNA contains the exogenous sequence to be inserted instead of the endogenous target sequence to be removed as well as sufficiently long stretches of nucleotide flanking this exogenous sequence, which are essentially identical to the Target sequence flanking the intended sequence to be removed. These flanking sequences may then recombine (X) with the Target DNA through the cellular process of HR, thus replacing a stretch of DNA in the Target DNA and in effect bringing about a replacement of an undesired endogenous sequence by a desired exogenous sequence. Upon successful recombination and replacement of the desired exogenous sequence, the SCNA binding sites on the Target nucleic acid may be designed to be abolished, thus ending the action of the complex. In occasions when perfect re-ligation by NHEJ occurs, the complex may continue to recleave the same sequence for repeated attempts at recombination.

Figure 13:
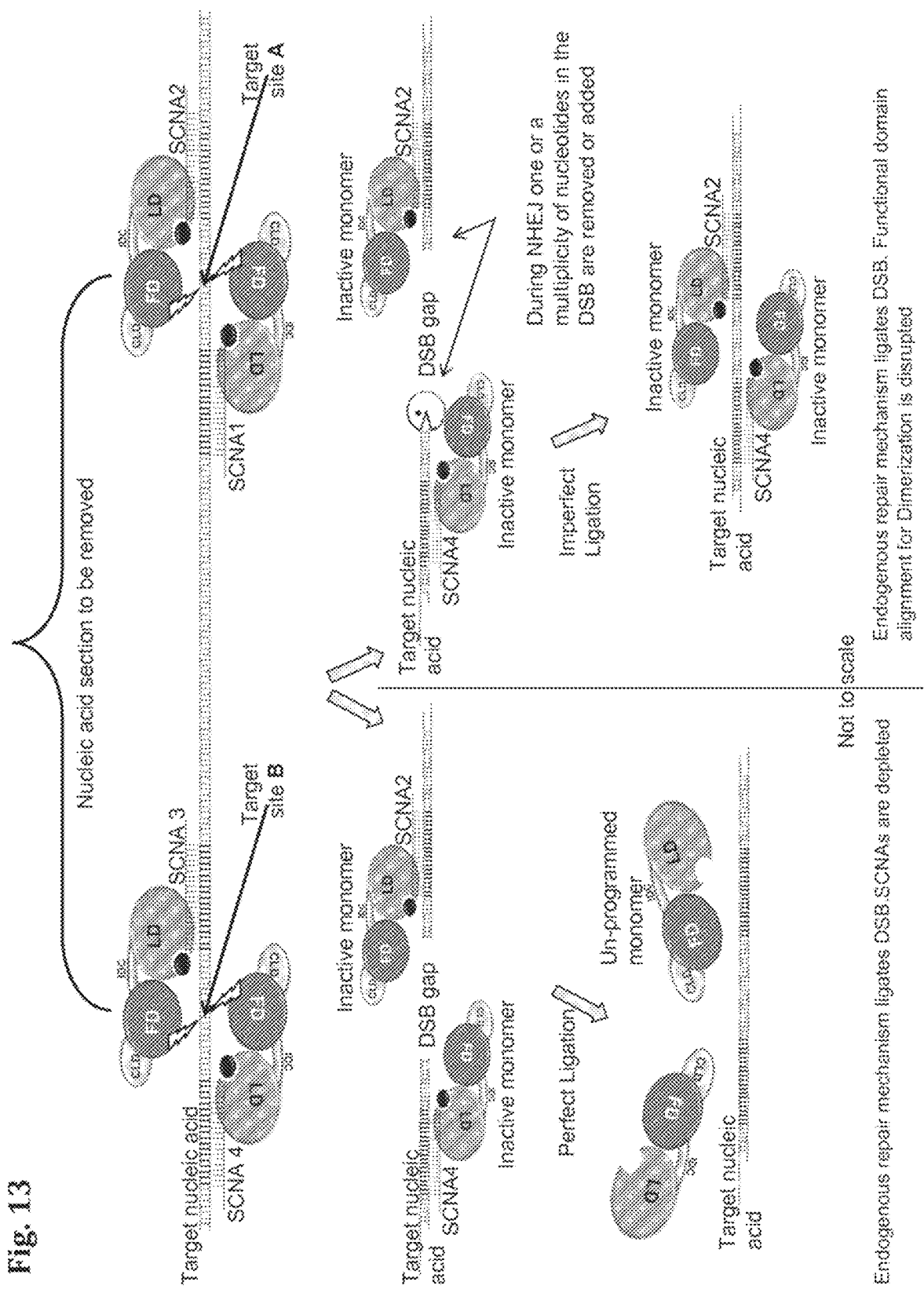
FIG. 13 is a schematic illustration (not to scale) demonstrating the use of a programmed molecular complex to create a deletion of one or a consecutive multiplicity of nucleotides from a Target nucleic acid, according to some embodiments.

Reference is now made to FIG. 13, which is a schematic illustration (not to scale) demonstrating the use of a programmed molecular complex to create a deletion of one or a consecutive multiplicity of nucleotides from a target nucleic acid, according to some embodiments. As shown in the non limiting example presented in FIG. 13, the Functional Domain of the protein moiety is derived from a nuclease, and the deletion is achieved through the creation of two dsDNA breaks (DSBs) in the Target nucleic acid at two predefined locations. SCNA-programmed molecular complexes self-assemble by SCNA base-pairing with corresponding target sequences. Upon assembly of the components of the complex, the Functional Domains are dimerized and the nucleases are activated, cleaving the target nucleic acid at the target site, which may be located at or near the midpoint between each pair of SCNA molecules creating DSBs. Concomitant or sequential cleavage of both sites essentially eliminates, or deletes, the sequence in between. Cellular Non homologous end-joining (NHEJ) repair mechanisms attempt to repair the DSB and while doing so may: 1) make a perfect ligation of the target DNA flanking the deleted sequence, while the activate complex may continue to recleave the same sequence until depletion of complex components (left hand panel); 2) make a perfect re-ligation of each separate DSB—while the complex may continue to recleave the same sequence for repeated attempts at deletion until depletion of complex components; 3) remove one or a multiplicity of nucleotides ("pacman" figure, right hand panel) in the DSB gap, thus narrowing the distance between the SCNAs and abolishing Functional Domain dimerization, thereby ending the action of the complex; or 4) add one or a multiplicity of nucleotides in the DSB gap thus widening the distance between the SCNAs and abolishing Functional Domain dimerization, thereby ending the action of the complex.

Figure 14:
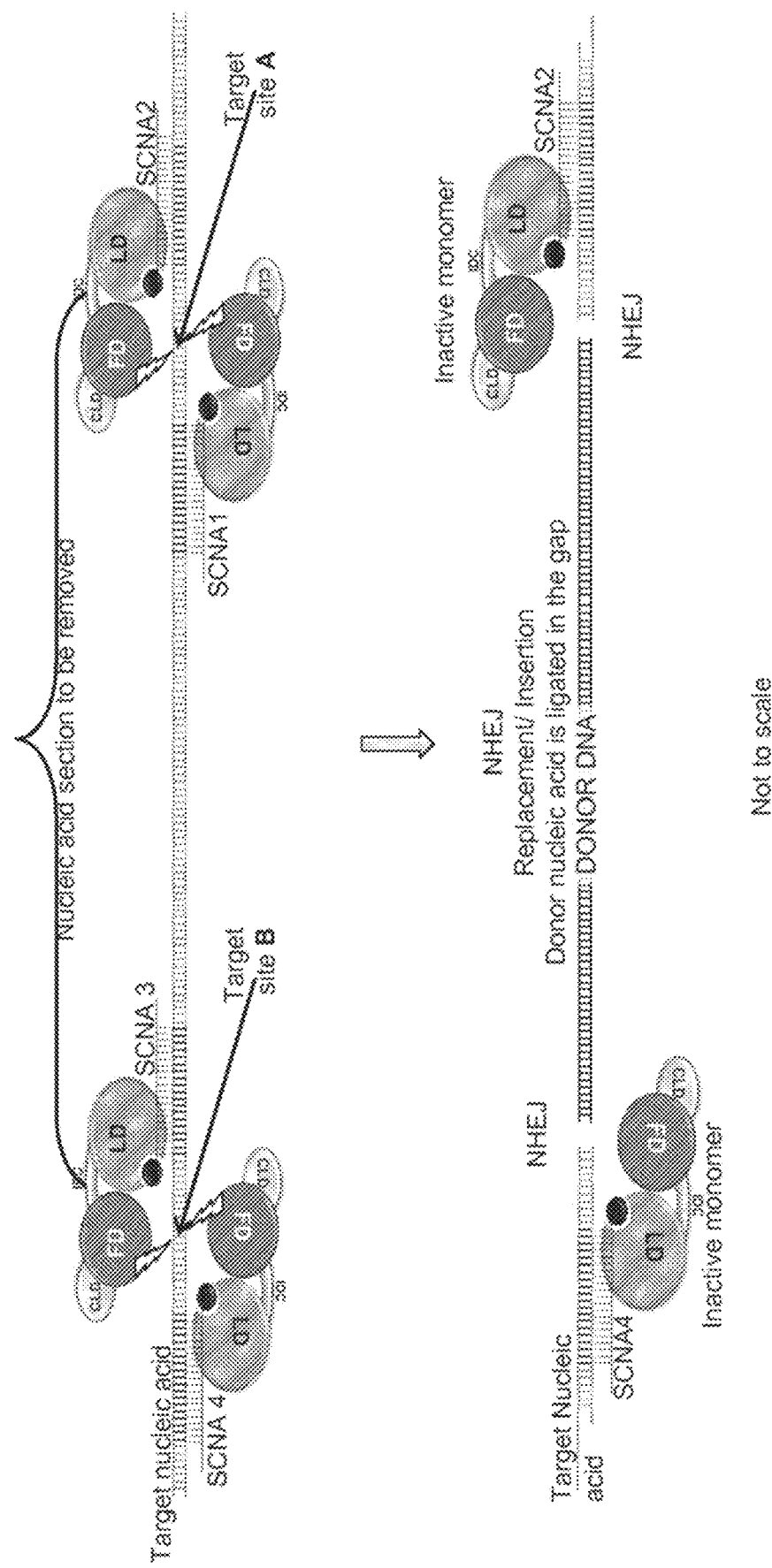
FIG. 14 is a schematic illustration (not to scale) demonstrating the use of a programmed molecular complex to replace one or a multiplicity of nucleotides in a Target nucleic acid using a supplied Donor nucleic acid, according to some embodiments.

Reference is now made to FIG. 14, which is a schematic illustration demonstrating the use of a programmed molecular complex to replace one or a multiplicity of nucleotides in a Target nucleic acid using a supplied Donor nucleic acid, according to some embodiments. As shown in the non limiting example presented in FIG. 13, the Functional Domain of the protein moiety is derived from a nuclease, and the replacement is achieved through the creation of two dsDNA breaks (DSBs) in the Target nucleic acid in two predefined locations (target sites), creating a deletion, and supplying a linear or linearized DNA Donor to fill the gap. SCNA-programmed molecular complexes self-assemble by SCNA base-pairing with corresponding target sequences. Upon assembly of the components of the complex, the Functional Domains are dimerized and the nucleases are activated, cleaving the target at or near the midpoint between each pair of SCNA molecules, thereby creating DSBs. Concomitant or sequential cleavage of both sites essentially eliminates, or deletes, the sequence region in between. Cellular Non homologous end-joining (NHEJ) repair mechanisms attempt to repair the DSB and while doing so may: 1) make a perfect pair of ligations of the Donor into the Target abolishing Functional Domain dimerization, thereby ending the action of the complex; 2) make a perfect ligation of the target nucleic acid sequence flanking the deleted sequence—whereas the complex may continue to recleave the same sequence for repeated attempts at replacement until depletion of complex components; 3) make a perfect re-ligation of each separate DSB, whereas the complex may continue to recleave the same sequence for repeated attempts at replacement until depletion of complex components; 4) remove one or a multiplicity of nucleotides in a DSB gap, thus narrowing the distance between the SCNAs and abolishing Functional Domain dimerization, thereby ending the action of the complex; or 5) add one or a multiplicity of nucleotides in a DSB gap thus widening the distance between the SCNAs and abolishing Functional Domain dimerization thereby ending the action of the complex.

Genetic Diseases

According to some embodiment, the compositions and methods of the present invention can be used to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods disclosed herein. Exemplary genetic diseases include, but are not limited to, achondroplasia, achromatopsia, acid maltase deficiency, acquired immunodeficiencies, adenosine deaminase deficiency (OMIM No. 102700), adrenoleukodystrophy, aicardi syndrome, alpha-I antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, Fanconi's anemia, fibrodysplasia ossificans progressive, fragile X syndrome, galactosemis, Gaucher's disease, generalized gangliosidoses (e.g., GM1), hemochromatosis, hemoglobinopathies (e.g., sickle cell anemia, the hemoglobin C mutation in the 6.sup.th codon of beta-globin, alpha-thalassemia, beta-thalassemia), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, lysosomal storage diseases (e.g., Gaucher's disease, GM1, Fabry disease and Tay-Sachs disease), Marfan syndrome, Moebius syndrome, mucopolysaccahidosis (e.g. Hunter's disease, Hurler's disease), nail patella syndrome, nephrogenic diabetes insipdius, neurofibromatosis, Neimann-Pick disease, osteogenesis imperfecta, porphyria, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

The following examples are presented in order to more fully illustrate some embodiments of the invention. They should, in no way be construed, however, as limiting the broad scope of the invention.

EXAMPLES

Example 1

In-Vivo System as Bioassay for Tuning Components of the Molecular Complex

This example describes a bioassay suitable for testing and optimizing permutations in the design and use of the programmable molecular complex, such as, for testing its activity in different organisms or cells, for testing different delivery methods, and for testing the editing functions of mutation, replacement, deletion and insertion.

The experiments shown in the examples below are for the detection of gene targeting and specific cleavage by a composition of the programmable molecular complex, which includes a modified nuclease as the effector domain of the protein moiety.

Visual reporter systems are used, based on repair of a STOP codon which is placed inside the reporter coding sequence. The reporter in these examples is Green Fluorescent Protein (GFP). When targeted, a double strand breaks (DSB) formed by the activated complex is repaired, (presumably through NHEJ pathway as exemplary illustrated in FIG. 10), abolishing the STOP codon and restoring GFP activity. This assay may thus give a good indication of gene targeting efficiency. This assay is known also as the "STOP GFP" assay. This visual assay is designed to target plasmid or genomic DNA in-vivo. In the following examples, an *Arabidopsis* protoplast based bioassay is used. In the described bioassay, the aforementioned reporter systems are delivered into protoplasts on a plasmid, co-delivered with the plasmid expressing the protein moiety of the molecular complex in-vivo and co-delivered with a pair of ssDNA Specificity Conferring Nucleic Acids (SCNA) modified, in this example, with a terminal (NHS-Ester-)-Digoxigenin (DIG). A second modification for exonuclease protection, (phosphorothioate), is added at the opposite terminus (here marked with an asterisk). The plasmid vectors used herein comprise plant promoters.

Protein Sequence and Properties

The molecular complex designed for this application is composed of two sequences of homologous nucleic acids for specificity determination (SCNAs) and a chimeric protein component containing a nuclease which binds to the SCNAs in vivo. The resulting cleavage of the predetermined target site (STOP codon) of the target nucleic acid (GFP coding sequence) results in its desired mutation, by endogenous processes. The programmable molecular complex in this example consists of 2 identical monomers of a protein moiety and two different SCNA molecules (as schematically illustrated in FIGS. 1A and 2A). In this example the protein moiety contains an amino-acid sequence modified from a FokI nuclease domain as the Functional Domain; an amino-acid sequence adapted from anti-DIG (Digoxigenin) single-chain variable fragment (scFv) immunoglobin (DIG-ScFv) similar to that described in (Huston et. al, 1988) as Linking Domain; an SV40NLS (SEQ ID NO: 3, PKKKRKV) as a nuclear localization domain and a ~15 Å inter-domain connector (SEQ ID NO:7, GGSGG). The nucleic acid sequence encoding for the protein moiety is inserted into suitable expression vectors (pUC based vectors (pSAT)), including a NOS or 35S promoter.

The in-vivo binding between the specificity-conferring nucleic acid and the Linking domain of the protein moiety, in this example, is the result of a non-covalent interaction which can be described as an antibody-antigen interaction; single-chain antibody-antigen; antibody or single-chain antibody-hapten interaction.

In this example, the nucleic acid end-modification of the SCNA is an NHS-Ester linked Digoxigenin (DIG) that is attached to the 5' or 3' position of the SCNA oligonucleotide.

Amino-acid sequence (one letter code) of the protein moiety of the molecular complex (NLS-FokI-nuclease sequence With Digoxygenin ScFv) is as designated in SEQ ID NO: 12, and is encoded by the sequence as set forth in SEQ ID NO: 13.

SCNA Properties and Sequence

The length of the SCNA of the complementary, target-base-pairing oligonucleotide is preferentially at least 18 bases. The SCNA can also contain a small number (e.g. 1-6, in one example 6, in other example, 2) of non-target-base-pairing nucleotides (N's) of any sequence composition that serve as a spacer between the DIG-NHS terminal-modifier and the target-complementary nucleotides. As detailed above, due to histones occupying minor grooves of DNA in chromosomal DNA, some constraints on SCNA spacing may exist. Thus, SCNAs are preferably designed to fit in the target DNA major groove by modulating the distance between SCNAs, to enable an orientation of the target helix that allows Linking Domains of a dimerized programmable molecular complex to bind. Choice of interdomain connector between the globular Functional Domain and the Linking Domain (in the example shown here is GSLEGGSGG (SEQ ID NO: 14)) also influences the optimal SCNA distance as it either restricts or permits movement in the "hinge" between these two domains. Addition of non-target-base-pairing nucleotides ("N's") changes both the distance between SCNAs and the rotational orientation on the target helix as it changes the flexibility of the SCNA relative to the protein and the helix. These unpaired nucleotides are not constrained to the target DNA major groove.

The results of spatial measurements taken from computerized 3D models for the anti-DIG-ScFv-NHS-Ester-DIG system with the GSLEGGSGG (SEQ ID NO: 14) interdomain linker, as shown in this example, yielded that the expected optimal distance between SCNAs is, in the presence of 2 N's in the SCNA, about 23-26 nucleotides. Cleavage is predicted to occur about ±2 nucleotides to left and to the right of the 11$^{th}$, 12$^{th}$ or 13$^{th}$ nucleotide, counting from after the last nucleotide hybridizing with the SCNA on either side, taking into account the 4 base 5' overhang created by dsDNA cleavage by the dimerized construct. This criterion suggests that if the targeted sequence is, for this 24 nucleotide example: AAAAAAAAAAYYYYYY-YYYXXXXXXXYYYYYYYYYCCCCCCCCCC, where Y+X represents the number of nucleotides between the SCNA base-pairing sites, then the designed SCNAs base-pair with areas A and C and the cleavage resulting in DSB is in or adjacent to the X area. The SCNAs can be complementary to either sense or antisense strands, but are chosen preferably to base-pair with the sense (untranscribed) sequence. Both SCNAs can base-pair with the same strand, as the protein moiety's position is situated at the "near end" of the SCNA as defined by the 5' or 3' modification of the primer being at the "near end" (as illustrated in FIG. 2A). Distance optimization between SCNAs, as well as preferred strand, are one of several criteria tested in this bioassay.

Target nucleic acid (GFP coding sequence), containing a target site (STOP codon, (TAG)) includes the nucleotide sequence set forth in SEQ ID NO: 15 ("STOP-GFP"), where the TAG stop codon is located at nucleotide 878:

The mCherry donor for examples 1B and 1C includes a promoter-less and terminator-less coding sequence, set forth in SEQ ID NO: 16:

The following target site sequence is targeted in examples 1A through 1C:

Examples 1A-C "First Target" Sequence

```
GTCGACAACTAGTCCAGATCT      (SEQ ID NO: 17)
```

SCNA Sequences
Modification symbols are: Phosphorothioate-bonds=*; 5' DIG=/5DigN/; 3'DIG=/3DigN/).
Tested Paired SCNA Combinations for 1A-1C "First Target":
Sense SCNA:
GFP_918_SR1: /5DigN/ NNNNNNGTGTCCAAGGGCGAGGAGCTG*T; (the nucleic acids only are designated herein as SEQ ID NO: 18)
GFP_896_SL1:
T*TTACGAACGATAGCCATGGCCNNNNNN/3DigN/
(the nucleic acids only are designated herein as SEQ ID NO: 19)
A second Sense paired combination, employing a 24 bp target gap and a shorter SCNA linker according to the prediction results:
GFP_920_SR1: /5DigN/ NNGTCCAAGGGCGAGGAGCTGTT*C (the nucleic acids only are designated herein as SEQ ID NO: 20)
GFP_895_SL1: A*TTTACGAACGATAGCCATGGCNN/ 3DigN/(the nucleic acids only are designated herein as SEQ ID NO: 21)
Anti-Sense SCNA:
GFP_918_ASR1:
C*AGCTCCTCGCCCTTGGAGACNNNNNN/3DIGN/
(the nucleic acids only are designated herein as SEQ ID NO: 22)
GFP_896_ASL1: /5DIGN/ NNNNNNGGCCATGGCTATCGTTCGTA*A (the nucleic acids only are designated herein as SEQ ID NO: 23)
A second Anti-sense paired combination, employing a 24 bp target gap and a shorter SCNA linker according to the prediction results:
GFP_920_ASR1:
G*AACAGCTCCTCGCCCTTGGACNN/3DIGN/(the nucleic acids only are designated herein as SEQ ID NO: 24)
GFP_895_ASL1: /5DIGN/ NNGCCATGGCTATCGTTCGTAAA*T (the nucleic acids only are designated herein as SEQ ID NO: 25)
Combinations of sense and anti-sense pairs:
GFP_918_SR1: /5DigN/ NNNNNNGTGTCCAAGGGCGAGGAGCTG*T (the nucleic acids only are designated herein as SEQ ID NO: 18)
GFP_896_ASL1: /5DIGN/ NNNNNNGGCCATGGCTATCGTTCGTA*A (the nucleic acids only are designated herein as SEQ ID NO: 23)

A second Anti-sense paired combination, employing a 24 bp target gap and a shorter SCNA linker according to the prediction results:
GFP_920_SR1: /5DigN/ NNGTCCAAGGGCGAGGAGCTGTT*C/ (the nucleic acids only are designated herein as SEQ ID NO: 20)
GFP_895_ASL1: /5DIGN/ NNGCCATGGCTATCGTTCGTAAA*T (the nucleic acids only are designated herein as SEQ ID NO: 25)
GFP_918_ASR1: C*AGCTCCTCGCCCTTGGAGACNNNNNN/3DIGN/ (the nucleic acids only are designated herein as SEQ ID NO: 22)
GFP_896_SL: T*TTACGAACGATAGCCATGGCCNNNNNN/3DigN/ (the nucleic acids only are designated herein as SEQ ID NO: 19)
A second Anti-sense paired combination, employing a 24 bp target gap and a shorter SCNA linker according to the prediction results:
GFP_920_SL1: A*TTTACGAACGATAGCCATGGCNN/3DigN/ (the nucleic acids only are designated herein as SEQ ID NO: 21)
GFP_895 ASR1: G*AACAGCTCCTCGCCCTTGGACNN/3DIGN/ (the nucleic acids only are designated herein as SEQ ID NO: 24)
"First target" for example 1C is identical to the 1A and 1B target.
"Second target" for example 1C: GACTCTAAGCTTGGGTCTAGA (SEQ ID NO: 26)
SCNAs for Example 1C:
A combination, utilizing a 24 bp target gap and a short SCNA linker:
Sense:
GFP_1658_SR: /5DIGN/ NNTCCGCAAAAATCACCAGTCTC*T (the nucleic acids only are designated herein as SEQ ID NO: 27)
GFP_1633_SL: G*CATGGACGAGCTGTACAAGTCNN/3DIGN/ (the nucleic acids only are designated herein as SEQ ID NO: 28)
Antisense:
GFP_1658_ASR: A*GAGACTGGTGATTTTTGCGGANN/3DIGN/ (the nucleic acids only are designated herein as SEQ ID NO: 29)
GFP_1633_ASL: /5DIGN/ NNGACTTGTACAGCTCGTCCATG*C (the nucleic acids only are designated herein as SEQ ID NO: 30)
As in example 1A-C "first target" SCNAs these four example 1C "second target" SCNAs may be paired using one "left" (L) and one "right" (R) SCNA from the list above.
Delivery
Bioassay setup: *Arabidopsis* protoplast preparation is based on Wu et. al. (Wu et. al., 2009):
Plant material: *Arabidopsis* grown under 16 hr day optimal light (150 microEinstein·m-2·s-1) at 22 degrees C.
Leaves: 3-5 week old plants (W~2 cm L~5 cm).
Working Solutions:
Enzyme Solution:
1% Cellulase, 0.25% Macerozyme, 0.4M Mannitol, 10 mM CaCl2, 20 mM KCl, 0.1% BSA, 20 mM MES pH5.7. Heat 50-55 degrees C. 10 minutes to inactivate proteases and then filter. Use fresh. 10 ml/7-10 peeled leaves (1-5 gr)/dish.
Modified W5 Solution:
154 mM NaCl, 125 mM CaCl2, 5 mM KCl, 5 mM Glucose, 2 mM MES pH5.7. Wash twice with 25 ml/plate, +twice 3 ml for transfection wash+1 ml resuspension
Modified MMg Solution:
(Resuspension Solution) 0.4M Mannitol, 15 mM MgCl2, 4 mM MES pH5.7.
Modified TEAMP Transfection Buffer (PEG Solution):
40% PEG MW 4000, 0.1M CaCl2, 0.2M Mannitol volume=1:1 of 200 microliter protoplasts in MMg+volume of DNA
BSA:
1% BSA
Working Protocol:
1. Preheat waterbath to 50-55 degrees C., cool swing-out centrifuge, chill W5 and MMg, and cut tips.
2. Prepare fresh BSA coated plates (1.25 ml 1% BSA/well in water, incubate on bench till ready)
3. Make fresh enzyme solution 10 ml/treatment.
4. Pick 7-10 leaves, must not be wet. 10 leaves should yield ~4-5 transformations.
5. Tape upper epidermis with Time-tape, lower with Magic tape. Easier without gloves. Easier to peel if petiole is stuck to time-tape only.
6. 0.22 μm-filter 10 ml fresh enzyme solution into each petri dish
7. Peel and discard Magic tape. Transfer Time-tape side to petri dish
8. Gently shake on platform shaker 40 rpm 20-60 min in light until protoplast release (check empirically)
9. Centrifuge in 50 ml tubes 100×g 3 min in swing-out rotor
10. Wash twice with 25 ml cold W5 solution.
11. Ice 30 min, count during this time in hemocytometer using light microscope
12. Centrifuge and resuspend in MMg solution to 2-5×10^5 cells/ml (about 1 ml).
Transfection:
1. Make fresh PEG sol for transfection in 2 ml tube
2. Pour off BSA from 6-well plates and dry
3. Mix ~5×10^4 protoplasts (2×10^4-1×10=) in 0.2 ml MMg solution with a mixture of Target plasmid DNA, Protein Moiety expressing plasmid DNA and SCNAs ssDNA to a total of 30-40 microgram at RT in 15 ml round-bottom (snap-cap) tubes.
4. Add equal volume (0.2 ml protoplasts+midiprep vol.) of fresh PEG sol
5. Incubate RT 5 min
6. Wash by slowly adding 3 ml W5 solution, 1 ml at a time, and mixing
7. Centrifuge 100×g in swing-out 1 min
8. Repeat wash and pellet
9. Resuspend in 1 ml W5 solution
10. Pour into BSA-coated plates
11. Grow protoplasts under 16 hr day optimal light (150 microEinstein·m^−2 s^−1) at 22 degrees C., replacing media as needed.
Protoplasts suspended in W5 solution are screened for GFP/mCherry activity 3 days after transfection using an automated flow-cytometer (FACS). GFP is detected by excitation at 488 nm with emission detected by 530/30 filter. mCherry excitation and emission are 561 nm and 610/20 filter. Threshold and compensation factors are set to exclude any false positives.

Example 1A

Point Mutation by Induced DSB

In this example, cleavage of the target results in a Double-Strand-Break (DSB) in the plasmid DNA target. This DSB is designed to be created in the STOP codon site, which is digested and is repaired by the NHEJ repair mechanism as set forth in the exemplary illustration of FIG. 10 (mutation). NHEJ is prone to mutations, and some of these mutations may abolish the STOP codon and restore an open reading frame resulting in an active GFP open reading frame (ORF). GFP is then detected by means of microscopy or flow cytometer (FACS), enabling the measurement of system efficiency and comparison between variables for its improvement.

When targeting a STOP-GFP transgene previously stably introduced into the *Arabidopsis* genome (instead of a plasmid), genome-modified plants can be regenerated from GFP expressing protoplasts.

Example 1B

Specific Integration into an Induced Genomic DSB

Similar to the example 1A, the in-frame GFP stop codon sequence is targeted with the programmed molecular complex. In this application a linear dsDNA donor is added, comprising a promoter-less, terminator-less mCherry reporter gene containing only the CDS. Following transfection as described, mCherry expressing protoplasts are detected by red fluorescence by means of microscopy or flow cytometer (FACS), enabling the measurement of system efficiency and comparison between variables for its improvement. The mCherry excitation and emission are 561 nm and 610/20 filter. Since the donor DNA contains a promoter-less mCherry, its activity can be achieved by promoter trapping. Thus, the targeted GFP cassette is cleaved to form a DSB wherein any linear DNA may be ligated. Since excess of the mCherry CDS linear dsDNA is supplied, it is trapped in the DSB, causing, in some cases, translation in frame of the mCherry protein. Targeted plasmids with such specific insertion of the mCherry into the GFP targeted sequence are further analyzed by PCR with the following primers: one binding the target plasmid DNA sequence, and one binding the inserted DNA:

```
35SF:      CTATCCTTCGCAAGACCCTTCC  (SEQ ID NO: 31)

mCherryR:  TTATCTTGTACAGCTCGTCCAT  (SEQ ID NO: 32)
```

Similarly, a bacterial antibiotic resistance (NPT-II coding cassette, without an origin of replication) is provided into the protoplasts as a linear dsDNA. This DNA is inserted instead of the mCherry CDS of examples 1B and 1C, and screened by extracting total DNA from protoplasts, transforming the DNA including plasmids with or without insertions into *E. coli*, and growing these on a medium containing Kanamycin. Resistant bacteria have plasmids that trapped the NPT-II cassette. To assess the specificity of the insertion into the predetermined GFP target site, the GFP-target site is PCR-amplified with primers spanning the expected insertion site. Specific insertion causes a significant shift in size of the PCR product on an agarose gel. Efficiency of insertion is calculated by dividing the number of Kanamycin resistant colonies by the number of Ampicillin resistant colonies (Ampicillin resistance is encoded on the target plasmid) in a duplicate-plating experiment. Specificity is calculated by repeating the experiment omitting or replacing components of the programmable molecular complex (e.g. GFP-targeting SCNAs) and comparing to unmodified experiments.

Example 1C

Gene Replacement Through NHEJ Repair Mechanism

In this example, the GFP coding sequence is replaced with mCherry CDS via endogenous NHEJ. To delete an extensive section of target DNA via the NHEJ strategy, two DSBs are created. To target the beginning and the end of the GFP CDS, two sets of SCNAs are used in conjunction with the mCherry linear dsDNA donor. Since the donor DNA contains promoter-less mCherry, its activity can be achieved by promoter trapping. The targeted GFP cassette can therefore trap the mCherry CDS. The mCherry is analyzed by FACS or microscope with excitation and emission detected at 561 nm and 610/20 filters, respectively.

mCherry positive protoplast are sorted by FACS and subsequently subjected to DNA extraction, direct transformation of the total DNA which includes plasmids into *E. coli*, growth on antibiotic containing media, and performing two colony-PCR reactions on each bacterial colony with two primer sets:

```
35SF:
                             (SEQ ID NO: 31)
CTATCCTTCGCAAGACCCTTCC mCherryR:
                             (SEQ ID NO: 32)
TTATCTTGTACAGCTCGTCCAT
and

35S-T-R-SEQ:
                             (SEQ ID NO: 33)
CCCTATAAGAACCCTAATTCCC mCherryF:
                             (SEQ ID NO: 34)
ATGGTGAGCAAGGGCGAGGA
```

Colonies which produce an amplification product in both PCR reactions contain a plasmid which has been targeted in *Arabidopsis* protoplasts to produce a correctly oriented replacement event through the NHEJ repair pathway, and are further sequenced for verification.

When targeting a GFP transgene previously stably introduced into the *Arabidopsis* genome (instead of a plasmid), no such direct transformation of *E. coli* is performed. Instead, genomic DNA is amplified directly by PCR from single protoplasts using said primers. Alternatively, genome-modified plants can be regenerated from non-GFP expressing, mCherry expressing protoplasts, portions of which can be similarly analyzed.

Example 2

DNA Double Strand Break Induction Mutation and Insertion, in a Monocotyledon Cereal Plant Genome Targeting IPK1 in Maize for Knockout.

The IPK1 gene, encodes inositol-1,3,4,5,6-pentakisphosphate 2-kinase which is involved in phytate biosynthesis in maize seeds. Phytate, when fed to non-ruminant livestock, is an anti-nutritional component that contributes to environmental phosphorus pollution. Targeting IPK1 may reduce the seed phosphorus by 75%. Two paralogous *Zea mays* IPK genes sharing 98% sequence identity exist in the maize genome. In this example, the IPK1 sequence based on Genbank Accession #: EF447274 is targeted.

Target Site in the Target Nucleotide Sequence:

```
In IPK1 exon 2:
                             (SEQ ID NO: 35)
TTCTCAAGTCATGAGCAACTC
```

Protein Sequence and Properties

The resulting cleavage of the predetermined Target site IPK1 by the programmed molecular complex, result in its mutation or in insertion of a donor DNA into the DSB created by the programmed complex, as desired, aided by endogenous processes. The programmable molecular complex here consists of 2 identical monomers of a protein moiety and two different SCNA molecules. In this example, the protein moiety is identical to that of example 1.

In this example the nucleic acid end-modification of the SCNA is an NHS-Ester linked Digoxigenin (DIG) that is attached to the 5' or 3' position of the oligonucleotide.

SCNA Properties and Sequence

The rational design of the SCNA is essentially as described in Example 1. The length of the SCNA of the complementary, target-base-pairing oligonucleotide is preferentially at least 18 bases. The SCNA can also contain a small number (e.g. 1-6, in one example 6, in other example, 2) of non-target-base-pairing nucleotides (N's) of any sequence composition that serve as a spacer between the DIG-NHS terminal-modifier and the target-complementary nucleotides.

SCNA Nucleotide Sequences Flanking the IPK1 Target Site

Combinations of the following "R" and "L" SCNAs employing a 21 bp target gap are tested:

IPK1-SR-1710: /5DIGN/ NNNNNNCTGTGGGGCCATATCCCAGAA*C (the nucleic acids only are designated herein as SEQ ID NO: 36)

IPK1-SL-1688: G*CGGGCACCGAGTTGTATTGTANNNNNN/3DIGN/ (the nucleic acids only are designated herein as SEQ ID NO: 37)

IPK1-ASR-1710: G*TTCTGGGATATGGCCCCACAGNNNNN/3DIGN/ (the nucleic acids only are designated herein as SEQ ID NO: 38)

IPK1-ASL-1688: /5DIGN/ NNNNNNTACAATACAACTCGGTGCCCG*C (the nucleic acids only are designated herein as SEQ ID NO: 39)

A second set of paired "R" and "L" SCNAs combination, employing a 24 bp target gap and a shorter SCNA linker according to the prediction results:

IPK1-SR-1712: /5DigN/ NNGTGGGGCCATATCCCAGAAC*T (the nucleic acids only are designated herein as SEQ ID NO: 40)

IPK1-SL-1687: A*GCGGGCACCGAGTTGTATTGTNN/ 3DigN/ (the nucleic acids only are designated herein as SEQ ID NO: 41)

IPK1-ASL-1687: /5DigN/ NNACAATACAACTCGGTGCCCGC*T (the nucleic acids only are designated herein as SEQ ID NO: 42)

IPK1-ASR-1712: A*GTTCTGGGATATGGCCCCACNN/ 3DigN/ (the nucleic acids only are designated herein as SEQ ID NO: 43)

SCNAs comprise modified ssDNA. Modification symbols are: Phosphorothioate-bonds=*; 5' DIG=/5DigN/; 3'DIG=/ 3DigN/.

Experiment 2A

IPK1 Knockout and GFP Expression in Protoplasts

In this experiment, genomic DSB in Maize plants and specific integration of GFP sequence into the IPK1 gene forming a knockout mutation and expression of GFP in the IPK1 locus are tested. The programmed molecular complex forms the genomic DSB in the IPK1 sequence, initiating the integration of the donor DNA into the IPK1 sequence through homologous recombination.

This example, 2A, is performed on maize protoplasts which are analyzed by FACS for GFP activity.

Working Protocol:

Protoplast Preparation:

A transient expression assay using maize mesophyll protoplasts (Sheen, 2001) is used with electroporation-induced nucleic-acid delivery in addition or alternatively to a Polybrene-induced delivery protocol:

Transfection Based on (Antonelli & Stadler, 1989):

Freshly isolated protoplasts (about $2 \times 10^6$) are incubated for about 6 to 12 h with about 20-50 microgram of transfecting DNA comprising modified-ssDNA SCNAs, a plasmid encoding the Protein Moiety, Donor DNA (where applicable), and 30 microgram of the polycation Polybrene (hexadimethrine bromide). At the end of the incubation period, the transfection mixture is diluted by addition of growth medium and the cells are then incubated further for about 30 h before being assayed for transient gene expression:

1. Prepare protoplasts, and resuspend $2 \times 10^6$ cells in 0.5 ml Murashige Skoog-based growth medium with 8% mannitol (MS2D8M).

2. For each experiment, prepare a fresh Polybrene (Aldrich) stock solution (10 mg/ml in phosphate buffered saline, pH 7.0). This is an extremely hygroscopic chemical and the manufacturer's safety instructions must be rigorously applied. The stock solution is then diluted to yield a final concentration of 30 microgram Polybrene in 0.1 ml MS2D8M.

3. The desired concentration of transfecting DNA-plasmid DNA and modified ssDNA-SCNAs—is suspended in 0.4 ml MS2D8M.

4. Mix the 0.1 ml (30 microgram) Polybrene solution with the resuspended protoplasts and transfer to a 60 mm Petri dish.

5. Immediately add (dropwise) the 0.4 ml DNA suspension. The protoplast/Polybrene/DNA mixture (total volume 1.0 ml) is rotated gently (25 rpm) on a gyratory shaker for 15 min and then incubated (stationary) at 28 C for 6 h.

6. After the 6 h incubation, dilute the above mixture with 4.0 ml MS2D8M, seal the Petri dish, and follow procedures for assaying transient gene expression or for selection of stable transfectants.

Detection:

Transfected maize protoplasts suspended in MS2D8M solution are analyzed by flow-cytometer using Fluorescence-activated cell sorting (FACS), 3 days after transfection with Polybrene. GFP is detected by excitation at 488 nm with emission detected by 530/30 filter. Threshold and compensation factors are set to exclude any false positives. FACS is used to separate targeted cells for further analysis.

The protoplasts are subjected to analysis by extraction of genomic DNA and its amplification by PCR using the primers 1F and 1R below and subsequent digestion with BspHI of the PCR product. BspHI uncleavable products of more or less similar size to wild-type result from precise targeting events coupled with imprecise re-ligation, larger sized PCR-products result from insertions into the target site as desired.

```
Primer 1F:  GAGCTAGATAGCAGATGCAGAT  (SEQ ID NO: 44)

Primer 2R:  CTCCAGAAAATCCCTAGAAACA  (SEQ ID NO: 45)
```

Alternatively, the PCR product is subjected to CEL I Enzymatic Mutation Detection Assay, in accordance with the instructions in the SURVEYOR Mutation Detection Kit (Transgenomics, USA). This assay is used to evaluate the effectivity of mutation of IPK1 DNA by gene targeting by the programmed molecular complex.

Donor Sequence for Experiment 2A:

GFP is fused to IPK1 sequence and thus GFP expression can happen only by precise homologous recombination (HR). The sequence of the entire donor sequence is as set forth in SEQ ID NO: 46. The sequence homologous to IPK1 necessary for recombination is nucleotides 1-621 and 1960-2610 of SEQ ID NO:46, and the GFP cassette is encoded by nucleotides 622-1959.

Experiment 2B

IPK Knockout and Bar Insertion, Delivery to Calli

In this experiment, genomic DSB in Maize plants and specific integration of the herbicide bar resistance gene conferring resistance to Bialaphos (Phosphinothricin; Glufosinate-Ammonium; its analogues or commercial herbicides such as Basta, Bayer Crop Science) into the IPK1 gene forming knockout mutation and expression of bar in the IPK1 locus, are tested. The programmed molecular complex forms the genomic DSB in the IPK1 sequence initiating the integration of the donor DNA into the IPK1 sequence through homologous recombination.

This example is performed on maize calli which are transfected by DNA bombardment and then grown under Bialaphos (Basta) selection.

Working Protocol:
1. Formation of embryogenic callus: Immature embryos 1.6 mm to 1.8 mm (Plants A188XB73 or A188XB84) Growth conditions: Light 10 microEinstein/m^2/sec 24 degrees C. on N6 medium containing 2 mg/L glycine, 2.9 g/L L-proline, 100 mg/L casein hydrolysate, 13.2 mg/L dicamba or 1 mg/L 2.4D, 20 g/L sucrose, pH 5.8. Solidified with 2 g/L Gelgro.
2. Bombardment of plasmid DNA and modified ssDNA-SCNAs into calli based on the method used by (Gordon-Kamm et. al., 1990).
3. Transfer calli to growth condition as described in example 2A, with final concentration of 2.5 mg/L Bialaphos in the medium (B0178 Gold Biotechnology, 1328 Ashby Rd., St. Louis, Mo. 63132 U.S.A.).
4. Calli are moved into new medium every 2 weeks.
5. Calli grown for 2 month on Bialaphos are resistant to the herbicide and can be subjected to PCR analysis or regeneration.
6. Regenerated plants are both resistant to Basta and have reduced levels of phytate.

Detection and Analysis:

Calli bombarded with the modified ssDNA-SCNA, the plasmid encoding the programmable molecular complex protein moiety and the donor DNA containing bar resistance CDS expression cassette are grown on regeneration medium containing 2.5 mg/L Bialaphos. Only calli that include cells where the bar gene coding sequence are integrated into the IPK1 locus through HR are able to grow under these conditions, therefore, plant material still proliferating after 1 month on this medium is deemed genome-modified as desired.

By this design, while the bar resistance cassette integrates into the genome by HR to function properly, the *Corynebacterium diphtheria* toxin A (DT-A) cassette is an autonomous cassette that expresses the DT-A under heat shock (HS) conditions (42 degrees C.). Thus, for further analysis, calli is split into HS induced calli and uninduced calli. Only calli which contain a perfect HR event do not express the DT-A. Calli that contain randomly integrated plasmid, which contains both the donor DNA and the DT-A cassette express the DT-A and consequently die.

Further, calli are subjected to PCR analysis using the primers 1F and 1R shown in example 2A, followed by digestion of the product, as above, with BspHI.

Donor Sequence for Experiment 2B:

The Donor plasmid contains both a bar resistance cassette, to be inserted into the IPK1 cleavage site, and a DT-A cassette which should not recombine into the IPK1 locus, as a non-specific integration event marker: The bar resistance cassette is flanked by sequences homologous to IPK1 (nts. 1-621 and 2338-2988 of SEQ ID NO:47) necessary for HR, while the DT-A cassette is located outside the homologous sequence flanked site. The bar cassette (nts. 622-2337 of SEQ ID NO: 47) contains a CaMv 35S constitutive promoter; the *Streptomyces hygroscopicus* bar gene CDS for phosphinothricin acetyl transferase conferring glufosinate ammonium resistance (nts. 1526-2078 of SEQ ID NO:47); and the NOS terminator—downstream from the bar CDS.— The entire 2B Donor sequence is set forth in SEQ ID NO: 47.

On the same plasmid, a second cassette encoding diphtheria toxin A, DT-A, (from GenBank: AB535096.1) under the control of a Heat-shock inducible promoter (HS-Promotor of *Arabidopsis* HSP18.2 from GenBank: X17295.1) and terminated with a NOS terminator has the sequence as set forth in SEQ ID NO: 48.

Example 3

Induction of Predetermined Chromosomal Double Strand Breaks (DSBs) in Living Cells of *Arabidopsis*

The enzyme Phytoene Desaturase (PDS) is involved in the conversion of phytoene to zeta-carotene in carotenoid biosynthesis. Disruption of *Arabidopsis* phytoene desaturase results in albino and dwarf phenotypes. This phenotype is explained by impaired chlorophyll, carotenoid, and gibberellin biosynthesis. Thus, a mutation in this gene is phenotypically detectable.

Experiment 3A

In this example, a chromosomal double-strand break (DSB) in the endogenous PDS gene is specifically induced in order to create a point mutation through a frameshift, thus knocking out the function of the gene by utilizing the NHEJ endogenous pathway.

Experiment 3B

In this example, a chromosomal double-strand break (DSB) specifically induced in the endogenous PDS gene in order to create an Insertion of a mCherry Donor sequence into an endogenous PDS sequence to knock out PDS by assisted homologous recombination using the programmable molecular complex.

For examples 3A-3B, an *Arabidopsis* protoplast based bioassay is used. In this bioassay the protoplasts are delivered with a plasmid expressing the protein moiety of the molecular complex in-vivo and co-delivered with a pair of ssDNA Specificity Conferring Nucleic Acids (SCNA) modified, in this example, with a terminal Fluorescein (6-carboxy-Fluorescein, 6-FAM), each SCNA having such a modification at either the 3'-terminus or the 5'-terminus (/36-FAM/and /56-FAM/, respectfully). A second modification for exonuclease protection, such as phosphorothioate, is added at the opposite terminus, as may internal phosphorothioate bonds for endonuclease protection. In this example, the coding sequences for the Protein Moiety and the Donor DNA are concomitantly delivered on a single plasmid using a PEG transfection protocol (Wu et. al., 2009). Modified ssDNA SCNAs are synthetically produced and delivered together with the plasmid using PEG as above.

Protein Sequence and Properties

In this example, the protein moiety, encoded on a plasmid, contains an amino-acid sequence adapted from a FokI nuclease domain as the Functional Domain; an amino-acid sequence adapted from anti-Fluorescein single-chain variable fragment (scFv) immunoglobin (Protein Data Bank accession codes 1X9Q, 1FLR_H), as Linking Domain; an SV40NLS (PKKKRKV: SEQ ID NO: 3) as a nuclear localization domain and a ~15 Å inter-domain connector (GGSGG: SEQ ID NO: 7).

Thus, the protein moiety of the molecular complex described in this example has the amino-acid sequence as set forth in SEQ ID NO: 49 and is encoded by the nucleotide sequence as set forth in SEQ ID NO:50.

The specificity-conferring nucleic acid (SCNA) of this example is modified by the addition of a Fluorescein-ScFv/6-FAM, 6-carboxyfluorescein-Fluorescein dT which includes a C6-linker to one end of each SCNA.

SCNA Properties and Sequence

The design of the SCNA is essentially as described in Example 1. The length of the SCNA of the complementary, target-base-pairing oligonucleotide is preferentially at least 18 bases. The SCNA can also contain a small number (e.g. 1-6, in one example 6, in other example, 2) of non-target-base-pairing nucleotides (N's) of any sequence composition that serve as a spacer between the 6-FAM terminal-modifier and the target-complementary nucleotides.

Target Sequence:

The target sequence is: GTCCTGCTAAGCCTTTGAAAG (SEQ ID NO: 51), Located on Exon 2 of the *Arabidopsis* PDS Sequence (GI:5280985, gene d13145c, protein id="CAB 10200.1).

SCNA Sequence Options:

SCNAs may be targeted to either strand, thus, for the shown target, 4 SCNA pairing options exist:

Sense (S) SCNAs:

PDS-SL1-846:
GCATCCTTCCGTAGTGCTCCTCNNNNNN/36-FAM/ (the nucleic acids only are designated herein as SEQ ID NO: 52)

PDS-SR1-868: /56-FAM/NNNNNNTTGTAAT-TGCTGGTGCTGGTAT (the nucleic acids only are designated herein as SEQ ID NO: 53)

Anti-sense (AS) SCNAs:

PDS-ASL1-846: /56-FAM/NNNNNNGAGGAGCAC-TACGGAAGGATGC (the nucleic acids only are designated herein as SEQ ID NO: 54)

PDS-ASR1-868: ATACCAGCACCAGCAATTA-CAANNNNNN/36-FAM/ (the nucleic acids only are designated herein as SEQ ID NO:217)

Mixed strand SCNAs:

PDS-SL1-846:
GCATCCTTCCGTAGTGCTCCTCNNNNNN/36-FAM/ (the nucleic acids only are designated herein as SEQ ID NO: 52)

PDS-ASR1-868: ATACCAGCACCAGCAATTA-CAANNNNNN/36-FAM/ (the nucleic acids only are designated herein as SEQ ID NO:217)

PDS-SR1-868: /56-FAM/NNNNNNTTGTAAT-TGCTGGTGCTGGTAT (the nucleic acids only are designated herein as SEQ ID NO: 53)

PDS-ASL1-846: /56-FAM/NNNNNNGAGGAGCAC-TACGGAAGGATGC (the nucleic acids only are designated herein as SEQ ID NO: 54)

A second set of paired "R" and "L" SCNAs combinations, employing a 24 bp target gap and a shorter SCNA linker according to the prediction results:

PDS-SL2-845: TGCATCCTTCCGTAGTGCTCCTNN/36-FAM/ (the nucleic acids only are designated herein as SEQ ID NO: 55)

PDS-SR2-870: /56-FAM/NNGTAAT-TGCTGGTGCTGGTATGT (the nucleic acids only are designated herein as SEQ ID NO: 56)

PDS-ASL2-845: /56-FAM/NNAGGAGCACTACG-GAAGGATGCA (the nucleic acids only are designated herein as SEQ ID NO: 57)

PDS-ASR2-870: ACATACCAGCACCAGCAATTACNN/36-FAM/ (the nucleic acids only are designated herein as SEQ ID NO: 58)

PDS-SL2-845: TGCATCCTTCCGTAGTGCTCCTNN/36-FAM/ (the nucleic acids only are designated herein as SEQ ID NO: 55)

PDS-ASR2-870: ACATACCAGCACCAGCAATTACNN/36-FAM/ (the nucleic acids only are designated herein as SEQ ID NO: 58)

PDS-SR2-870: /56-FAM/NNGTAAT-TGCTGGTGCTGGTATGT (the nucleic acids only are designated herein as SEQ ID NO: 56)

PDS-ASL2-845: /56-FAM/NNAGGAGCACTACG-GAAGGATGCA (the nucleic acids only are designated herein as SEQ ID NO: 57)

/56-FAM/ symbolizes a 5'-modification on the SCNA ssDNA comprising of 6-FAM (6-carboxy-Fluorescein). /36-FAM/ symbolizes a 3'-modification on the SCNA ssDNA comprising of 6-FAM (6-carboxy-Fluorescein). N symbolizes any nucleotide.

Donor sequence is DONOR PD-MCHERRY-S having the sequence as set forth in SEQ ID NO: 59 (mCherry encoding ORF is at nucleotides 662-1372 of SEQ ID NO:59).

Delivery

Bioassay setup: *Arabidopsis* protoplast preparation is based on (Wu et. al., 2009) and is similar to that of example 1 with differences in the transfection step:

Transfection:

1. Make fresh PEG sol for transfection in 2 ml tube
2. Pour off BSA from 6-well plates and dry
3. Mix ~5×10^4 protoplasts (2×10^4-1×10^5) in 0.2 ml MMg with a mixture of Donor plasmid DNA (where relevant), Protein Moiety expressing plasmid DNA and SCNAs ssDNA to a total of 30-40 microgram at RT in 15 ml round-bottom (snap-cap) tubes. Alternatively Donor DNA and Protein-moiety expressing DNA are constructed and delivered on a single plasmid.
4. Add equal volume (0.2 ml protoplasts+midiprep vol.) of fresh PEG sol
5. Incubate RT 5 min
6. Wash by slowly adding 3 ml W5, 1 ml at a time, and mixing 7. Centrifuge 100×g in swing-out 1 min
8. Repeat wash and pellet
9. Resuspend in 1 ml W5 solution
10. Pour into BSA-coated plates
11. Grow protoplasts under 16 hr day optimal light (150 microEinstein·m^−2·s^−1) at 22 degrees C., replacing media as needed.

Analysis

In experiment 3A, DNA from pooled protoplasts is analyzed by PCR and restriction fragment analysis of the PCR product.

The PCR is conducted with the primers:

```
PCR Primer2F:
                                (SEQ ID NO: 60)
TGGTTGTGTTTGGGAATGTTTCT;
and PCR Primer2R:
                                (SEQ ID NO: 61)
TATCCAAAAGATATCTTCCAGTAAAC
```

Abolishment of cleavage with the restriction enzyme DdeI in at least a portion of the amplified DNA indicates at least some successful gene targeting and directed mutation of the genomic template.

In experiment 3B a Donor DNA encoding mCherry is fused in frame to the endogenous PDS gene. mRNA produced from this gene encodes a disrupted PDS fused to a full mCherry immediately followed by a STOP codon ("PD-mCherry"). Protoplasts suspended in W5 solution are screened for mCherry activity 3 days after transfection using an automated flow-cytometer (FACS) machine. PDS-modified protoplasts are detected by FACS analysis, where an insertion of mCherry donor is detectable by mCherry fluorescence using a 561 nm excitation wavelength and detection of 590-630 nm emission. Threshold and compensation factors are set to exclude any false positives.

Further characterization in both experiments is achieved by regenerating protoplasts on suitable media and examining their subsequent phenotypic character, where bleached plants or calli indicate successful gene-targeting.

Example 4

In-Vivo Genomic DNA Targeting and Gene-Replacement in the Dicotyledonous Plant Tobacco Replacement of the ALS gene in tobacco and producing herbicide resistant plants: Acetolactate synthase (ALS) is an enzyme in the biosynthetic pathways of valine, leucine, and isoleucine in plants. Mutations in this gene result in resistance to several herbicides. For example, mutations in the SuRB gene in tobacco have been shown to provide the following herbicide resistances: S647T—imazaquin, P191A—chlorsulfuron, W568L—chlorsulfuron and imazaquin In this example, the Tobacco ALS is targeted in order to replace the wild-type gene with a herbicide tolerant mutated version by assisted homologous-recombination mediated gene replacement.

Expression and assembly of the programmed molecular complex in tobacco plants is, performed here in two steps. Delivery of the protein moiety is achieved by infecting a Tobacco plant with a Tobacco Rattle Virus (TRV)-based viral protein expression vector such as a vector modified from pTRV2 (Vainstein et. al., 2011) for the delivery and expression of the programmable protein moiety in-planta.

Delivery of SCNA into plants expressing the protein moiety is achieved by infecting the plants with *Agrobacterium* carrying a T-DNA encoding both a pair of RNA-SCNAs and a Donor sequence.

The RNA-SCNAs in this example bind the Linking Domain of the Protein Moiety of the Molecular complex using the 20-mer boxB RNA hairpin binding sequence from bacteriophage Phi21 (SEQ ID NO: 62: 5'-UUCACCUC-UAACCGGGUGAG-3') as the "SCNA nucleotide motif" schematically exemplified in FIG. 1B.

The Linking Domain in this example is derived from the RNA-binding protein (RBP) bacteriophage Phi21 NProtein (SEQ ID NO: 63: N'-GTAKSRYKARRAELIAER-C'). In the example shown here the hairpin is not on the target but rather on the SCNA, and the action of the binding protein is thus not limited to a specific recognition site on the target RNA itself, but can be used to target any sequence, including DNA, depending exclusively on the variable SCNA target base-pairing sequence adjacent to the invariable RBP-binding hairpin.

The target nucleic acid (gene) in this example is SuRB (GenBank accession GI: 19778) and the desired amino acid mutation is P191A—conferring chlorsulfuron resistance. Thus:

```
Unaltered original Sequence:
                                (SEQ ID NO: 64)
GGTCAAGTGCCACGTAGGATG Induced Mutation:
                                (SEQ ID NO: 65)
GGTCAAGTGGCGCGCAGGATG
```

The Sequence of the Components of the Protein Moiety:
Components:
1. Bacteriophage Phi21 NProtein (SEQ ID NO: 63: GTAKSRYKARRAELIAER) at or near the N' terminus as in the full-length N-protein the RNA-binding peptide is situated at the N-terminus.
2. FokI nuclease

```
                                (SEQ ID NO: 66)
(VKSELEEKKSELRHKLKYVPHEYIELIEIARNSTQDRILEMKVMEFFM

KVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGN

YKAQLTRLNHITNCNGAVLSVEELLIGGEMIKAGTLTLEEVRRKFNNGEI

NF)
```

3.

```
SV40-NLS: (SEQ ID NO: 67: MPKKKRKV)
```

4. Interdomain connectors: various poly-amino-acid linkers are tested for optimal function of the programmed molecular complex.

Two options for protein assembly are tested in this example:
1. The first option, (as set forth in SEQ ID NO: 68), in which the Phi21 NProtein is assembled in the N' terminus of the protein moiety of the programmable molecular construct and the nuclear localization signal, SV40NLS, is located at the C' terminus and the interdomain linker is GGSGG (SEQ ID NO: 7). This protein assembly is encoded by the nucleic acid sequence as set forth in SEQ ID NO: 69.

Spatial measurements taken from computerized 3D models for the C' Phi21 NP version in conjunction with the BoxB RNA hairpin system and the GGSGGESK (SEQ ID NO: 74) interdomain linker, as shown in this example, yielded that the expected optimal distance between SCNAs is, in the presence of a single "N" in the SCNA, about 26-30 nucleotides. Cleavage is predicted to occur about ±2 nucleotides to left and to the right of the $13^{th}$-$17^{th}$ nucleotide, counting starts after the last nucleotide hybridizing with the SCNA on either side, taking into account the 4 base 5' overhang created by dsDNA cleavage by the dimerized construct. This criterion suggests that if the targeted sequence is 28 nucleotide in this example:

$A_1A_1A_1A_1A_1A_1A_1A_1A_1A_1$YYYYYYYYYY-XXXXXXXXYYYYYYYYYYYC$_1$C$_1$C$_1$C$_1$C$_1$C$_1$C$_1$C$_1$C$_1$C$_1$ where Y+X represents the number of nucleotides between the SCNA base-pairing sites, then the designed SCNAs base-pair with areas $A_1$ and $C_1$ and the cleavage resulting in DSB is in or adjacent to the X area. The SCNAs can be complementary to either sense or antisense strands, but are chosen preferably to base-pair with the sense (untranscribed) sequence. Both SCNAs can base-pair with the same strand, as the protein moiety's position is situated at the "near end" of the SCNA as defined by the 5' or 3' modification of the primer being at the "near end".

SCNA Sequence Options:

SCNAs base-pair to sequences flanking the target site that is to be cleaved on either strand, thus, for the shown target, utilizing a 28 bp target gap: 4 SCNA pairing options exist:

Sense (S) SCNA pair:

```
SuRB_P191_SR1 586:
                                    (SEQ ID NO: 70)
UUCACCUCUAACCGGGUGAGNGGUACUGAUGCUUUUCAGGAAA

SuRB_P191_SL1 557:
                                    (SEQ ID NO: 71)
AUAGCGUCCCCAUUGUUGCUAUNUUCACCUCUAACCGGGUGAG
```

Antisense (AS) SCNA pair:

```
SuRB_P191_ASR1 586:
                                    (SEQ ID NO: 72)
UUUCCUGAAAAGCAUCAGUACCNUUCACCUCUAACCGGGUGAG

SuRB_P191_ASL1 557:
                                    (SEQ ID NO: 73)
UUCACCUCUAACCGGGUGAGNAUAGCAACAAUGGGGACGCUAU
```

And all combinations of sense and antisense pairs always choosing one Right (R) and one Left (L) SCNA:

The second option for protein assembly tested in this example, assembled with the Phi21 nProtein at the C' of the protein and the SV40NLS at the N' of the protein moiety. In this construct an interdomain connector of the sequence: GGSGGESK (SEQ ID NO: 74) is used:

The Assembled Phi21 NP-based programmable protein moiety of this example has the amino acid sequence as set forth in SEQ ID NO: 75 and is encoded by the nucleic acid sequence as set forth in SEQ ID NO: 76.

Results of spatial measurements taken from computerized 3D models for the C' Phi21 NP version in conjunction with the BoxB RNA hairpin system and the GGSGGESK (SEQ ID NO: 74) interdomain linker, as used in this example, yielded that the expected optimal distance between SCNAs is, in the presence of 1 N in the SCNA, about 22-24 nucleotides. Cleavage is predicted to occur about ±2 nucleotides to left and to the right of the $11^{th}$, $12^{th}$ or $13^{th}$ nucleotide, counting from after the last nucleotide hybridizing with the SCNA on either side, taking into account the 4 base 5' overhang created by dsDNA cleavage by the dimerized construct. This criterion suggests that if the targeted sequence is, for this 23 nucleotide example:

$A_1A_1A_1A_1A_1A_1A_1A_1A_1A_1$YYYYYYYYXXX-XXXXYYYYYYYYC$_1$C$_1$C$_1$C$_1$C$_1$C$_1$C$_1$C$_1$C$_1$C$_1$.

where Y+X represents the number of nucleotides between the SCNA base-pairing sites, then the designed SCNAs base-pair with areas $A_1$ and $C_1$ and the cleavage resulting in DSB is in or adjacent to the X area. The SCNAs can be complementary to either sense or antisense strands, but are chosen preferably to base-pair with the sense (untranscribed) sequence. Both SCNAs can base-pair with the same strand, as the protein moiety's position is situated at the "near end" of the SCNA as defined by the 5' or 3' modification of the primer being at the "near end".

SCNA Sequence Options:

SCNAs base-pair to sequences flanking the target site to be cleaved on either strand, utilizing a 31 bp target gap, result in 4 SCNA pairing options:

Sense (S) SCNA Pair:

```
SuRB_P191_SR1-588:
                                    (SEQ ID NO: 77)
UUCACCUCUAACCGGGUGAGUACUGAUGCUUUUCAGGAAACU

SuRB_P191_SL1-556:
                                    (SEQ ID NO: 78)
GAUAGCGUCCCCAUUGUUGCUAUUCACCUCUAACCGGGUGAG
```

Antisense (AS) SCNA Pair:

```
SuRB_P191_ASR1-588:
                                    (SEQ ID NO: 79)
AGUUUCCUGAAAAGCAUCAGUAUUCACCUCUAACCGGGUGAG

SuRB_P191_ASL1-556:
                                    (SEQ ID NO: 80)
UUCACCUCUAACCGGGUGAGUAGCAACAAUGGGGACGCUAUC
```

Combinations of Sense and Antisense Pairs:

```
SuRB_P191_SR1-588:
                                    (SEQ ID NO: 77)
UUCACCUCUAACCGGGUGAGUACUGAUGCUUUUCAGGAAACU

SuRB_P191_ASL1-556:
                                    (SEQ ID NO: 80)
UUCACCUCUAACCGGGUGAGUAGCAACAAUGGGGACGCUAUC

SuRB_P191_SL1-556:
                                    (SEQ ID NO: 78)
GAUAGCGUCCCCAUUGUUGCUAUUCACCUCUAACCGGGUGAG

SuRB_P191_ASR1-588:
                                    (SEQ ID NO: 79)
AGUUUCCUGAAAAGCAUCAGUAUUCACCUCUAACCGGGUGAG
```

A second set of paired "R" and "L" SCNAs combinations, employing a 23 bp target gap and a short (a single N) SCNA linker according to the prediction results:

Sense (S):

```
SURB_P191_SR2-584:
                                    (SEQ ID NO: 81)
UUCACCUCUAACCGGGUGAGNUCGGUACUGAUGCUUUUCAGGA
```

-continued

SURB_P191_SL2-560:
(SEQ ID NO: 82)
GCGUCCCCAUUGUUGCUAUAACNUUCACCUCUAACCGGGUGAG

Antisense (AS)

SuRB_P191_ASR2-584:
(SEQ ID NO: 83)
UCCUGAAAAGCAUCAGUACCGANUUCACCUCUAACCGGGUGAG

SuRB_P191_ASL2-560:
(SEQ ID NO: 84)
UUCACCUCUAACCGGGUGAGNGUUAUAGCAACAAUGGGGACGC

Or combinations of "R" and "L" SCNAs from the second set.
UUCACCUCUAACCGGGUGAG (SEQ ID NO:62) is the sequence of the 20-mer boxB RNA hairpin binding sequence from bacteriophage Phi21, and functions as the Linking-domain-binding segment of the SCNA (schematically marked as "SCNA nucleotide motif" in FIG. 1B).
Coding sequence of the ALS SURB CDS (unaltered) is set forth in SEQ ID NO: 85.
DONORI P191A:
donor has altered nucleotide sequence to create a Proline to Alanine (P191A) mutation and to enable restriction enzyme analysis. The sequence of this donor is set forth as SEQ ID NO: 86. Altered sequence is as set forth in nucleotides 544-591 of SEQ ID NO: 86.

Method:
In this example, natural host plants *Petunia*, *Nicotiana tabacum* or *N. benthamiana* plants are first inoculated with a pTRV-based or pTRVdelta2b-based vector (Vainstein et. al., 2011), which is designed to express, in this example, the programmable molecular construct under the control of a viral subgenomic promoter. About 5-21 days after infection, plant leaves are collected and plant sap, used here as inoculum, is extracted by crushing the leaves in phosphate buffer (20 mM, pH 6.8), optionally supplemented with a nonionic wetting agent such as Silwet L-77 (about 0.015%). Clearing the solution by centrifugation and/or cheesecloth is optionally followed by 0.22 µm filtering. Filtering is necessary for injection into tissue-culture grown plants. Concomitantly, a portion of a leaf is analyzed for stability of the viral construct by extracting RNA, reverse transcribing the RNA using a primer 3' from the foreign gene insertion site, amplifying the cDNA by PCR using primers spanning the foreign gene insertion site and electrophoresing side by side with a similarly PCR amplified pTRV plasmid originally used for inoculation. Target tobacco plants, about 1 month old, are then infected by lightly abrading their leaves with carborundum and rubbing the sap on the leaf surface. These plants may be grown in-vitro or otherwise. TRV-based self-replicating vector carrying the programmable molecular complex infects the plant and spreads systemically to leaves, meristems and non-inoculated tissues and organs. While still unprogrammed the said complex is inactive as a nuclease.

Once the TRV-based self-replicating vector has spread systemically throughout the plant (about 5-7 days), hence, expressing the programmable protein moiety of the molecular complex, leaf-disks are excised under sterile conditions. Leaf disk transient expression is done in a manner similar to (Gallois & Marinho, 1995). Briefly, disks are vacuum infiltrated with a suitable strain of *Agrobacterium* (e.g. EHA105) pre-transformed with one binary plasmid (e.g. pRCS, pSOUP+pGreen, or other suitable binary vector) encoding between its RB and LB sequences one of the combinations of two SuRB_P191 SCNA transcripts shown above (see also FIG. 9 and FIG. 8A for schematic illustrations), under the control of two, identical or different, constitutive plant promoters such as CaMV 35S or NOS or OCS and carrying also the Donor1 P191A sequence. SCNAs are transcribed upon T-strand import into the cell, assemble with the programmable protein to form a programmed molecular complex which is then imported into the nucleus where it specifically cleaves a DSB in the SurB locus in the tobacco genomic DNA. Donor DNA from the T-DNA then recombines with the SurB gene near this DSB bringing about the desired mutation. Leaf disks are placed on selection medium containing 420 nM chlorsulfuron as described by Kochevenko (Kochevenko & Willmitzer, 2003) and in the detailed protocol below. *Agrobacterium* is killed with a suitable antibiotic (Carbenicillin 250 ug/ml+Vancomycin 250 ug/ml), and callus developing from leaf-disks is permitted to form shoots grown into herbicide resistant genome-modified plants. Regenerating plants are screened for chlorsulfuron resistance on Murashige and Skoog medium containing 420 nM chlorsulfuron as described by Kochevenko et. al. Only plants that grow on chlorsulfuron have an altered ALS gene, indicating that ALS was targeted by the programmed molecular complex and that the Donor was properly recombined into the correct location.

Analysis enabling resolving of successful gene-replacement events is achieved by conducting PCR on genomic DNA extracted from portions of Tobacco regenerants. On the altered sequence, the AgeI restriction enzyme site is abolished and BssHII and KpnI sites are added. Thus amplifying a PCR fragment encompassing the replacement site in the SuRB gene and digestion of the PCR fragment with AgeI, BssHII and KpnI provides a diagnostic pattern enabling recognition of successful gene replacement. These plants are further screened to eliminate those that have unwanted integrated T-DNA by DNA extraction and PCR amplification of a non-SuRB region of the SCNA-encoding T-DNA.

Detailed *Agrobacterium* Transformation Protocol:
1. Collect 2 ml overnight *Agrobacterium* culture (transformed with a binary plasmid encoding the SCNA transcripts and carrying the Donor DNA).
2. Resuspend in 4 ml Induction medium (IL: 10.5 g K2HPO4, 4.5 g KH2PO4, 1 g (NH4)2SO4, 0.5 g NaCitrate, 1 g glucose, 4 g fructose, 4 g glycerol, 0.12 g MgSO4, 1.95 g MES pH5.6), add Acetosyringone to final concentration of 100 µM.
3. Grow at 30 degrees C. for 6 h.
4. Collect bacteria by centrifugation 3000 g 5 min.
5. Resuspend in infiltration medium (10 mM MgSO4, 10 mM MES pH5.6) containing 200 µM Acetosyringone to final OD600 0.4.
6. Take leaf discs of 4-12 mm diameter and incubate in the bacterial infiltration solution (step 5) for 30 min.
7. Place leaf discs on regeneration medium (IL: 4.3 g MS, 30 g sucrose, 100 mg Myo-inositol, pH 5.6, 10 g Agar, add NAA and BA to final concentration of ~100 microgram/L NAA and 3 mg/L BA). Incubate for 48 h at 20-25 degrees C.
8. Move leaf discs to new regeneration medium containing the antibiotic carbenicillin (0.3 mg) and the herbicide chlorsulfuron (420 nM). Move to new medium every 21 days.
9. Cut shoots above 10 mm and move to ½ MS medium for rooting (IL: 2.15 g MS, 10 g Sucrose, 0.5 g MES pH=5.7 with KOH, 10 g Agar).

Example 5

Targeted Chemical Modification of DNA Using a Programmed Molecular Complex

In this example, specific methylation of DNA in a predetermined location is tested.

DNA methylation is catalyzed by DNA methyltransferases, which transfer a methyl group (—CH3) from S-adenosyl-L-methionine to the C-5 position of cytosine residues. Three active DNA methyltransferases, DNMT1, DNMT3A, and DNMT3B, have been identified in humans and mice. Methylation in these examples is of DNA on the Cytosine of a CpG sequence. These enzymes belong to a class of S-adenosylmethionine-dependent methyltransferases (SAM or AdoMet-MTase), class I; AdoMet-MTases are enzymes that use S-adenosyl-L-methionine (SAM or AdoMet) as a substrate for methyltransfer, creating the product S-adenosyl-L-homocysteine (AdoHcy).

DNMT3A

Both the DNMT1 and DNMT3 families of methyltransferases contain the highly conserved C-5 methyltransferase motifs at their C termini, but they show no sequence similarity in their N-terminal regions. DNMT3A also binds deacetylases and is recruited by a sequence-specific repressor to silence transcription. DNMT3A associates with the histone deacetylase HDAC1 using its ATRX homology domain. This domain of DNMT3A represents an independent transcriptional repressor domain whose silencing functions require HDAC activity. DNMT3A acts as a co-repressor protein carrying deacetylase activity and can be targeted to specific regulatory foci via its association with DNA-binding transcription. DNMT3A also cooperates with RP58 to repress transcription in a methylation-independent manner. In this example, methyltransferase activity is localized to a specific locus using SCNAs.

In this example a portion of the C' of DNMT3A is used to construct a methyltransferase-based programmable molecular complex. The PWWP domains which target DNMT3A to pericentric heterochromatin, the Zinc-finger domains, the ADD domains, the ATRX region which causes its association the histone deacetylase HDAC1, and the whole regulatory N'-part of the protein are removed, keeping the region comprising the AdoMet_MTase region (www.uniprot.org Q9Y6K1). The C-terminus of DNMT3A and B contain the catalytic domain. In DNMT3A the active site is C710 (numbering is based on the translated GenBank accession AF067972.2).

DNMT3A forms a DNMT3L:DNMT3A:DNMT3A:DNMT3L heterotetramer complex. DNMT3L is inactive as a methylase, and DNMT3A can dimerize and is active without DNMT3L. DNMT3A is functional in the homodimeric form. The complex shows specific contacts at the DNMT3A homodimer interface (dimer interface) and dimerization brings two enzyme active sites separated by approximately one helical turn, in B-form DNA. Thus, a programmed molecular complex dimer localized to a specific locus by the SCNA, can bring about methylation of cytosines at CpG sites about 10-11 base pairs apart. To further restrict DNMT3A interactions with DNMTL, the mutation R729A in the C' terminal AdoMet_MTase region is used in this example. The DNMT3A mutants that form dimers instead of tetramers on DNA are R771A, E733A, R729A, F732A, and Y735A.

In order to test the capability of the molecular complex of this example to perform directed specific methylation on a predetermined DNA sequence, a plasmid is used as the target nucleic acid. Directed methylation of different locations on the gene encoding the mCherry on both strands is tested on the pSAT6-mCherry plasmid by methylation sensitive restriction analysis.

Detection of transfected cells, is done by FACS analysis at wavelength 561 nm excitation and emission detected by 610/20 filter.

Protein Moiety Construction:

In this example, the protein, encoded on the delivered plasmid, contains an amino-acid sequence adapted from the AdoMet_MTase region containing the catalytic site of a methyltransferase based on human DNA (cytosine-5)-methyltransferase 3A (DNMT3A PDB accession 2QRV is used to elucidate 3D structure). A mutation, R729 or R771 (based on the translated GenBank AF067972.2 numbering) is added to abolish tetramerization with the regulatory DNMTL without disrupting DNMT3A dimerization or reducing Kcat. The amino acid sequence (translated according to GenBank AF067972.2) of the methyltransferase region of this example is set forth in SEQ ID NO: 87 (DNMT3A AdoMet_MTase region R729A)

An amino-acid sequence adapted from anti-Fluorescein single-chain variable fragment (scFv) immunoglobin (Protein Data Bank accession codes 1X9Q, 1FLR_H), is used in this example as Linking Domain; an SV40NLS (PKKKRKV: SEQ ID NO: 3) is used as a nuclear localization domain and inter-domain connectors such as a flexible inter-domain connector (SEQ ID NO. 14: GSLEGGSGG) are utilized in this example for their attachment. The protein moiety has the amino-acid sequence set forth in SEQ ID NO: 88, encoded by the nucleic acid sequence set forth as SEQ ID NO: 89:

The Target sequence for the methylation assay is based on a mCherry coding cassette cloned into the MCS site of pSAT6-MCS (AY818383.1 GI:56553596) and includes the nucleotide sequence as set forth in SEQ ID NO: 90. The mCherry coding sequence (cds) is as set forth in nucleotides 952-1671 of SEQ ID NO: 90.

SCNA Sequence Used in this Experiment:

SL898: TCGAGCTCAAGCTTCGAATTCTNNNNNN/36-FAM/ (the nucleic acids only are designated herein as SEQ ID NO: 91).

SR951: /56-FAM/NNNNNNGATGGT-GAGCAAGGGCGAGGAG (the nucleic acids only are designated herein as SEQ ID NO: 92).

3'- and 5'-6FAM (6 carboxy-Fluorescein) Linking-domain-binding-sites are labeled, by /36-FAM/ and /56-FAM/ respectively. Though one SCNA is sufficient for DNA methylation, it is possible to use more than one SCNA, spaced correctly to allow protein dimerization to enhance specificity.

Experimental Procedure

A double transfection strategy is utilized to allow the expression of the protein moiety of the molecular complex before introduction of SCNAs and Target DNA.

*Arabidopsis* protoplast preparation is based on Wu (Wu et. al., 2009) and is similar to that of example 1 with differences in the transfection step:

Transfection:

1. Make fresh PEG sol for transfection in 2 ml tube
2. Pour off BSA from 6-well plates and dry
3. Mix ~5×10^4 protoplasts (2×10^4-1×10^5) in 0.2 ml MMg with about 20 microgram Protein-Moiety-expressing plasmid DNA at RT in 15 ml round-bottom (snap-cap) tubes.
4. Add equal volume (0.2 ml protoplasts+midiprep vol.) of fresh PEG sol 5. Incubate RT° 5 min
6. Wash by slowly adding 3 ml W5, 1 ml at a time, and mixing
7. Centrifuge 100×g in swing-out 1 min
8. Repeat wash and pellet
9. Resuspend in 1 ml W5
10. Pour into BSA-coated plates
11. Grow protoplasts under 16 hr day optimal light (150 microEinstein·m^–2·s^–1) at 22 degrees C., replacing media as needed.
12. About 16 Hrs. later, retransfection of these cells is done, by repetition of steps 1-11 replacing the plasmid of step 3 with plasmid encoding the mCherry Target and with relevant SCNAs (total about 20 microgram).
13. mCherry expression and methylation status of extracted plasmids is analyzed 48 h later.

Analysis

Analysis of CpG methylation status of target DNA are performed by two methods:

A) Digested DNA from pooled protoplasts is analyzed by PCR amplification. Digestion is performed using the methylation sensitive restriction enzymes SmaI (CC CGGG), SalI (GTCGAC) or SacII (CCGCGG). The SmaI, SalI, SacII cluster is used as a CpG site for the methylase. CpG dinucleotides underlined. Methylated DNA does not cleave with these enzymes. Thus, the MCS sequence spanning the cleavage sites of these enzymes is amplified and the product measured by Quantitative PCR returning a measure of the methylation efficiency versus samples lacking components of the molecular complex or deliberately containing non-specific SCNAs, scarcely amplified due to complete cleavage resulting from non-methylation.

B) DNA from pooled protoplasts is converted by bisulphite prior to PCR amplification, cloning and sequencing, to analyze the methylation status of a number of target and non-target control sequences. Bisulphite sequencing is done as described in the EZ DNA Methylation-Gold Kit (ZYMO, USA) suitable for methylated DNA detection and is used for further analysis.

Example 6

Targeted Genome Modification in Humans: CCR5 Gene Deletion in Human Hematopoietic Stem Cells C—C chemokine receptor type 5 (CCR5, GenBank Acc. Nr. NT_022517.18) is a chemokine receptor expressed and displayed on the surface of T cells, macrophages, dendritic cells and microglia. A mutation of this gene—CCR5-Δ32, which consists of a 32 base deletion, results in a frame-shift mutation which introduces 31 new amino-acids at the C'-terminus of the truncated protein, and confers resistance to smallpox and some types of Human Immunodeficiency Virus (HIV). This allele is found in about 10% of Europeans but is rare in other groups.

In the following example, CCR5 or portions of this gene are deleted from hematopoietic stem cells (HSC) extracted from HIV infected patients that do not have the Δ32 allele.

The protein moiety is composed of a nuclease-based Functional Domain (modified FokI nuclease domain, as above) and an RNA-motif-binding Linking Domain (derived from the BIV TAT protein minimal BIV TAT peptide SGPRPRGTRGKGRRIRR (SEQ ID NO: 93) domain, where the linking domain of the protein moiety binds the particular RNA sequence UUCAGCUCGUGUAGCU-CAUUAGCUCCGAGCU (SEQ ID NO: 94) which is the BIV TAR loop 1. Delivery of the nucleic acid encoding for the protein moiety is performed concomitantly with the delivery of the specificity conferring nucleic acid (SCNA) by Adenoviral vector, for their transient expression. Adenoviruses do not integrate into the host genome.

Upon introduction and expression in the target cells (HSC), the molecular complexes self-assemble on the CCR5 target gene, allowing the protein moieties to dimerize and cleave the CCR5 sequence, to cause a deletion of portions of this gene, as intended. Following this genetic modification, the thus created gene-modified HSCs, or their descendants are autologously retransplanted to the patient. Cells which have been modified are enriched by selection by removing CCR5 displaying cells prior to grafting. CCR5 mutated T-cells and macrophages develop from these HSCs becoming resistant to HIV infection. Most of the Adenovirus and the molecular complex components clear from the HSCs before grafting, having completed their function.

Functionally preventing the display of CCR5 can be achieved through this system in several different ways, using different SCNA types and locations, as detailed below:

In the Δ32 allele, 32 nucleotides of the 3' of the CCR5 CDS are missing, resulting in a frame-shift deletion. The deleted sequence is: TTCCATACAGTCAGTATCAAT-TCTGGAAGAA (SEQ ID NO: 95). To delete this sequence from CCR5 expressing cells, SCNAs derived from the following sequences (shown without Linking-domain-binding modification) are used:

```
ATCAATTCTGGAAGAATTTCCA;    (SEQ ID NO: 96)

TCATTACACCTGCAGCTCTCAT.    (SEQ ID NO: 97)
```

In this example, where the Linking Domain-binding modification on a transcribed SCNA utilizes the BIV TAR, the complete sequences of the SCNA sequences are: SCNA distance option 1, Utilizing a 16 bp gap and no SCNA internal "N" linker:

```
CCR5_D32_SR_3321:
                                       (SEQ ID NO: 98)
UUCAGCUCGUGUAGCUCAUUAGCUCCGAGCUAUCAAUUCUGGAAGAAUU

UCCA

CCR5_D32_SL_3304:
                                       (SEQ ID NO: 99)
UCAUUACACCUGCAGCUCUCAUUUCAGCUCGUGUAGCUCAUUAGCUCCG

AGCU
```

SCNA distance option 2, employing a 27 bp target gap and 2 "N" linker nucleotides:

```
CCR5_D32_SR_3319:
                                       (SEQ ID NO: 100)
UUCAGCUCGUGUAGCUCAUUAGCUCCGAGCUNNGUAUCAAUUCUGGAAGA

AUUUC

CCR5_D32_SL_3291:
                                       (SEQ ID NO: 101)
CAAAAAGAAGGUCUUCAUUACACNNUUCAGCUCGUGUAGCUCAUUAGCU

CCGAGCU
```

These SCNAs are designed to allow modification/cleavage in the TTTCCATACAGTCAGTATCAATTCTG-GAAGAA target sequence (SEQ ID NO: 102). Cleavage and DSB formation mediated by these pairs alone can, in some cases, through endogenous mechanisms, cause a mutation that can lead to a frame shift. In order to make wider deletions in the CCR5 gene pairs of SCNAs targeting at least two targets on CCR5 are used:

Deletion of substantially all of the CCR5 coding sequence are induced by using CCR5-ATG region binding SCNAs and CCR5-STOP codon region binding SCNAs, concomitantly.

ATG SCNAs:
Targeted Area Between SCNAs (ATG Underlined):

(SEQ ID NO: 103)
CAGGGTGGAACAAGATGGATTATCAAGTGTC.

SCNA Distance Option 1 Utilizing a 31 bp Target Gap and No SCNA Internal "N" Linker:

CCR5_SR_2779:
(SEQ ID NO: 104)
UUCAGCUCGUGUAGCUCAUUAGCUCCGAGCUAAGUCCAAUCUAUG

ACAUCAAU;

CCR5_SL_2747:
(SEQ ID NO: 105)
AAGAUCACUUUUUAUUUAUGCAUUCAGCUCGUGUAGCUCAUUAGCUCC

GAGCU..

SCNA Distance Option 2, Based on the Computational Results, Employing a 27 bp Target Gap and 2 "N" Linker Nucleotides:

CCR5_SR_2777:
(SEQ ID NO: 106)
UUCAGCUCGUGUAGCUCAUUAGCUCCGAGCUNNUCAAGUCCAAUCUAUG

ACAUCA

CCR5_SL_2749:
(SEQ ID NO: 107)
GAUCACUUUUUAUUUAUGCACANNUUCAGCUCGUGUAGCUCAUUAGCUCC

GAGCU

STOP SCNAs:
Targeted Area Between SCNAs (STOP Codon Underlined):

(SEQ ID NO: 108)
ATATCTGTGGGCTTGTGACACGGACTCAAGT

SCNA Distance Option 1 Utilizing a 31 bp Target Gap and No SCNA Internal "N" Linker:

CCR5_SR_3884:
(SEQ ID NO: 109)
UUCAGCUCGUGUAGCUCAUUAGCUCCGAGCUGGGCUGGUGACCCAGUCAG

AGU;

CCR5_SL_3802:
(SEQ ID NO: 110)
CCGAUCCACUGGGGAGCAGGAAUUCAGCUCGUGUAGCUCAUUAGCUCCGA

GCU

SCNA Distance Option 2, Based on Computational Results, Employing a 27 bp Target Gap and 2 "N" Linker Nucleotides:

CCR5_SR_3833:
(SEQ ID NO: 111)
UUCAGCUCGUGUAGCUCAUUAGCUCCGAGCUNNUGGGCUGGUGACCCAGU

CAGAG

CCR5_SL_3805:
(SEQ ID NO: 112)
AUCCACUGGGGAGCAGGAAAUANNUUCAGCUCGUGUAGCUCAUUAGCUCC

GAGCU

The protein moiety of the molecular complex is expressed via a nucleotide sequence carried in an Adenovirus-based expression system, such as, Adeno-X™ Adenoviral System 3 (Clontech Laboratories (CA, USA)) and used according to manufacturer instructions. Alternatively, the protein moiety is delivered by naked RNA transfection.

The Protein Moiety Amino-Acid Sequence for this Example:
Functional Domain: derived from the FokI nuclease subunit (as above).
Linking Domain: minimal BIV TAT peptide SGPRPRGTRGKGRRIRR (SEQ ID NO: 93) domain.
Cellular Localization Domain: Nuclear localization signal (NLS) domain of SV40 (SV40NLS).
FokI nuclease subunit:

(SEQ ID NO: 66)
VKSELEEKKSELRHKLKYVPHEYIELIEIARNSTQDRILEMKVMEFFMKV

YGYRGKHLGGSRKPDGAIYTVGSPIDYGVIVDTKAYSGGYNLPIGQADEM

QRYVEENQTRNKHINPNEWWKVYPSSVTEFKFLFVSGHFKGNYKAQLTRL

NHITNCNGAVLSVEELLIGGEMIKAGTLTLEEVRRKFNNGEINF;

SV40NLS:
(SEQ ID NO: 67)
MPKKKRKV;

BIV TAT peptide:
(SEQ ID NO: 93)
SGPRPRGTRGKGRRIRR.

Interdomain connector:
(SEQ ID NO: 113)
GSGGSGP

The Assembled BIV TAT-based programmable protein moiety of this example has the amino acid sequence as set forth in SEQ ID NO: 114, which is encoded by the nucleic acid sequence as set forth in SEQ ID NO: 115.

Spatial measurements taken from computerized 3D models for the BIV-TAT-TAR system with the GGSGGGP (SEQ ID NO: 116) interdomain linker, as used in this example, yielded that the expected optimal distance between SCNAs is, in the presence of 2 N's in the SCNA, is about 26-28 nucleotides. Cleavage is predicted to occur about ±2 nucleotides to left and to the right of the $12^{th}$, $13^{th}$ or $14^{th}$ nucleotide, counting starts after the last nucleotide hybridizing with the SCNA on either side, taking into account the 4 base 5' overhang created by dsDNA cleavage by the dimerized construct. This criterion suggests that if, as in this example, the targeted sequence is, 27 nucleotides: AAAAAAAAAAYYYYYYYYYYXXXXXXXYY-YYYYYYYYCCCCCCCCCC, where Y+X represents the number of nucleotides between the SCNA base-pairing sites, then the designed SCNAs base-pair with areas A and C and the cleavage resulting in DSB is in or adjacent to the X area (target site). The SCNAs can be complementary to either sense or antisense strands, but are preferably chosen to base-pair with the sense (untranscribed) sequence. Both SCNAs can base-pair with the same strand, as the protein moiety's position is situated at the "near end" of the SCNA as defined by the 5' or 3' modification of the primer being at the "near end".

Detection and selection of CCR5 non-expressing/presenting cells vs. wild type CCR5 expressing cells is performed by FACS analysis, using a monoclonal mouse anti-Human CCR5 antibody (R&D systems Catalog nr. FABSP1).

Example 7

Programmable Nucleic-Acid Base-Pairing Targeted Transcriptional Activator

In this example, a protoplast system in the monocot maize (Marrs & Urioste, 1995; Rhodes et. al., 1988) is used as a bioassay. In this system maize protoplasts are electroporated to introduce a plasmid for transient expression. These protoplasts may then be regenerated if so desired.

In this example, a protein moiety composed of the Gal4 transcriptional activator domain, excluding the UAS binding domain, and a linking domain composed of the anti-Fluorescein ScFV, together with a Fluorescein-modified SCNA, is used to activate the expression of a reporter gene. In this example, used here, the DNA binding domain of the Gal4 is removed and replaced with a Linking Domain of the protein moiety.

In the first example, two reporter plasmids are used, which can express GFP (option 1) or β-glucoronidase (GUS, option 2) only if a transcriptional activator is bound to a sequence upstream from a TATA box. In this example, this sequence is a 6x-UAS, known to be activated by Gal4 protein.

In the second example, the UAS sequences are removed from the target nucleic acid and the SCNA binds at minus 62 (62 nt downstream from the TATA box), thus essentially attaining the same result but without any natural promoter. In the maize protoplast bioassay system the protein moiety shown below and the SCNA can be co-transfected using electroporation.

Protein moiety amino acid sequence: comprising an N' nuclear-targeted Gal4 activation domain fused via an inter-domain connector to an anti-Fluorescein ScFv is designated herein as SEQ ID NO: 132 and is encoded by the nucleotide sequence as set for the in SEQ ID NO: 157.

The first example utilizes a target plasmid with 6 UAS repeats:
The target plasmid contains, in the following order (5'→3'), a 6UAS promoter region followed by a TATA box and is designated herein in SEQ ID NO: 180:

GGACTGTAGAGGTTCCGGGTGACAGCCCTCCGACGGGTGACAGCCCTCCG

ACGGGTGACAGCCCTCCGAATTCTAGAGGATCCGGGTGACAGCCCTCCGA

CGGGTGACAGCCCTCCGACGGGTGACAGCCCTCCGAATTCGAGCTCGGTA

CCCGGGGATCTGTCGACCTCGATCGAGATCTTCGCAAGACCCTTCCTCTA

TATA;

A spacer having the sequence:

(SEQ ID NO: 192)
AGGAAGTTCATTTCATTTGGRGAGGACACGCTGAACC;

Option 1:
A GFP coding sequence set forth in SEQ ID NO: 193.
Option 2:
A β-glucoronidase (GUS) coding sequence, set forth in SEQ ID NO: 194.
A 35S-Terminator Sequence:

(SEQ ID NO: 195)
GTCCGCAAAAATCACCAGTCTCTCTCTACAAATCTATCTCTCTCTATTTT

TCTCCAGAATAATGTGTGAGTAGTTCCCAGATAAGGGAATTAGGGTTCTT

ATAGGGTTTCGCTCATGTGTTGAGCATATAAGAAACCCTTAGTATGTATT

TGTATTTGTAAAATACTTCTATCAATAAAATTTCTAATTCCTAAAACCAA

AATCCAGTGAC

Two different orientations of SCNA are supplied in separate experiments to choose the more effective of the two: UAS-sequence binding SCNA
Sense: CGGGTGACAGCCCTCCGANNNNNN/36-FAM/ (the nucleic acids only are set forth herein in SEQ ID NO: 196)
Anti-sense: /5-6FAM/NNNNNNTCGGAGGGCTGT-CACCCG (the nucleic acids only are set forth herein in SEQ ID NO: 197)

The end modification of the SCNAs is 6-carboxy fluorescein (6FAM). 5' or 3' modification shown as /5-6FAM/ or /3-6FAM/ respectively. N represents any nucleotide.

The second example utilizes a target plasmid lacking a promoter for controlling expression of the reported gene: The target plasmid contains, in the following order, a plasmid backbone sequence followed by a TATA box:

(SEQ ID NO: 198)
TCTTCGCTATTACGCCAGCTGGCGAAAGGGGGATGTGCTGCAAGGCGATT

AAGTTGGGTAACGCCAGGGTTTTCCCAGTCACGACGTTGTAAAACGACGG

CCAGTGCCACCCATAATACCCATAATAGCTGTTTGCCAACCGGTTCTAT

ATA;

A Spacer Sequence (SEQ ID NO: 199):

AGGAAGTTCATTTCATTTGGRGAGGACACGCTGAACC;

Option 1:
the GFP ORF, as set forth in SEQ ID NO: 200.
Option 2:
β-glucoronidase (GUS) coding sequence, as set forth in SEQ ID NO: 201.
A 35S Terminator Sequence (SEQ ID NO: 202):
Two different orientations of SCNA are used:
SCNA: options (minus 62):
GCCAGGGTTTTCCCAGTCACGANNNNNN/36-FAM/ (the nucleic acids only are set forth herein in SEQ ID NO: 203)
/5-6FAM/NNNNNNTCGTGACTGGGAAAACCCTGGC (the nucleic acids only are set forth herein in SEQ ID NO: 204)

Maize protoplasts are tested for GFP expression (option 1) using microscopic or flow-cytometric methods. GFP positive cells indicate the functioning of the programmed complex. The percentage of GFP positive cells allows the calculation of relative efficiencies between experiments conducted to improve different parameters of the system. Absence of GFP in cells missing the proper components of the complex (e.g. by using control non-specific SCNAs) allows to measure the limits of specificity.

Maize protoplasts are tested for GUS expression (option 2) by staining the cells with X-Gluc in 0.45M mannitol and incubating overnight at 37° C., and detected using a microscope. GUS positive cells (stained blue) indicate the functioning of the programmed complex. The percentage of GUS positive cells allows us to calculate relative efficiencies between experiments conducted to improve different parameters of the system. Absence of GUS in cells missing the proper components of the complex (e.g. by using control non-specific SCNAs) allows us to measure the limits of specificity.

Example 8

Gene-Targeting in Organellar DNA

In Eukaryotes, organelles such as mitochondria and plastids contain their own genomes. Furthermore, in plants, they may also contain sub-genomic circular DNAs. Modifying mitochondrial DNA can have implications for treatment of human disease and for agricultural uses, among others. Challenges for these modifications include, among other technical hurdles, the delivery and activation of a reasonably efficient, sequence-specific system necessary for gene-editing into the organelle.

PCF in *Petunia*

Cytoplasmic male sterility (CMS) is a valuable plant trait used extensively by commercial seed companies as a method of protecting their seed lines. Thus it is advantageous to either repair CMS in existing lines or create CMS in new lines. Cytoplasmic male sterility can be due to the failure of plants to produce functional anthers, pollen, or male gametes as the result of specific nuclear and mitochondrial interactions. In the examples shown here a characterized cytoplasmic male sterility trait in *Petunia* which is caused by a combined deletion and insertion into the atp9 gene in mitochondrial DNA which encodes the subunit 9 of an ATPase, is used. This results in disruption of the proton-translocating function of the mitochondrial ATPase multi-protein complex leading to male sterility.

The protein moiety of the programmable molecular complex of this example is designed to harbor a mitochondrial localization signal to ensure the localization of the programmed molecular complex inside the mitochondria. Other methods to transfer nucleic acids into mitochondria include the use of liposomes or electroporation. Plant mitochondria, and specifically in a plant from the solanaceae which includes *Petunia*, actively import DNA via the permeability transition pore complex. The process is restricted to double-strand DNA, but has no obvious sequence specificity. Donor sequences can be delivered, for example, either as linear purified PCR fragments, linearized plasmids, or as circular plasmids, depending on the method of delivery. Expression from plasmids, electroporated into isolated wheat mitochondria, for example, is very efficient when using a mitochondria-compatible promoter such as the 882 bp of *T. timopheevi* cox II mitochondrial promoter containing the initiation region described by (Hanic-Joyce and Gray, 1991). Selection of cells containing a replacement or insertion event can be achieved by a Chloramphenicol resistance operon encoded in the Donor DNA.

In the following examples (8A-8C) the protein moiety comprises:

A Linking Domain derived from BIV TAT peptide comprising the amino-acid sequence SGPRPRGTRGKGRRIRR (SEQ ID NO: 93);
A Functional Domain derived from FokI nuclease comprising the amino-acid sequence (SEQ ID NO: 66)
VKSELEEKKSELRHKLKYVPHEYIELIEIARNSTQDRILEMKVMEFFMKV

YGYRGKHLGGSRKPDGAIYTVGSPIDYGVIVDTKAYSGGYNLPIGQADEM

QRYVEENQTRNKHINPNEWWKVYPSSVTEFKFLFVSGHFKGNYKAQLTRL

NHITNCNGAVLSVEELLIGGEMIKAGTLTLEEVRRKFNNGEINF;

a Cellular Localization Domain derived from the *Arabidopsis* Lipoic acid synthase and comprising the amino-acid sequence MHSRSALLYRFLRPASRCFSSSS (SEQ ID NO:6) which is a mitochondrial localization signal (MLS).

Interdomain connector:
(SEQ ID NO: 113)
GSGGSGP

The Assembled BIV TAT-based programmable protein moiety of this example has the amino acid sequence set forth in SEQ ID NO: 205, which is encoded by the nucleotide sequence set forth in SEQ ID NO:206.

The results of spatial measurements taken from computerized 3D models for the BIV-TAT-TAR system with the GGSGGGP (SEQ ID NO: 116) interdomain linker, of this example, show that the expected optimal distance between SCNAs, in the presence of 2 N's in the SCNA, is about 26-28 nucleotides. Cleavage is predicted to occur about ±2 nucleotides to left and to the right of the $12^{th}$, $13^{th}$ or $14^{th}$ nucleotide, counting starts after the last nucleotide hybridizing with the SCNA on either side, taking into account the 4 base 5' overhang created by dsDNA cleavage by the dimerized construct. This criterion suggests that if the targeted sequence is, for example, the following 27 nucleotides:

$A_1A_1A_1A_1A_1A_1A_1A_1A_1A_1$YYYYYYYYYYYXXX-XXXXYYYYYYYYYYYC$_1$C$_1$C$_1$C$_1$C$_1$C$_1$C$_1$C$_1$C$_1$C$_1$.

where Y+X represents the number of nucleotides between the SCNA base-pairing sites, then the designed SCNAs base-pair with areas $A_1$ and $C_1$ and the cleavage resulting in DSB is in or adjacent to the X area. The SCNAs can be complementary to either sense or antisense strands, but are chosen preferably to base-pair with the sense (untranscribed) sequence. Both SCNAs can base-pair with the same strand, as the protein moiety's position is situated at the "near end" of the SCNA as defined by the 5' or 3' modification of the primer being at the "near end".

The SCNA Linking-Domain-binding RNA sequence used in this example is derived from the BIV TAR loop 1 comprising the nucleic acids sequence UUCAGCUCGU-GUAGCUCAUUAGCUCCGAGCU (SEQ ID NO: 117). The SCNA may thus be either directly delivered to isolated mitochondria (by electroporation of mitochondria in the presence of a DNA encoding the SCNA under a bacterial promoter) or delivered to the cytoplasm (by *Agrobacterium* mediated transient transcription) and "pulled" into the mitochondria by the protein moiety bound to it and comprising an MLS.

After expression of the programmable molecular complex, mitochondria are isolated and a Donor DNA is transfected into the isolated mitochondria.

The following examples are performed, each having 2 options for SCNA distances:

1. Forming a CMS phenotype without a donor DNA (8A).
2. Targeting atp9 to form a pcf-like mutant using a Donor DNA with Chloramphenicol resistance (8B).
3. Repairing a pcf (CMS) phenotype, reforming ATP9 and restoring fertility and concomitantly using a Donor DNA with Chloramphenicol resistance (8C).
Target nucleic acid sequences for these examples include:
"ATP9": *Petunia* x *hybrida* X *Petunia axillaris* subsp. *parodii* mitochondrial ATP synthase subunit 9, GenBank acc. Nr. Y00609.1 GI:297475.
"pcf": Cytoplasmic male sterility (CMS) in *Petunia axillaris* subsp. *Parodii*, CMS-associated fusion protein (CMS-afp), NADH dehydrogenase subunit 3 (nad3), and ribosomal protein S12 (rps12) genes, complete cds; mitochondrial, GenBank acc. Nr. M16770.1 GI:1256946.

Example 8A

Directed DNA-Mutation in Organellar DNA, without Organelle Isolation

Targeting ATP9 to form a mutation which causes CMS by creating a non-functional protein ATP9 protein.
The SCNAs are designed to form a single DSB in the target site, that is repaired by the endogenous NHEJ repair pathway, creating frameshifts in part of the coding sequence.
ATP9 Target site: GCAAAACAATTATTTGGTTATGC-CATTTTGG (SEQ ID NO: 118).
SCNA distance option 1, 31 bp target gap:
ATP9 target site flanking SCNAs:

```
ATP9_ASL_705:
                                       (SEQ ID NO: 119)
UUCAGCUCGUGUAGCUCAUUAGCUCCGAGCUCAAUGAUGGAUUUCGCGCC

ACG

ATP9_ASR_737:
                                       (SEQ ID NO: 120)
UUAGCUUCGGUUAGAGCAAAGCUUCAGCUCGUGUAGCUCAUUAGCUCCGA

GCU
```

SCNA distance option 2, employing a 27 bp target gap:

```
ATP9_ASL_707:
                                       (SEQ ID NO: 121)
UUCAGCUCGUGUAGCUCAUUAGCUCCGAGCUGCCAAUGAUGGAUUUCGCG

CCA

ATP9_ASR_735:
                                       (SEQ ID NO: 122)
AGCUUCGGUUAGAGCAAAGCCCUUCAGCUCGUGUAGCUCAUUAGCUCCGA

GCU
```

*Petunia* leaves are inoculated using a standard leaf infiltration method as known in the art, with *Agrobacterium* harboring T-DNA derived from a binary vector plasmid encoding the protein moiety, and the RNA-SCNAs (as schematically shown in FIG. 8A). After transfection, the components of the Programmed molecular complex are expressed in the cytoplasm, self-assemble, and are then localize to the mitochondria by the mitochondrial import machinery, via the MLS exhibited on the surface of protein moiety. The programmed molecular complex (comprising the protein moiety and the targeting SCNA) then targets the ATP9 gene in mitochondrial DNA thus forming mutated mitochondria.

For analysis, 48 hours after the transfection, DNA is purified from the plants and the ATP9 sequence is amplified by PCR using primers:

```
ATP9atgF:
                                       (SEQ ID NO: 123)
ATGTTAGAAGGTGCAAAATCAA ATP9p2R:
                                       (SEQ ID NO: 124)
CTAACGGACTTGGAATACGAAT
```

The PCR product is then subjected to CEL I Enzymatic Mutation Detection Assay (SURVEYOR Mutation Detection Kit (Transgenomics, USA)). This assay is used to evaluate the effectivity of mutation of mitochondrial DNA by gene targeting with a programmed molecular complex.

Example 8B

Directed DNA-Insertion in Organellar DNA

In this example, ATP9 is targeted to form a pcf-like mutant by inserting a Donor DNA containing the selection marker chloramphenicol into the ATP9 locus.
Method: as in Example 8A, *Petunia* leaves are inoculated using a standard leaf infiltration method with *Agrobacterium* harboring T-DNA derived from a binary vector plasmid encoding the protein moiety of the programmed molecular complex, and the SCNAs. After transfection, the components of the Programmed molecular complex are expressed in the cytoplasm, self-assemble, and are localize into the mitochondria by the mitochondrial import machinery via the MLS exhibited on the surface of protein moiety. After about 12-72 Hrs infiltrated leaves are used for mitochondrial preparation. A plasmid vector or a linear PCR product comprising the Donor DNA of this example, is delivered by electroporation into isolated mitochondria. The electroporated mitochondria are then transplanted into fresh *Petunia* protoplasts by microinjection. The injected protoplasts are regenerated on Chloramphenicol selection media allowing only the PCF like mitochondria to survive in the cells.
The 8B DONOR DNA (atp9 changed to pcf-like) is set forth in SEQ ID NO: 125:
Results and Analysis:
The programmed molecular complex cleaves the atp9 gene in its coding sequence, downstream of the region homologous to pcf. This results in homologous recombination (HR) between the pcf-like Donor and the cleaved atp9 gene. A pcf male sterile genotype in the mitochondrial genome is thus recreated. Further, the donor contains a chloramphenicol resistance cassette allowing selection for mitochondria resistant to chloramphenicol. Injected protoplasts which are able to regenerate on selection media containing chloramphenicol contain the DNA-modified targeted mitochondria. Callus resulting from these protoplasts is capable of shoot differentiation, and ultimately whole plants are formed resulting in regenerated plants containing only the targeted mitochondria. Male sterile *Petunia* is thus achieved by regenerating plants from calli containing chloramphenicol resistant mitochondria.

Example 8C

Directed DNA-Replacement in Organellar DNA

In this example, pcf mutant is targeted to form an active repaired ATP9 sequence using a Donor DNA containing a resistance to Chloramphenicol.

In this example, the Donor DNA is designed to be integrated by HR into the pcf locus, creating a STOP codon to recreate an intact ATP9 protein devoid of the superfluous amino-acid sequence causing the pcf disorder. A Chloramphenicol resistance cassette (AY230218.1 GI:30267504) in the Donor DNA is used for selection of repaired mitochondria. The CDS on the donor are in an operon based design. The chloramphenicol sequence is shown in underlined lowercase.

Method: A plasmid vector comprising the Donor DNA of this example, the SCNA shown in example 8C and the protein moiety of example 8A are delivered by electroporation into isolated mitochondria, in this example on a single plasmid similar in design to that schematically shown in FIG. 9.

Similarly to example 8B, the electroporated mitochondria are transplanted into Petunia protoplasts by microinjection. The protoplasts are sown on Chloramphenicol selection media. Callus resulting from these protoplasts is capable of shoot differentiation (Frearson et. al., 1973), and ultimately whole plants are formed resulting in regenerated plants containing only the targeted mitochondria. These Petunia plants are screened for male-fertility.

8C sequences:
Target site in pcf: AGACTTACATCAC-GATGTCTTTTTCTTCGTT (SEQ ID NO: 126)
SCNAs flanking target site:
SCNA distance option 1, 31 bp target gap:

```
CMS_ASL_704:
                                         (SEQ ID NO: 127)
UUCAGCUCGUGUAGCUCAUUAGCUCCGAGCUGUUAUUUGUAUACCUAACA
CGG.

CMS_ASR_736:
                                         (SEQ ID NO: 128)
AUACGAAAACCAAAAUCAGAAUUUCAGCUCGUGUAGCUCAUUAGCUCCGA
GCU.
```

SCNA distance option 2, based on computational results, employing a 27 bp target gap:

```
CMS_ASL_706
                                         (SEQ ID NO: 129)
uucagcuCGUGUAGCUCAUUAGCUCCGagcuCUGUUAUUUGUAUACCUAA
CAC CMS_ASR_734
                                         (SEQ ID NO: 130)
ACGAAAACCAAAAUCAGAAUAAUUCAGCUCGUGUAGCUCAUUAGCUCCGA
GCU
```

Example 9

Genomic Modification of Mammalian Cells: Preventing FAS Receptor Mediated Death

The FAS receptor (FasR) also known as apoptosis antigen 1 (APO-1, APT, TNFRSF6, CD95), is a protein that in humans is encoded by the TNFRSF6 gene located on chromosome 10 in humans (GenBank accession NC_000010 REGION: 90750288 . . . 90775542 GPC_000000034 VERSION NC_000010.10 GI:224589801). The Fas receptor is a death receptor displayed on the surface of cells that leads to programmed cell death (apoptosis) by forming the death-inducing signaling complex (DISC) upon ligand binding. Membrane-anchored Fas ligand trimer on the surface of an adjacent cell causes trimerization of Fas receptor. Fas ligand or FasL (CD95L) is a homotrimeric type II transmembrane protein. Soluble FasL is less active than its membrane-bound counterpart and does not induce receptor trimerization and DISC formation. Upon ensuing death domain (DD) aggregation, the receptor complex is internalized and initiates a cascade of events through caspases, eventually leading to DNA degradation, membrane blebbing, and other hallmarks of apoptosis. This event can also be mimicked by binding of an agonistic Fas antibody, used in the example here.

Eight splice variants of FasR are known, which are translated into seven isoforms of the protein. Apoptosis-inducing Fas receptor is dubbed isoform 1 and is a type 1 transmembrane protein. Fas protein has 319 amino acids, is divided into 3 domains: an extracellular domain, a transmembrane domain, and a cytoplasmic domain. The extracellular domain has 157 amino acids and is rich in cysteine residues. The transmembrane and cytoplasmic domains have 17 and 145 amino acids respectively. Exons 1 through 5 encode the extracelluar region which can interact with FasR trimer. Exon 6 encodes the transmembrane region. Exons 7-9 encode the intracellular region.

Protein Sequence and Properties

The protein moiety is as described in Example 3.

Thus, the protein moiety of the molecular complex described in this example has the amino-acid sequence set forth in SEQ ID NO: 49.

The specificity-conferring nucleic acid (SCNA) of this example is modified by the addition of a Fluorescein-ScFv/6-FAM, 6-carboxyfluorescein-Fluorescein dT which includes a C6-linker to one end of each SCNA.

SCNA Properties and Sequence

The length of the SCNA of the complementary, target-base-pairing oligonucleotide is preferentially at least 18 bases. The SCNA can also contain a small number (e.g. 0-6, in this example 6) of non-target-base-pairing nucleotides (N's) of any sequence composition that serve as a spacer between the 6-FAM terminal-modifier and the target-complementary nucleotides.

The results of spatial measurements taken from computerized 3D models for the anti-Fluorescein-ScFv-6-FAM system with the GGSGG (SEQ ID NO: 7) interdomain linker, as used in this example, yielded that the expected optimal distance between SCNAs is, in the presence of 2 N's in the SCNA, about 23-26 nucleotides. Cleavage is predicted to occur about ±2 nucleotides to left and to the right of the $11^{th}$, $12^{th}$ or $13^{th}$ nucleotide, counting from after the last nucleotide hybridizing with the SCNA on either side, taking into account the 4 base 5' overhang created by dsDNA cleavage by the dimerized construct. This criterion suggests that if the targeted sequence is, for this 24 nucleotide example: AAAAAAAAAAYYYYYYY-YYXXXXXXYYYYYYYYYYCCCCCCCCCC, where Y+X represents the number of nucleotides between the SCNA base-pairing sites, then the designed SCNAs base-pair with areas A and C and the cleavage resulting in DSB is in or adjacent to the X area. The SCNAs can be complementary to either sense or antisense strands, but are chosen preferably to base-pair with the sense (untranscribed) sequence. Both SCNAs can base-pair with the same strand, as the protein moiety's position is situated at the "near end" of the SCNA as defined by the 5' or 3' modification of the primer being at the "near end".

Target Site Sequence:

The target sequences examples are:

A) Exon 1 starts at 347, target sequence is: GGG-CATCTGGACCCTCCTACC (SEQ ID NO: 133)

SCNAs:

SCNA distance option 1, 21 bp target gapSL351:
A*GGATTGCTCAACAACCATGCTNNNNNN/36-FAM/ (the nucleic acids only are set forth herein in SEQ ID NO: 134)

SR373: /56-FAM/NNNNNNTCTGGTGAGCCCTCTCCTGCC*C (the nucleic acids only are set forth herein in SEQ ID NO: 135)

SCNA distance option 2, based on computational results, employing a 24 bp target gap and a shorter SCNA "N" linker:

SL349: G*GAGGATTGCTCAACAACCATGNN/36-FAM/ (the nucleic acids only are set forth herein in SEQ ID NO: 136)

SR374: /56-FAM/NNCTGGTGAGCCCTCTCCTGCCC*G (the nucleic acids only are set forth herein in SEQ ID NO: 137)

Exon 2 starts at 12499, target sequence is: TACGTCTGTTGCTAGATTATC (SEQ ID NO: 138)

B)

SCNAs:

SCNA distance option 1, 21 bp target gap:
SL12503: A*TGCTTTTATTTTACAGGTTCTNNNNNN/36-FAM/ (the nucleic acids only are set forth herein in SEQ ID NO: 139)

SR12525: /56-FAM/NNNNNNGTCCAAAAGTGTTAATGCCCA*A (the nucleic acids only are set forth herein in SEQ ID NO: 140)

SCNA distance option 2, based on computational results, employing a 24 bp target gap and a shorter SCNA "N" linker:

SL12501: TCATGCTTTTATTTTACAGGTTNN/36-FAM/ (the nucleic acids only are set forth herein in SEQ ID NO: 141)

SR12526: /56-FAM/NNTCCAAAAGTGTTAATGCCCAA*G (the nucleic acids only are set forth herein in SEQ ID NO: 142)

Exon 2 Target for restriction analysis: CAGTTGAGACTCAGAACTTGG (SEQ ID NO: 143)

C)

SCNAS:

SCNA distance option 1, 21 bp target gap
SL12595: G*GAATTGAGGAAGACTGTTACTANNNNN/36-FAM/ (the nucleic acids only are set forth herein in SEQ ID NO: 144)

SR12617: /56-FAM/NNNNNNAAGGCCTGCATCATGATGGCCAATTCT*C (the nucleic acids only are set forth herein in SEQ ID NO: 145)

SCNA distance option 2, based on computational results, employing a 24 bp target gap and a shorter SCNA "N" linker:

SL12594: G*GAATTGAGGAAGACTGTTACTNN/36-FAM/ (the nucleic acids only are set forth herein in SEQ ID NO: 146)

SR12619: /56-FAM/NNGGCCTGCATCATGATGGCCAA*T (the nucleic acids only are set forth herein in SEQ ID NO: 147)

Primers for analysis of example C:

FAS_E2F: CATGCTTTTATTTTACAG; (SEQ ID NO: 148)

FAS_E2R: CTGTGACTTTCACTGTAATC (SEQ ID NO: 149)

PCR-amplification of the target with these primers forms (in unmodified DNA) a 227 bp PCR product digested with DdeI forming fragments of 127 bp and 100 bp. DdeI digestion is abolished by accurate targeting.

Exon 9 target: CAATTGTGAATTCACATAGAA (SEQ ID NO: 150)

D)

SCNAs:

SCNA distance option 1, 21 bp target gap
SL24524: G*GTGTCATATTATACAATATTTNNNNNN/36-FAM/ (the nucleic acids only are set forth herein in SEQ ID NO: 151)

SR24546: /56-FAM/NNNNNNAACATTAAATTATAATGTTTG*A (the nucleic acids only are set forth herein in SEQ ID NO: 152)

SCNA distance option 2, based on computational results, employing a 24 bp target gap and a shorter SCNA "N" linker:

SL24522: T*TGGTGTCATATTATACAATATNN/36-FAM/ (the nucleic acids only are set forth herein in SEQ ID NO: 153)

SR24547: /56-FAM/NNACATTAAATTATAATGTTTGA*C (the nucleic acids only are set forth herein in SEQ ID NO: 154)

Primers for analysis of example D:
FAS_E9F CTTTGTTTATAACTCTGAGAAG (SEQ ID NO: 155)
FAS_E9R TCAAAATGCTTTTGATGCCTGA (the nucleic acids only are set forth herein in SEQ ID NO: 156)

PCR-amplification of the target with these primers forms (in unmodified DNA) a 240 bp PCR product digested with EcoRI forming fragments of 134 bp and 106 bp. EcoRI digestion is abolished by accurate targeting.

/56-FAM/ and /36-FAM/symbolize a 5'-modification or a 3'-modification respectively on the SCNA ssDNA comprising of 6-FAM (6-carboxy-Fluorescein). N symbolizes any nucleotide. Phosphorothioate-bonds are symbolized by an asterisk (*).

While each SCNA pair can cause a mutation that knocks out the FAS receptor, deletion of a whole stretch of DNA resulting from targeting more than one site in the gene can disable the activity of FASR outright. Thus, for example, using the SCNAs in examples A-C may result in mutations abolishing FasR activity, while using any of these SCNAs together with the SCNA of example D leads to a major genomic deletion that abolishes FasR activity.

Assay:

A bioassay for detecting an induced specific mutation in Human genomic DNA is as follows: HeLa and Jurkat Cells are transfected with a plasmid encoding the protein moiety of the programmable molecular complex together with the relevant ssDNA SCNAs using the transfection agents (Mirus, USA) TransIT-HeLaMONSTER or TransIT-LT1 for formulating the plasmid DNA and TransIT-Oligo for formulating the SCNA ssDNA. Once incubated for the allotted time, both sets of formulated DNA-transfection-agent mixes are supplied simultaneously to the cells, to target chromosomal FasR. To determine the efficiency of gene-targeting cells are tested for their sensitivity to FasL in a protocol modified from (Kotlo et. al., 2003): Transfected cells are plated in duplicates 20-24 h prior to the treatment with a combination of 200 ng/ml anti-FasR agonistic antibody (Anti-Fas mAb, clone 2R2 Cat. No.: MC-121, Kamiya Biomedical Company, or monoclonal anti CD95 Clone 7C11, Cat. No.: PN IM2387 Beckman-Coulter) and optionally, a sensitizing agent such as Dicumarol 100 micromolar. Seventeen hours post-treatment, the number of viable, trypan blue excluding cells that remain attached to the plate following rinsing with PBS is determined or alternatively propidium iodide exclusion staining is done to evaluate intact living cells by Flow cytometry (FACS). Cells in which the FAS gene is targeted and disabled, do not go through a death-induction process, do not stain, but rather multiply. Thus, a comparison between induced, specifically targeted cells versus non-specifically targeted cells (e.g. no SCNAs or non-FAS SCNAs) evaluates gene targeting success in human cells. Surviving or FACS-sorted cell-lines are analysed by PCR amplification of genomic DNA in the targeted FasR regions followed by restriction fragment analysis and sequencing to identify induced mutations.

Example 10

Editing Plasmid DNA Sequence In-Vivo. Antibiotic Resistance Modification

Figure 15:
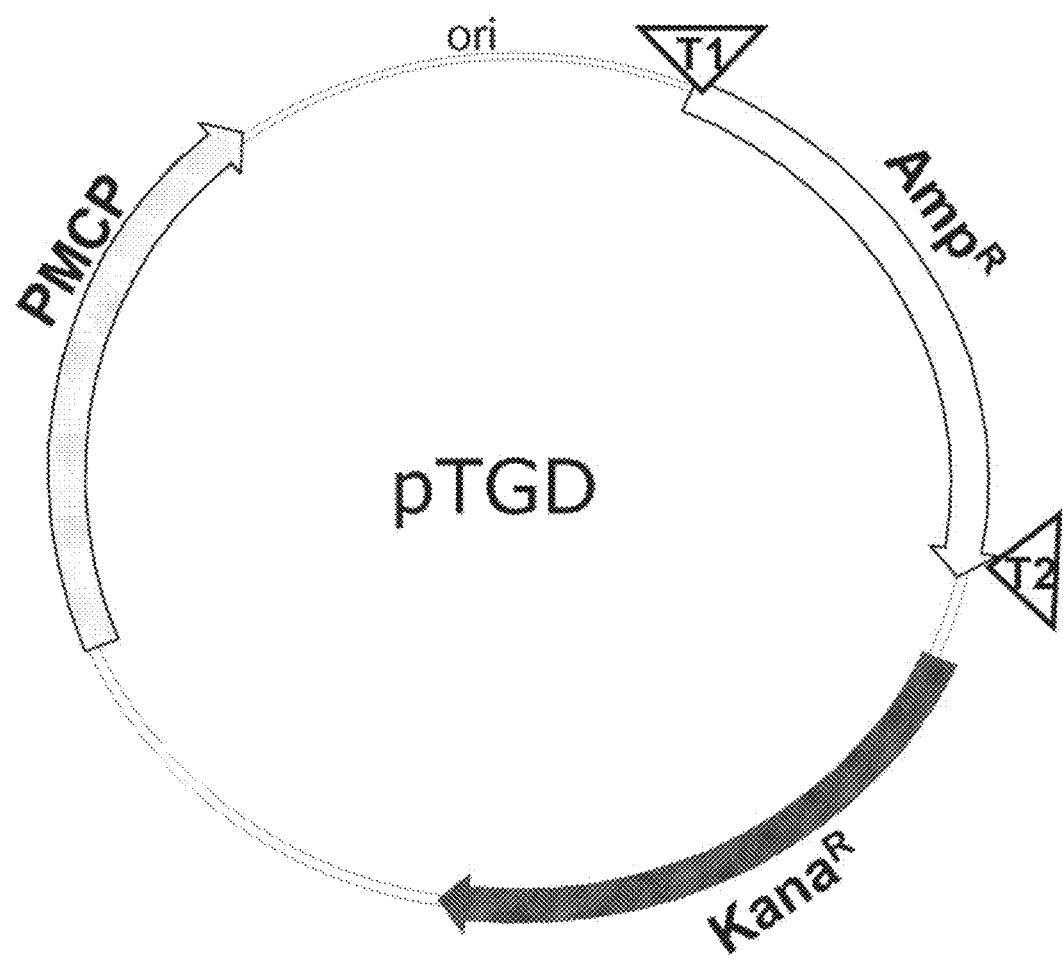
FIG. 15 shows a schematic illustration of a non-limiting example of a delivery vehicle or vector (not to scale) for concomitant delivery of the programmable molecular complex protein (PMCP) to a susceptible target Eukaryotic cell together with a target sequence to test its activity, according to some embodiments, and as detailed in Example 10.

This example is for a bioassay suitable for testing and fine-tuning permutations in the basic design of the programmable molecular complex; for testing its application in different organisms or cells; for testing different delivery methods; and for testing the editing functions of mutation, replacement, deletion and insertion.
Bacterial selectable marker genes are used to determine the gene targeting efficiency when targeting plasmid DNA.
In these examples an *Arabidopsis* protoplast based bioassay is used. In this bioassay, protoplasts are delivered with the reporter system and the molecular complex on a plasmid, co-delivered with paired ssDNA SCNA modified with a terminal Digoxigenin (NHS Ester) (DIG), one SCNA having such a modification at the 3'-terminus and the other at the 5'-terminus. A second modification for exonuclease protection, such as phosphorothioate, may be added at the opposite terminus.
Protein Sequence and Properties
The protein moiety is as described in Example 1.
In this example, the nucleic acid end-modification of the SCNA is an NHS-Ester linked Digoxigenin (DIG), attached to the 5' or 3' position of the oligonucleotide. Amino-acid sequence (one letter code) of the protein moiety of the molecular complex (NLS-FokI-nuclease sequence With Digoxygenin ScFv is set forth in (SEQ ID NO: 12):
SCNA Properties and Sequence
The length of the SCNA of the complementary, target-base-pairing oligonucleotide is preferentially at least 18 bases. The SCNA can also contain a small number (e.g. 1-6, in one example 6, in other example, 2) of non-target-base-pairing nucleotides ("N's") of any sequence composition that serve as a spacer between the DIG-NHS terminal-modifier and the target-complementary nucleotides.
Results of spatial measurements taken from computerized 3D models for the anti-DIG-ScFv-NHS-Ester-DIG system with the GSLEGGSGG (SEQ ID NO: 14) interdomain linker, as shown in this example, yielded that the expected optimal distance between SCNAs is, in the presence of 2 N's in the SCNA, about 23-26 nucleotides. Cleavage is predicted to occur about ±2 nucleotides to left and to the right of the $11^{th}$, $12^{th}$ or $13^{th}$ nucleotide, counting from after the last nucleotide hybridizing with the SCNA on either side, taking into account the 4 base 5' overhang created by dsDNA cleavage by the dimerized construct. This criterion suggests that if the targeted sequence is, for this 24 nucleotide example: AAAAAAAAAAYYYYYYYYYXX-XXXXYYYYYYYYYCCCCCCCCCC, where Y+X represents the number of nucleotides between the SCNA base-pairing sites, then the designed SCNAs base-pair with areas A and C and the cleavage resulting in DSB is in or adjacent to the X area. The SCNAs can be complementary to either sense or antisense strands, but are chosen preferably to base-pair with the sense (untranscribed) sequence. Both SCNAs can base-pair with the same strand, as the protein moiety's position is situated at the "near end" of the SCNA as defined by the 5' or 3' modification of the primer being at the "near end".
Detection Assay:
The target plasmid pTGD (schematically represented in FIG. 15) comprises 4 main sections:
1. The target ampicillin resistance cassette (AmpR).
2. Constitutive selection Kanamycin (Km) resistance cassette (KanR).
3. Origin of replication (ori).
4. The programmable molecular complex protein moiety encoding sequence cassette (PMCP) including a promoter suitable for the test organism, in this example, plants.
5. T1 and T2-target sequences 1 and 2.

This plasmid multiplies in bacterial cells such as *E. coli* cells. In this example the SCNAs, the target plasmid pTGD encoding the programmable molecular complex protein moiety and a donor DNA (in examples 10B, 10C) are delivered into *Arabidopsis* protoplasts. 48 hours after transfection, DNA is extracted from the transfected protoplasts (Kit A1120 Promega Corp.) and transformed into *E. coli* bacterial competent cells (Kit L3002 Promega Corp.). The transfected bacteria are spread on LB medium containing Kanamycin in a concentration of 100 microgram/ml. Colonies are grown for about 16 h at 37 degrees C. The colonies are then transferred in replica to Ampicillin (100 microgram/ml) or Tetracycline (100 microgram/ml) LB plates and grown for another 16 h at 37 degrees C.
Analysis:
Colonies from each replica are counted. Number of Kanamycin resistant colonies suggests total plasmid number which also represents total target number. Colonies which are not resistant to Ampicillin are colonies that contain a plasmid successfully targeted validating the editing functions of "Mutation" or "Deletion". Colonies resistant to Tetracycline but not to Ampicillin represent integration of the donor DNA into the target plasmid by NHEJ validating the editing function of "Replacement". Colonies that are resistant to both Ampicillin and Tetracycline are colonies containing plasmids that were targeted, had the donor integrated into the Ampicillin target sequence, but did not replace it validating the editing function of "Insertion".
Plasmids are then subjected to PCR and sequence analysis for verification of the results with the primers:

| A961F: | TAGGGCGCTGGCAAGTGTAG | (SEQ ID NO: 158) |
| A2161R: | CATAACACCCCTTGTATTAC | (SEQ ID NO: 159) |

Experiments

Example 10A

Targeted Mutation in the AMPR Cassette

The detection assay is performed essentially as described above ("detection assay") with the following additional details: pTGD plasmid is transfected together with SCNAs flanking target sequence 1 (SEQ ID NO: 161) to *Arabidopsis* protoplasts. DNA is purified and transformed into *E. coli* competent cells which are spread on LB Kan medium. A replica is made on LB AMP plates. Colonies that lost resistance to AMP contain a targeted plasmid.

Example 10B

The detection assay is performed essentially as described above ("detection assay") with the following additional details: pTGD plasmid is transfected together with SCNAs flanking target sequence 1 and a linear dsDNA Tetracycline (Tet) donor, produced as a PCR product, into *Arabidopsis* protoplasts. DNA is purified and transformed into *E. coli* competent cells which are spread on LB Km medium. A replica is made on both LB AMP and on LB Tet plates. Colonies that lost resistance to AMP contain a targeted plasmid. Colonies resistant to Tet represent plasmids containing specifically integrated donor DNA.

Example 10C

The detection assay is performed essentially as described above ("detection assay") with the following additional details: pTGD plasmid is transfected together with SCNAs directed against target sequence 1 and SCNAs against target sequence 2 (SEQ ID NO: 170), together with the Tetracycline (Tet) donor DNA to *Arabidopsis* protoplasts. DNA is purified and transformed into *E. coli* competent cells which are spread on LB Km medium. A replica is made on LB AMP and on LB Tet plates. Colonies that lose resistance to AMP contain a targeted plasmid. Tet resistant colonies represent specifically integrated donor DNA. The AMP sensitive colonies are subjected to PCR analysis with primers A961F and A2161R.

Colonies that contain a plasmid incorporating the Tet donor (ca. 1.9 Kb) instead of the AMP (ca. 860 bp) target sequence demonstrate gene replacement events.

Colonies sensitive to both AMP and to Tet demonstrate gene deletion through NHEJ.

Colonies resistant to both Tet and AMP contain a plasmid incorporating the TetR donor without deletion of the Amp resistance cassette and demonstrate targeted donor integration or "insertion".

Delivery

Bioassay setup: *Arabidopsis* protoplast preparation is based on Wu et. al. (2009), and is similar to that of example 1 with differences in the transfection step:

Transfection:
1. Make fresh PEG sol for transfection in 2 ml tube
2. Pour off BSA from 6-well plates and dry
3. Mix ~5×10^4 protoplasts (2×10^4-1×10≡) in 0.2 ml MMg with a mixture of plasmid comprising the Target plasmid DNA and the Protein Moiety expressing DNA, the ssDNA SCNAs and the linear dsDNA Donor to a total of 30-40 microgram at room temperature in 15 ml round-bottom (snap-cap) tubes.
4. Add equal volume (0.2 ml protoplasts+midiprep vol.) of fresh PEG sol
5. Incubate RT° 5 min
6. Wash by slowly adding 3 ml W5, 1 ml at a time, and mixing
7. Centrifuge 100×g in swing-out 1 min
8. Repeat wash and pellet
9. Resuspend in 1 ml W5 solution.
10. Pour into BSA-coated plates
11. Grow protoplasts under 16 hr day optimal light (150 microEinstein·m^−2·s^−1) at 22 degrees C., replacing media as needed.

Protoplasts are then subjected to DNA extraction as described in the Detection Assay.

Targeted AmpR Cassette is as set forth in SEQ ID NO: 160. SCNA pairs are chosen one left (L) and one right (R) irrespective of sense (S) or antisense (AS) strand: Choice of SCNA pair combination is a tested parameter in the experiment.

Target sequence T1 on AMPR cassette: TATGAGTATTCAACATTTCCG (SEQ ID NO: 161) (ATG start codon is underlined)

Set 1 of AMP Targeting SCNAs:
Option 1—Utilizing a 21 bp Target Gap:
pTGD_130_SL:
A*ATAATATTGAAAAAGGAAGAGNNNNNN/3DIGN/ (the nucleic acids only are set forth herein in SEQ ID NO: 162)
pTGD_152_SR: /5DIGN/ NNNNNNTGTCGCCCTTATTCCCTTTTT*T (the nucleic acids only are set forth herein in SEQ ID NO: 163)
pTGD_130_ASL: /5DIGN/ NNNNNNCTCTTCCTTTTTCAATATTAT*T (the nucleic acids only are set forth herein in SEQ ID NO: 164)
pTGD_152_ASR: A*AAAAGGGAATAAGGGCGACANNNNNN/3DIGN/ (the nucleic acids only are set forth herein in SEQ ID NO: 165)

Option 2—paired combinations, employing a 24 bp target gap and a shorter SCNA linker according to the prediction results: AMP_129_SL:
C*AATAATATTGAAAAAGGAAGANN/3DIGN/ (the nucleic acids only are set forth herein in SEQ ID NO: 166)
AMP_154_SR: /5DIGN/ NNTCGCCCTTATTCCCTTTTTTG*C (the nucleic acids only are set forth herein in SEQ ID NO: 167)
AMP_129_ASL: /5DIGN/ NNTCTTCCTTTTTCAATATTATT*G (the nucleic acids only are set forth herein in SEQ ID NO: 168)
AMP_154_ASR:
G*CAAAAAAGGGAATAAGGGCGANN/3DIGN/ (the nucleic acids only are set forth herein in SEQ ID NO: 169)

Target sequence T2 on AMPR cassette: AGCATTGGTAACTGTCAGACC (SEQ ID NO: 170)

Set 2 of AMP Targeting SCNAs:
Option 1 utilizing a 21 bp target gap:
pTGD_981_SL:
G*AGATAGGTGCCTCACTGATTANNNNNN/3DIGN/ (the nucleic acids only are set forth herein in SEQ ID NO: 171)
pTGD_1003_SR: /5DIGN/ NNNNNNAAGTTTACTCATATATACTTT*A (the nucleic acids only are set forth herein in SEQ ID NO: 172)
pTGD_981_ASL: /5DIGN/ NNNNNNTAATCAGTGAGGCACCTATCT*C (the nucleic acids only are set forth herein in SEQ ID NO: 173)
pTGD_1003_ASR:
T*AAAGTATATATGAGTAAACTTNNNNNN/3DIGN/ (the nucleic acids only are set forth herein in SEQ ID NO: 174)

Option 2 paired combinations, employing a 24 bp target gap and a shorter SCNA linker according to the prediction results:
AMP_980_SL: T*GAGATAGGTGCCTCACTGATTNN/3DIGN/ (the nucleic acids only are set forth herein in SEQ ID NO: 175)

AMP_1005_SR: /5DIGN/ NNGTTTACTCATATATACTTTAG*A (the nucleic acids only are set forth herein in SEQ ID NO: 176)
AMP_980_ASL: /5DIGN/ NNAATCAGTGAGGCACCTATCTC*A (the nucleic acids only are set forth herein in SEQ ID NO: 177)
AMP_1005_ASR: T*CTAAAGTATATATGAGTAAACNN/3DIGN/ the nucleic acids only are set forth herein in SEQ ID NO: 178)
Donor:
Donor sequence encoding Tetracycline resistance from Cloning vector pSoup, EU048870.1 GI:155733614 is as set forth in SEQ ID NO: 179.

Example 11

Construction of the Programmable Molecular Complex to Act with a Pair of Connected SCNA Sequences In this example, the programmable molecular complex is designed to operate with a single nucleic acid molecule incorporating dual target sequence binding nucleic acid sequences, here designated as a connected pair of Specificity Conferring Nucleic Acid sequences (SCNA sequences) as schematically illustrated in FIGS. 4A and 4B.

In this example, a disrupted GFP target sequence is repaired by removal or mutation of a STOP codon. The resulting cleavage of the predetermined Target GFP leads to point mutation that may restore GFP activity.

In these examples, an *Arabidopsis* protoplast based bio-assay, in which the protoplasts are delivered with the reporter system (target plasmid), protein moiety expressing plasmid, co-delivered with either: For example 12A (schematically illustrated in FIG. 4A)—A nucleic acid encoding an RNA, RNA composed of two SCNA sequences modified, in this example, by the 20-mer boxB RNA hairpin binding sequence from bacteriophage Phi21 (SEQ ID NO: 62: 5'-UUCACCUCUAACCGGGUGAG-3') and an "SCNA Connector", a non-target hybridizing stretch of nucleotides of undefined sequence or length. One SCNA having such a modification at the 3'-terminus and the other at the 5'-terminus of the RNA molecule. The RNA-SCNAs in this example bind the Linking Domain of the Protein Moiety of the two Molecular complexes using the 20-mer boxB RNA hairpin binding sequence from bacteriophage Phi21 (5'-UUCACCUCUAACCGGGUGAG-3'(SEQ ID NO: 62), or: In example 11B schematically illustrated in FIG. 4B) a modified ssDNA SCNA containing sequence, in this example, modified on both the 5' and the 3' termini by addition of terminal Digoxigenin (NHS Ester) (DIG) molecules and an "SCNA Connector", a non-target hybridizing stretch of nucleotides of undefined sequence or length.
Protein Sequence and Properties The protein moiety in example 11A, contains an amino-acid sequence derived from a FokI nuclease domain as the Functional Domain, Linking Domain in derived from the RNA-binding protein (RBP) bacteriophage Phi21 NProtein (SEQ ID NO: 63: N'-GTAKSRYKARRAELIAER-C'), an SV40NLS (PKKKRKV: SEQ ID NO: 3) as a nuclear localization domain and an inter-domain connector (SEQ ID NO: 14: GSLEGGSGG).

The protein moiety in example 11B contains an amino-acid sequence adapted from a FokI nuclease domain as the Functional Domain; an amino-acid sequence adapted from anti-DIG single-chain variable fragment (scFv) immuno-globin (DIG-ScFv) similar to that described in (Huston et. al., 1988) as Linking Domain; an SV40NLS (PKKKRKV: SEQ ID NO: 3) as a nuclear localization domain and an inter-domain connector (SEQ ID NO: 14: GSLEGGSGG).

The nucleic acid end-modifications of the SCNA are NHS-Ester linked Digoxigenin (DIG) and are attached to both the 5' and the 3' position of the oligonucleotide.

Example 11A

Phi21NP Based Programmable Molecular Complex Protein Moiety Sequence

Components:
Bacteriophage Phi21 NProtein
(SEQ ID NO: 63: GTAKSRYKARRAELIAER) at or near the N' terminus as in the full-length N-protein the RNA-binding peptide is situated at the N-terminus.
FokI Nuclease:

```
                                    (SEQ ID NO: 66)
VKSELEEKKSELRHKLKYVPHEYIELIEIARNSTQDRILEMKVMEFFMKV

YGYRGKHLGGSRKPDGAIYTVGSPIDYGVIVDTKAYSGGYNLPIGQADEM

QRYVEENQTRNKHINPNEWWKVYPSSVTEFKFLFVSGHFKGNYKAQLTRL

NHITNCNGAVLSVEELLIGGEMIKAGTLTLEEVRRKFNNGEINF

SV40-NLS:  (PKKKRKV: SEQ ID NO: 3)
```

Interdomain connectors: various poly-amino-acid linkers are tested for optimal function of the programmed molecular complex.
Amino-acid sequence of the protein moiety of the molecular complex: In this example, the Phi21 NProtein (amino acid sequence as set forth in SEQ ID NO:68) is assembled in the N' terminus of the protein moiety of the programmable molecular construct and the nuclear localization signal, SV40NLS, is located at the C' terminus and the interdomain linker is GGSGG (SEQ ID NO: 7).

Example 11B

Amino-Acid Sequence (One Letter Code) of the Protein Moiety of the Molecular Complex (NLS-FokI-Nuclease with Digoxygenin ScFv, is Set Forth in SEQ ID NO: 12)

SCNA Properties and Sequence

The SCNA length of the complementary, target-base-pairing oligonucleotide can be at any predetermined length. For example, the length is at least 18 bases. The SCNA can also contain a small number (preferably 0-6, more preferably 1-2) of non-target-base-pairing nucleotides (N's) of any sequence composition that serve as a spacer between the A) Phi21 boxB RNA hairpin terminal modifier in example 11A or 11B) DIG-NHS terminal-modifier in example 12B, and the complementary nucleotides. In these examples, the SCNAs are connected by a non-target-base pairing sequence designated the "SCNA Connecter" in FIG. 14 or X(n) in the sequences of this example. X(n) signifies an undetermined length of RNA nucleotides connecting the two specificity conferring regions to each other. For linear DNA the expected optimal length (n) is about, 35-73 nucleotides (nts), while both longer (above 73 nts) and shorter (4-34 nts) SCNA connectors are applicable. In the examples given here n=40 nucleotides.

The SCNAs can be complementary to either sense or antisense strands, but are chosen preferably to base-pair with the sense (untranscribed) sequence though two options are shown here for each example. Both SCNA sequences can base-pair with the same strand, as the protein moiety position is situated at the "near end" of the SCNA as defined by the 5' or 3' modification of the primer being at the "near end".

Target "STOP GFP" containing plasmid for the assays of Examples 11A and 11B contains the nucleic acid sequence as set forth in (SEQ ID NO: 181).

Example 11A

Phi21NP Based

Sense or antisense hybridizing dual SCNAs are constructed:
Sense Connected SCNAs:
GFP-921SR-X(n)-892SL BOXBPHI
UUCACCUCUAACCGGGUGAGNUCCAAGGGC-GAGGAGCUGUUCA (SEQ ID NO: 207)-X(n)-AC-CAUUUACGAACGAUAGCCAUN
UUCACCUCUAACCGGGUGAG (designated as SEQ ID NO: 208).
Anti-Sense Connected SCNAs:

```
GFP-921ASR-X(n)-892ASL BOXBPHI
                                        (SEQ ID NO: 209)
UUCACCUCUAACCGGGUGAGNAUGGCUAUCGUUCGUAAAUGGU (SEQ ID NO: 210)
-X(n)-UGAACAGCUCCUCGCCCUUGGANUUCACCUCUAACCGGGUGAG
```

The 20-mer boxB PHI sequence 5'-UUCACCUC-UAACCGGGUGAG-3' (SEQ ID NO: 62) is underlined. Specificity-conferring sequences on the dual SCNA are marked in the schematic drawings of FIGS. 4A-B as SCNA1 and SCNA2. N's signify a short stretch (0-6) of any nucleotide, X(n) signifies a non-target hybridizing stretch of nucleotides of undefined sequence or length (SCNA Connector).

Example 11B

Sense or antisense hybridizing dual SCNAs are constructed:
Sense Connected SCNAs:
GFP-919SR-X(n)-894SL-DIG
/5DigN/NNTGTCCAAGGGCGAGGAGCTGTT (the nucleic acids only are designated as SEQ ID NO: 211)
—X(n)-CATTTACGAACGATAGCCATGGNN/3DigN/
(the nucleic acids only are designated as SEQ ID NO: 212)
Antisense Connected SCNAs:
GFP-919ASR-X(n)-894ASL-DIG
/5DigN/NNCCATGGCTATCGTTCGTAAATG (the nucleic acids only are designated as SEQ ID NO: 213)-X(n)-AACAGCTCCTCGCCCTTGGACANN/3DigN/ (the nucleic acids only are designated as SEQ ID NO: 214)

Modification symbols are those used in the Integrated DNA Technology (IDT) website (5' DIG=/5DigN/; 3'DIG=/3DigN/), X(n) signifies a non-target hybridizing stretch of nucleotides of undefined sequence or length (SCNA Connector).
Delivery Bioassay setup: *Arabidopsis* protoplast preparation is based on Wu et. al. (Wu et. al., 2009) and is similar to that of example 1 with differences in the transfection step:

Transfection:
1. Make fresh PEG sol for transfection in 2 ml tube
2. Pour off BSA from 6-well plates and dry
3. Mix ~$5 \times 10^4$ protoplasts ($2 \times 10^4$-$1 \times 10^5$) in 0.2 ml MMg with a mixture of plasmid comprising the Target plasmid DNA and the Protein Moiety expressing DNA and the dual-SCNA expressing plasmid (For example 12A) or dual SCNA containing ssDNA (For example 12B) of 30-40 µg at RT° in 15 ml round-bottom (snap-cap) tubes.
4. Add equal volume (0.2 ml protoplasts+midiprep vol.) of fresh PEG sol
5. Incubate RT° 5 min
6. Wash by slowly adding 3 ml W5, 1 ml at a time, and mixing
7. Centrifuge 100×g in swing-out 1 min
8. Repeat wash and pellet
9. Resuspend in 1 ml W5 solution
10. Pour into BSA-coated plates
11. Grow protoplasts under 16 hr day optimal light (150 µE·m−2·s−1) @22° C., replacing media as needed.

Protoplasts are then subjected to FACS or DNA extraction as described below.
Results: Point Mutation by Induced DSB.

In this example, cleavage of the target by the molecular complex results in a Double-Strand-Break (DSB) in the plasmid DNA target. This DSB is created in the STOP codon site, which is digested and is repaired by endogenous NHEJ repair mechanism. NHEJ is prone to mutations, and some of these mutations may abolish the STOP codon and restore an open reading frame resulting in an active GFP open reading frame (ORF). GFP is then detected by means of microscopy or flow cytometer (FACS), enabling the measurement of system efficiency and comparison between variables for its improvement.
Analysis:

The gene targeting efficiency is determined as the percentage of positive GFP cells. Protoplasts suspended in W5 solution are screened for GFP activity 3 days after transfection using an automated flow-cytometer (FACS). GFP is detected by excitation at 488 nm with emission detected by 530/30 filter. Threshold and compensation factors are set to exclude any false positives.

The target sequence is a STOP codon coupled with a diagnostic restriction site (SpeI AC<u>TAG</u>T, STOP underlined) in the GFP coding sequence. When successfully targeted, the STOP codon and diagnostic restriction site are abolished by a deletion, an insertion or a point mutation event. Repair in a specific frame can also restore GFP expression. The assay is analyzed by FACS as described herein below or by purifying plasmid DNA from the protoplasts using a plasmid miniprep kit (Bioneer K3030) as following: protoplasts in W5 solution are precipitated, and lysed by addition of 250 ul Buffer 1 and proceeding with the protocol as for bacterial pellets in the manufacturer's instructions. The region between the SCNAs is amplified from resulting plasmid preparation by PCR. PCR products are exhaustively cleaved with SpeI. After electrophoresis uncleaved products are excised from the gel, cloned into a T/A cloning vector (pUC57/T Fermentas) and individual clones are sequenced to detect different mutation events.

Example 12

Bioassay for Determination of Optimal SCNA Distances

Figure 16:
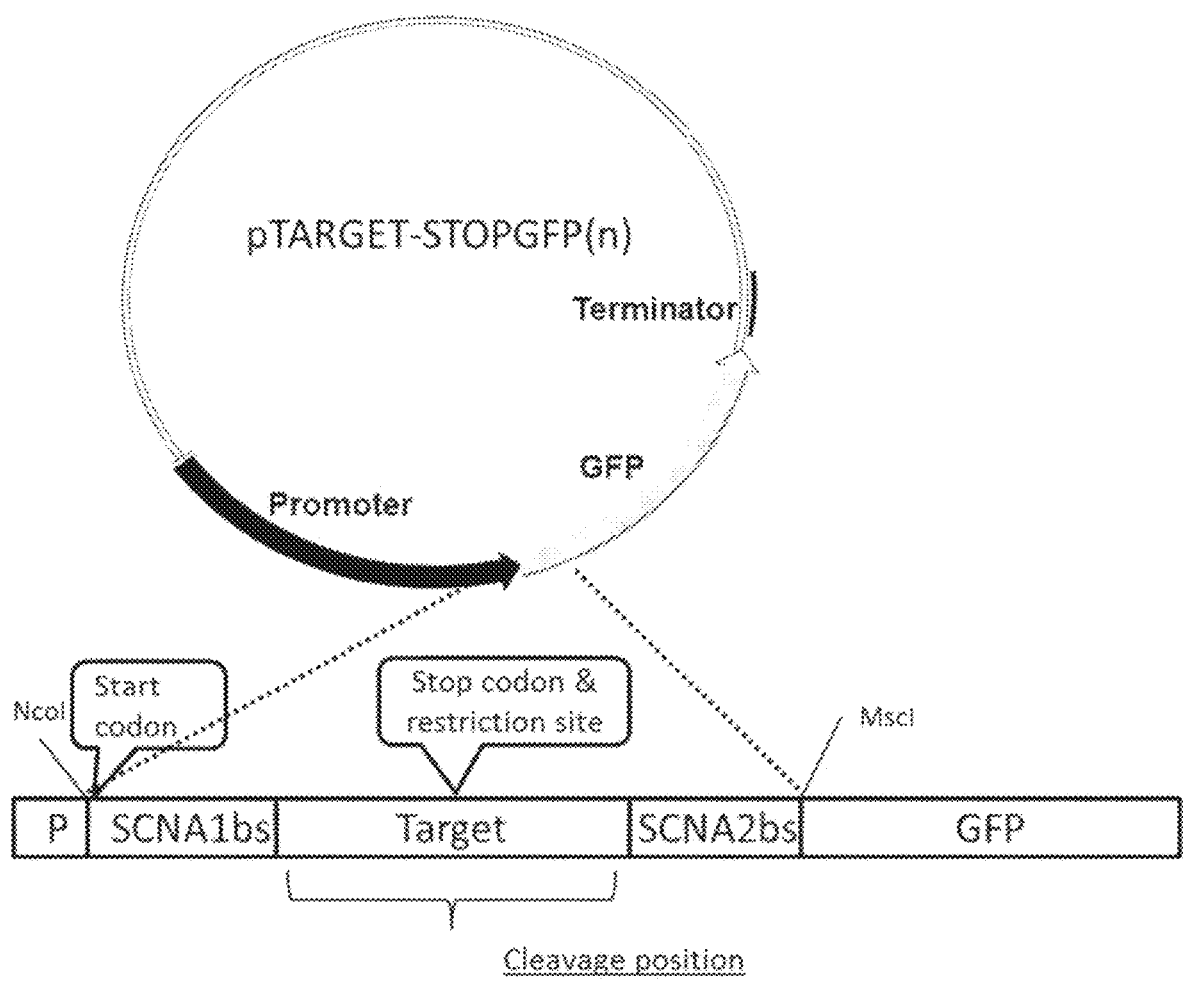
FIG. 16 shows a schematic drawing (not to scale) of parameters to empirically determine the optimal distance between SCNA pairs and to test capability of different types of programmed molecular complexes to specifically cleave a target DNA, as detailed in Example 12.

To determine optimal SCNA distances from potential target sites, for each different target type or programmable molecular complex type, a set of target plasmids (pTAR-GET-STOPGFP(n), FIG. 16.) containing a disrupted GFP reporter coding sequence (STOP-GFP) are created. In an artificial N' leader and in the GFP coding sequence (CDS) two SCNA binding sequences (SCNAbs) are inserted, which flank a target sequence with variable lengths forming series of plasmids designated as pTARGET-STOPGFP(1-8) (FIG. 16). Inserts, as outlined in FIG. 16 are inserted using the restriction enzymes NcoI and MscI. The target sequence is a STOP codon coupled with a diagnostic restriction site (SpeI AC<u>TAG</u>T (SEQ ID NO:215) or BclI <u>TGA</u>TCA (SEQ ID NO:216), STOP underlined) in the artificial N' leader.

Other components of the plasmid include 1) a promoter operably linked to the GFP sequence. Assay can be conducted in different Eukaryotes. In this example, a plant promoter such as NosP is used for conducting the experiment in *Arabidopsis* protoplasts. 2) a pair of SCNA binding sites (SCNA1bs and SCNA2bs); 3) a Target site containing a STOP codon; 4) a GFP coding sequence and 5) a transcription terminator sequence, in this example NosT.

The schematic cartoon (not to scale) shown in FIG. 16, illustrates a set of eight exemplary constructs in a set of plasmids pTarget-STOPGFP(n), containing a disrupted Green Fluorescent Protein (GFP) reporter coding sequence (STOPGFP), where "n" signifies a serial number as shown in the table in FIG. 16. The set of inserts of variable length and composition are delineated by an NcoI restriction site encompassing the start codon and an MscI site at the opposite end. SCNA1bs is located in the GFP-artificial N' leader and SCNA2bs is located in the GFP coding sequence. The target sequence is a STOP codon coupled with a diagnostic restriction site (SpeI AC<u>TAG</u>T (SEQ ID NO:215) or BclI <u>TGA</u>TCA (SEQ ID NO:216), STOP underlined) and a frameshift (except in n=5) in the artificial N' leader. Sequences of the target site spacers are shown in Example 12. In the table, "n" signifies the plasmid serial number. The distance between SCNAbs in base-pairs (bp) is shown followed by the relevant diagnostic restriction site in parenthesis. Desired cleavage positions on the top and bottom strands, due to expected four bp 5' overhangs, are shown, where ±2 numbers are in even-numbered inserts and ±3 numbers in odd-numbered inserts, due to uncertainty caused by the positioning of the catalytic location "on" a nucleotide instead of between nucleotides. In some cleavage events endogenous repair mechanisms may cause imperfect repair causing the deletion, mutation or addition of non-templated nucleotides. Some of these repaired sequences may cause the abolishment of the STOP codon and of the diagnostic restriction site coupled with a frame shift restoring GFP expression. The minimal restoring events, addition or deletion of nucleotides or point mutations, are shown in the rightmost column of the table.

Recognition Sequence of SCNA1 Binding in Insert:

```
ATCTCAAGTCTCTAGGACTGGT       (SEQ ID NO: 182)
```

Recognition Sequence of SCNA2 Binding in GFP Sequence:

```
ATCTGTGAGCAAAGGCGAGGAG       (SEQ ID NO: 183)
```

As outlined in FIG. 16:

NcoI/MscI insert for n=1:

```
                                          (SEQ ID NO: 184)
CCATGGGATCTCAAGTCTCTAGGACTGGTCTTCAAAATCTTTCTCACTAG

TTTCTACGATCTTGGCCA
```

NcoI/MscI insert for n=2:

```
                                          (SEQ ID NO: 185)
CCATGGGATCTCAAGTCTCTAGGACTGGTCAAAATCTTTCTCACTAGTTT

CTACGCTGGCCA
```

NcoI/MscI insert for n=3:

```
                                          (SEQ ID NO: 186)
CCATGGGATCTCAAGTCTCTAGGACTGGTAATCTTTCTCACTAGTTACGC

TGGCCA
```

NcoI/MscI insert for n=4:

```
                                          (SEQ ID NO: 187)
CCATGGGATCTCAAGTCTCTAGGACTGGTAATCTTTCTTGATCAGTCTGG

CCA
```

NcoI/MscI insert for n=5:

```
                                          (SEQ ID NO: 188)
CCATGGGATCTCAAGTCTCTAGGACTGGTAATCTTTCTTGATCAGCTGG

CCA
```

NcoI/MscI insert for n=6:

```
                                          (SEQ ID NO: 189)
CCATGGGATCTCAAGTCTCTAGGACTGGTAATCTTTCTTGATCACTGG

CCA
```

NcoI/MscI insert for n=7:

```
                                          (SEQ ID NO: 190)
CCATGGGATCTCAAGTCTCTAGGACTGGTCTTTCTCACTAGTTCTGGCCA
```

NcoI/MscI insert for n=8:

```
                                          (SEQ ID NO: 191)
  CCATGGGATCTCAAGTCTCTAGGACTGGTCTTCACTAGTGGCCA
```

Each molecular complex is co transfected into *Arabidopsis* protoplasts as described herein below:

Delivery

Bioassay setup: *Arabidopsis* protoplast preparation is based on (Wu et. al.) and is similar to that of example 1 with differences in the transfection step:

Transfection:
1. Make fresh PEG sol for transfection in 2 ml tube
2. Pour off BSA from 6-well plates and dry
3. Mix ~5×10^4 protoplasts (2×10^4-1×10^5) in 0.2 ml MMg with a mixture of Donor plasmid DNA (where relevant), Protein Moiety expressing plasmid DNA and SCNAs ssDNA to a total of 30-40 microgram at RT° in 15 ml round-bottom (snap-cap) tubes. Alternatively Donor DNA and Protein-moiety expressing DNA are constructed and delivered on a single plasmid.
4. Add equal volume (0.2 ml protoplasts+midiprep vol.) of fresh PEG sol
5. Incubate RT° 5 min
6. Wash by slowly adding 3 ml W5, 1 ml at a time, and mixing
7. Centrifuge 100×g in swing-out 1 min
8. Repeat wash and pellet
9. Resuspend in 1 ml W5 solution
10. Pour into BSA-coated plates
11. Grow protoplasts under 16 hr day optimal light (150 microEinstein·m^−2·s^−1) at 22 degrees C., replacing media as needed.

Analysis:

The gene targeting efficiency of each form of the molecular complex is tested on the pTARGET-STOPGFP(n) plasmid series.

When successfully targeted, the STOP codon and diagnostic restriction site are abolished by a deletion, an insertion or a point mutation event (FIG. 16). Repair in a specific frame can also restore GFP expression (FIG. 16). The assay is analyzed by FACS or by purifying plasmid DNA from the protoplasts using a plasmid miniprep kit (Bioneer K3030) as following: protoplasts in W5 solution are precipitated, and lysed by addition of 250 ul Buffer 1 and proceeding with the protocol as for bacterial pellets in the manufacturer's instructions. The "spacer" region is amplified from resulting plasmid preparation by PCR. PCR products are exhaustively cleaved with SpeI (37° C.) or BclI (50° C.) as appropriate. After electrophoresis, uncleaved products are excised from the gel, cloned into a T/A cloning vector (pUC57/T Fermentas) and individual clones are sequenced to detect different mutation events.

The gene targeting efficiency is then determined as the percentage of positive GFP cells. Protoplasts suspended in W5 solution are screened for GFP activity 3 days after transfection using an automated flow-cytometer (FACS). GFP is detected by excitation at 488 nm with emission detected by 530/30 filter. Threshold and compensation factors are set to exclude any false positives.

Controls included in the experiment are 1) use of illegitimate (non-base pairing) SCNAs to control for non-specific cleavage, 2) use of a pTARGET-STOPGFP missing one target binding site to control for non-dimer action, 3) use of pTARGET-GFP, a similar plasmid without the GFP-disrupting STOP codon and having an in-frame GFP as a positive control, 4) use of pTARGET-STOP-I-SceI-GFP, a plasmid similar to pTARGET-STOPGFP but containing an I-SceI restriction site near the GFP-disrupting STOP codon, in conjunction with pSAT4-NLS-I-SceI, a plasmid expressing a nuclear localized I-SceI restriction enzyme in plant cells, as a comparative heterologous system control.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES

1. Schierling B, Dannemann N, Gabsalilow L, Wende W, Cathomen T, Pingoud A. (2012). A novel zinc-finger nuclease platform with a sequence-specific cleavage module. Nucleic Acids Res. 2012 March; 40(6):2623-38.
2. Eisenschmidt K, Lanio T, Simoncsits A, Jeltsch A, Pingoud V, Wende W, Pingoud A. (2005). Developing a programmed restriction endonuclease for highly specific DNA cleavage. Nucleic Acids Res. 2005 Dec. 14; 33(22): 7039-47.
3. Kubo T, Kanno K, Ohba H, Rumiana B, Fujii M. (2004). Control of intracellular delivery of oligonucleotides by signal peptides and genetic expression in human cells. Nucleic Acids Symp Ser (Oxf). 2004; (48):303-4.
4. Jinek M, Chylinski K, Fonfara I, Hauer M, Doudna J A, Charpentier E. (2012). A programmable dual-RNA-guided DNA endonuclease in adaptive bacterial immunity. Science. 2012 Aug. 17; 337(6096):816-21.
5. Hanic-Joyce P J, Gray M W (1991) Accurate transcription of a plant mitochondrial gene in vitro. Mol Cell Biol 11: 2035-2039
6. Vainstein A, Marton I, Zuker A, Danziger M, Tzfira T (2011) Permanent genome modifications in plant cells by transient viral vectors. Trends in Biotechnology 29: 363-369
7. Gallois P, Marinho P (1995) Leaf disk transformation using *Agrobacterium tumefaciens*-expression of heterologous genes in tobacco. Methods Mol Biol 49: 39-48
8. Kochevenko A, Willmitzer L (2003) Chimeric RNA/DNA oligonucleotide-based site-specific modification of the tobacco acetolactate syntase gene. Plant Physiol 132: 174-184
9. Marrs K A, Urioste J C (1995) Transient Gene Expression Analysis in Electroporated Maize Protoplasts. Vol. 55, pp 133-145.
10. Kotlo K U, Yehiely F, Efimova E, Harasty H, Hesabi B, Shchors K, Einat P, Rozen A, Berent E, Deiss L P (2003) Nrf2 is an inhibitor of the Fas pathway as identified by Achilles' Heel Method, a new function-based approach to gene identification in human cells. Oncogene 22: 797-806
11. Huston J S, Levinson D, Mudgett-Hunter M, Tai M S, Novotny J, Margolies M N, Ridge R J, Bruccoleri R E, Haber E, Crea R, et. al. (1988) Protein engineering of antibody binding sites: recovery of specific activity in an anti-digoxin single-chain Fv analogue produced in *Escherichia coli*. Proc Natl Acad Sci USA 85: 5879-5883
12. Wu F H, Shen S C, Lee L Y, Lee S H, Chan M T, Lin C S (2009) Tape-*Arabidopsis* Sandwich—a simpler *Arabidopsis* protoplast isolation method. Plant Methods 5: 16.
13. Antonelli N M, Stadler J (1989) Chemical methods for direct gene transfer to maize protoplasts: I. Efficient transient expression after treatment with the polycation Polybrene Maize News letter 63: 21-22
14. Sheen J (2001) Signal transduction in maize and *Arabidopsis* mesophyll protoplasts. Plant Physiol 127: 1466-1475
15. Gordon-Kamm W J, Spencer™, Mangano M L, Adams T R, Daines R J, Start W G, O'Brien J V, Chambers S A, Adams W R, Jr., Willetts N G, Rice T B, Mackey C J, Krueger R W, Kausch A P, Lemaux P G (1990) Transformation of Maize Cells and Regeneration of Fertile Transgenic Plants. Plant Cell 2: 603-618.

The invention claimed is:

1. A method for modifying a predetermined target site within a target deoxyribonucleic acid (DNA) molecule in a plant host cell by a nucleo-protein molecular complex, the method comprising delivering to the plant host cell:
   (a) a programmable polypeptide, or a nucleic acid sequence encoding the programmable polypeptide, the polypeptide comprising:
      (i) an effector domain, wherein the effector domain is a nuclease; and
      (ii) a linking domain that is capable of interacting with a specificity conferring nucleic acid (SCNA),
      wherein the linking domain is devoid of a specific target-nucleic acid binding site, and wherein (A) the linking domain directly binds the SCNA or (B) the linking domain indirectly binds the SCNA; and
   (b) a synthetic specificity-conferring nucleic acid (SCNA) molecule, or a nucleic acid encoding the SCNA, the SCNA molecule comprising:
      (i) a nucleotide sequence complementary to a region of the target DNA molecule; and
      (ii) a recognition region capable of specifically attaching to the linking domain of the programmable polypeptide;

wherein the presence of the programmable polypeptide and the SCNA in the plant host cell enables attachment of the programmable polypeptide to the SCNA, forming in the plant host cell a nucleo-protein molecular complex, wherein the SCNA provides the specificity and binding capability of the nucleo-protein molecular complex to the predetermined target site within the target DNA molecule within the plant host cell, thereby enabling the nucleo-protein molecular complex to bind to the target DNA molecule, wherein the nucleo-protein molecular complex cleaves the target DNA molecule and wherein the nucleo-protein molecular complex does not comprise any of: an effector domain of a recombinase, digoxigenin (DIG), an anti-DIG single-chain variable fragment immunoglobin (DIG-ScFv)-DIG interaction, an antibody-antigen interaction, or a single chain antibody-antigen interaction.

2. The method of claim 1, wherein the target DNA molecule is genomic DNA.

3. The method of claim 1, wherein the target nucleic acid sequence is an extra-chromosomal nucleic acid sequence, selected from the group consisting of a nucleic acid in mitochondria, chloroplast, amyloplast, and chromoplast.

4. The method of claim 1, wherein the SCNA comprises a nucleic acid molecule selected from the group consisting of a single-stranded RNA, a double-stranded RNA, or a combination thereof.

5. The method of claim 1, wherein the interaction between the SCNA and the target DNA molecule is through base pairing selected from the group consisting of a full double helix base pairing, a partial double helix base pairing, a full triple helix base pairing, a partial triple helix base pairing, and D-loops.

6. The method of claim 1, wherein the recognition region of the SCNA comprises a RNA secondary or tertiary structure.

7. The method of claim 1, wherein the recognition region of the SCNA comprises a nucleotide motif capable of interacting with the linking domain of the polypeptide.

8. The method of claim 1, wherein the association between the recognition region of the SCNA and the linking domain is a nucleic acid-protein interaction.

9. The method of claim 1, wherein the interaction between the nucleotide motif and the linking domain is a RNA-motif-binding linking domain interaction with a RNA structure.

10. The method of claim 1, wherein the linking domain comprises a polypeptide which binds a structural RNA motif on the SCNA.

11. The method of claim 1, wherein the programmable polypeptide is expressed in the plant host cell.

12. The method of claim 1, wherein the programmable polypeptide and the SCNA are expressed in the plant host cell.

13. The method of claim 1, wherein the programmable polypeptide is expressed in the plant host cell.

14. The method of claim 1, wherein the programmable polypeptide and the SCNA are expressed in the plant host cell.

15. The method of claim 1, wherein the effector domain of the nucleo-protein molecular complex cleaves the target DNA molecule.

16. The method of claim 1, wherein the linking domain indirectly binds the SCNA through a modification on the SCNA.

* * * * *